United States Patent
Albert et al.

(10) Patent No.: US 12,171,938 B1
(45) Date of Patent: Dec. 24, 2024

(54) APPARATUS, METHODS, AND SYSTEMS FOR DELIVERY AND ADMINISTRATION OF PHARMACEUTICAL, THERAPEUTIC AND COSMETIC SUBSTANCES TO USERS

(71) Applicant: MICRONEB TECH HOLDINGS, INC., St Petersburg, FL (US)

(72) Inventors: Pradeep Albert, Sarasota, FL (US); Christine Nichols, Largo, FL (US); David J. Condron, Seminole, FL (US); Brian Artze, Gulfport, FL (US); Fadi Saba, St Petersburg, FL (US); Jesse Klein, Clearwater, FL (US); Vijay Vad, New York, NY (US)

(*) Notice: Subject to any disclaimer, the term of this patent is extended or adjusted under 35 U.S.C. 154(b) by 0 days.

(21) Appl. No.: 18/630,093

(22) Filed: Apr. 9, 2024

Related U.S. Application Data

(63) Continuation-in-part of application No. 18/529,978, filed on Dec. 5, 2023, and a continuation-in-part of
(Continued)

(51) Int. Cl.
  *A61M 16/00* (2006.01)
  *A01C 21/00* (2006.01)
  (Continued)

(52) U.S. Cl.
  CPC ......... *A61M 16/0084* (2014.02); *A01C 21/00* (2013.01); *A61C 19/063* (2013.01);
  (Continued)

(58) Field of Classification Search
  CPC A61M 16/0084; A61M 11/005; A61M 16/14; A61M 2210/0625; A61M 2210/0631; A61M 2210/0637
  See application file for complete search history.

(56) References Cited

U.S. PATENT DOCUMENTS

| 5,487,378 A | 1/1996 | Robertson et al. |
| 5,584,285 A | 12/1996 | Sater et al. |
| (Continued) | | |

FOREIGN PATENT DOCUMENTS

| CN | 215608554 U | 1/2022 |
| CN | 110708972 B | 2/2023 |
| (Continued) | | |

*Primary Examiner* — Bradley J Osinski
(74) *Attorney, Agent, or Firm* — Derek Fahey; The Plus IP Firm, PLLC

(57) ABSTRACT

Apparatus, methods, and systems for delivery and administration of pharmaceutical, therapeutic and cosmetic substances to users. The method includes providing a removable capsule having an atomizer, inserting the removable capsule in a channel of a base unit of a device. The channel is in fluid communication with a mixing chamber of the base unit, and the base unit defines openings on the base unit configured to receive a portion of a conduit and a removable air mover unit. Further, the method includes dispensing, using the atomizer, the at least one medication from the removable capsule to the mixing chamber of the base unit, and using the removable air mover unit, causing air and the at least one medication within the mixing chamber to be conveyed from the mixing chamber to the conduit such that air and the at least one medication dispensed from the removable capsule exits the conduit.

15 Claims, 72 Drawing Sheets

Related U.S. Application Data application No. 18/373,142, filed on Sep. 26, 2023, now Pat. No. 11,944,742, which is a continuation-in-part of application No. 18/449,838, filed on Aug. 15, 2023, now Pat. No. 11,925,748, which is a continuation-in-part of application No. 18/224,502, filed on Jul. 20, 2023, now Pat. No. 11,844,900, which is a continuation-in-part of application No. 18/207,242, filed on Jun. 8, 2023, now Pat. No. 11,850,356.

(60) Provisional application No. 63/437,568, filed on Jan. 6, 2023.

(51) Int. Cl.

| | | |
|---|---|---|
| A61C 19/06 | (2006.01) | |
| A61D 7/04 | (2006.01) | |
| A61F 9/00 | (2006.01) | |
| A61M 11/00 | (2006.01) | |
| A61M 16/14 | (2006.01) | |
| A61M 25/00 | (2006.01) | |

(52) U.S. Cl.
CPC ......... *A61F 9/0008* (2013.01); *A61M 11/005* (2013.01); *A61M 16/14* (2013.01); *A61M 25/0082* (2013.01); *A61D 7/04* (2013.01); *A61M 2205/14* (2013.01)

(56) References Cited

U.S. PATENT DOCUMENTS

| | | |
|---|---|---|
| 5,716,002 A | 2/1998 | Haack et al. |
| 5,791,134 A | 8/1998 | Schneider et al. |
| 6,014,970 A | 1/2000 | Ivri et al. |
| 6,978,779 B2 * | 12/2005 | Haveri .................. A61M 16/08 128/204.22 |
| 7,219,668 B2 | 5/2007 | Flynn |
| 7,954,728 B2 | 6/2011 | Weng et al. |
| 8,141,551 B2 | 3/2012 | Wachter |
| 8,596,263 B2 | 12/2013 | Piper |
| 9,168,555 B2 | 10/2015 | Tsai et al. |
| 10,300,228 B2 | 5/2019 | Minskoff |
| 11,135,379 B2 | 10/2021 | Pell et al. |
| 11,344,686 B2 | 5/2022 | Pell et al. |
| 11,364,225 B2 | 6/2022 | Pell et al. |
| 11,690,963 B2 | 7/2023 | Danek |
| 11,724,047 B2 | 8/2023 | Lahoud et al. |
| 2011/0168175 A1 | 7/2011 | Dunne et al. |
| 2013/0061849 A1 | 3/2013 | Lemper |
| 2016/0151589 A1 | 6/2016 | Ohrt et al. |
| 2016/0271357 A1 | 9/2016 | Islava et al. |
| 2016/0339198 A1 | 11/2016 | Fraser et al. |
| 2018/0311228 A1 | 11/2018 | Havercroft |
| 2019/0143053 A1 | 5/2019 | Chen et al. |
| 2020/0197299 A1 | 8/2020 | Pell et al. |
| 2020/0306466 A1 | 10/2020 | Pell et al. |
| 2021/0022406 A1 | 1/2021 | Minami et al. |
| 2022/0400746 A1 | 12/2022 | Lahoud et al. |

FOREIGN PATENT DOCUMENTS

| | | |
|---|---|---|
| CN | 218682023 U | 3/2023 |
| CN | 116139372 A | 5/2023 |
| DE | 102016118013 A1 | 3/2017 |
| EP | 3199191 B1 | 7/2020 |
| EP | 3247435 B1 | 3/2021 |
| GB | 2442267 A | 4/2008 |
| WO | 2010100557 A1 | 9/2010 |
| WO | 2017125846 A1 | 7/2017 |
| WO | 2017192767 A1 | 11/2019 |
| WO | 2022200487 A1 | 9/2022 |

* cited by examiner

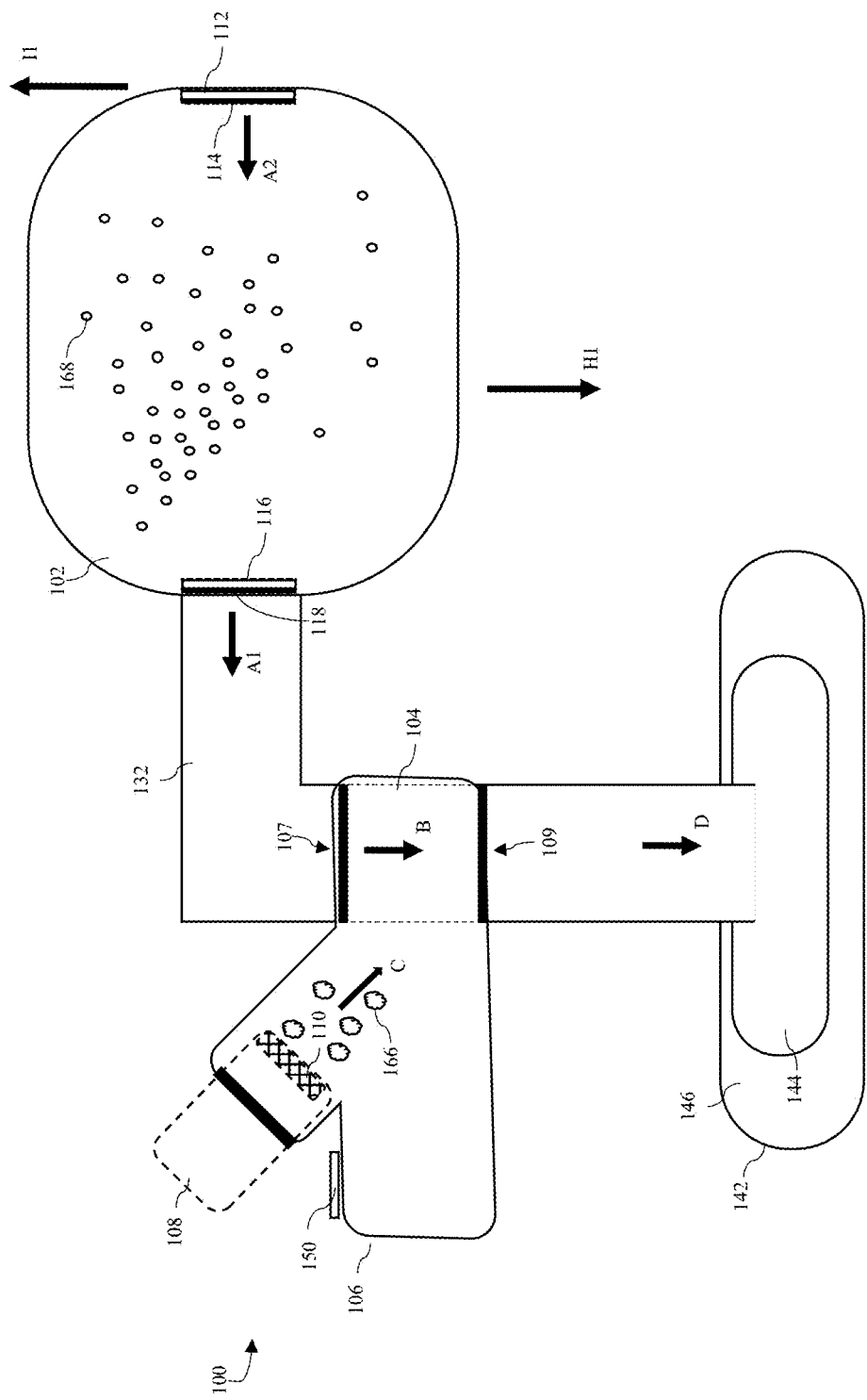

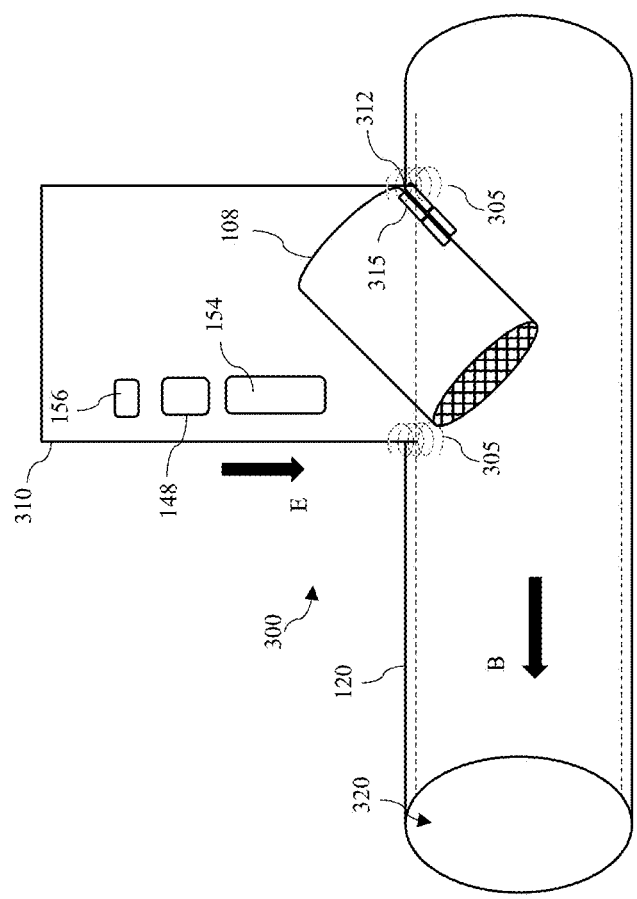

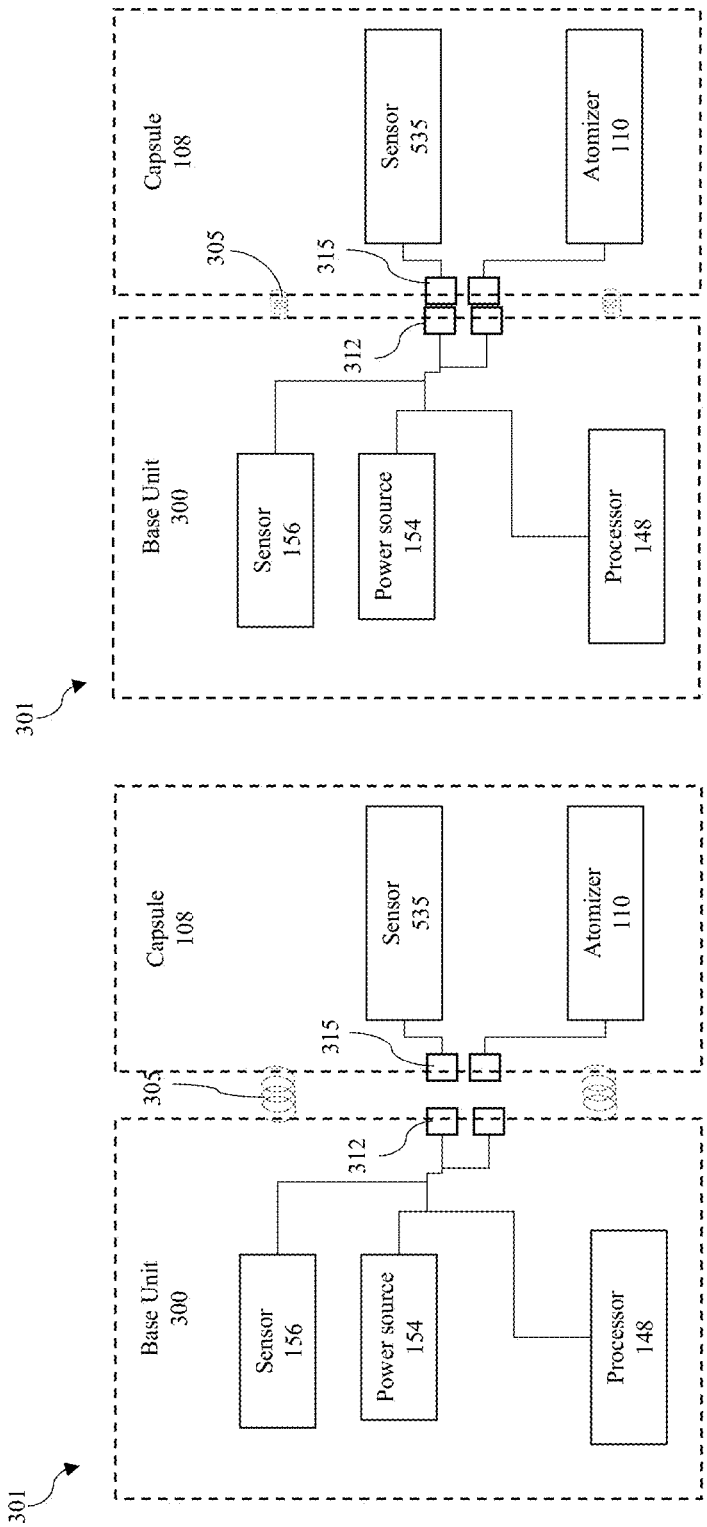

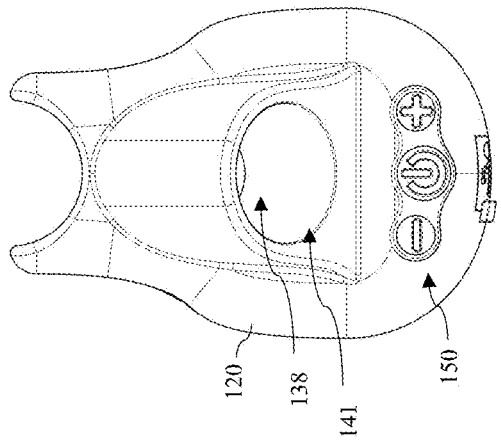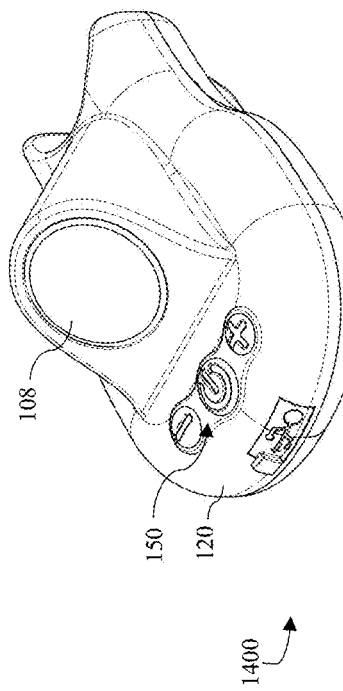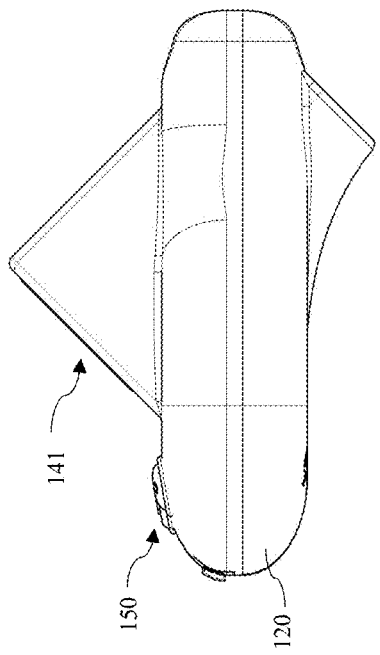

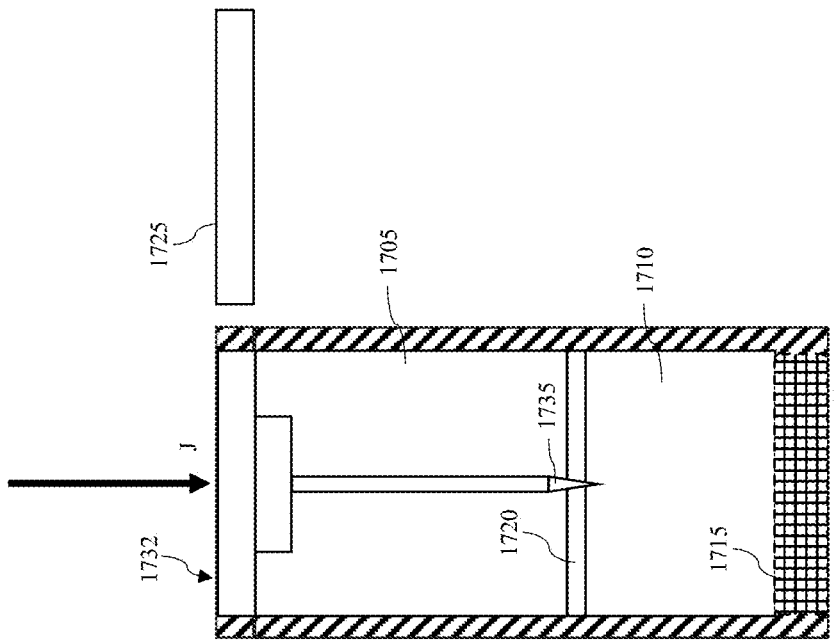
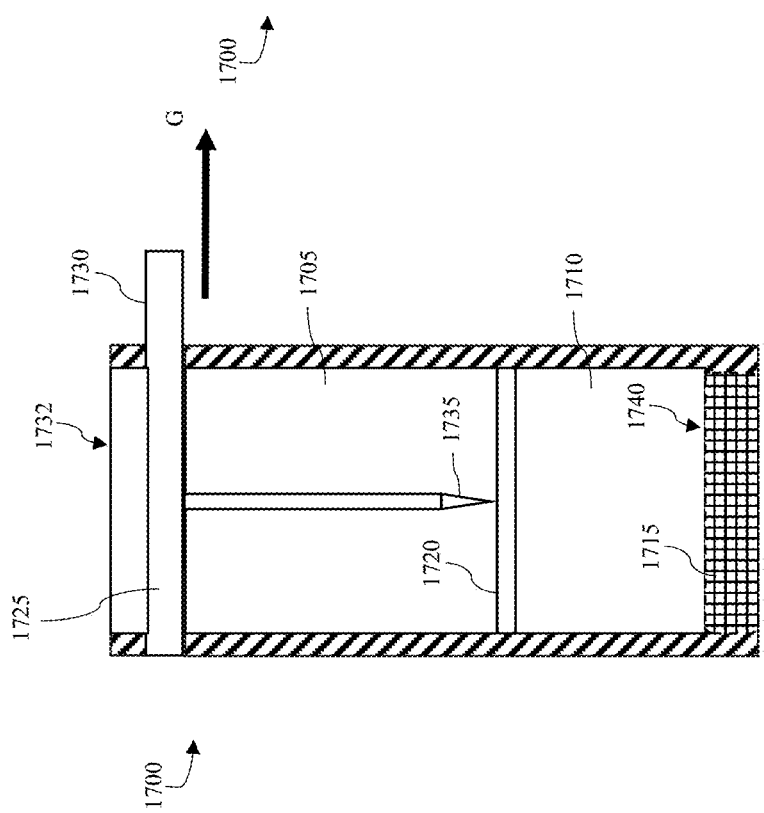
FIG. 17B
FIG. 17A

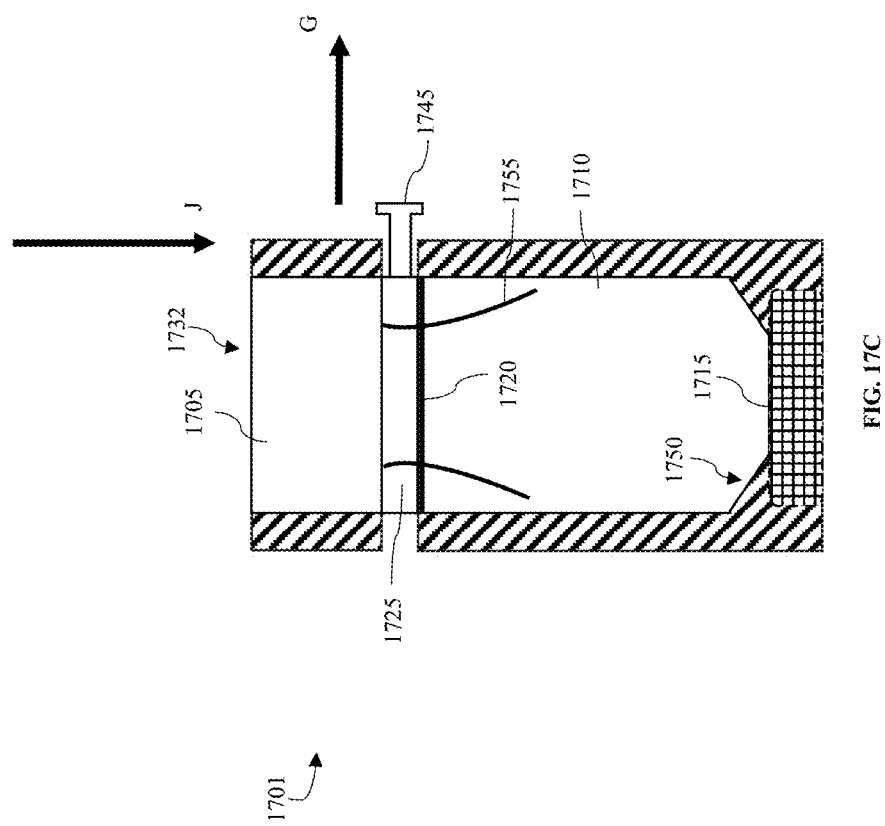

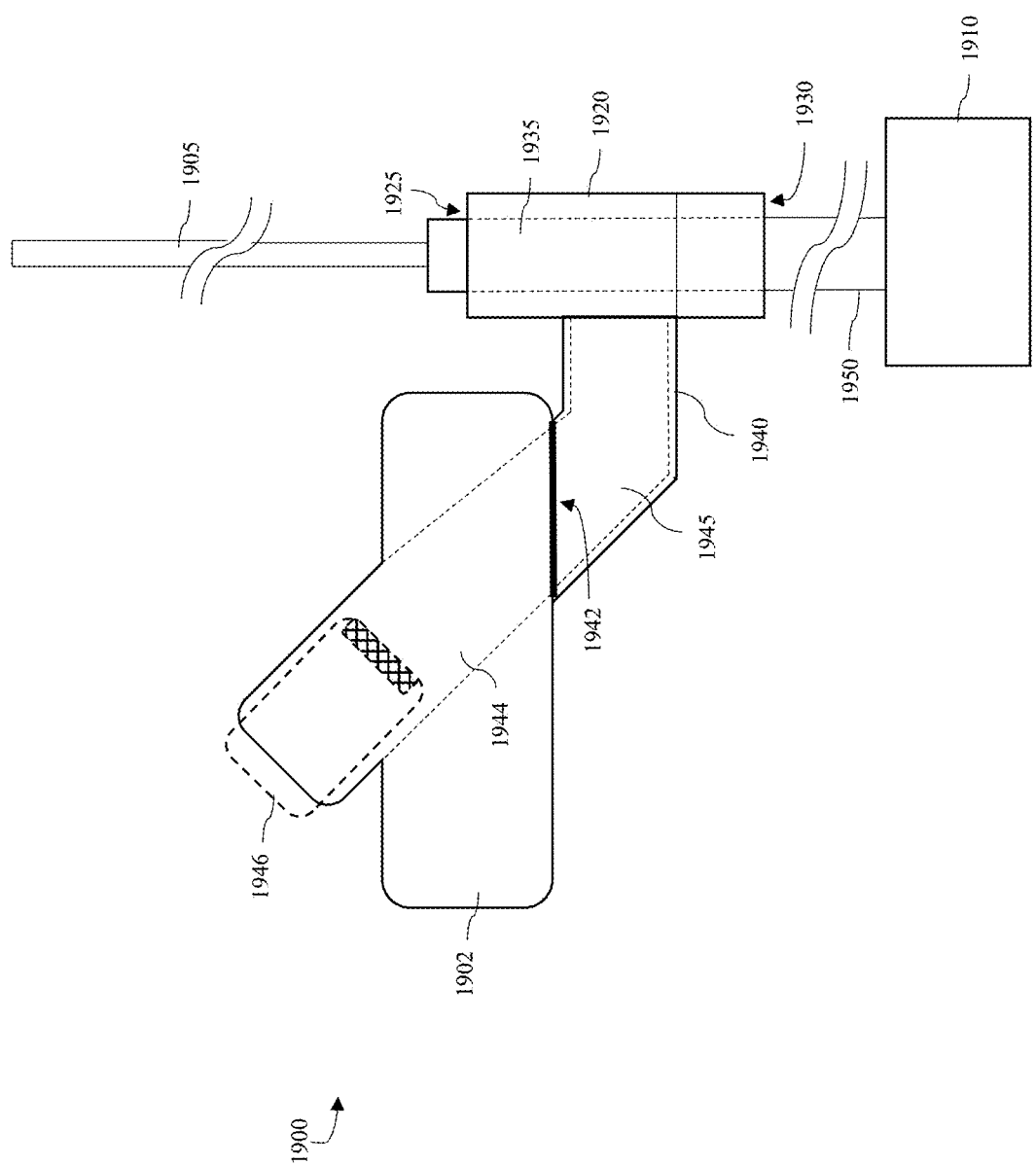

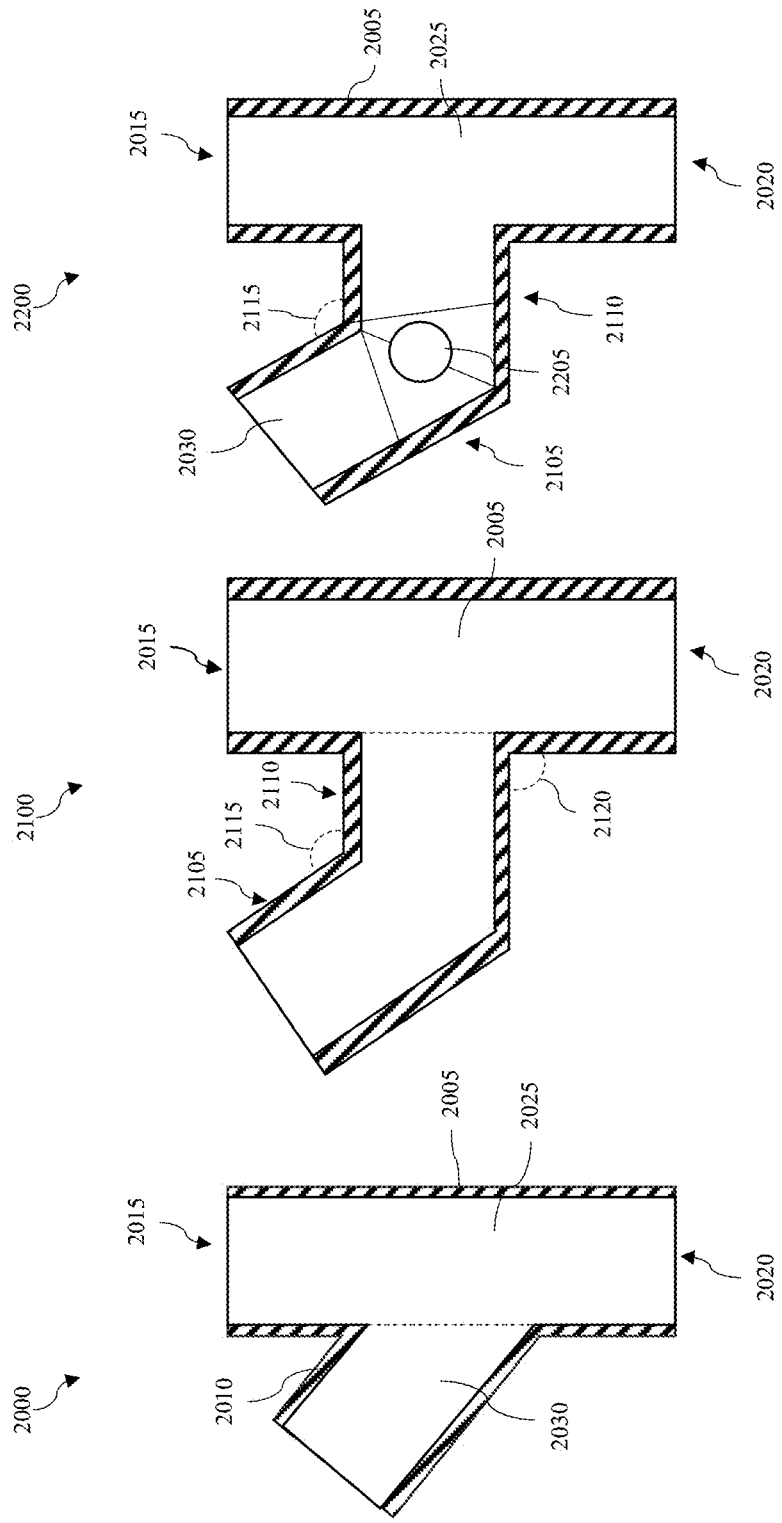

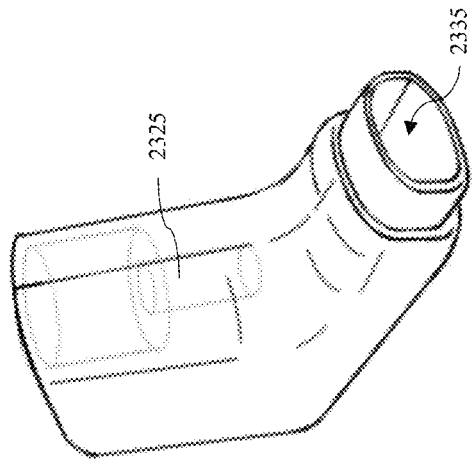
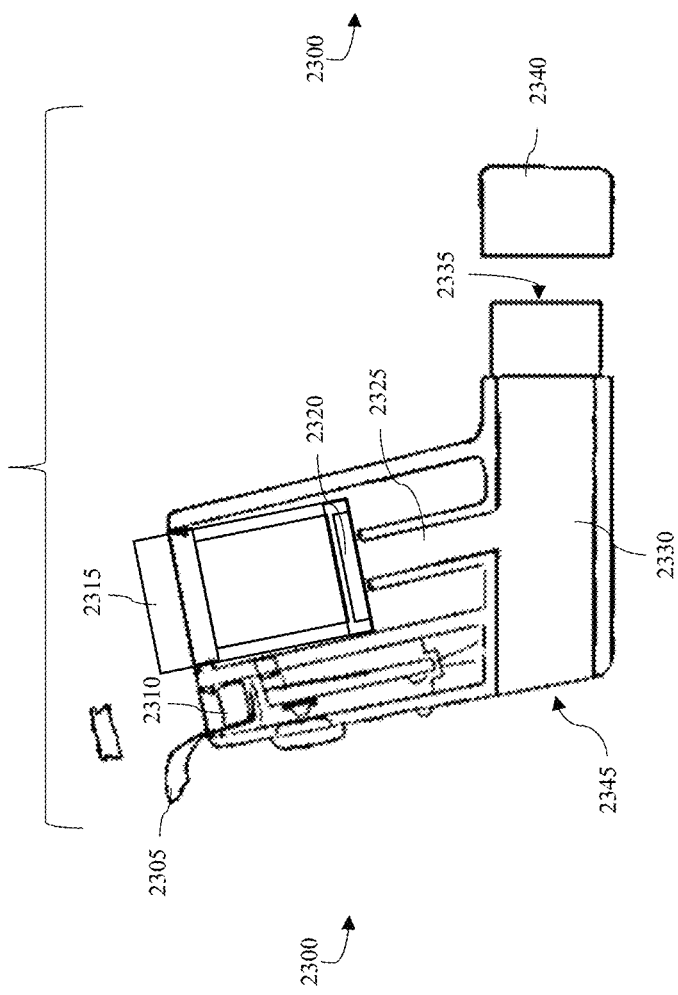
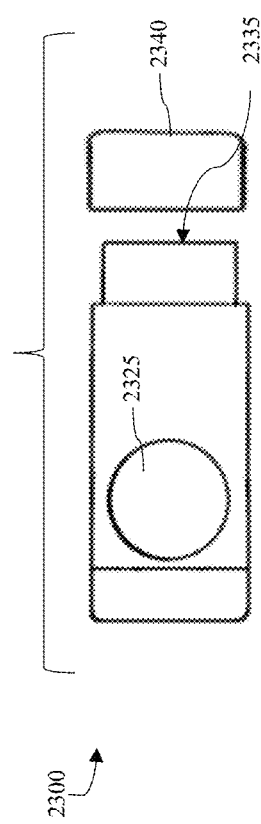

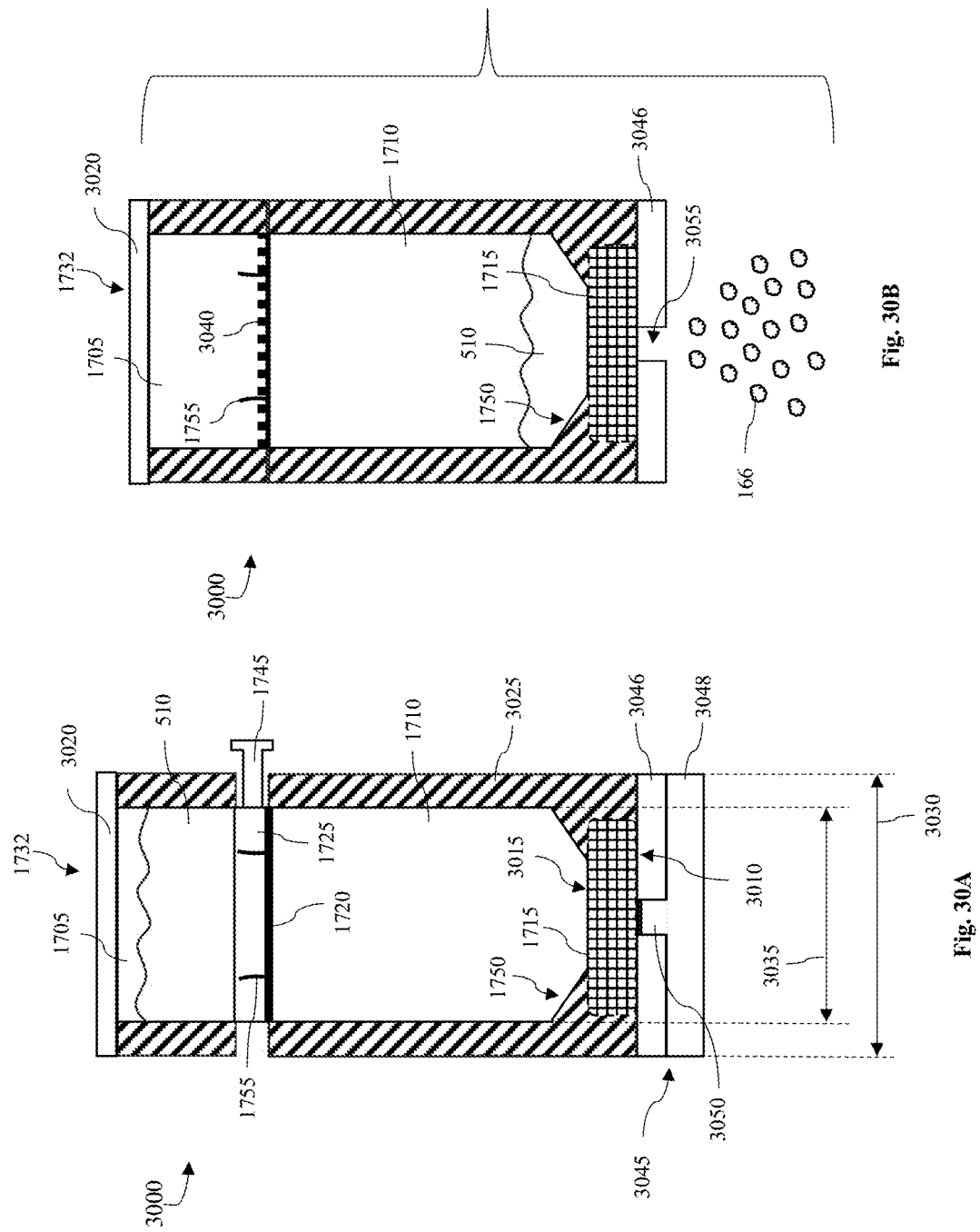

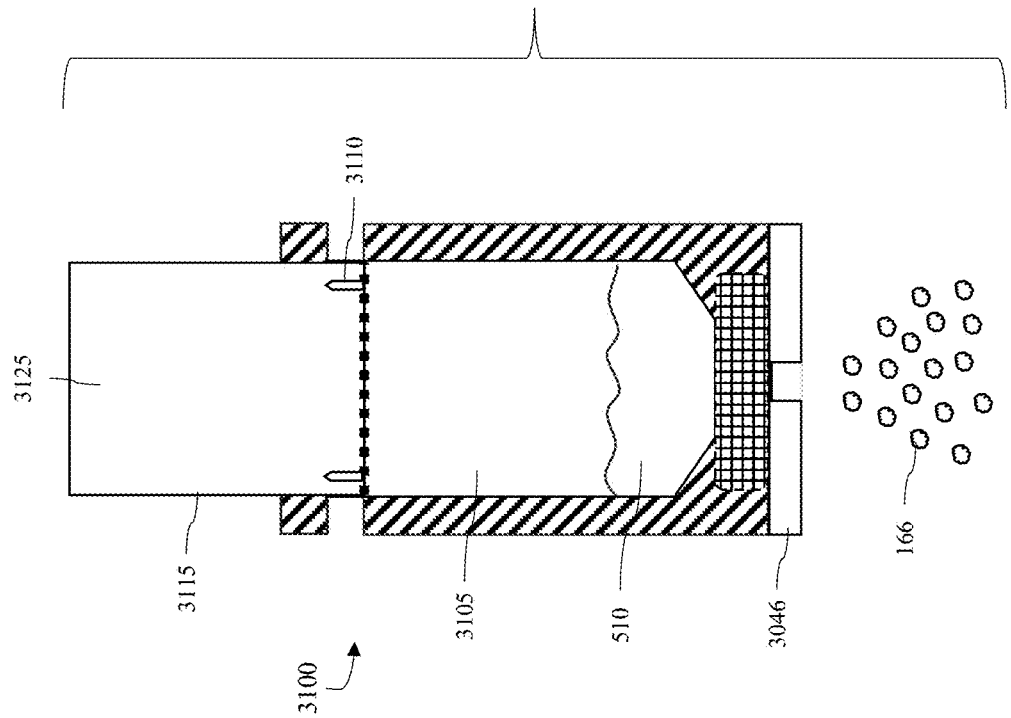
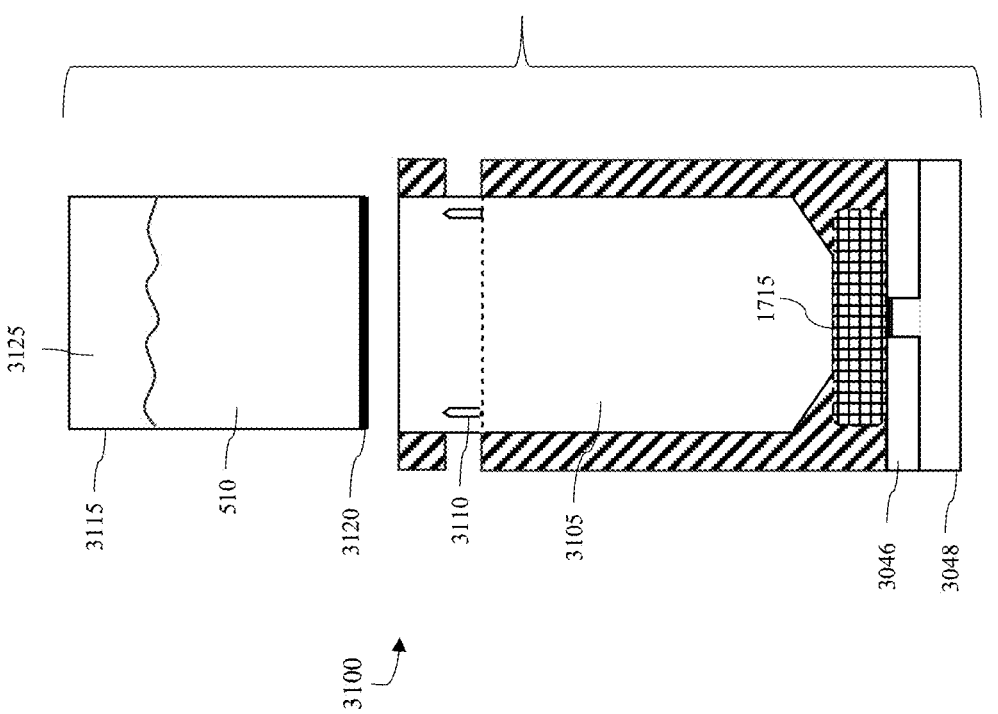
Fig. 31A
Fig. 31B

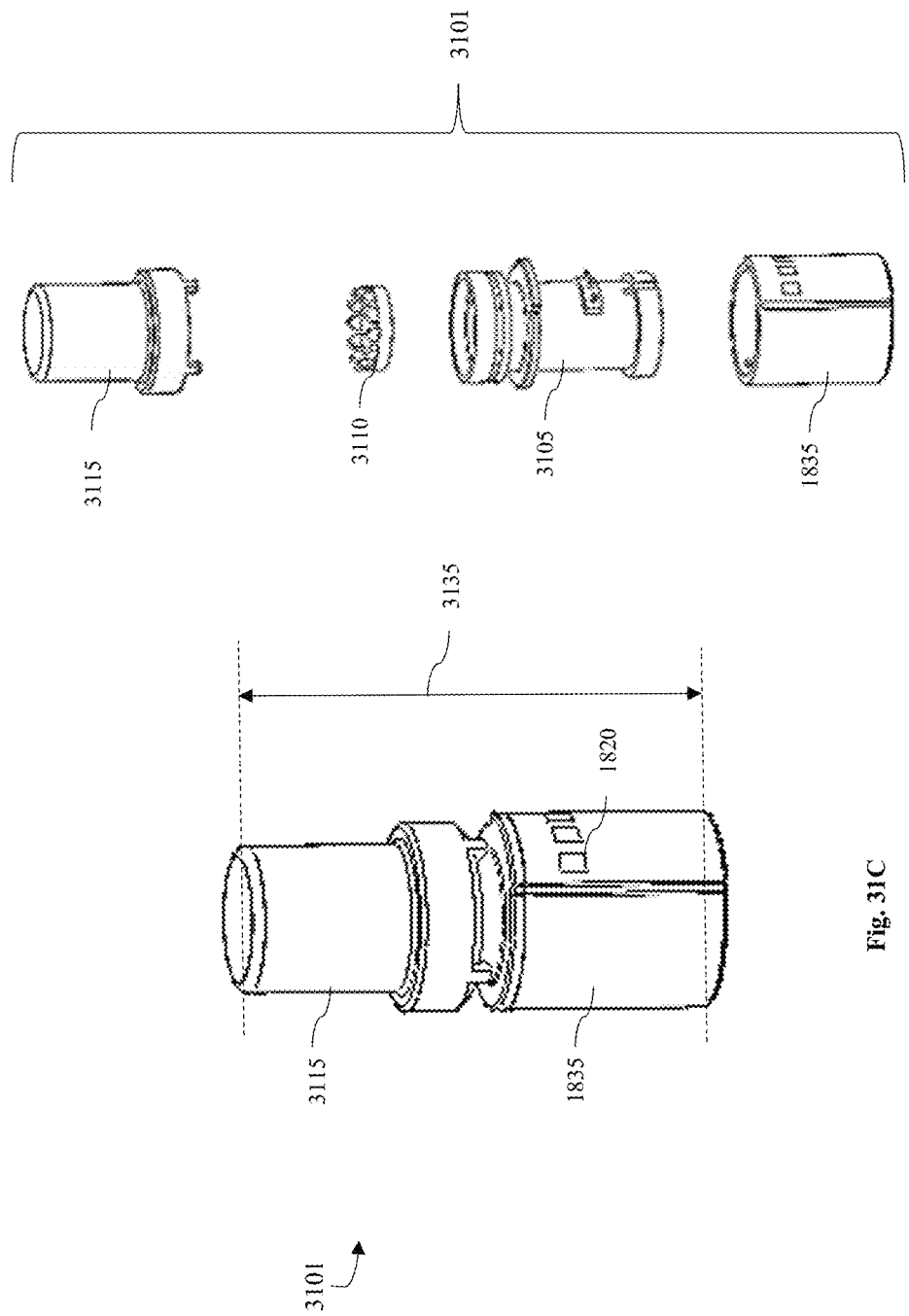

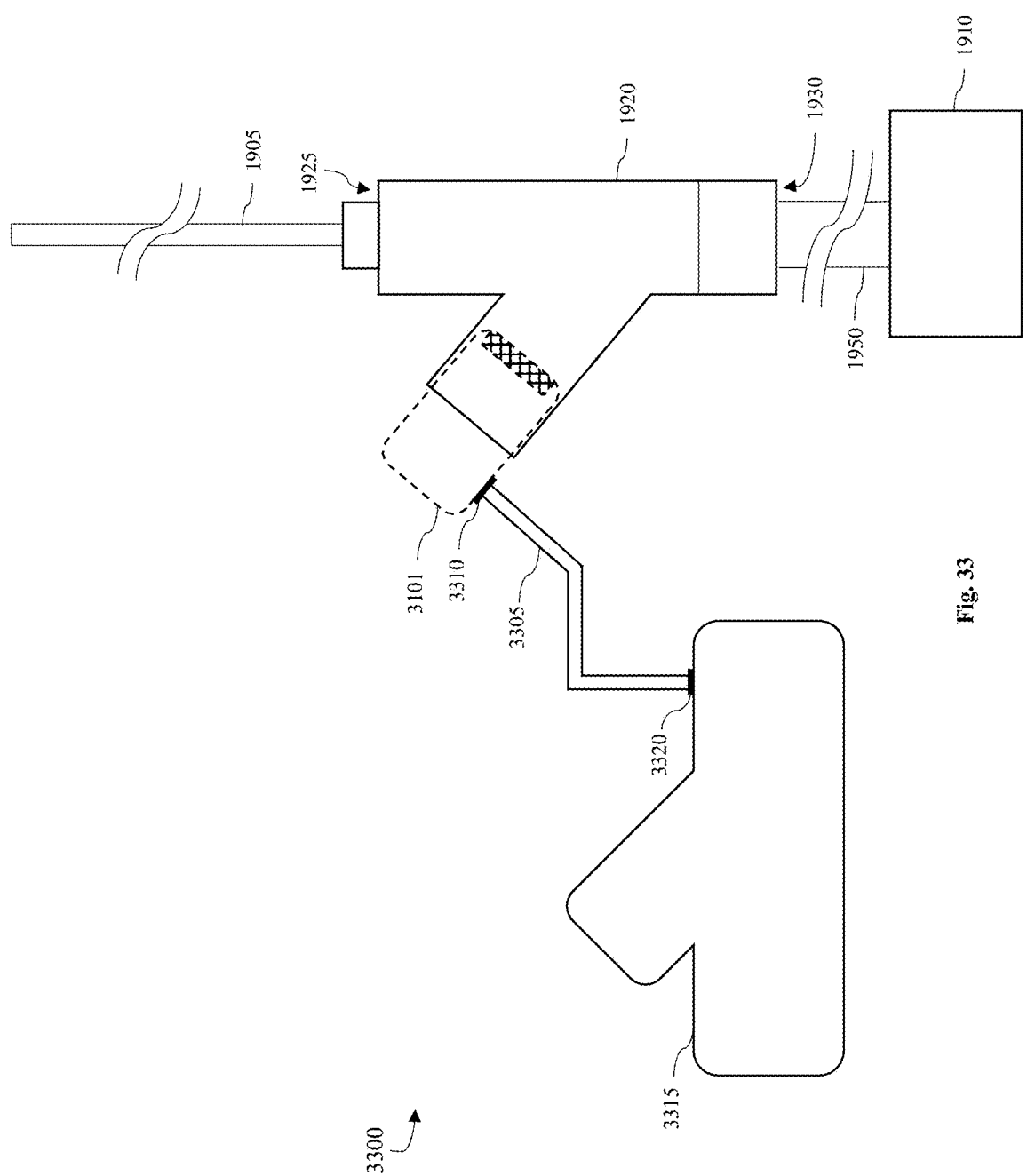

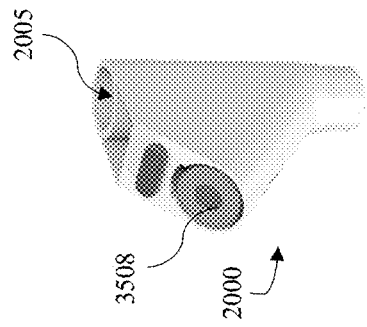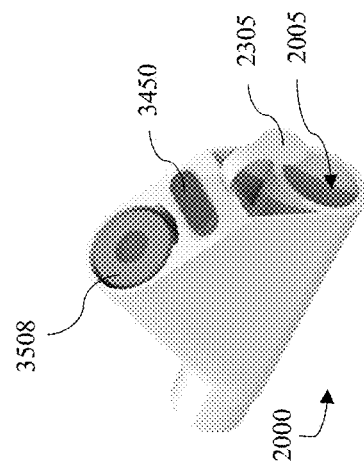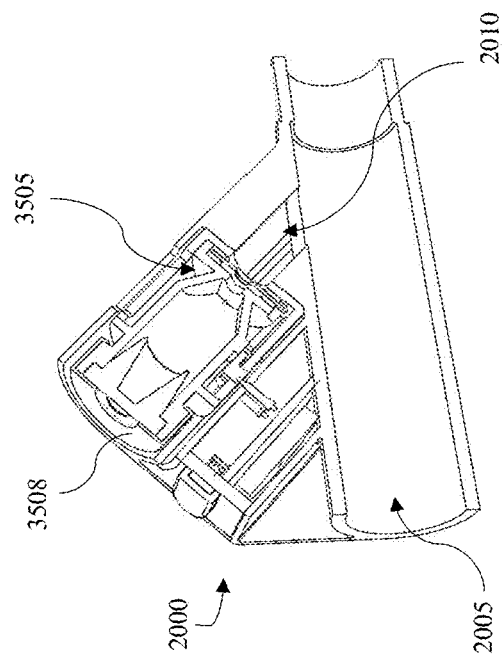
Fig. 35B
Fig. 35C
Fig. 35A

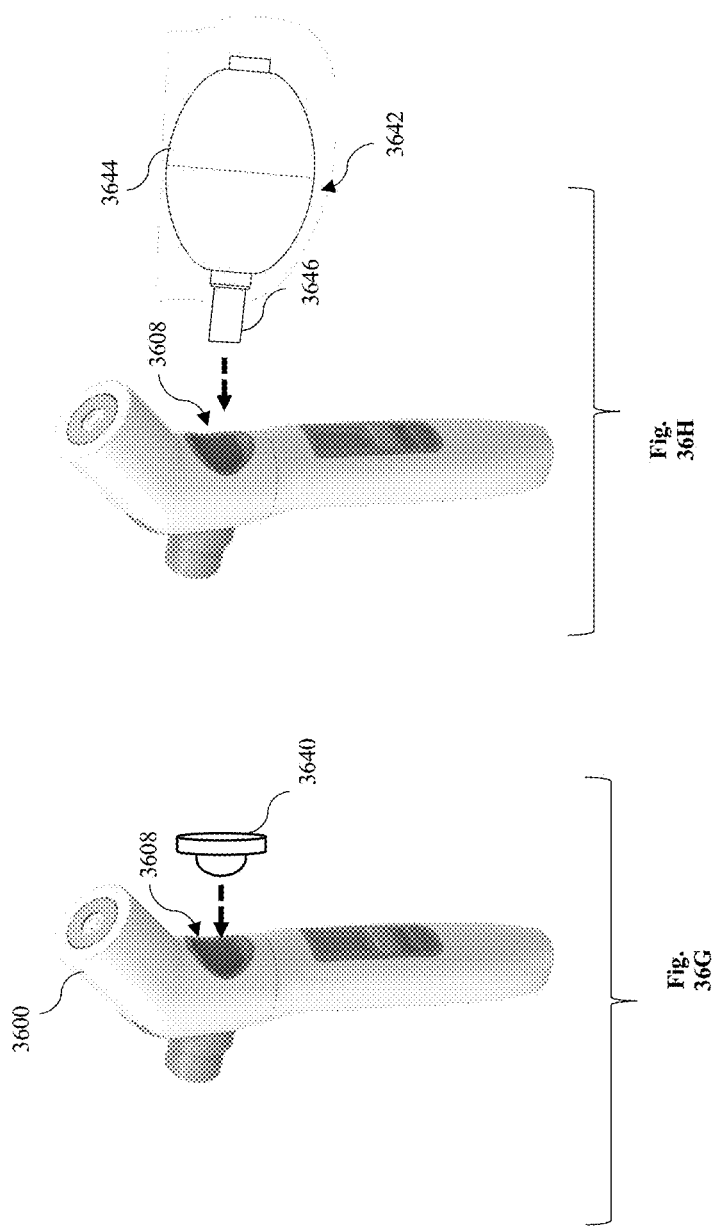

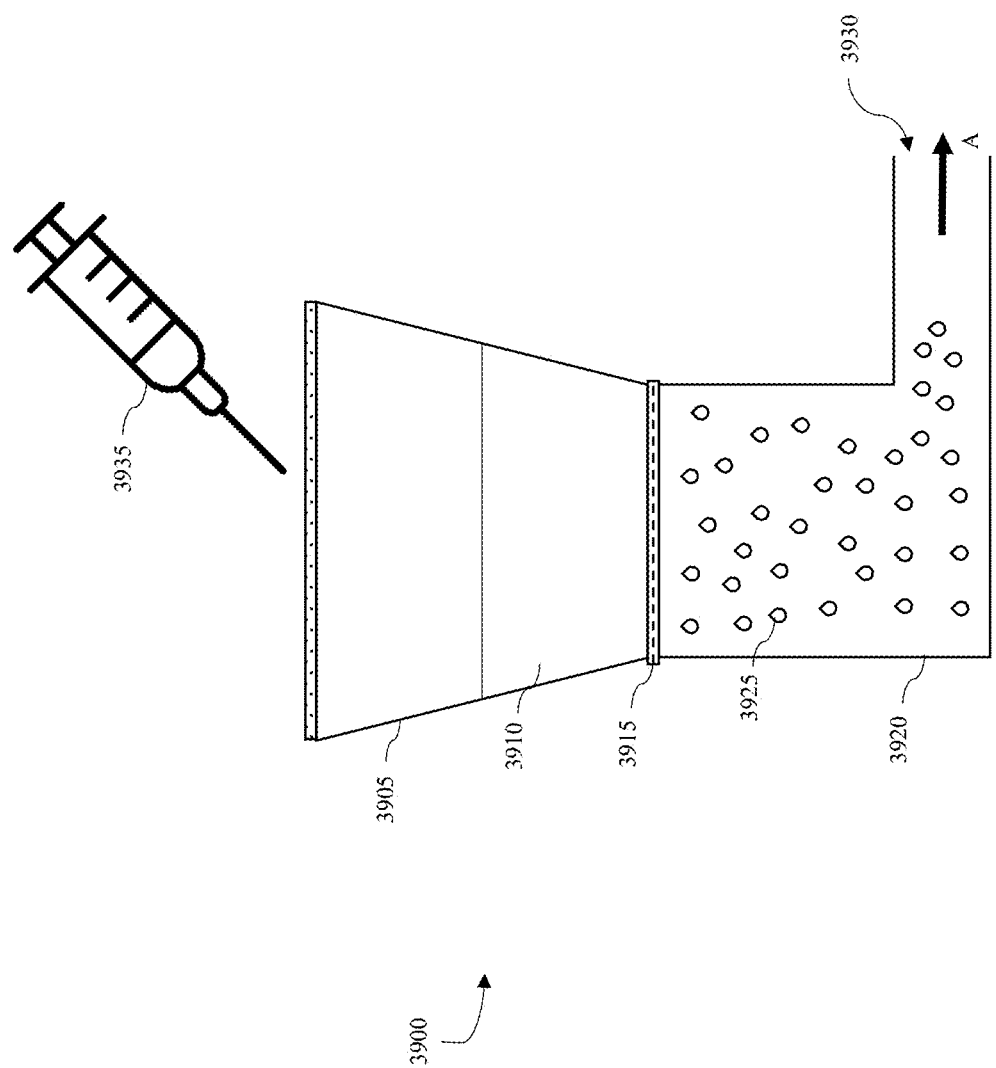

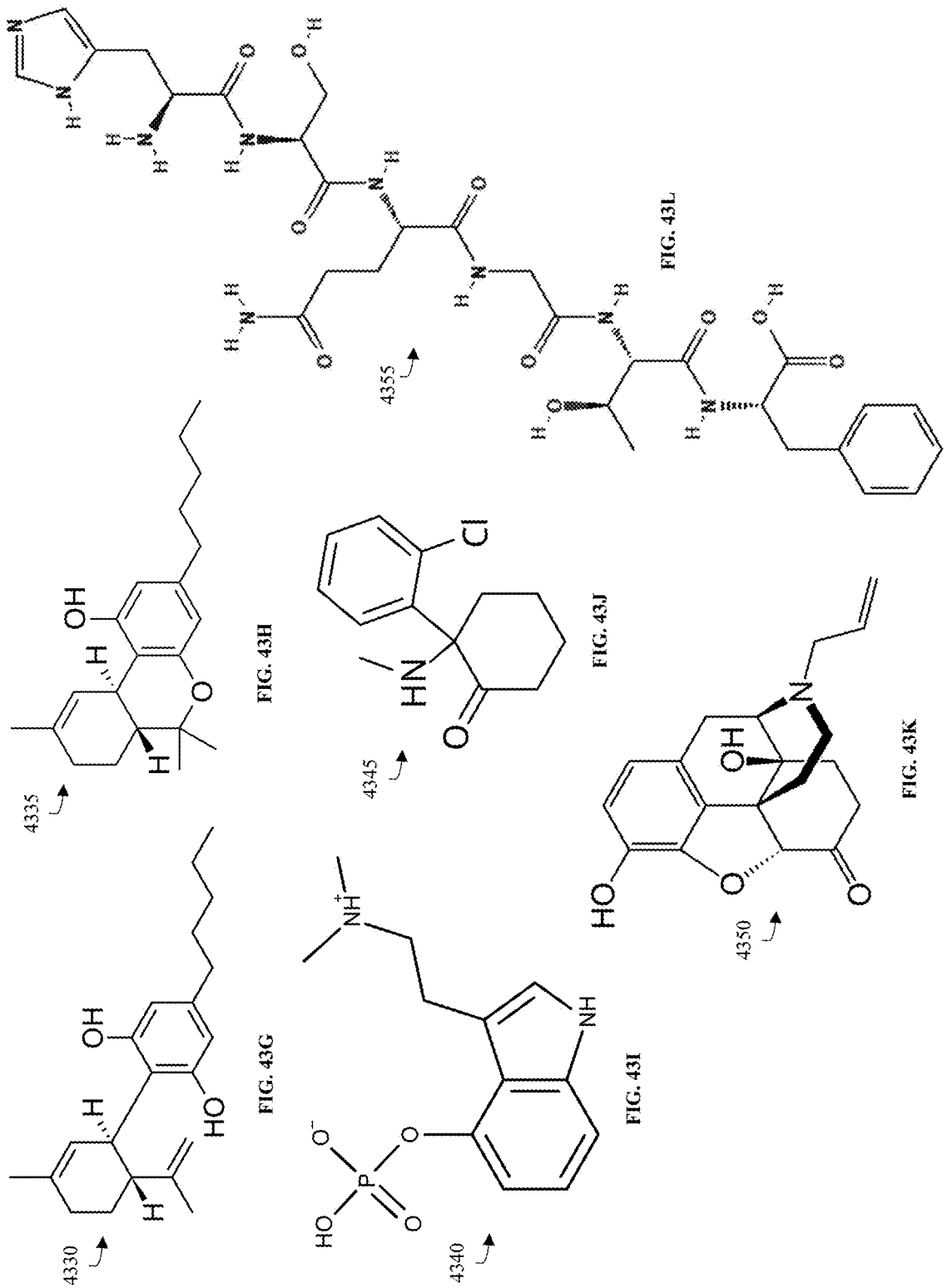

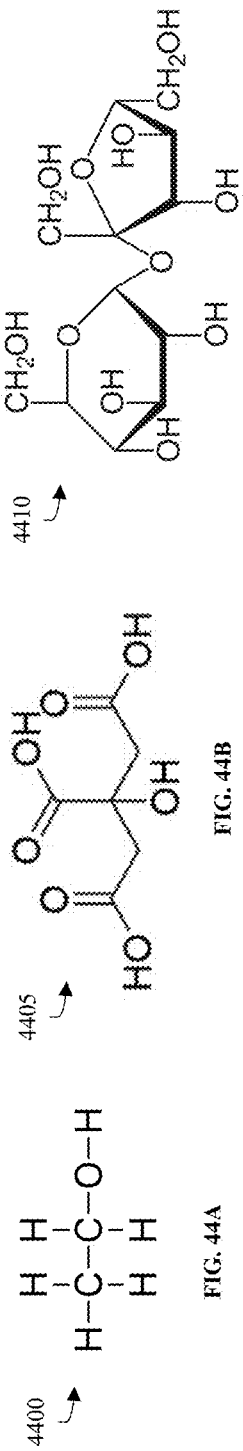
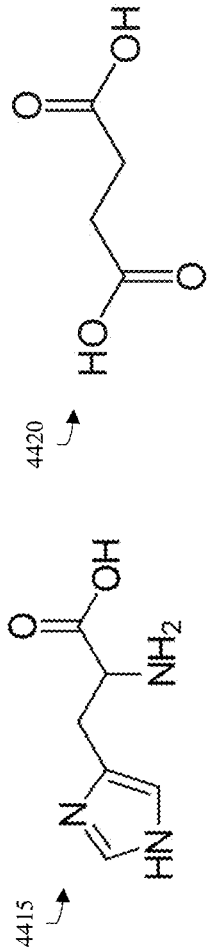
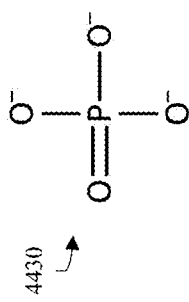
FIG. 44A
FIG. 44B
FIG. 44C
FIG. 44D
FIG. 44E
FIG. 44F
FIG. 44G

APPARATUS, METHODS, AND SYSTEMS FOR DELIVERY AND ADMINISTRATION OF PHARMACEUTICAL, THERAPEUTIC AND COSMETIC SUBSTANCES TO USERS

REFERENCE TO RELATED APPLICATIONS

This application is a continuation in part application of U.S. Non-Provisional application Ser. No. 18/529,978 titled "Apparatus, Methods, and Systems for Providing Pharmaceutical Compositions and Administering Medications to Patients" and filed Dec. 5, 2023, which claims the benefit of U.S. Provisional Application Ser. No. 63/437,568 titled "Compositions, Methods, and Systems for Providing a Nebulized Solution" and filed Jan. 6, 2023.

The U.S. Non-Provisional application Ser. No. 18/529,978 is also a continuation in part application of U.S. Non-Provisional application Ser. No. 18/373,142 titled "Apparatus, Methods, and Systems for Administering a Medication to an Animal" and filed Sep. 16, 2023, which is a continuation in part application of U.S. Non-Provisional application Ser. No. 18/449,838 titled "Apparatus, Methods, and Systems for Administering a Medication to a Patient" and filed Aug. 15, 2023, which is a continuation in part application of U.S. Non-Provisional application Ser. No. 18/224,502 titled "Apparatus, Methods, and Systems for Administering a Medication to a Patient" and filed Jul. 20, 2023, which is a continuation in part application of U.S. Non-Provisional application Ser. No. 18/207,242 titled "Apparatus, Methods, and Systems for Administering a Medication to a Patient" and filed Jun. 8, 2023, the subject matter of each of which is incorporated herein by reference.

CROSS-REFERENCES

Not applicable.

STATEMENT REGARDING FEDERALLY SPONSORED RESEARCH OR DEVELOPMENT

Not applicable.

INCORPORATION BY REFERENCE OF MATERIAL SUBMITTED ON A COMPACT DISK

Not applicable.

TECHNICAL FIELD

The present disclosure relates to the field of mesh nebulizers, and more specifically to the field of mesh nebulizers for administering medications.

BACKGROUND OF THE INVENTION

A mesh nebulizer, also known as a vibrating mesh nebulizer, is a type of device used to deliver medication in a fine mist or aerosol form, which makes it easier for patients to inhale the medication directly into their lungs. This is particularly useful for the treatment of respiratory diseases like asthma, COPD (chronic obstructive pulmonary disease), or cystic fibrosis. The "mesh" in the name refers to a key component of the nebulizer: a small plate with multiple tiny holes, or a "mesh". This mesh vibrates at high frequencies, causing the liquid medication to be pushed through the tiny holes in the mesh, creating a fine mist or aerosol that can be inhaled. Mesh nebulizers are generally more efficient and portable than traditional jet nebulizers. They tend to be quiet, lightweight, and capable of nebulizing a wide range of medications. However, they can be more expensive, and the mesh plate can become blocked over time, requiring replacement. Proper cleaning and maintenance are important to keep the device functioning properly.

Inhalers are another form of medical devices that are used to deliver medication directly into the lungs. They are commonly used to treat conditions like asthma and chronic obstructive pulmonary disease (COPD). There are two main types of inhalers: metered-dose inhalers (MDIs) and dry powder inhalers (DPIs). MDIs use a chemical propellant to push the medication out of the inhaler. The user pushes down on the top of the inhaler and inhales at the same time to ensure the medication reaches the lungs. MDIs also can be used with a spacer, a tube-like device which provides a space for the medication to mix with air before reaching the lungs. This makes it easier for the medication to be inhaled and is especially helpful for children or people who have difficulty coordinating their breath with the release of the medication. DPIs do not use a chemical propellant. Instead, the medication is in a powder form, which the user inhales. Because they require a strong, quick inhalation to get the medication into the lungs, DPIs can be harder for some people to use than MDIs. Inhalers can deliver a variety of medications. However, the effectiveness of inhalers depends significantly on correct usage. Mistakes in technique can result in less medication reaching the lungs. These mistakes could include breathing too quickly or not deeply enough, not shaking the inhaler before use, or not using a spacer if needed. Some inhalers, especially newer or brand-name inhalers, can be quite expensive, potentially posing a financial burden.

Despite the various advancements in the field of medication delivery via capsules, there exist several challenges that continue to impact both patient compliance and the overall effectiveness of the treatment. One major challenge is the management of precise dosage control. In many instances, the ability to ensure a patient receives the exact dose of medication prescribed is crucial for the treatment's efficacy. However, it is a common problem that current capsule systems might not always deliver the accurate dose due to the limitations in the mechanism of action or variability in user technique. Further, many capsule systems for medication delivery require intricate instructions for use, which can lead to user errors. This is particularly relevant in instances where capsules need to be loaded into a device, such as an inhaler, where improper loading could result in suboptimal medication delivery. User-friendliness and ease of use are paramount in designing such systems, and any complexity can lead to misuse or non-compliance.

The potential for contamination is another issue that is often encountered in these systems. This can occur during the loading of the capsule into the delivery device or during the process of administering the medication itself. Both scenarios can compromise the sterility of the medication, leading to potential health risks. Another concern with these systems is the difficulty of integrating modern technologies such as sensors and connectivity features. The inclusion of these technologies could enhance the performance and functionality of the capsule systems by enabling real-time monitoring, improving dosage control, or allowing for personalized treatments. However, the integration of such features in a compact and user-friendly form remains a significant challenge. Regarding the specific use of medicine vials, while their adoption has provided a convenient way to store and administer liquid medication, issues arise in terms of potential wastage and the need for preservatives. Many vials are single-use to maintain sterility, but this can lead to medication wastage if the full vial content is not used. Additionally, the need for preservatives in multi-dose vials to prevent microbial contamination can lead to potential allergic reactions or side effects.

A common challenge observed in prior art pertaining to medication delivery via capsules revolves around the lack of interchangeability. A significant number of the pre-existing capsule systems are designed for a specific medication or a particular type of medication. This can be due to the unique physical or chemical properties of the medication, such as particle size in case of inhaled medication, or stability considerations for certain biologics. The lack of a standardized, universal system restricts the ability to switch between different medications using the same delivery device, limiting the versatility of the treatment options. Moreover, the case of transportation is another aspect that remains wanting in many prior art capsule systems. Certain systems, particularly those requiring intricate loading or handling procedures, can prove cumbersome to transport, and potentially fragile. This is a critical consideration for patients who need to carry their medication for use throughout the day, or during travel. Ideally, medication delivery systems should be robust, compact, and portable, making them convenient for users to carry and use as required. Non-invasive administration of medication is an essential aspect of patient compliance and comfort. In the prior art, many delivery systems, particularly for certain conditions, might require invasive procedures such as injections, which can cause discomfort or distress to patients. These methods also raise potential issues of sterility and can increase the risk of infection. Therefore, there is a persistent need for delivery systems that can efficiently administer medication in a non-invasive manner, such as inhalation or oral administration, without compromising on the medication's efficacy.

Referring to compositions, methods, and systems for treating opioid dependency and opioid overdose, opioid dependency is a chronic condition characterized by a physical and psychological reliance on opioids. This dependency often arises from prolonged opioid use, whether for medical or non-medical reasons. The treatment of opioid dependency is complex, involving a gradual weaning process to mitigate withdrawal symptoms and reduce reliance on the drug. Effective management of opioid dependency requires a carefully calibrated approach to medication, often necessitating tailored dosages and controlled administration to support gradual reduction in opioid use.

In contrast, opioid overdose presents an acute emergency scenario. Overdosing on opioids can lead to critical symptoms such as respiratory depression, unconsciousness, and, in severe cases, death. Rapid intervention is crucial in these situations. Medications such as naloxone have been developed to counteract the life-threatening effects of an opioid overdose. The swift administration of such medications can reverse the overdose symptoms, making speed and efficiency in drug delivery systems critical for successful emergency response.

Both these aspects—the chronic management of opioid dependency and the acute response to opioid overdose-highlight the need for versatile and effective pharmaceutical solutions. These solutions must be adaptable to different scenarios, ranging from controlled, gradual dosage for dependency treatment to rapid, emergency administration for overdoses. The development of such treatments and delivery systems is central to addressing the complexities and urgent needs posed by the opioid crisis.

Naloxone is a critical drug in the fight against opioid overdose. As an opioid antagonist, it rapidly reverses the effects of opioid overdose, including respiratory depression, sedation, and hypotension, by displacing opioids from receptor sites in the brain. Its life-saving capabilities have been recognized globally, with its use in emergency settings being pivotal for immediate response to opioid overdoses. For broader accessibility, especially in non-medical environments, naloxone is also formulated for intramuscular or subcutaneous injection, frequently deployed using auto-injectors. Furthermore, nasal spray formulations of naloxone have gained prominence due to their needle-free, user-friendly nature, significantly enhancing public health responses to opioid overdoses.

A pressing issue in contemporary public health is the increasing incidence of Xylazine, traditionally a veterinary sedative, being ingested by humans, often unknowingly, through its incorporation into street drugs. Xylazine, not approved for human use, poses significant health risks when consumed by humans, leading to profound sedation, respiratory depression, and other severe side effects. The contamination of street drugs with Xylazine has become a dangerous trend, contributing to a rise in drug-related emergencies and complications. This emerging problem highlights an urgent need for effective measures to counteract the effects of Xylazine in humans. While Naloxone, commonly used to reverse opioid overdose, is ineffective against Xylazine, the potential role of Yohimbine, an alpha-2 adrenergic receptor antagonist, comes into focus. Given Yohimbine's efficacy in reversing Xylazine's effects in veterinary contexts, there is a growing interest in exploring its applicability for similar use in humans. The development of a safe and effective antidote or treatment protocol involving Yohimbine could be pivotal in addressing the complications arising from Xylazine ingestion in humans. This situation underscores the need for rapid response from the medical community and drug regulatory authorities to mitigate this emerging public health concern. Tolazoline, a vasodilator and an alpha-adrenergic antagonist, is known for reversing the effects of sedatives and for its use in various medical applications. Its potential contribution to opioid overdose treatment is intriguing, given its pharmacological profile, which could complement the actions of other agents in managing the effects of opioid toxicity. Tolazoline is typically administered intravenously, especially in hospital environments for diagnosing vascular disorders and treating skin ulcers. In neonatal care, particularly in veterinary medicine, tolazoline is used intravenously to reverse sedative effects in neonates.

Albuterol, primarily known for treating bronchospasm in conditions like asthma and chronic obstructive pulmonary disease, works by relaxing the muscles in the airways and increasing airflow to the lungs. Albuterol is most effectively delivered through inhalation using metered-dose inhalers or nebulizers. This method ensures direct lung delivery, providing swift symptom relief. Additionally, albuterol is available in oral forms, including tablets and liquid preparations, though these are less common compared to inhalation routes. In severe cases, intravenous administration of albuterol may be warranted, albeit in a strictly monitored hospital setting.

Each of these active ingredients has a unique profile and mechanism of action, making them valuable in addressing various aspects of opioid overdose and dependency. However, the inherent limitations in prior art related to interchangeability, transportability, and non-invasive administration pose significant barriers to optimal patient care. The need for more adaptable, easily transportable, and less invasive delivery systems persists, driving the continuous pursuit for innovation in this field. As a result, there exists a need for improvements over the prior art and more particularly for improved, user-friendly, and reliable capsule systems and pharmaceutical compositions that can provide accurate dosing, maintain sterility, and integrate modern technologies for enhanced monitoring and control.

BRIEF SUMMARY OF THE INVENTION

An apparatus, method, and system for administering at least one substance to a to a subject is disclosed. This Summary is provided to introduce a selection of disclosed concepts in a simplified form that are further described below in the Detailed Description including the drawings provided. This Summary is not intended to identify key features or essential features of the claimed subject matter. Nor is this Summary intended to be used to limit the claimed subject matter's scope.

In one embodiment, the method involves providing a removable capsule having an atomizer, and inserting the removable capsule in a channel of a base unit of a device. The channel is in fluid communication with a mixing chamber of the base unit, and the base unit defines openings on the base unit configured to receive a portion of a conduit and a removable air mover unit. The removable air mover unit is electrically connected directly to the base unit. Further, the method includes dispensing, using the atomizer, the at least one substance from the removable capsule to the mixing chamber of the base unit. In the mixing chamber, the at least one substance is combined with air. The method includes using the removable air mover unit, causing air and the at least one medication within the mixing chamber to be conveyed from the mixing chamber to the conduit such that air and the at least one substance dispensed from the removable capsule exits the conduit.

In one embodiment, a system for administering at least one substance to a body part of a user is disclosed. The system comprises a removable capsule comprising the at least one substance wherein the at least one substance is a biological agent, and an atomizer disposed directly adjacent to a capsule chamber of the removable capsule, wherein the at least one medication contacts the atomizer within the capsule chamber. The system includes a base unit of a device comprising a mixing chamber and a plurality of openings in fluid communication with the mixing chamber, and a removable air mover unit attached to the base unit of the device via an opening of the said plurality of openings on the base unit, wherein an outward surface of the removable air mover unit abuts an inner wall of the opening that receives the removable air mover unit. The removable air mover unit is in fluid communication with the mixing chamber of the base unit, the removable air mover unit is configured such that air conveyed from the removable air mover unit moves into the mixing chamber, and the removable air mover unit is in direct electrical connection with the base unit of the device and a first electrical contact is disposed on the outward surface of the removable air mover unit and a second electrical contact is disposed on the inner wall of the opening of the base unit for providing electrical communication between the removable air mover unit and the base unit. Further, the system includes a conduit connected to the base unit and in fluid communication with mixing chamber, the conduit configured to convey the at least substance to the body part of the user Additional aspects of the disclosed embodiment will be set forth in part in the description which follows, and in part will be obvious from the description, or may be learned by practice of the disclosed embodiments. The aspects of the disclosed embodiments will be realized and attained by means of the elements and combinations particularly pointed out in the appended claims. It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute part of this specification, illustrate embodiments of the disclosure and together with the description, explain the principles of the disclosed embodiments. The embodiments illustrated herein are presently preferred, it being understood, however, that the disclosure is not limited to the precise arrangements and instrumentalities shown, wherein:

FIG. 1 is a diagram of a side view of a system for administering medication to a patient, according to a first embodiment;

FIG. 1A is a diagram of a side view of a system for administering medication to a patient, wherein the resilient air bladder is deflated by the force of a rescuer, according to a first embodiment;

FIG. 1B is a diagram of a side view of an attachment for administering medication to a patient, according to a first embodiment;

FIG. 2 is a diagram of a side view of a system for administering medication to a patient, according to a second embodiment;

FIG. 3A is a diagram of a side view of a system for administering medication to a patient, according to a third embodiment, wherein a biasing element is in an extended state;

FIG. 3B is a diagram of a side view of a system for administering medication to a patient, according to the third embodiment, wherein a biasing element is in a compressed state;

FIG. 3C is a diagram illustrating the main electrical components of the system for administering medication to a patient, wherein biasing elements are in an extended state, according to the third embodiment;

FIG. 3D is a diagram illustrating the main electrical components of the system for administering medication to a patient, wherein biasing elements are in a compressed state, according to the third embodiment;

FIG. 4 is a diagram illustrating the main electrical components of a system for administering medication to a patient, according to an example embodiment;

FIG. 5 is a diagram of a front view of a capsule, according to a first example embodiment;

FIG. 6A is a diagram illustrating the main electrical components of the capsule, wherein an electrical insulator in form of a tab is positioned between two contacts, according to an example embodiment;

FIG. 6B is a diagram illustrating the main electrical components of the capsule, wherein an electrical insulator in form of a tab is removed from between two contacts, according to an example embodiment;

FIG. 7 is a diagram of an operating environment that supports a system of administering medication to a patient, according to an example embodiment;

FIG. 8 is a flowchart diagram illustrating steps for a method of administering medication to a patient, according to an example embodiment;

FIG. 14A is a perspective view of an attachment for administering medication to a patient, according to the first embodiment;

FIG. 14B is a top view of an attachment for administering medication to a patient, according to the first embodiment;

FIG. 14C is a side view of an attachment for administering medication to a patient, according to the first embodiment;

FIG. 17A is a cross-sectional side view of the capsule including a stop, according to a fourth example embodiment;

FIG. 17B is a cross-section of a side view of the capsule, wherein the stop is removed, according to a fourth example embodiment;

FIG. 17C is a cross-section of a side view of the capsule, according to a fifth example embodiment;

FIG. 19 illustrates a diagram of the device in operation for a patient in an intubated state, wherein the device is in attachment with an endotracheal tube and a ventilator, according to an example embodiment;

FIG. 20 is a cross-section of a modular tubular extension, according to a first example embodiment.

FIG. 21 is a cross-section of a modular tubular extension, according to a second example embodiment.

FIG. 22 is a cross-section of a modular tubular extension, according to a third example embodiment.

FIG. 23 illustrates the device for administering at least one medication to a patient in an unconscious state to a conscious state, according to an inhaler embodiment.

FIG. 24 illustrates the device for administering at least one medication to a patient in an unconscious state to a conscious state, according to the inhaler embodiment.

FIG. 25 illustrates the device for administering at least one medication to a patient in an unconscious state to a conscious state, according to the inhaler embodiment.

FIG. 30A is a cross-section of a side view of a capsule system for use with a medical device for administering at least one atomized medication to a patient, according to an example embodiment;

FIG. 30B is a cross-section of a side view of the capsule system, according to an example embodiment;

FIG. 31A is a cross-section of a side view of a capsule system including the removable container, according to an example embodiment;

FIG. 31B is a cross-section of a side view of the capsule system, wherein the removable container is inserted, according to an example embodiment;

FIG. 31C is a side perspective view of a capsule system including the removable container, according to an example embodiment;

FIG. 31D is an exploded perspective view of the capsule system including the removable container, according to an example embodiment;

FIG. 33 is a diagram of the capsule system for use with a medical device for administering at least one atomized medication to a patient, according to an example embodiment;

FIG. 35A is a cross-section of a perspective side view of the medical device, according to an example embodiment;

FIG. 35B is a perspective view of the medical device, according to an example embodiment;

FIG. 35C is a perspective view of the medical device, according to an example embodiment;

Figures 36A, 36B, 36C:
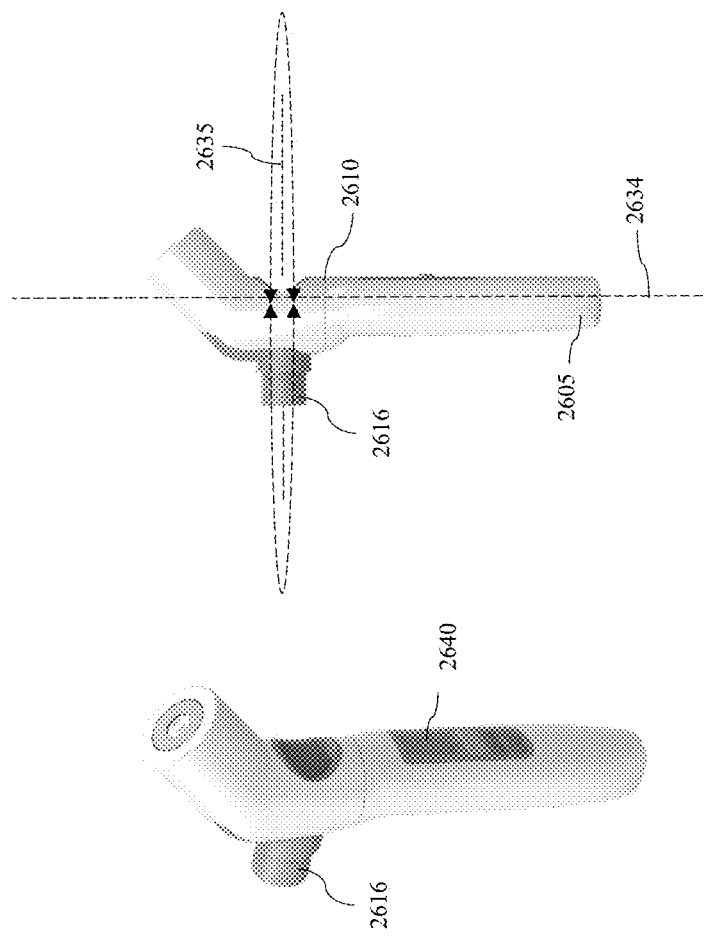
FIG. 36A is a perspective side view of the wand embodiment of the medical device, according to an example embodiment.
FIG. 36B is a side view of the wand embodiment of the medical device, according to an example embodiment.
FIG. 36C is a perspective side view of the wand embodiment of the medical device, according to an example embodiment.

FIGS. 36G, and 36H, illustrate a removable cap and a resilient bladder attached to a base unit of a device, according to another example embodiment.

Figure 36D:
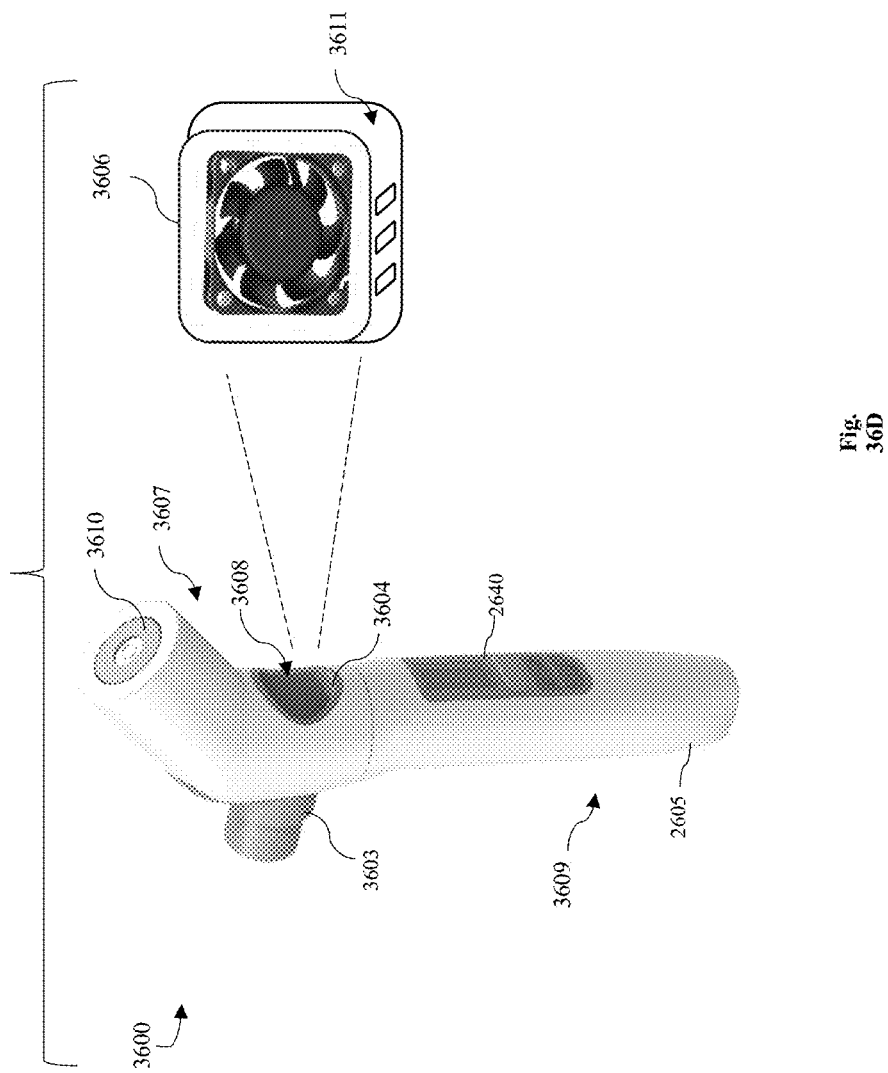
FIG. 36D is a perspective side view of a wand embodiment of the medical device having a removable air mover unit, according to another example embodiment.
Figure 36E:
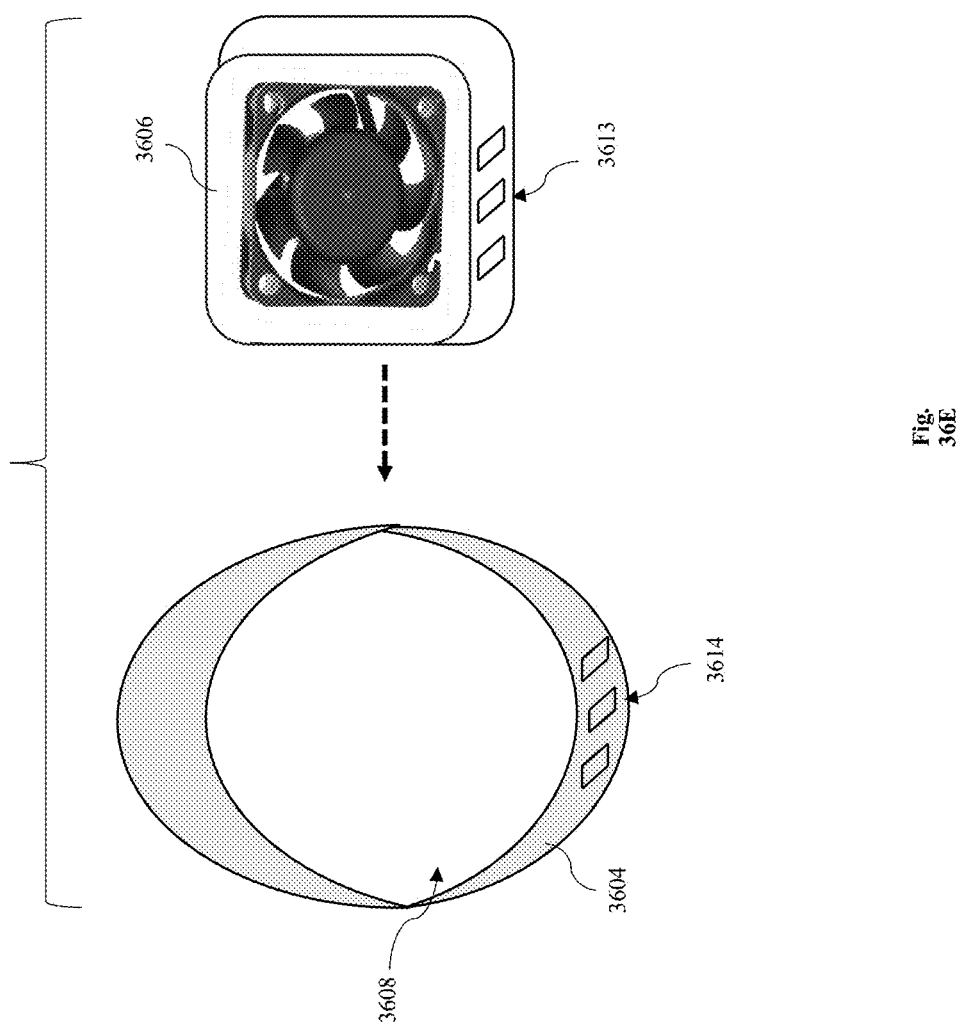
FIG. 36E is a schematic view of an opening of a device and an air mover unit, according to another example embodiment.
Figure 36F:
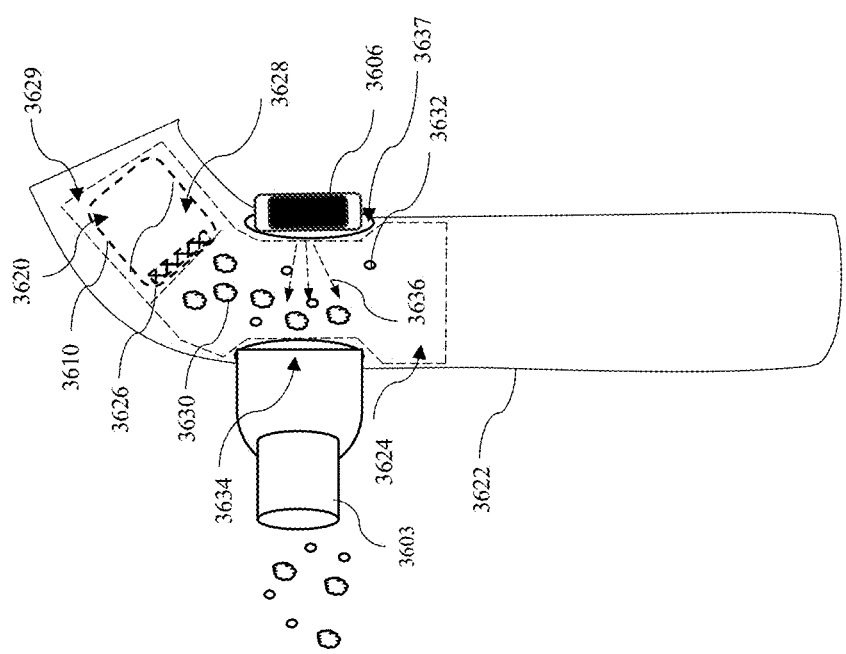
FIG. 36F illustrate schematic view of operation of a device for delivering medication, according to another example embodiment.
Figure 36I:
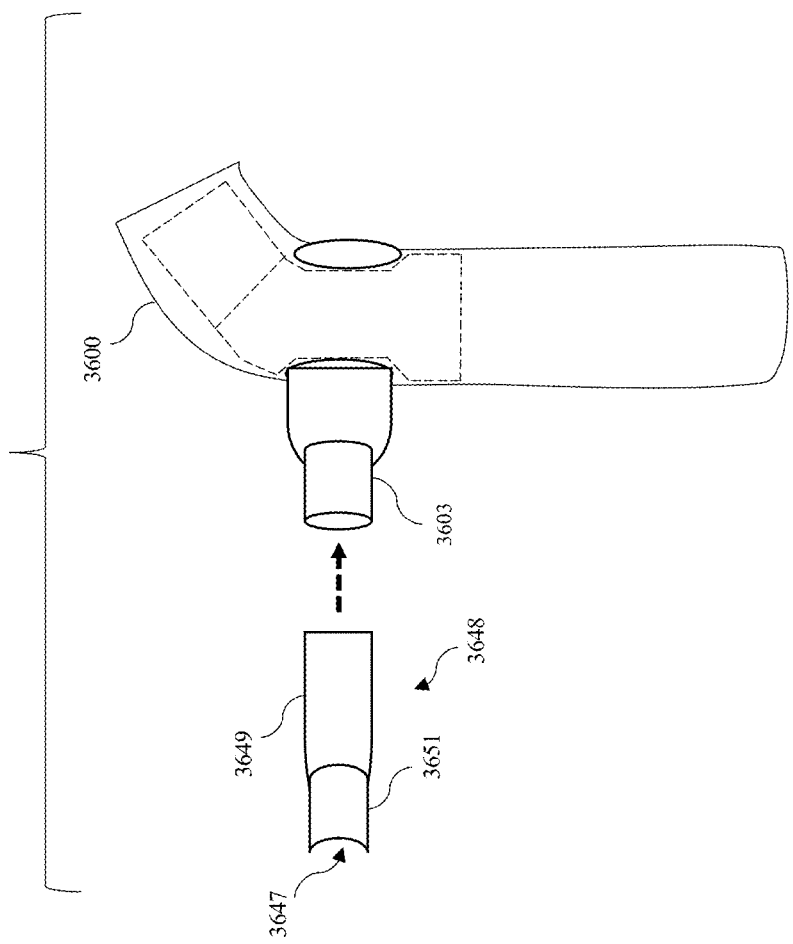
Figure 36J:
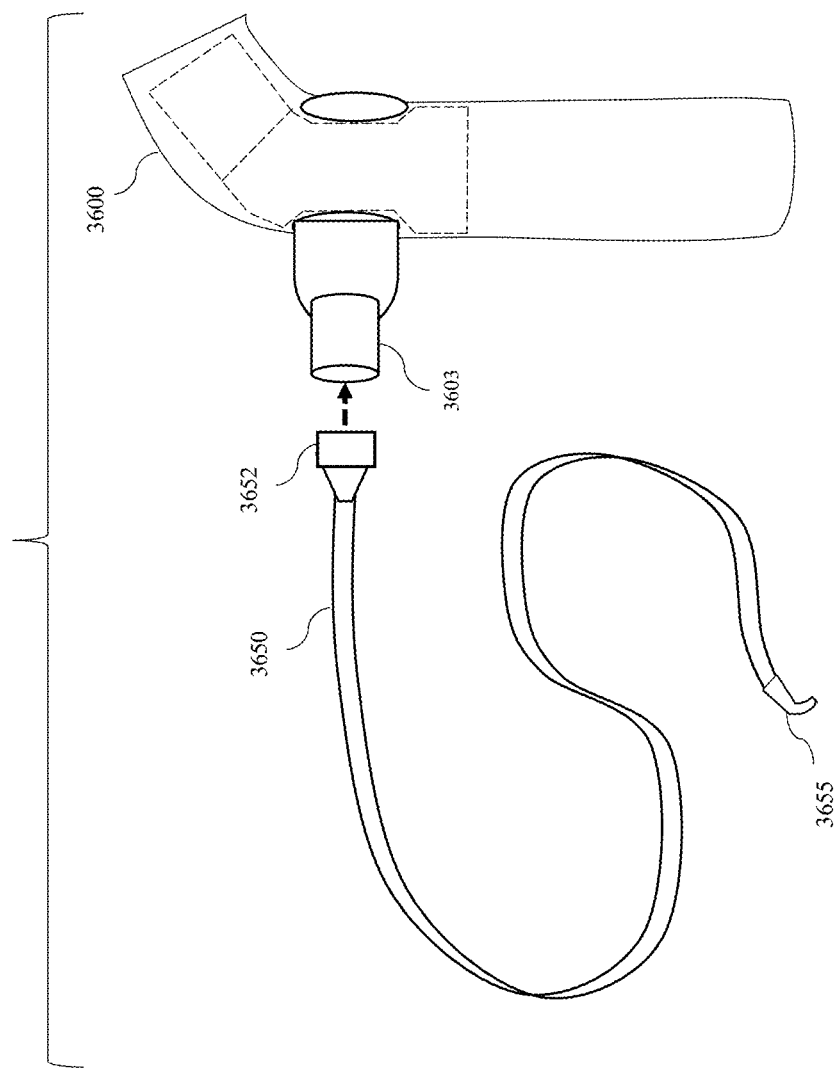
Figure 36K:
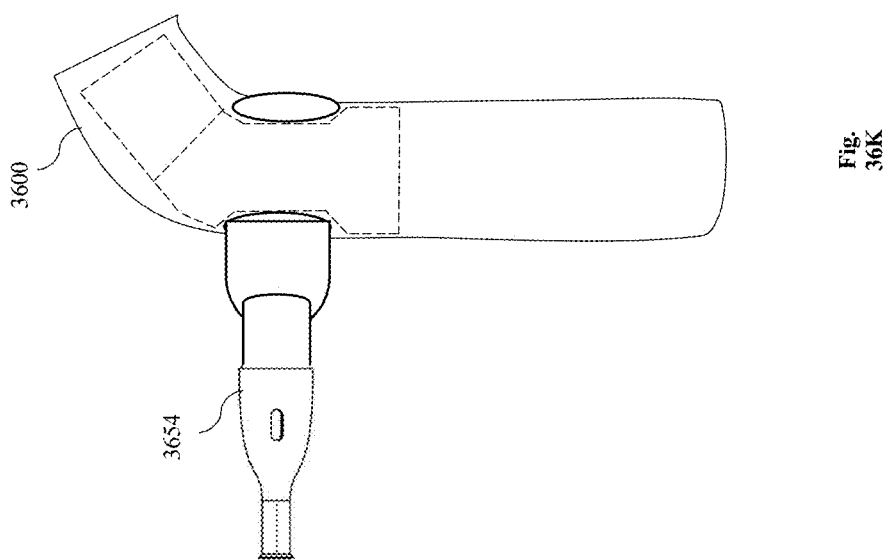

FIGS. 36I, 36J and 36K illustrate various additional components attached to a base unit of a device, according to another example embodiment.

Figure 36L:
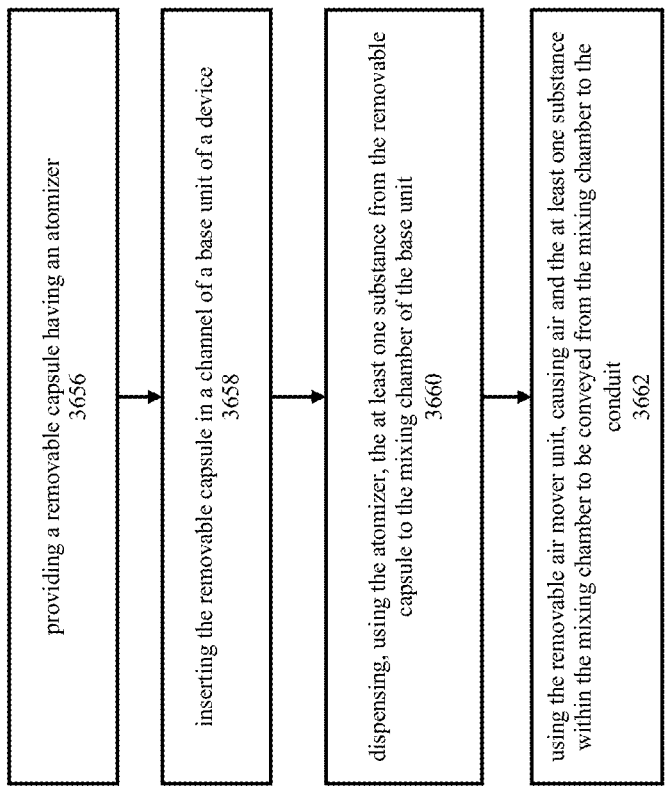

FIG. 36L is a flowchart diagram illustrating steps for a method for using the removable air mover unit, according to an example embodiment.

Figure 36M:
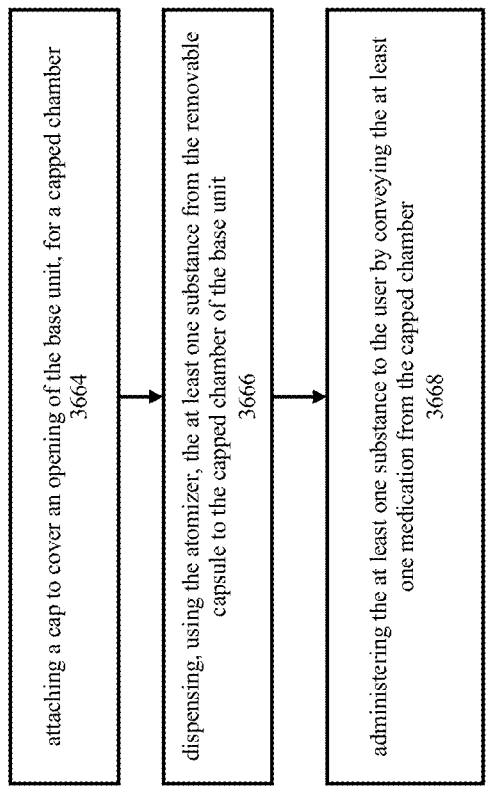

FIG. 36M is a flowchart diagram illustrating steps for a method for administering medication to a user from a capped chamber, according to an example embodiment.

Figure 36N:
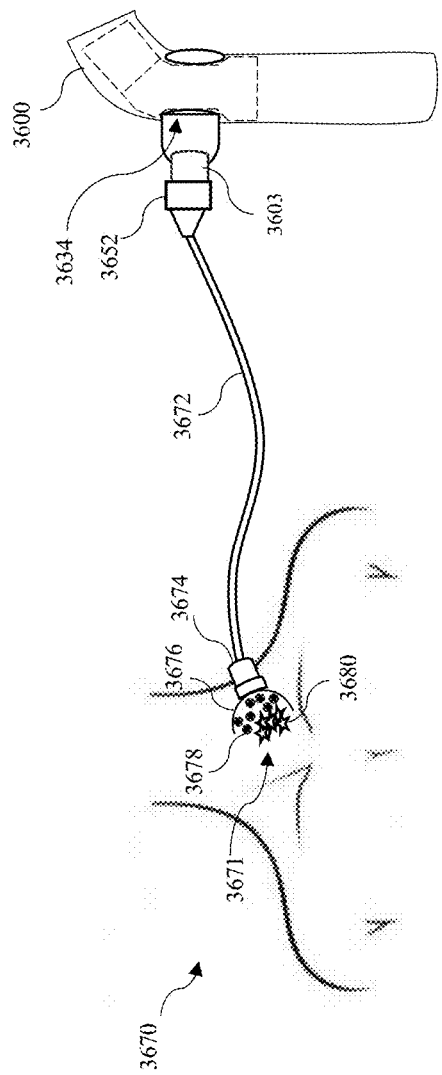

FIG. 36N illustrates a skin care cup and an elongated tube attached to a base unit of a device, according to another example embodiment.

Figure 37:
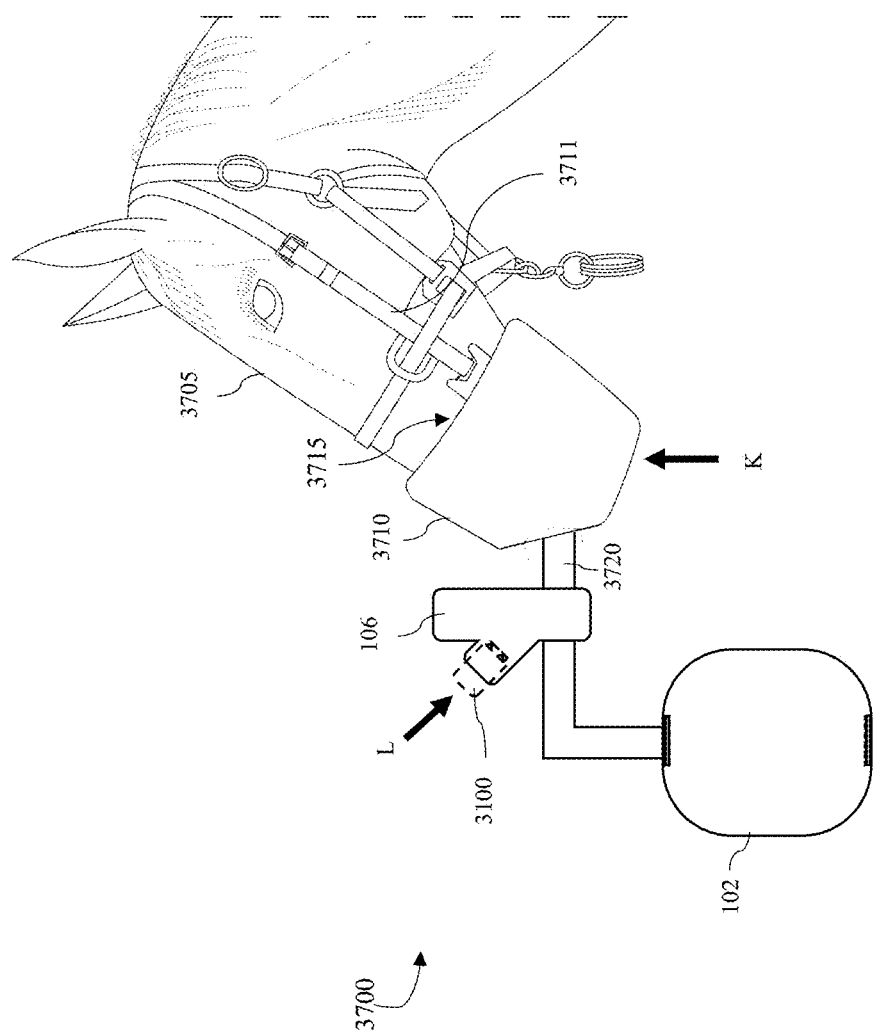

FIG. 37 illustrates a system for veterinary administration of at least one medication to an animal, according to an example embodiment.

Figure 38A:
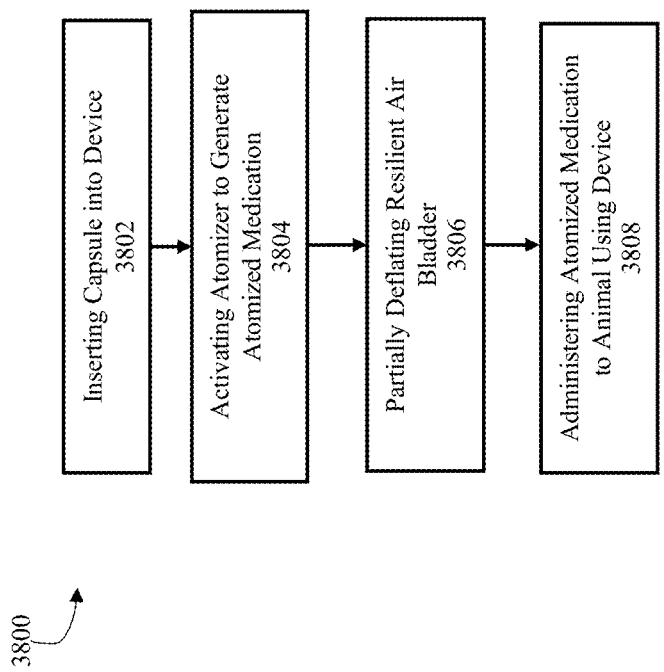

FIG. 38A a flowchart diagram illustrating steps for a method for veterinary administration of at least one medication to an animal, according to an example embodiment.

Figure 38B:
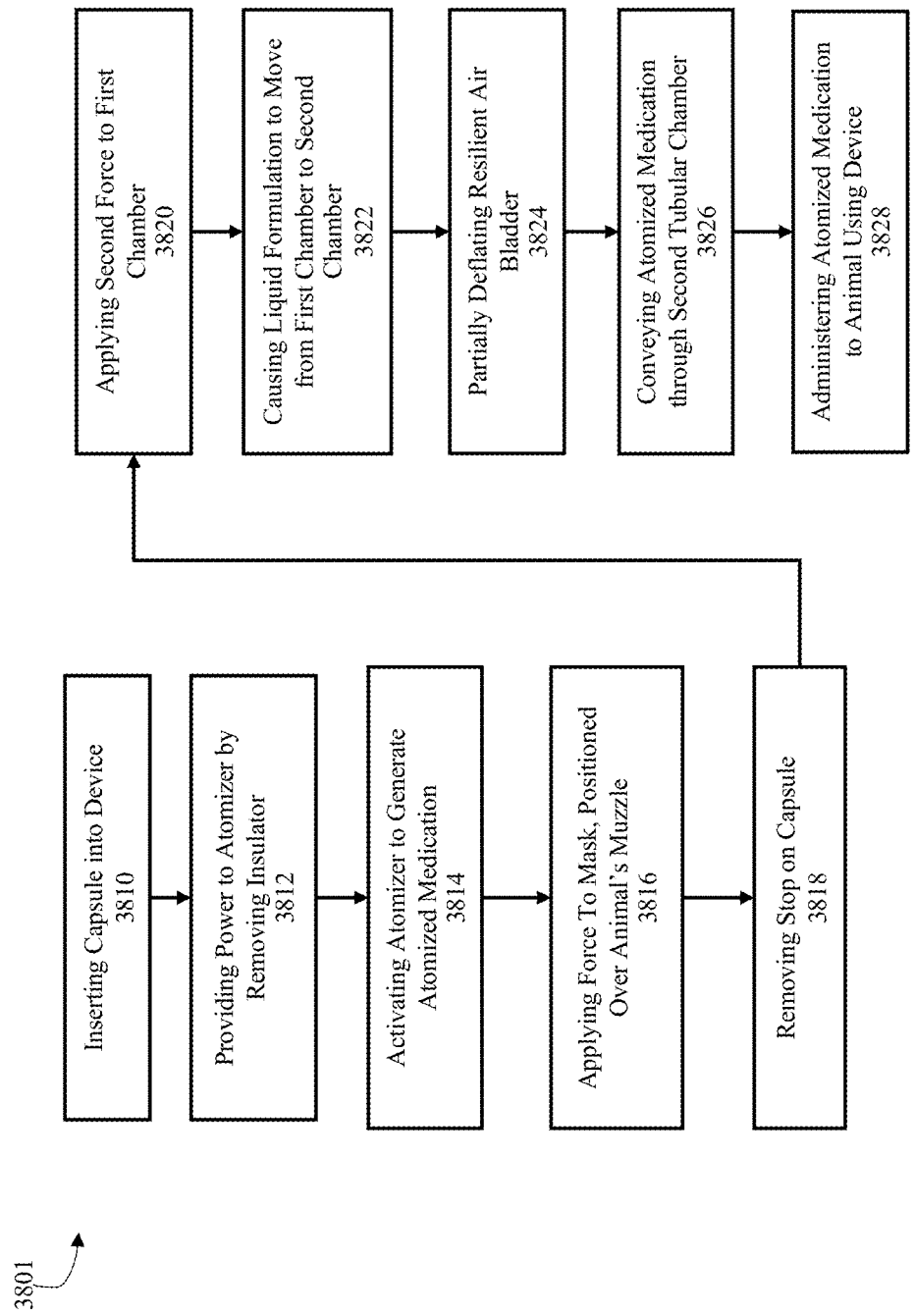

FIG. 38B a flowchart diagram illustrating steps for a method for veterinary administration of at least one medication to an animal, according to an example embodiment.

Figure 38C:
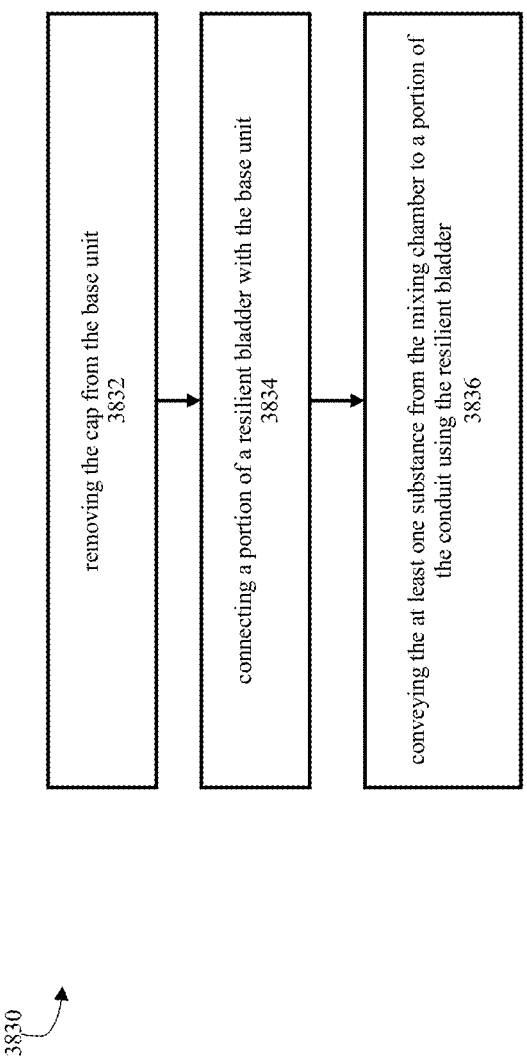

FIG. 38C is a flowchart diagram illustrating steps for a method for conveying medication using a resilient bladder, according to an example embodiment.

Figure 38D:
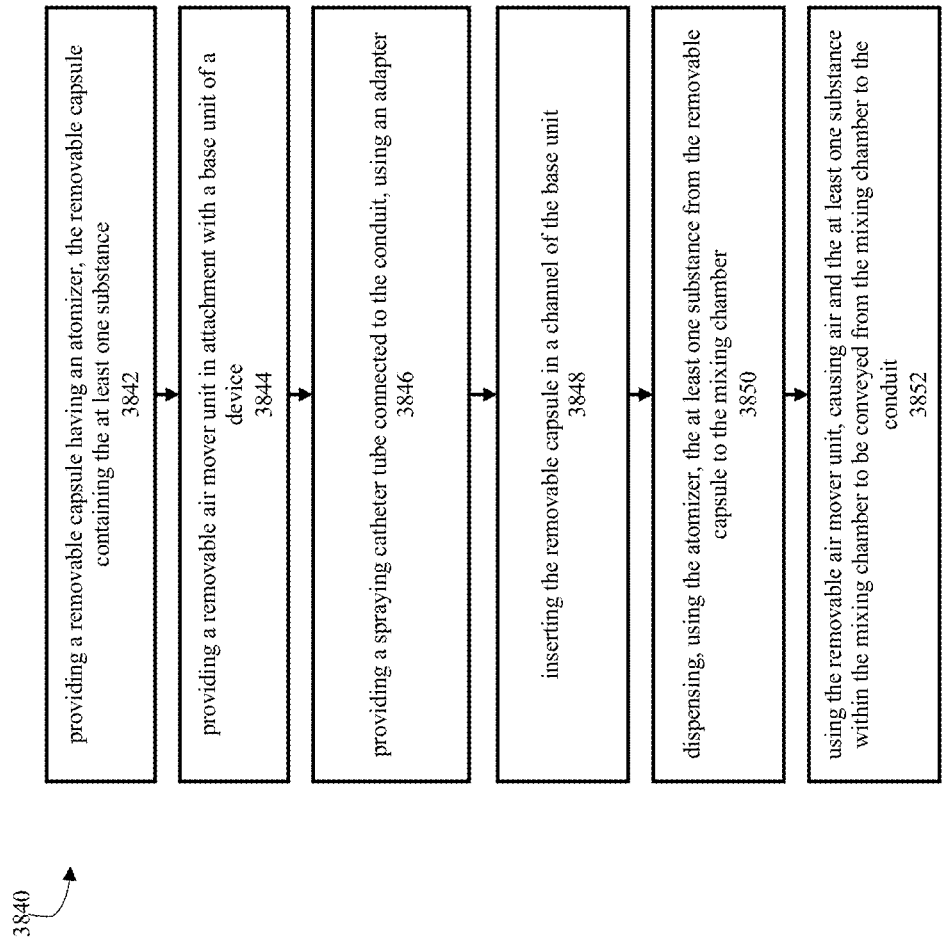

FIG. 38D a flowchart diagram illustrating steps for a method for using the removable air mover unit to convey a medication, according to an example embodiment.

Figure 38E:
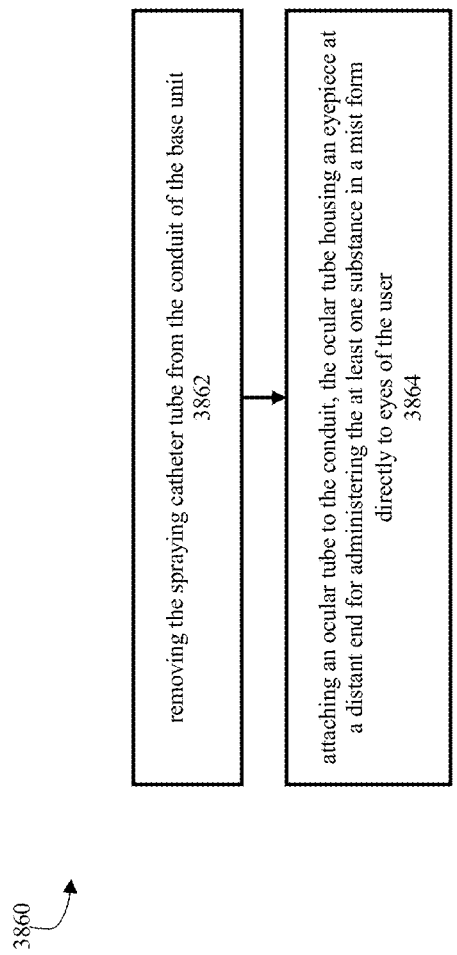

FIG. 38E a flowchart diagram illustrating steps for a method for attaching an ocular tube to the conduit for administration medication to a user, according to an example embodiment.

Figure 40:
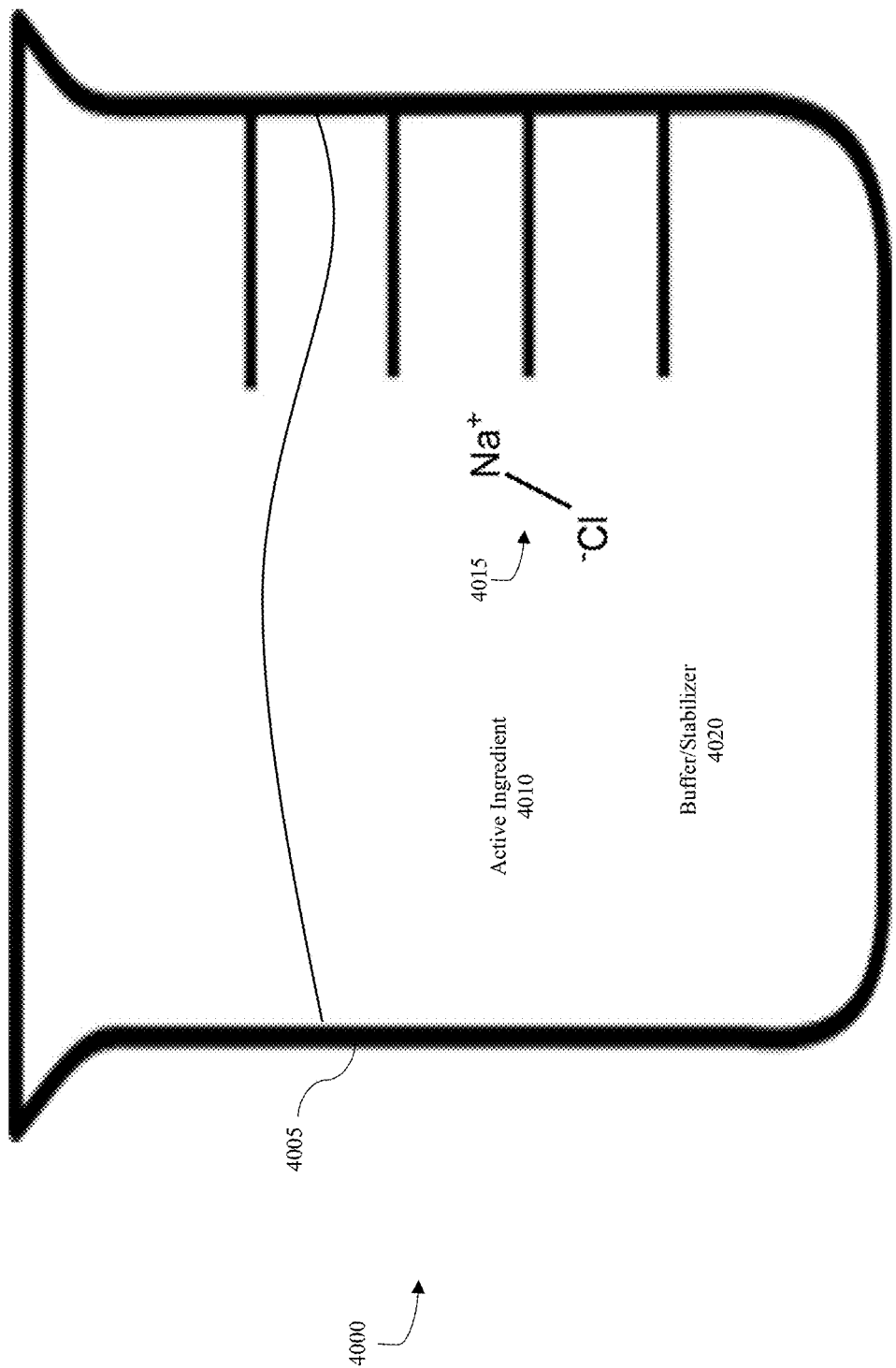
Figure 41:
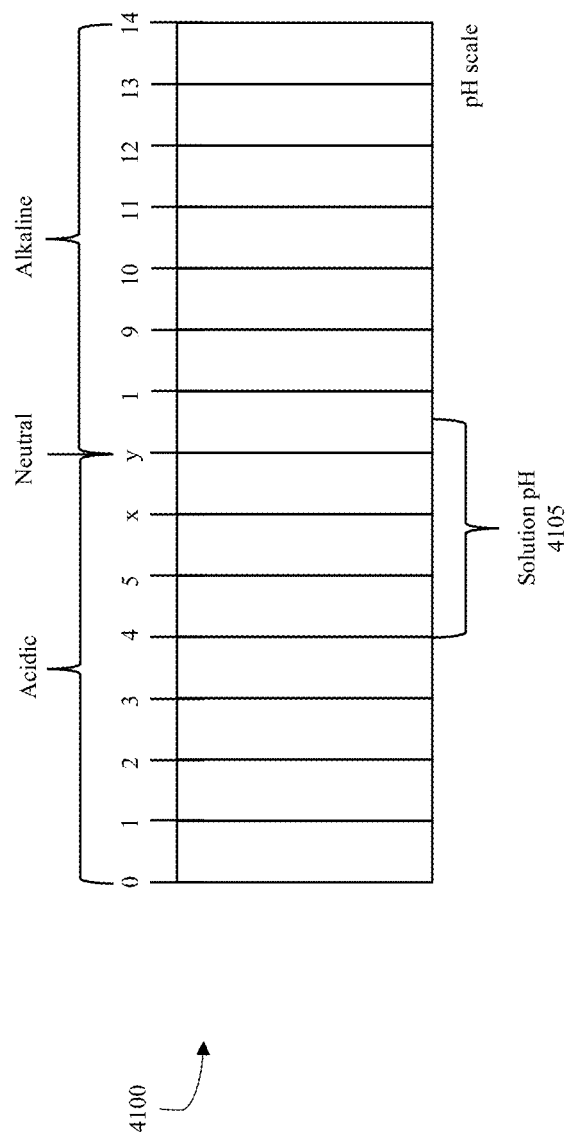
Figure 42:
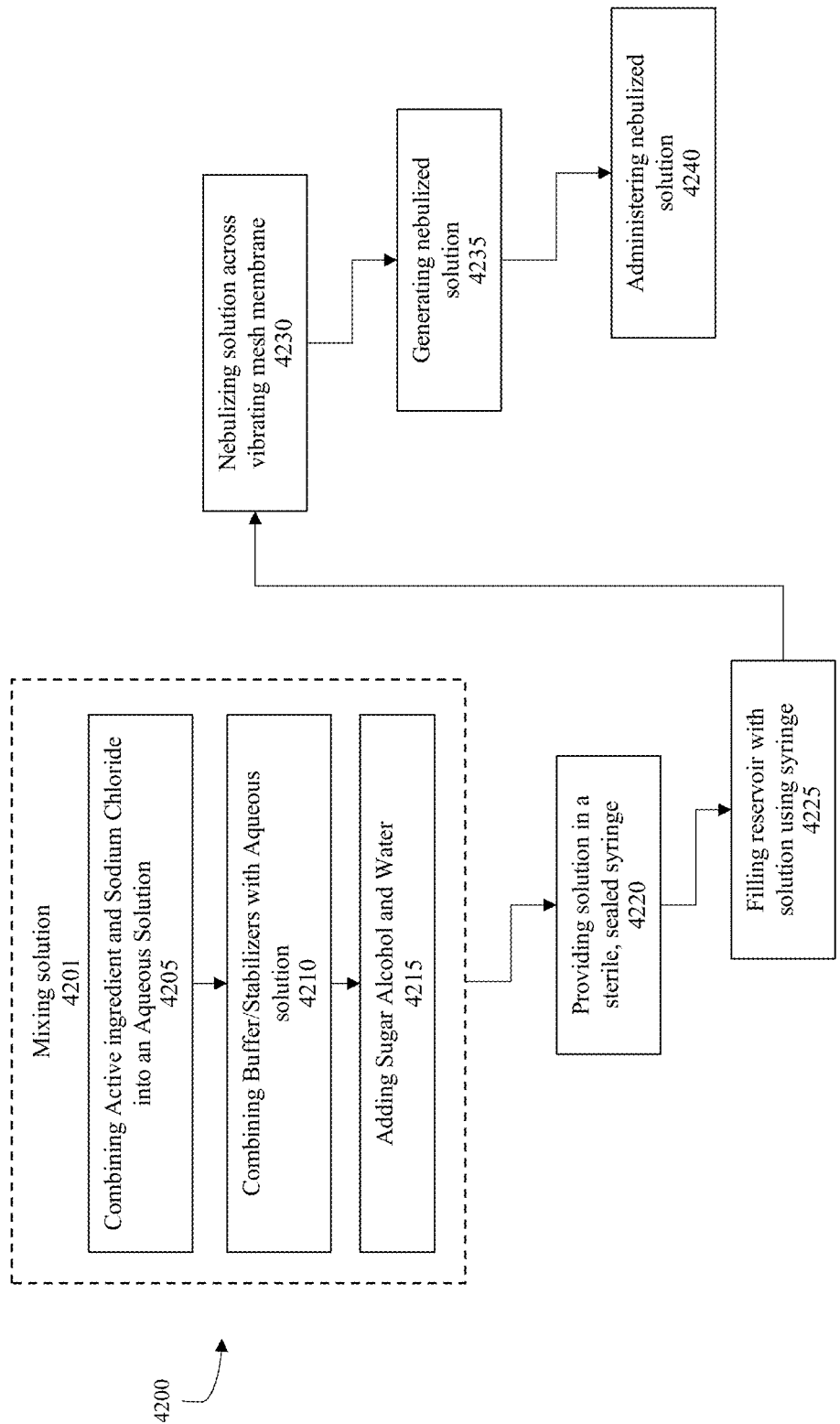

FIG. 39 is a side view of an active vibrating instrument, according to an example embodiment;

FIG. 40 is a side view of a beaker containing a solution for use with the active vibrating instrument, according to an example embodiment;

FIG. 41 is a block diagram of a pH scale, according to an example embodiment;

FIG. 42 is a flow diagram of a method of administering the solution for use with the active vibrating instrument, according to an example embodiment.

Figure 43A:
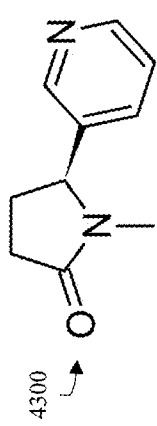
Figure 43D:
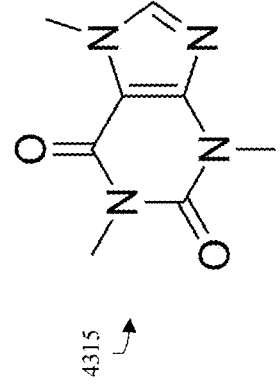
Figure 43E:
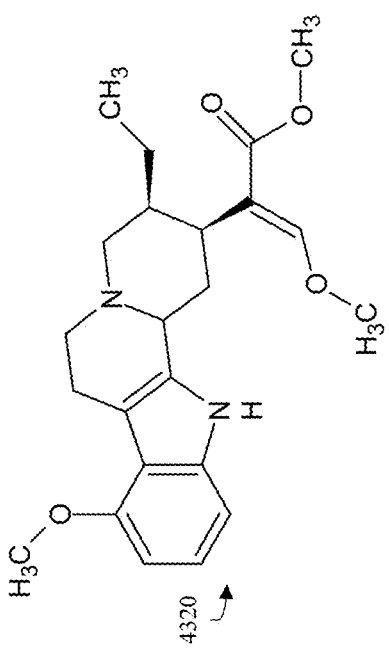
Figure 43B:
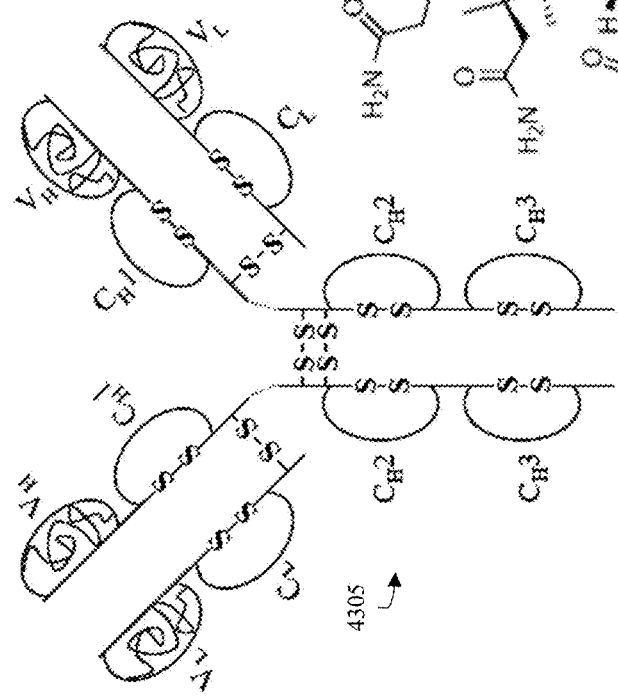
Figure 43F:
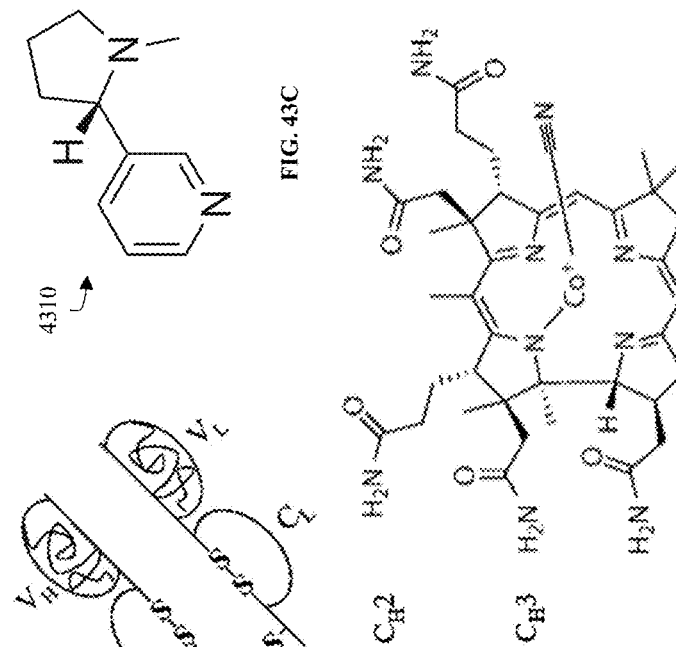
Figure 43C:
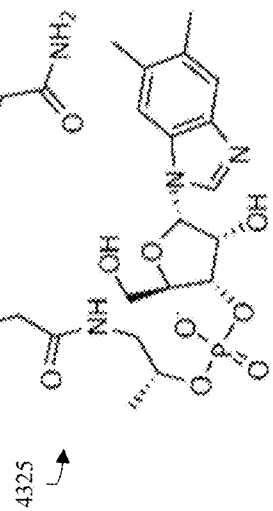
Figure 44H:
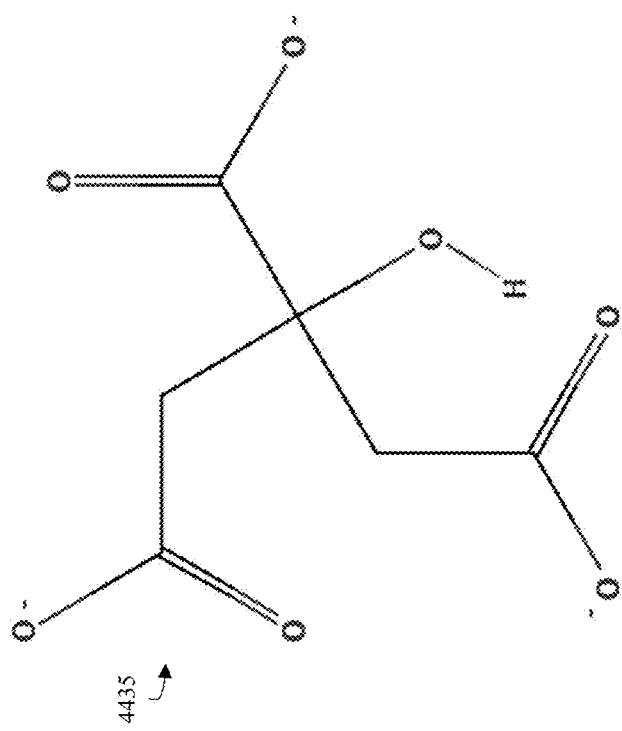
Figure 44I:
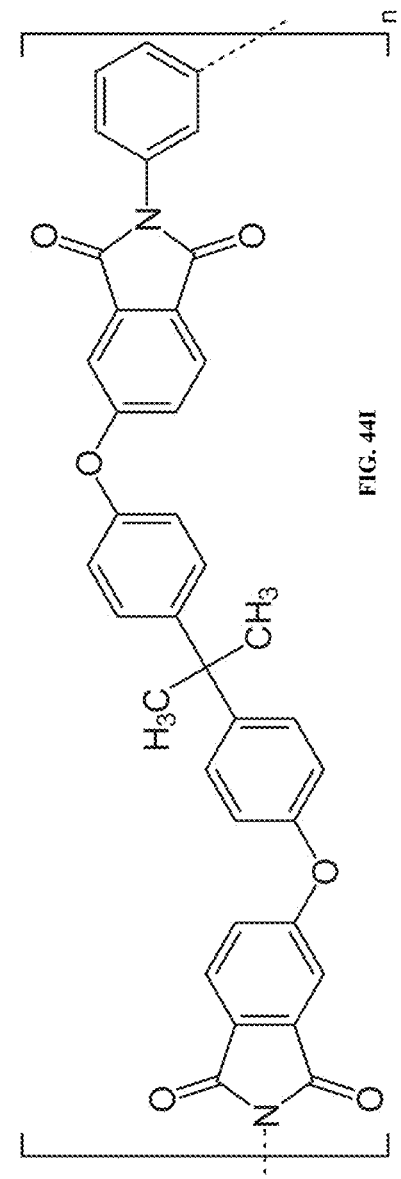
Figure 44K:
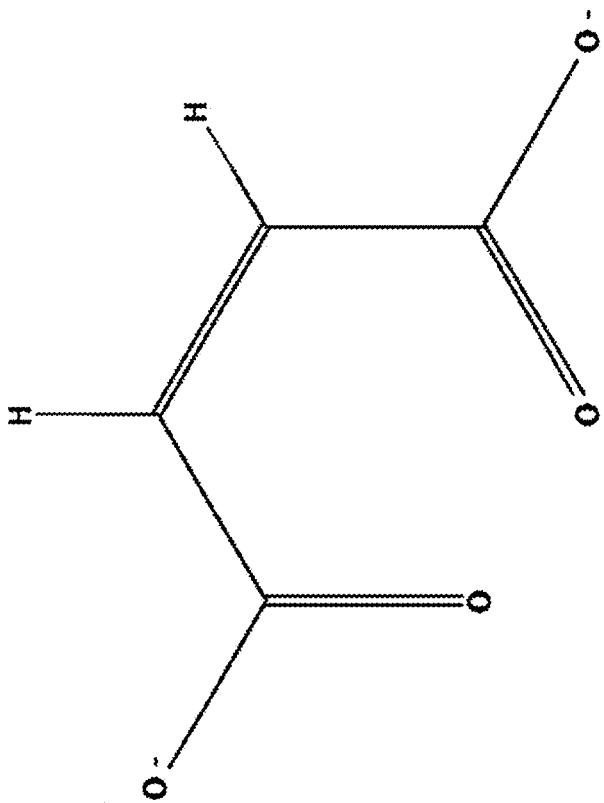
Figure 44J:
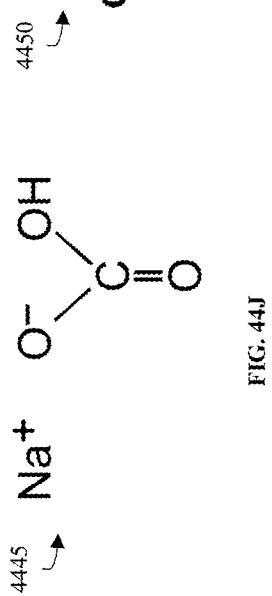
Figure 44L:
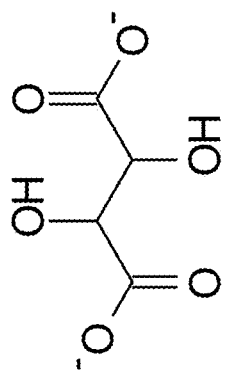
Figure 45:
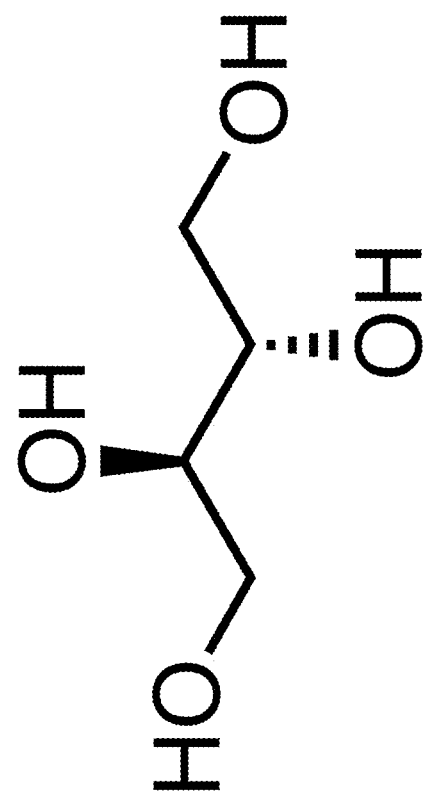
Figure 46:
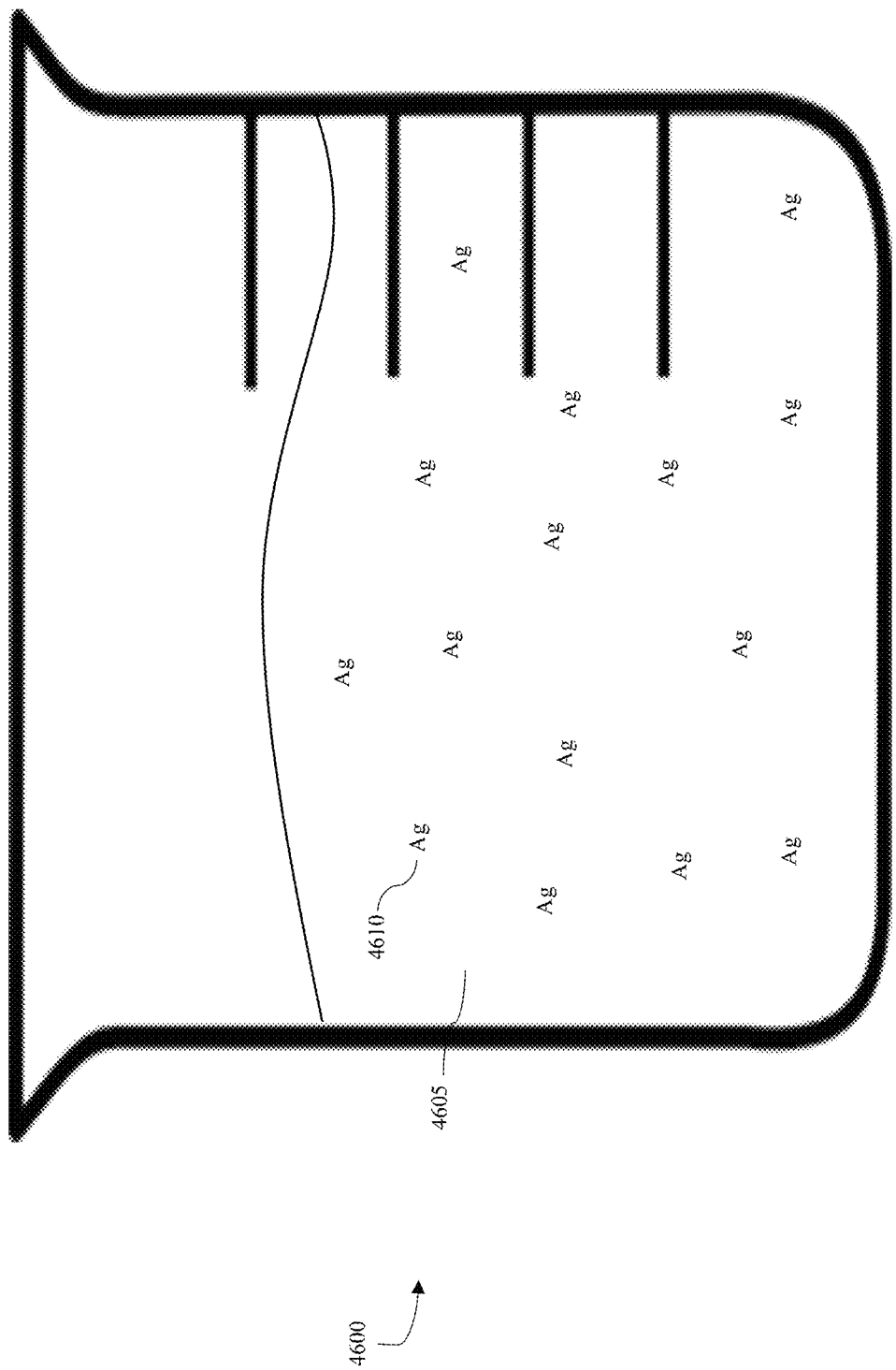

FIG. 43A is a perspective view of the molecular structure of cotinine, according to an example embodiment;

FIG. 43B is a perspective view of the molecular structure of adalimumab, according to an example embodiment;

FIG. 43C is a perspective view of the molecular structure of nicotine, according to an example embodiment;

FIG. 43D is a perspective view of the molecular structure of caffeine, according to an example embodiment;

FIG. 43E is a perspective view of the molecular structure of kratom, according to an example embodiment;

FIG. 43F is a perspective view of the molecular structure of vitamin B12, according to an example embodiment;

FIG. 43G is a perspective view of the molecular structure of cannabidiol, according to an example embodiment;

FIG. 43H is a perspective view of the molecular structure of tetrahydrocannabinol, according to an example embodiment;

FIG. 43I is a perspective view of the molecular structure of psilocybin, according to an example embodiment;

FIG. 43J is a perspective view of the molecular structure of ketamine, according to an example embodiment;

FIG. 43K is a perspective view of the molecular structure of naloxone (Narcan®), according to an example embodiment;

FIG. 43L is a perspective view of the molecular structure of glucagon, according to an example embodiment;

FIG. 44A is a perspective view of the molecular structure of ethyl alcohol, according to an example embodiment;

FIG. 44B is a perspective view of the molecular structure of citric acid, according to an example embodiment;

FIG. 44C is a perspective view of the molecular structure of sucrose, according to an example embodiment;

FIG. 44D is a perspective view of the molecular structure of histidine, according to an example embodiment;

FIG. 44E is a perspective view of the molecular structure of succinate, according to an example embodiment;

FIG. 44F is a perspective view of the molecular structure of acetate, according to an example embodiment;

FIG. 44G is a perspective view of the molecular structure of phosphate, according to an example embodiment;

FIG. 44H is a perspective view of the molecular structure of citrate, according to an example embodiment;

FIG. 44I is a perspective view of the molecular structure of polyetherimide, according to an example embodiment;

FIG. 44J is a perspective view of the molecular structure of sodium bicarbonate, according to an example embodiment;

FIG. 44K is a perspective view of the molecular structure of maleate, according to an example embodiment;

FIG. 44L is a perspective view of the molecular structure of tartrate, according to an example embodiment;

FIG. 45 is a perspective view of the molecular structure of a sugar alcohol, according to an example embodiment; and FIG. 46 is a side view of colloidal silver in a beaker, according to an example embodiment.

Figure 48:
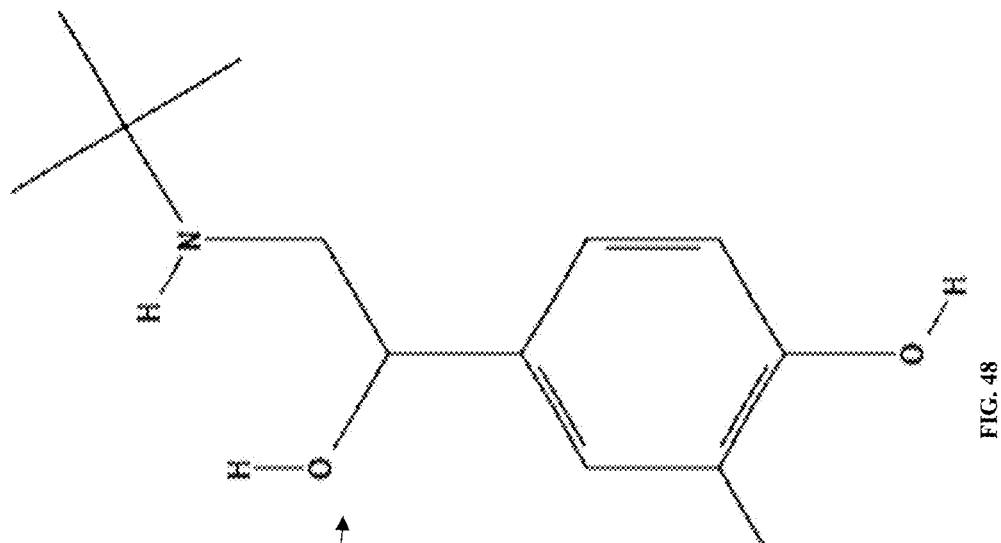
Figure 47:
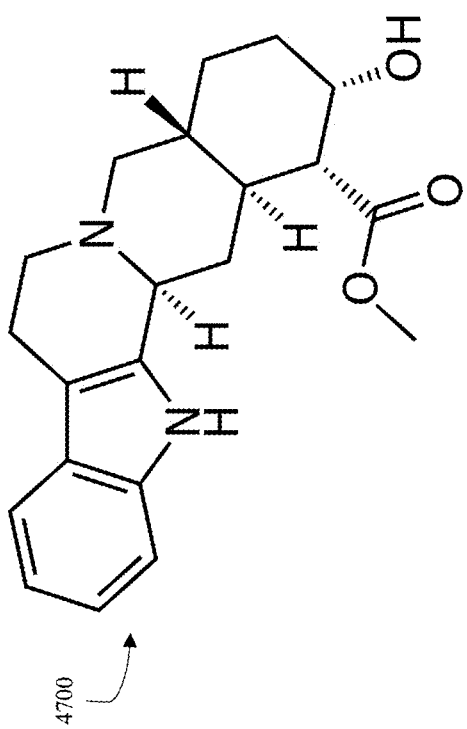
Figure 50:
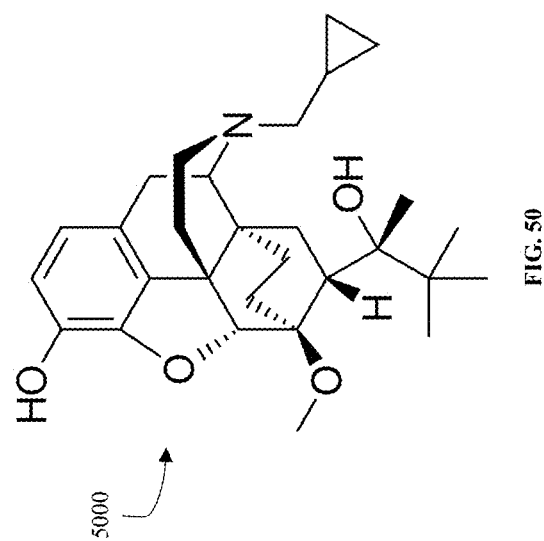
Figure 49:
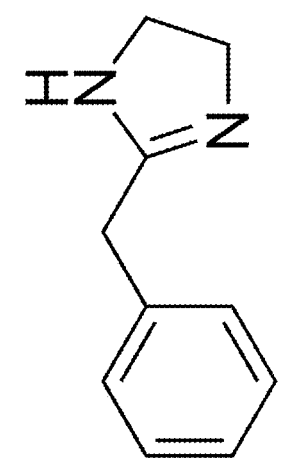

FIG. 47 is a perspective view of the molecular structure of yohimbine, according to an example embodiment;

FIG. 48 is a perspective view of the molecular structure of albuterol, according to an example embodiment;

FIG. 49 is a perspective view of the molecular structure of tolazoline, according to an example embodiment;

FIG. 50 is a perspective view of the molecular structure of buprenorphine, according to an example embodiment;

Like reference numerals refer to like parts throughout the various views of the drawings. FIGS. 11A through 16B, FIGS. 18A through 18D, FIGS. 31A through 31B, and FIGS. 34A through 36C are drawn to scale.

DETAILED DESCRIPTION

The following detailed description refers to the accompanying drawings. Whenever possible, the same reference numbers are used in the drawings and the following description to refer to the same or similar elements. While disclosed embodiments may be described, modifications, adaptations, and other implementations are possible. For example, substitutions, additions, or modifications may be made to the elements illustrated in the drawings, and the methods described herein may be modified by substituting reordering or adding additional stages or components to the disclosed methods and devices. Accordingly, the following detailed description does not limit the disclosed embodiments. Instead, the proper scope of the disclosed embodiments is defined by the appended claims.

Figure 15A:
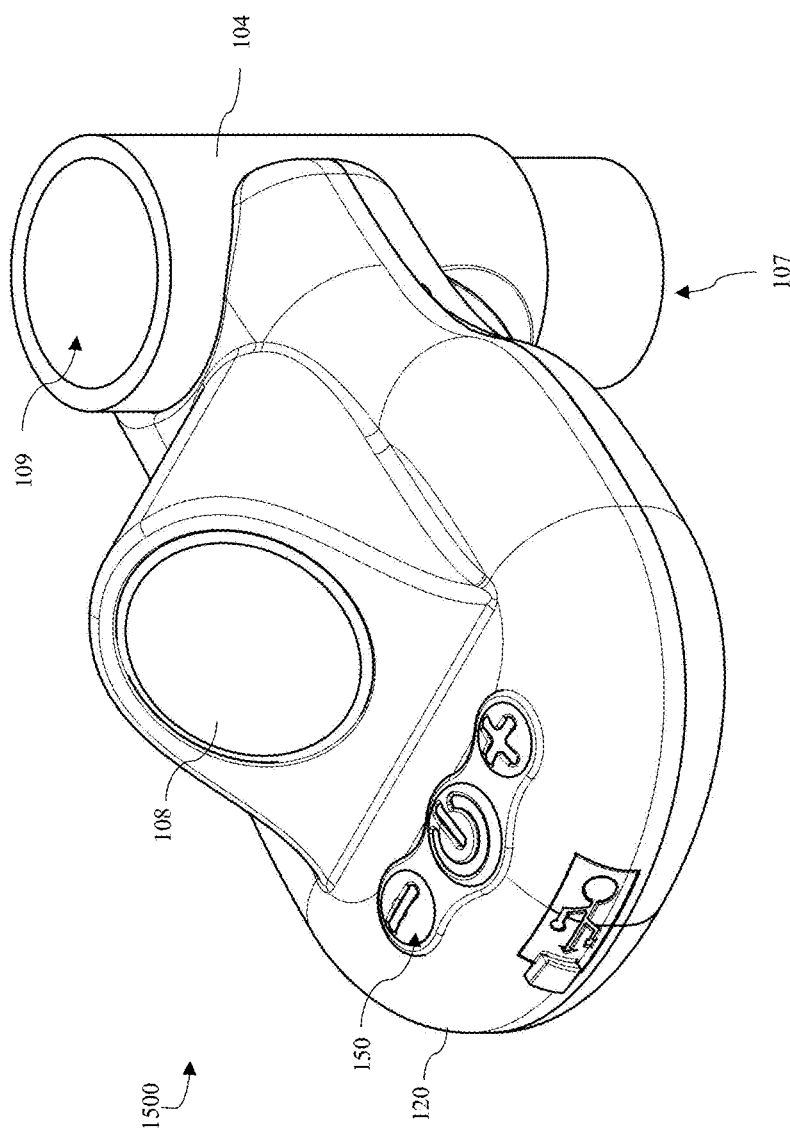
FIG. 15A is a perspective view of an attachment for administering medication to a patient, according to the first embodiment.
Figure 15B:
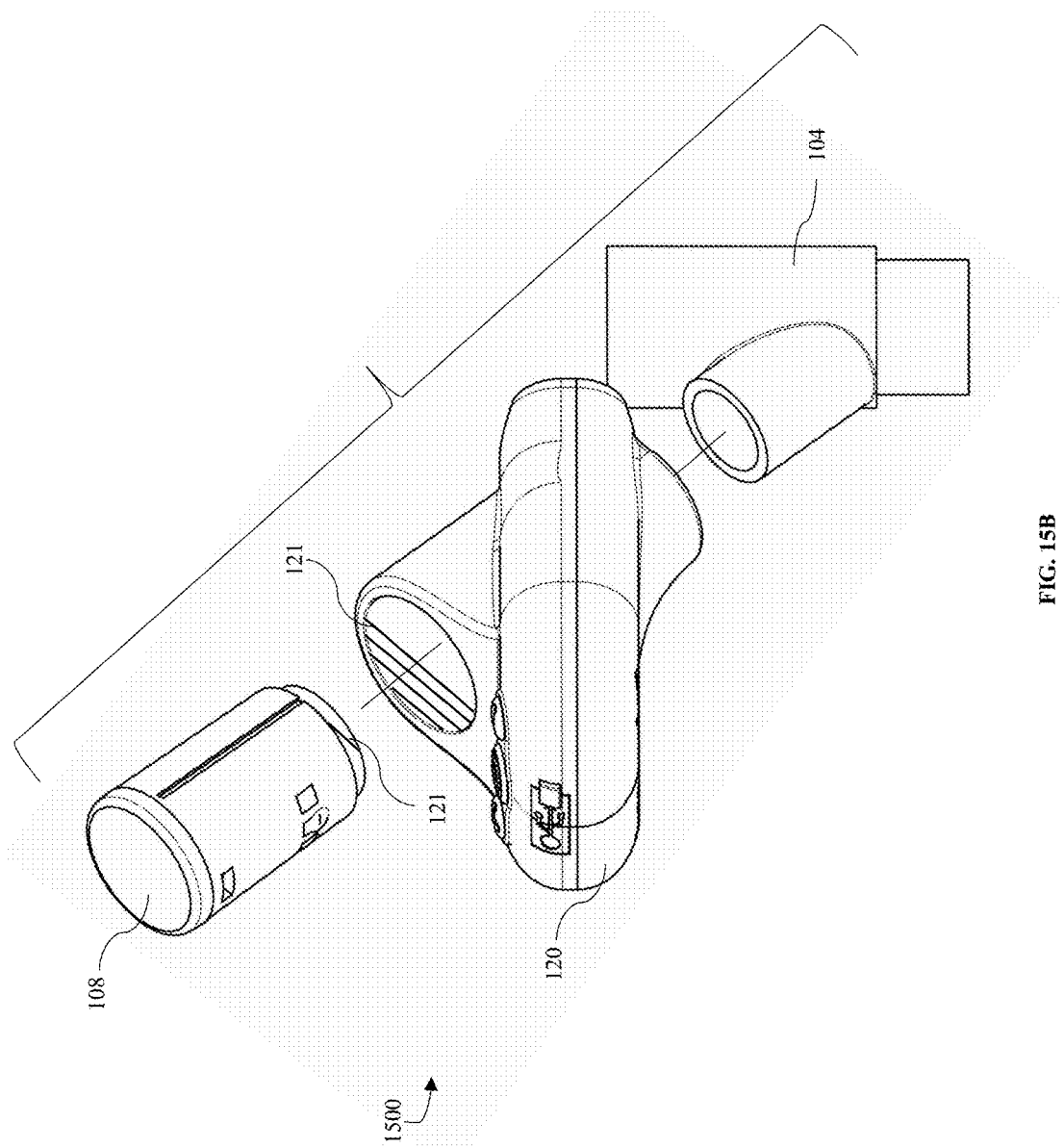
FIG. 15B is an exploded perspective view of an attachment for administering medication to a patient, according to the first embodiment.

The disclosed embodiments improve upon the problems with the prior art by providing a compact air mover unit that can be attached to the device. An air mover unit attached to a medical inhalation device optimizes the delivery mechanism of inhaled medication, enhancing the efficiency and effectiveness of the treatment process. The air mover unit creates a controlled flow of air to propel a mixture of medication toward the patient. This action ensures that the medication is delivered directly to the user's respiratory system in an optimal aerosolized form. Further, the incorporation of an air mover unit improves the consistency of dose delivery, enhancing the user's ability to receive the full therapeutic benefit of the medication, and reducing the physical effort required by the patient to inhale the medication, thereby improving the overall effectiveness of treatments.

Further, the disclosed embodiments provide the air mover unit with electrical contacts that can be easily connected to the device by enabling a quick and efficient electrical connection between the air mover unit and the device. This feature facilitates the immediate activation and control of the air mover unit upon attachment, streamlining the setup process and enhancing the device's overall usability. The design of the electrical contacts ensures a secure and reliable connection, providing for consistent operation of the air mover unit. Additionally, the disclosed embodiments improve over the prior art by providing the air mover unit that propels the mixture of medication through long flexible tubes, even those with multiple turns, without accumulating medications in the turns. This maintains a consistent and controlled airflow that ensures the aerosolized substance is delivered efficiently and uniformly. The air mover unit generates a flow of air to navigate the complexities of a tube's interior, including its length and any bends. Further, the air mover unit prevents the sedimentation of medication particles at the curves or turns of the tubing providing a seamless delivery.

The system also improves over the prior art by providing a device capable of receiving various modular attachments for medication, therapeutic and cosmetic purposes thereby offering a customizable and multifunctional tool that can cater to a wide range of user needs. This modular capability allows for the seamless interchange of attachments designed for specific treatments, enabling the device to administer a variety of medicated aerosols for respiratory conditions and deliver substances for cosmetic applications, such as moisturizers or treatments for skin conditions, through the same system. The system's ability to deliver and administer a diverse range of substances other than pharmaceuticals, including therapeutic and cosmetic substances, offers a significant advantage by broadening its applicability across various industries and use cases. Such a system provides users with a more comprehensive care solution, accommodating a wide array of health, wellness, and beauty needs through a single, innovative device. By catering to this broader spectrum of applications, the system stands out as a multifunctional tool that can deliver targeted treatments ranging from medical therapies to skincare routines, thereby meeting a wider range of consumer demands and expectations.

The disclosed embodiments improve over the prior art by providing a device to deliver exosomes as medication to users. The use of exosomes, which are vesicles derived from cells that can encapsulate and deliver therapeutic agents directly to specific cells or tissues, provide targeted therapy. The system increases the precision with which medications are delivered, minimizing off-target effects and enhancing the efficacy of treatments. Exosomes can carry a wide range of therapeutic agents, including drugs, RNA, or proteins, directly to diseased cells while sparing healthy tissues. This targeted delivery improves treatment outcomes and reduces the side effects and toxicity associated with conventional therapies.

The system also improves over the prior art because the medication is held in capsules that includes an atomizer that abuts the medication. Gravity forces the medication to be pressed against the medication to allow for efficient atomization. The capsule is compatible with the attachment because both include electrical contacts that, when paired up, provide electrical communication between the capsule and the attachment.

The disclosed system and methods described herein represents a significant improvement over prior art by incorporating a sophisticated capsule system for administering atomized medication. Specifically, the system comprises at least one chamber housing the medication, an atomizer to convert the medication into a fine mist, and various additional components such as sensors and electrical contacts. This design allows for a more controlled and precise delivery of medication, enabling targeted treatment with reduced risk of overdose or underdose.

In the general practice of medicine for humans, the disclosed invention offers significant improvements over prior art, particularly addressing concerns around modularity, interchangeability, and speed in administration. Modularity enables customization of medical devices to suit individual patient needs and particular medical conditions, allowing for a more targeted and efficient approach. With the invention's design, various components can be added or removed with case, thereby adapting the device to different scenarios and patient requirements. The interchangeability feature ensures that parts can be substituted without compromising the integrity or functionality of the device, thus increasing its utility and flexibility. This adaptability not only reduces costs by allowing components to be reused across different applications but also facilitates quick adjustments in emergency situations. Finally, the invention's design emphasizes rapid administration of medication, significantly reducing the time required to prepare and deliver treatments. This is particularly crucial in critical care situations, where every second can make a difference in patient outcomes. By addressing these key areas, the invention enhances the efficiency, adaptability, and responsiveness of medical treatment, setting a new standard in patient care.

Referring now to the Figures, FIG. 1A is a side view of a system 100 for administering at least one medication to a patient, according to a first embodiment. FIG. 1B is a side view of a base unit or an attachment 106 for administering medication to a patient, according to the first embodiment. Additionally, FIGS. 13 through 15B also depict views showing additional example embodiments. FIG. 13 is a side view of the system 1300, according to the first embodiment.

FIGS. 14A through 14C are various views of the housing 120 of the system 1400, according to the first embodiment. FIG. 15A is a perspective view of the device 1500, according to the first embodiment. FIG. 15B is an exploded perspective view of the device 1500, according to the first embodiment. The medication is in fluid form. FIG. 15B also includes mating threads 121 on the capsule 108 and the walls of the base unit so that the capsule may be rotated so that it moves into the base unit such that the capsule engages with an actuator that causes the atomizer to be powered thus atomizing the medication. In other embodiments, the threads 121 may be used to simply secure the capsule within the base unit. The system includes a resilient air bladder 102 in fluid communication with a tubular chamber 104 of a base unit. The tubular chamber is a hollow enclosed space within the base unit. The resilient air bladder supplies the system with fresh air. Other types of cardiopulmonary devices configured to supply air into the system may be used and are within the spirit and scope of the present invention. The resilient air bladder is a resuscitation bag, which is commonly used by medical professionals.

The base unit is the attachment 106 that including receiving sections 107 and 109 that provides modular fittings such that commonly used medical components, such as medical face masks or medical mouthpieces, and modular cardiopulmonary devices may be attached. The base unit may also be described herein as a device or medical device. Each of the receiving sections includes an opening into the first channel. The first channel may have a cross-sectional shape defining a circle, but other shapes may be used and are within the spirit and scope of the present invention and as such the openings of the receiving sections 107 and 109 may also be a circular shaped opening. The attachment is configured for connecting to a modular cardiopulmonary device. The modular cardiopulmonary device is defined by the resilient air bladder and at least a mask 142 or mouthpiece (205 in FIG. 2). Modular fittings refer to pre-manufactured parts or components that can be assembled, interchanged, or replaced with relative ease. They are designed to be used in different configurations to meet various requirements. The key advantage of modular fittings is their versatility and ease of use, as they allow for customization and flexibility. Modular fittings provide a standardized, interchangeable set of parts that can be used in a variety of configurations to meet different needs. Examples of modular fittings may include, but are not limited to, friction fit, male female fit, or screw fit. Other types of modular fittings configured to allow the attachment 106 to attach to modular cardiopulmonary devices may be included and are within the spirit and scope of the present invention. The modular fittings allow the user of the system to remove or attach different cardiopulmonary devices so that the user can clean and disinfect the devices between each patient.

A capsule 108 is in fluid communication with the tubular chamber and is configured for carrying the medication. In some embodiments, the capsule may include a sensor (156 in FIG. 2) for detecting the amount of medication within the capsule. An atomizer 110 is disposed at least proximate to the capsule and in fluid communication with the tubular chamber. The atomizer is configured to atomize the medication that is disposed within the capsule. The atomizer is configured to produce particles having a particle diameter ranging from about 1.5 micrometers (μm, or microns) to about 6 micrometers. The atomizer includes a vibrating mesh membrane. As the medication passes through the vibrating mesh membrane, the membrane nebulizes the medication to create a nebulized medication that includes a plurality of particles. The vibrating mesh membrane produces nebulized medication by vibrating at high frequency to trigger particle, or droplet, formation from the medication solution against an inner surface of the membrane on an outer surface of the membrane. The vibrating mesh membrane is a metal piece or plate having a plurality of openings extending through the piece, such that the metal piece, when electrically stimulated to undergo piezoelectric vibration, oscillates against the medication in the capsule 108, causing some of the medication to move through the openings and form small particles on or above the outer surface of the active mesh. The vibrating mesh membrane vibrates at between about 150 kHz and about 300 kHz upon electrical stimulation by an AC|DC current directed to the vibrating mesh membrane. However, other frequencies may be used and are within the spirit and scope of the present invention. The vibrating mesh membrane includes material such as pure titanium, platinum, or palladium, or alloys thereof or the like, or laminated layers of titanium, platinum, or palladium or the like, to produce a piezoelectric effect that results in mesh vibration and particle formation over the outer surface of the mesh in the mouthpiece interior volume. Piezoelectricity is the ability of a material to develop electric charge in response to applied mechanical stress.

The atomizer produces particles that are atomized droplets of the medication. Particles that are larger than 5 micrometers are unable to penetrate into the alveoli of the lungs and are thus of reduced efficiency in being rapidly absorbed by the circulatory system and/or body tissues. The ability of particles to penetrate into the lungs and be absorbed by the depends on the size of the particles. Inhalable particles, ranging in size from 1.5 micrometers to about 6 micrometers, penetrate into the lungs as far as the bronchi because the cilia of the lungs filter the inhalable particles from further travel into the lung volume. Particles ranging in size from 1.5 micrometers to about 5 micrometers are able to penetrate into the alveoli in the lungs and are readily absorbed through the alveoli into the circulatory system and body tissues.

The medication in the capsule is a fluid solution configured to treat patients for different situations. The solution includes an aqueous solution that includes an active ingredient and sodium chloride. When atomized by the atomizer in the capsule, the atomized medication is configured to break a patient's blood brain barrier. The active ingredient includes at least one of nicotine, caffeine, a plurality of vitamins, kratom, Vitamin B12, cotinine, adalimumab, cannabidiol ("CBD"), tetrahydrocannabinol ("THC"), psilocybin, cannabis, ketamine and any combination thereof. The active ingredient may also include exosomes, analgesics, antifungals, Benzodiazepines, Antiarrhythmic agents, anti-aging agents, rapamycin, metformin, calcium channel blockers, antibiotics, anti-inflammatory, anti-gout, alpha-beta-adrenergic agonists, Nitroglycerin, adrenergic bronchodilators, cardiovascular agents, central nervous system stimulants and/or depressants, diabetic agents, diuretics, immunologic agents, gastrointestinal agents, common biologics like Humira, Lantus, Remicade, Enbrel, vaccines, psychotherapeutic agents, opiate partial antagonists, opioids, pulmonary agents, hormonal agents, weight loss agents, vitamins/minerals/supplements, Antihyperlipidemics, PCSK9 Inhibitors, Evolocumab, Alirocumab, Inclisiran, Diuretics, Furosemide, Bumetanide, Torsemide, Beta-2 Adrenergic Agonists, Salmeterol, Long-Acting Beta Agonist, Vilanterol, Formoterol, Anticholinergics, Umeclidinium, Glycopyrrolate, Corticosteroid: Budesonide, Fluticasone, Bronchodilators, Tiotropium, Over-active Bladder Medications, Anticholinergics, Ditropan (oxybutynin), Tolterodine, Darifenacin, Muscarinic Antagonists, narcotic antagonists, Trospium, Fesoterodine, Migraine Therapyies, CGRP Receptor Blockers (gepants and monoclonal antibodies ((mAb)), Ubrelvy, Triptans, Ergots, Antiemetics, antagonists of the serotonin, histamine, muscarinic and neurokinin systems, Selective Serotonin 5-HT3 Antagonists, Zofran (ondansetron), Diabetic and Weight loss agents, GLP-1, Semaglutide, GIP+GLP-1, Mounjaro™ (Tirzepatide), Anticonvulsants, Pulmonary medications, Hormones, Biologics, Regenerative Drugs, all essential drugs and medicine as defined by World Health Organization, vitamins, caffeine and energy medications, all emergency medicine medications, integrative therapeutics, peptides, ozone, o2, white curcumin, exosomes, gene therapy vectors, erectile dysfunction medications, such as sildenafil citrate, tadalafil, Cialis®, Viagra®, future classes of therapeutics, Yohimbine, and Haloperidol. The active ingredient may also include preservatives, such as Sodium benzoate, and/or anti-yeast agents, such as potassium sorbate. Other preservatives for medication may be used and are within the spirit and scope of the present invention.

The solution further includes a buffer and/or stabilizer. The buffer helps stabilize and maintain the pH level of the solution. The active ingredient includes approximately up to 10% of the solution. Sodium chloride includes approximately between 10% to 90% of the solution. The buffer includes approximately between 1% to 5% of the total solution. The solution has a pH of approximately between 4 pH and 7.5 pH. The pH range is critical to decrease the effects that the active ingredient may have on the body when inhaled, e.g., an increased amount of acute toxicity which may be present in unprotonated active ingredients above a certain pH.

In a first example solution, the solution is for at least decreasing withdrawal symptoms of a person addicted to nicotine. Said solution includes cotinine being the active ingredient in the solution including approximately between 0.5% and 8% of the solution and a sugar alcohol including approximately between 0.5% to 3% of the solution. The solution further includes a buffer including ethyl alcohol and citric acid. The ethyl alcohol includes approximately between 0.1% to 3% of the solution, and the citric acid comprising approximately between 0.1% to 3% of the solution. Cotinine helps reduce symptoms of nicotine withdrawal. The sugar alcohol and citric acid act as sweeteners to counter the bitterness of cotinine when inhaled. In another embodiment, the solution of the first embodiment may be mixed with a small dose of nicotine.

In a second example solution, the solution is a pulmonary irrigation solution. The solution includes adalimumab being the active ingredient including approximately between 1% to 10% of the solution and a sugar alcohol including approximately between 0.1% to 1% of the solution. Adalimumab helps treat a variety of diseases by fighting infections or bacteria within the lungs. The solution further includes a stabilizer including polyol including approximately between 0.1% to 5% of the solution and surfactant comprising approximately between 0.1% to 5% of the solution. The solution may also include at least one of preservative (at 0.1% of the solution) and anti-mold and anti-yeast agent at (0.1% of the solution), The polyol is at least one of sucrose, histidine, and succinate. The surfactant is polyetherimide. At least one of the buffer and the stabilizer includes at least one buffer selected from the group consisting of histidine, succinate, phosphate, citrate, acetate, sodium bicarbonate, maleate, and tartrate buffers. The buffer does not include a combination of a citrate buffer and a phosphate buffer. This solution is intended for use in the induction of sputum production where sputum production is indicated, such as with Rheumatoid Arthritis, Ankylosing Spondylitis, ulcerative Colitis, Psoriasis, Psoriatic Arthritis, Cystic Fibrosis patients and Bronchoalveolar lavage procedures.

In a third example solution, the active ingredient is naloxone, also known as NARCAN®. Naloxone rapidly counters and/or reverses the effects of opioids. Naloxone is the standard treatment to counter opioid overdoses. Inhalation of naloxone through a portable AVI could quickly save the life of opioid users who overdose.

In a fourth example solution, the active ingredient is colloidal silver. Colloidal silver is a liquid solution including a plurality of silver particles. Colloidal silver treatment can heal a variety of infections, such as the common cold or respiratory infections.

In a fifth example solution, the active ingredient is glucagon. Glucagon is a hormone that raises blood glucose levels and the concentration of fatty acids in the bloodstream. Glucagon treatment helps people who suffer from hypoglycemia. Hypoglycemia occurs when the blood glucose levels are lower than the standard range.

An air inlet 112 and a first one-way valve 114 is in fluid communication with the resilient air bladder configured to allow fresh air to enter the resilient air bladder. The air inlet includes an opening on which first one-way valve 114 is mounted. An air outlet 116 and a second one-way value 118 is in fluid communication the resilient air bladder and the tubular chamber. The first one-way valve 114 allows fresh air outside the bladder to move into the air bladder through that valve and prevents air from moving out of the first one-way valve 114 when the first one-way valve moves between the deflated state to the fully inflated state.

Fresh air is forced in direction A1 through the second one-way valve and to the tubular chamber when the resilient air bladder deflates. The second one-way valve may be a check valve. The air bladder deflates when opposing forces in directions H1 and I1 are applied via squeezing the air bladder. When the resilient air bladder deflates, fresh air is expelled out of the air outlet 116 in direction A1, and the first one-way valve 114 prevents air from being pushed out from the resilient air bladder through the air inlet. Because the resilient air bladder must return to its original shape, the air bladder automatically inflates in directions H2 and I2 when the forces stop squeezing it. Shown in FIG. 1, when the resilient air bladder inflates, fresh air enters through the air inlet 112 in direction A2 and is drawn into the resilient air bladder, and the second one-way valve 118 prevents air from within the tubular chamber from entering the resilient air bladder thereby not causing air to be potentially sucked from a patient.

In one embodiment, the medical device is equipped with at least one sensor 172 (also shown in FIG. 34A) for monitoring fluid parameters various components of the device, thereby allowing for precise control and delivery of atomized medication. These sensors may be strategically placed in areas such as within tubular chambers, the mask attachment, or the capsule itself to gauge the various fluid parameters. The at least one sensor is configured to monitor and/or measure fluid parameters including but not limited to viscosity, density, pH, conductivity, turbidity, salinity, dissolved oxygen or nitrogen levels, particle size, temperature, and pressure within the device's system. For example, the at least one sensor may include sensors such as viscosity sensors, density sensors, pH sensors, conductivity sensors, turbidity sensors, salinity sensors, gas sensors for monitoring dissolved oxygen or nitrogen, particle size analyzers, temperature sensors, and pressure sensors, all of which can play pivotal roles in understanding and controlling the fluid parameters within the device.

For instance, pressure sensors may be used within the chambers to ensure that the fluid, such as a medication, is at the appropriate pressure for atomization. Additionally, the device may include sensors designed to measure fluid parameters, including the oxygen (O2) and carbon dioxide (CO2) content during inhalation and exhalation. These may encompass specific gas sensors like oxygen sensors, used to measure O2 content, and nondispersive infrared (NDIR) sensors for CO2 content. Such a configuration allows the device to adapt to the patient's respiratory needs and tailor the delivery of the medication, thereby optimizing treatment efficacy and patient comfort. These enhancements in sensor technology contribute to a more personalized and efficient means of administering medication compared to conventional methods.

These sensors can measure the viscosity, indicating the flow characteristics, and density, which helps in calculating the exact concentration of medication. The PH level of the fluid can be monitored to ensure its compatibility with the patient's needs. Electrical conductivity provides insights into the fluid's composition and purity, while turbidity sensors assess the clarity and potential contamination. The salt concentration or salinity is measured for certain medication types, and dissolved gases such as oxygen or nitrogen are monitored to ensure proper formulation. The particle size and distribution within the fluid are measured for determining how the medication may be absorbed by the body. Standard measurements of temperature and pressure are also undertaken, given their direct impact on fluid behavior, and thus the delivery and effectiveness of the medication.

For example, at least one of the sensors may be used to measure O2 inhaled by the patient and the CO2 exhaled by the patient over a period of time. Additionally, the data measured may be used to establish a metabolic signature or profile of the patient over time that can be used to create a baseline metabolic profile of the patient. The metabolic signature may be used to compare a with a second metabolic signature of the patient at a second period of time for the same patient or for other patients. In certain embodiments the second metabolic profile may be taken from different patients with certain known conditions, such as COVID, influenza, tuberculosis, heart disease. However, other conditions may be used to create the second metabolic profile for which is to be compared with other metabolic signatures of the patient taken over other periods of time. The periods of time, we be longer periods so that certain patterns and anomalies may be identified.

When the device is used with a resilient air bladder 102 to manually control the inhalation and exhalation of the patient, the sensors may be used for monitoring and regulating the pressure within the air bladder, assessing the flow rate of the inhalation and exhalation, detecting any abnormalities in the respiratory pattern, and ensuring that the prescribed dosage of atomized medication is delivered in synchronization with the patient's breathing cycle. Additionally, the sensors can provide feedback on various fluid parameters such as oxygen content, carbon dioxide content, and humidity, thus enhancing the efficiency and safety of the delivery system and allowing for timely adjustments to the medication delivery or respiratory support as required by the patient's condition.

The base unit further includes a housing 120 and a first channel 122 spanning from a first side 124 of the housing to a second side 126 of the housing. The housing may be comprised of metallic material such as carbon steel, stainless steel, aluminum, Titanium, other metals or alloys, composites, ceramics, polymeric materials such as polycarbonates, such as Acrylonitrile butadiene styrene (ABS plastic), Lexan™, and Makrolon™. other materials having waterproof type properties. The housing may be made of other materials and is within the spirit and the disclosure. The housing may be formed from a single piece or from several individual pieces joined or coupled together. The components of the housing may be manufactured from a variety of different processes including an extrusion process, a mold, casting, welding, shearing, punching, folding, 3D printing, CNC machining, etc. However, other types of processes may also be used and are within the spirit and scope of the present invention.

The system further includes a first longitudinal axis 128 of the first channel. A first end portion 130 of the first channel is configured to receive a portion of a conduit 132 that is in fluid communication with the air outlet of the resilient air bladder, and a second end portion 134 of the first channel configured to receive a portion of the mouthpiece or the mask 142. The first end portion and second end portion include openings configured to receive the conduit and mask, respectively. The channel may have walls that have smooth surfaces so that air and medication may easily move toward the user or provide a path for air and medication to be in fluid communication with the mouthpiece of the mask. The system further includes a second channel 138 disposed on the housing configured to receive a portion of the capsule 108 and a second longitudinal axis 140 defined by the second channel. In one embodiment, the second channel may be circular in shape, however other shapes may be used and are within the spirit and scope of the present invention. The base unit includes an opening 141 of the second channel that receives a portion of the capsule. The second longitudinal axis defines at most a 90-degree angle relative to the first longitudinal axis of the first channel. In the present embodiment, the angle 143 between the second longitudinal axis and first longitudinal axis is at a 45-degree angle. However, other angles that allow the medication to easily flow into the second channel may be used and are within the spirit and scope of the present invention.

The fresh air then moves through tubular chamber in direction B while the atomized medication moves through base unit in direction C such that the fresh air and the medication atomized by the atomizer mix together within the tubular chamber to create a mixture 170. The system further includes a mask 142 defining a mask chamber 144 within the mask. The mask is configured to be positioned over the patient's mouth and nose. The mask has a rim 146 extending about a periphery of the mask for forming a seal with the patient's face and a mouthpiece defining a tubular shaped body. The mixture 170 of the fresh air and the atomized medication flows towards the mask in direction D.

The system further includes a processor 148 housed by the housing of the base unit. Two electrical contacts 152 are positioned within the second channel. The capsule also includes two electrical contacts (shown in FIG. 2) that mate with the two electrical contacts within the second channel providing electrical communication with the power source 154 of the base unit. The power source may be a battery power source. In the present embodiment, the battery power source may be a battery power source, such as a standard dry cell battery commonly used in low-drain portable electronic devices (i.e., AAA batteries, AA batteries, etc.). Other types of batteries may be used including rechargeable batteries, aluminum air batteries, lithium batteries, paper batteries, lithium-ion polymer batteries, lithium iron phosphate batteries, magnesium iron batteries etc. Additionally, other types of battery applications may be used and are within the spirit and scope of the present invention. For example, a battery stripper pack may also be used. Additionally, other types of power sources may also be used and are within the spirit and scope of the present invention. In other embodiments, the power source may be an external power source. For example, the system may include a power cable that can connect to an electrical wall outlet. Other types of external power sources may be used and are within the spirit and scope of the present invention.

The base unit may also include a sensor 156 that detects whether a capsule is inserted into the second channel or not. The housing also houses a user interface 150. The user interface is configured to be acted on by a rescuer to start the atomizer to atomize the medication. The user interface may include controls to set or adjust the rate of medication to administer, to start or stop the atomizer, and/or to gain authorization to the base unit. The user interface may also include a graphical display configured to receive gestures such as touches, swipes, etc. to control the device. The user interface may also be controlled by receiving sound commands that are received by an audio sensor and then processed by the processor. The processor is configured for receiving a signal to start the atomizer to atomize the medication, sending a second signal to the atomizer to cause the atomizer to atomize the medication within the capsule and convey the atomized medication into the second channel, receiving a third signal from the sensor when the sensor detects that the medication within the capsule is less than a minimum threshold, and sending a fourth signal to turn off the atomizer after the third signal is received. For example, the minimum threshold may be an amount of fluid that is left in the container is less than $1/12$ the total of medication in the capsule. For example, the sensor may detect that minimum threshold amount of medication is within the capsule, send the signal to the processer, then the processor may send a signal to stop the atomizer.

In some embodiments, the system may include a storage case such as, but not limited to, a briefcase. The storage may be able to hold multiple attachments, or attachment 106, that can be charged by a power source within the storage case. The briefcase may require security measures to be unlocked. For example, unique codes or a fingerprint scanner may be used as a security measure. The storage case may include slots to hold a capsule that may be prefilled or non-prefilled with medication. The storage case would be very useful in medical emergencies.

Figure 2:
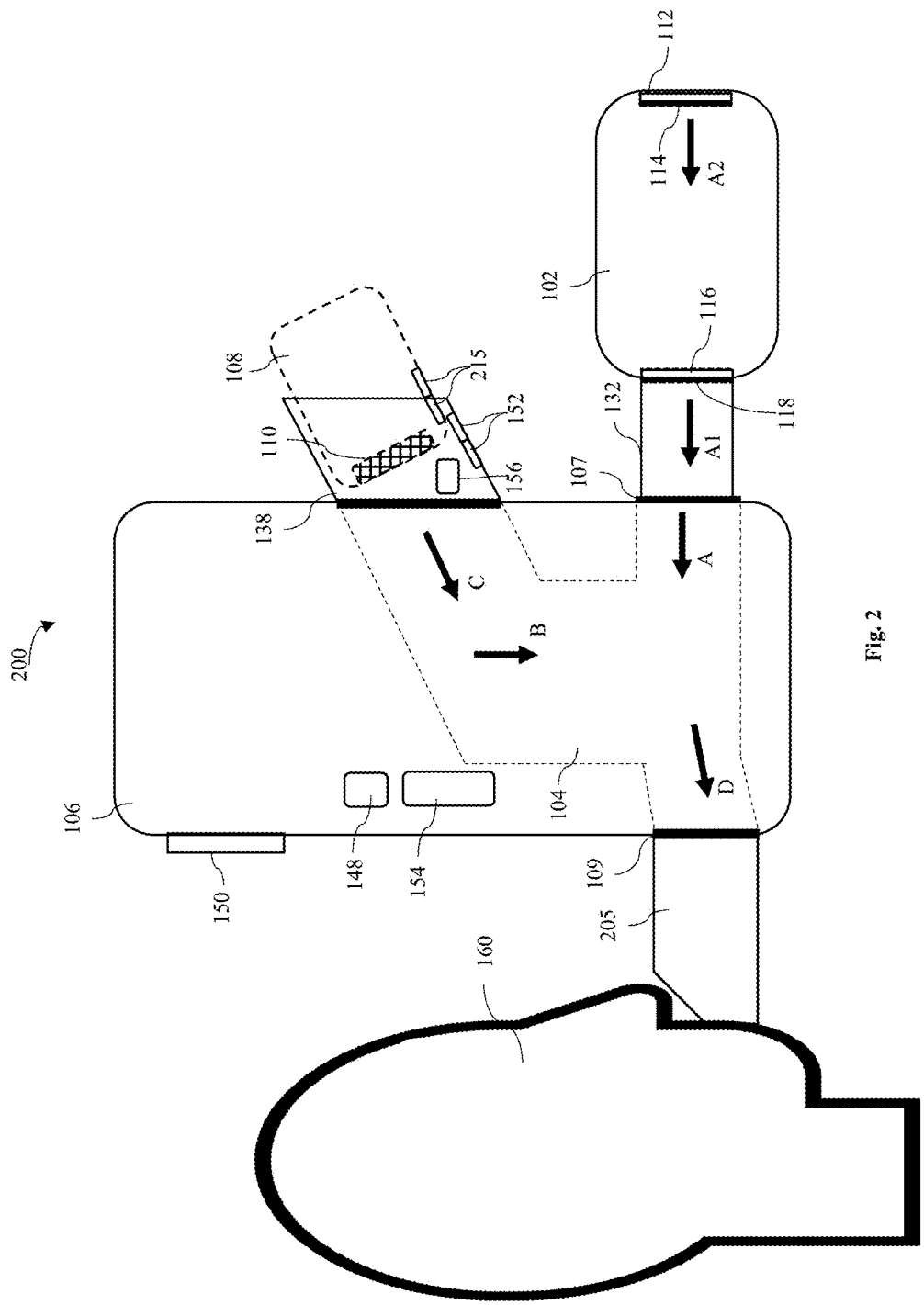

Referring now to FIG. 2, a side view of a system 200 for administering medication to a patient is shown, according to a second embodiment. Instead of the mask in the first embodiment, the second embodiment of the system for administering medication to a patient includes a mouthpiece 205. In one embodiment, the mouthpiece may be a tubular shaped body that is shaped to be inserted into a patient's mouth so that the user may inhale atomized medication into the patient's mouth.

The system 200 also includes electrical contacts 152 exposed on the inner surface of the second channel 138 that pair with electrical contacts 215 exposed on the outer surface of the capsule. When electrical contacts 152 and 215 are touching each other, the sensor 156 sends a signal to the processor 148, which sends a signal to turn on the power source 154. The power source then provides electrical power to the capsule 108 such that the atomizer begins atomizing the medication if there is electrical communication between contacts 152 and 215. The main difference between the first embodiment and the second embodiment is that they have different medical components (mask vs. mouthpiece) in attachment with the receiving sections 107 and 109 of the base unit. The system also includes an interface 150 on the second side of the base unit and is configured to allow the user to send signals to the processor to control the atomizer. The second embodiment allows a rescuer, medical professional, or in certain cases the patient to use the system on a patient that is positioned upright and is conscious, unlike the first embodiment, wherein the patient is laying down and may be unconscious. Upright means that the patient's body is substantially vertical so the patient's head 160 is substantially vertical.

Figure 3A:
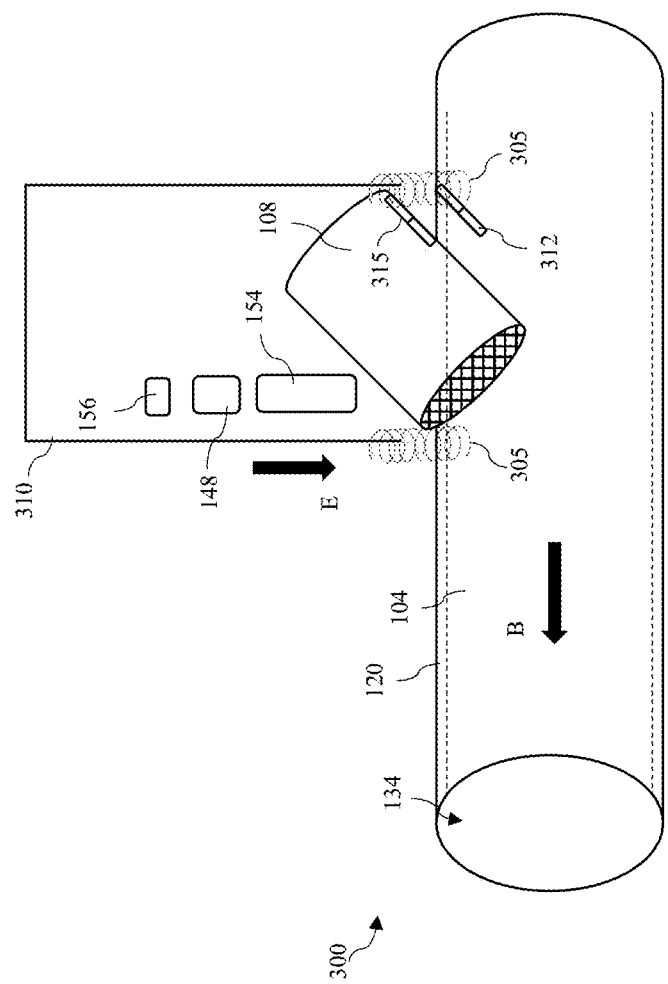
Figure 11B:
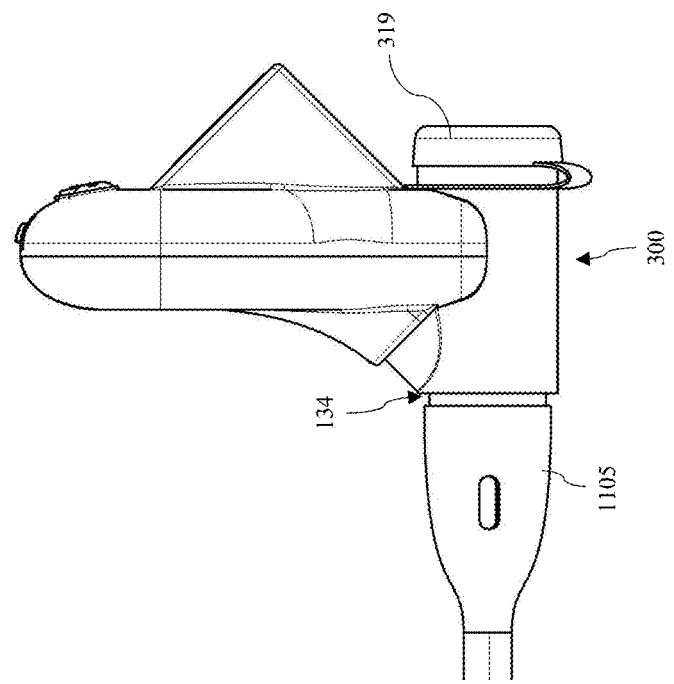
FIG. 11B is a side view of a system for administering medication to a patient, according to the third embodiment.
Figure 11A:
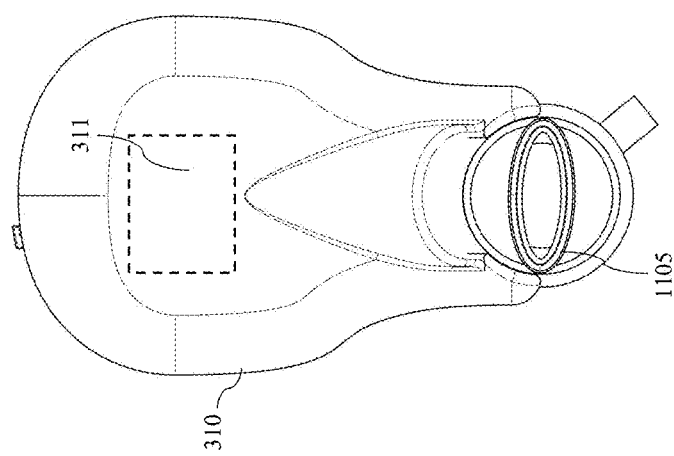
FIG. 11A is a front view of a system for administering medication to a patient, according to the third embodiment.

Referring now to FIGS. 3A through 3D, 11A, 11B, and 12, various views of a third embodiment of the system for administering medication to a patient are shown. FIG. 3A is a diagram of side view of the base unit 300 of the system for administering medication to a patient, according to the third embodiment. FIG. 3B is a diagram of a side view of the base unit 300 of the system for administering medication to a patient, according to the third embodiment. FIG. 3C is a diagram 301 illustrating the main electrical components of the system for administering medication to a patient, according to the third embodiment. FIG. 3D is a diagram 301 illustrating the main electrical components of the system for administering medication to a patient, according to the third embodiment. Additionally, FIGS. 11A through 12 also depict views of other examples of the third embodiment of the system for administering medication to a patient. FIG. 11A and FIG. 11B are various views of the system having a mouthpiece 1105 in attachment with the base unit 300, according to the third embodiment. FIG. 11A may include a graphical display 311 that is configured to provide visual instructions, warnings, maintenance items to the patient, such as when to start inhaling, when to stop inhaling, battery life of the device etc. when the device is in operation. The system may also include an audio component such as a speaker 314 to provide audio instructions (that are similar to the instructions provided by graphical display 311).

Figure 4:
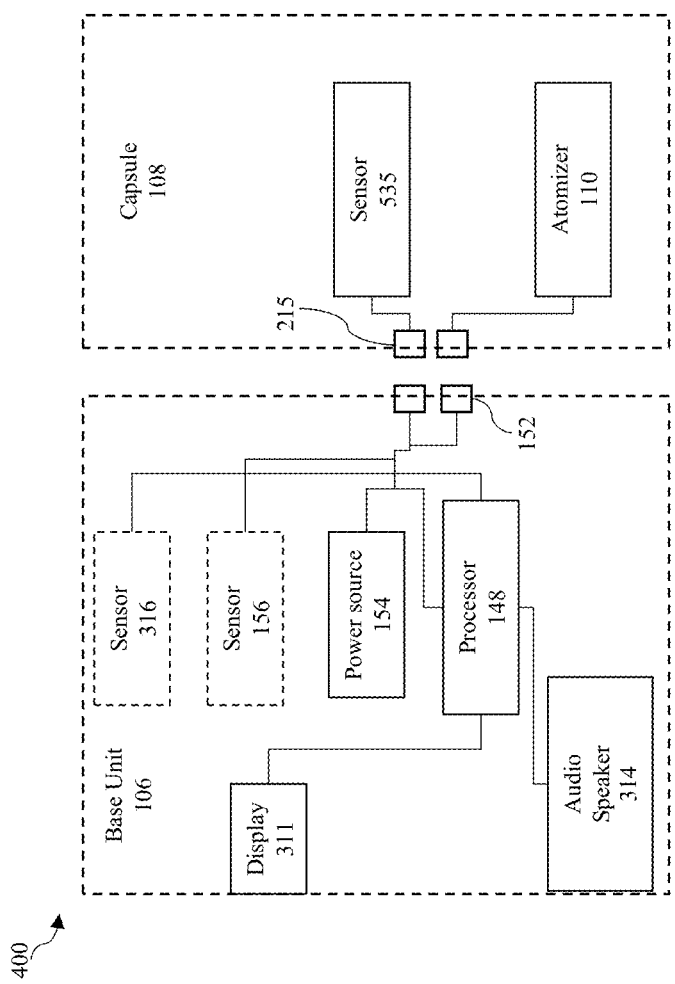

As shown in FIG. 4, the system may also include a sensor 316 for receiving audio commands from a user, such as when to start or stop the atomizer; however, other type of audio commands may be used and are within the spirit and scope of the present invention. The attachment may also include a cap 319 or cover that covers the opening of the receiving section. The cap may be configured to cover the opening so that when no bag is attached to the receiving section, the device may still be used as an atomizer for atomizing medication.

It is understood that the device may include at least one sensor, or a plurality of sensors, consistent with this disclosure. These sensors may be implemented in various locations and configurations within the device to monitor and measure vital parameters, fluid dynamics, and operational states, thereby contributing to the precise control and safety of the medication administration. While specific examples of sensor types and their applications have been described, these are not meant to be limiting. The incorporation of sensors within the device can be adapted to suit various needs and may extend beyond the examples provided herein. Such variations and adaptations are contemplated to be within the spirit and scope of the present invention, highlighting the flexibility and comprehensiveness of the system's design in catering to a wide range of requirements and scenarios in administering medication to patients.

Referring back to FIGS. 3A and 3B, the housing includes biasing elements 305 that are positioned between the housing 120 and an engaging element 310 that receives the capsule. In one embodiment, the biasing elements may be compressing springs. However, other biasing elements may be used and are within the spirit and scope of the present invention. The engaging element is a component that a user of the system interacts with to start the atomization of the medication. The engaging element is in attachment with the housing 120 of the base unit. The engaging element is similar to a button such that the user pushes down on the engaging element, which then interacts with the housing of the base unit. The engaging element may be comprised of metallic material such as carbon steel, stainless steel, aluminum, Titanium, other metals or alloys, composites, ceramics, polymeric materials such as polycarbonates, such as Acrylonitrile butadiene styrene (ABS plastic), Lexan™, and Makrolon™. other materials having waterproof type properties. The engaging element may be made of other materials and is within the spirit and the disclosure. The engaging element may be formed from a single piece or from several individual pieces joined or coupled together. The components of the engaging element may be manufactured from a variety of different processes including an extrusion process, a mold, casting, welding, shearing, punching, folding, 3D printing, CNC machining, etc. However, other types of processes may also be used and are within the spirit and scope of the present invention. The engaging element is shaped such that a user of the system can use one hand to push down on the engaging element. The third embodiment is convenient because it allows the user to self-administer medication.

A patient can push down or apply a force on the engaging element in direction E such that the engaging element moves towards the housing. When force in of line E is applied to overcome the expansion force of the spring, the engaging element 310 moves toward the housing to a certain extent so that the electrical contacts 312 of the housing and the electrical contacts 315 of the capsule contact each other to provide electrical communication between the power source and the atomizer in the capsule. The patient must provide enough force downward to hold down to allow the electrical contacts to remain in contact such that the atomizer continues to atomize the medication in the capsule. This causes the medication to be dispensed into the tubular chamber 104 for as long as electrical contacts of the housing are in contact with the electrical contacts of the capsule. The atomized medication then moves in direction B towards the end portion 320 of the base unit where a mouthpiece or mask may be attached to. The end portion 320 is similar to the first end portion 130 and the second end portion 134 such that it includes a receiving section with modular fittings. Referring back to FIG. 11B, the user may view the graphical display 311, which may provide instructions as to how long to apply force to cause the medication to be atomized by the device. Shown in FIGS. 11A and 11B, a mouthpiece 1105 is in attachment with the end portion 320.

Figure 12:
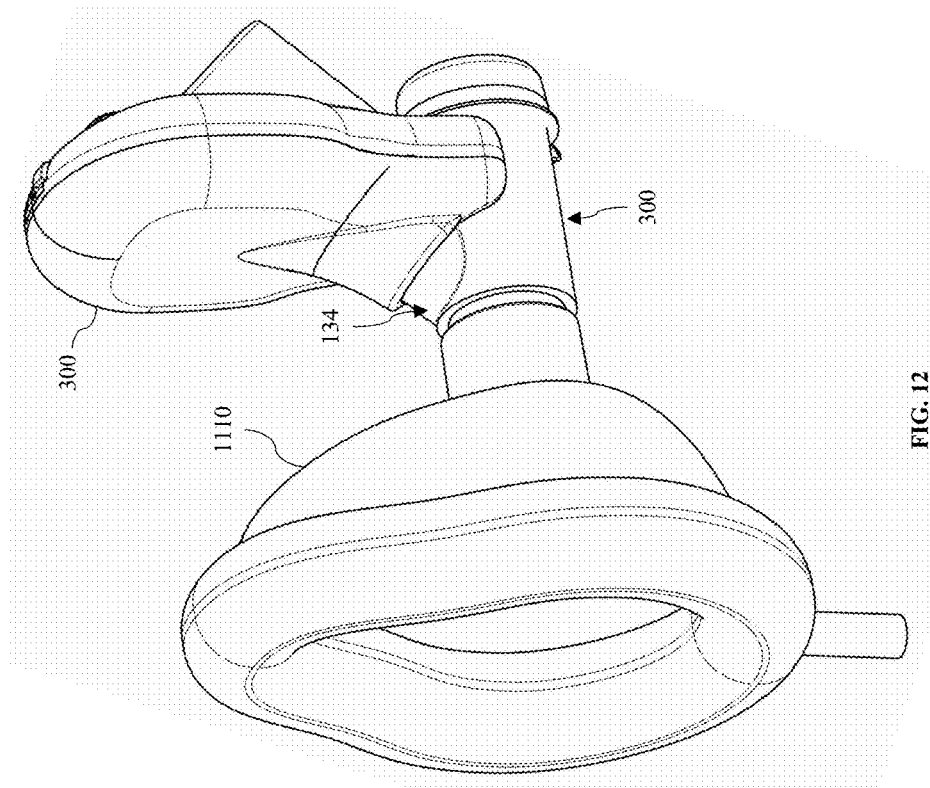
FIG. 12 is a perspective view of a system for administering medication to a patient, according to the third embodiment.
Figure 13:
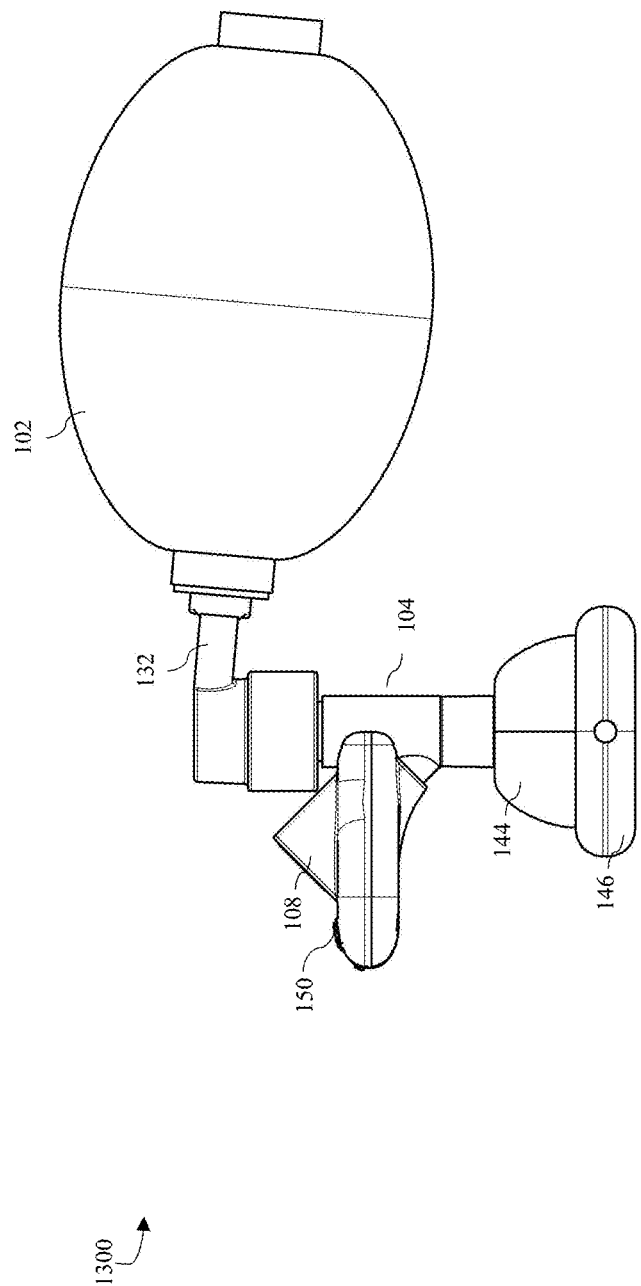
FIG. 13 is a side view of a system for administering medication to a patient, according to the first embodiment.

Referring to FIG. 12, a perspective view of system having a mask 1110 in attachment with the base unit 300, according to a third example embodiment is shown. In FIG. 12, a mask is in attachment with the end portion 320. The third embodiment can be easily used by one person as opposed to the first embodiment and second embodiment because only one hand is needed. A conscious patient can perform treatment on themselves when using the third embodiment. The capsule may also include a sensor 535, also shown in FIG. 5, that detects the amount of medication remaining in the capsule.

Figure 5:
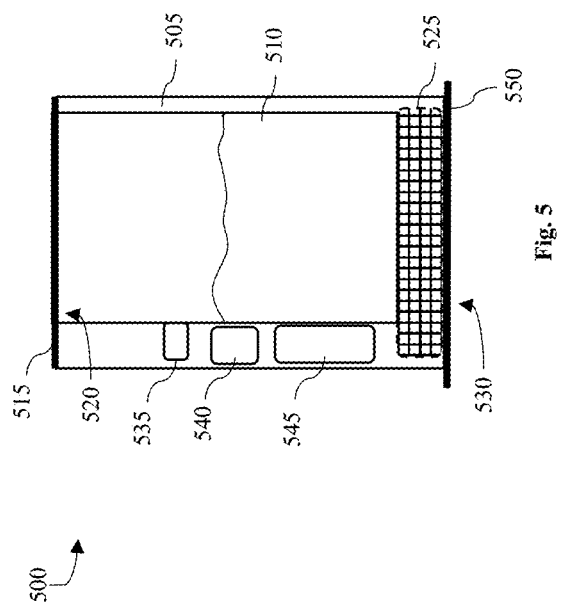
Figure 16B:
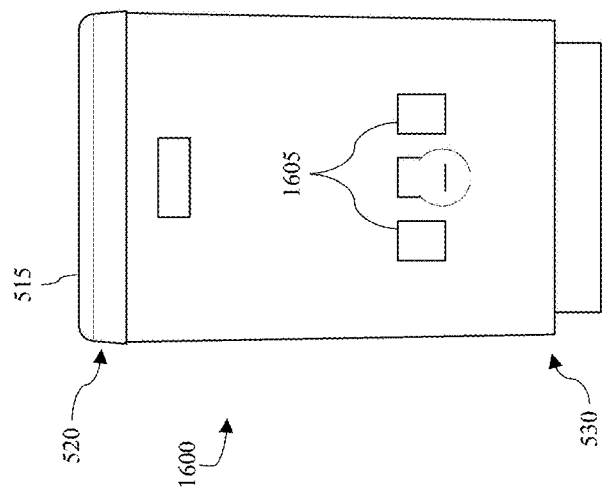
FIG. 16B is a front view of the capsule, according to a second example embodiment.
Figure 16A:
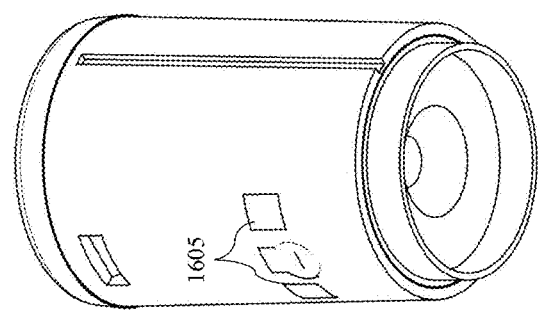
FIG. 16A is a bottom perspective view of the capsule, according to a second example embodiment.

Referring now to FIG. 5, FIGS. 16A and 16B, and FIGS. 18A through 18D, a single chamber capsule is shown, according to various example embodiments. FIG. 5 shows a front view of a capsule 500, according to first example embodiment. FIGS. 16A and 16B illustrate various views of a capsule 1600 according to a second example embodiment. Additionally, FIGS. 18A through 18D illustrates various views of capsule 1800, according to a third example embodiment. The capsule 1600 includes a different design of capsule 500. Capsule 1800 is a single chamber capsule having a refillable rubberized section and/or stopper and/or seal to receive at least one medication. Moreover, FIGS. 17A and 17B illustrate a fourth embodiment of a capsule having more than one chamber, namely, a first chamber for holding medication and a second chamber for atomizing the medication once the capsule is engaged and/or activated. Said chambers are initially separate until the capsule is engaged as to breach a divider or seal between the chambers enabling the first and second chamber to be in fluid communication with one another. This embodiment is further detailed below.

The capsule includes a capsule chamber 505 for housing the medication 510 and a rubber section 515 covering an open side 520 of the capsule. In the present embodiment, the capsule chamber can hold up to 20 milliliters of fluid. In other embodiments, the capsule chamber may hold other volumes of fluid, which are within the spirit and scope of the present invention. The rubber section allows for medication to be inserted into the capsule. A user of the capsule may add medication by inserting a syringe through the rubber section and using the syringe to dispense the medication into the capsule chamber 505. The capsule further includes the atomizer 525 proximate to a second side 530 of the capsule and a sensor 535 for detecting the amount of the medication in the capsule. In operation, the capsule chamber is above the atomizer and abuts the atomizer such that gravity allows the medication to go through the atomizer. Gravity forces the medication down such that the medication presses down against the atomizer. The sensor 535 may be a float sensor that measures the level of liquid in the capsule chamber. However, other sensors may be used and are within the spirit and scope of the present invention. After all the medication in the capsule chamber is dispensed through the atomizer, a maximum amount of the medication has been dispensed, or the maximum amount of time has passed, sensor 535 sends a signal to the processor to stop the atomizer. The float sensor is a continuous level sensor featuring a magnetic float that rises and falls as liquid levels change. The movement of the magnetic float creates a magnetic field that actuates a hermetically sealed reed switch located in the stem of the level sensor, triggering the switch to open or close. Other types of sensors configured to detect the amount of liquid in the capsule chamber may be used and are within the spirit and scope of the present invention. Additionally, the maximum amount of medication or time may be adjusted depending on the patient, medication and variety of other factors.

The capsule may also include a removeable covering 550, such as, but not limited to, a cap or seal, in attachment with the second side 530 of the capsule to preserve the medication and/or prevent the medication from leaking. The removeable covering allows users of the system to store capsules for emergency use or long-term use, depending on the type of removeable covering. In some embodiments, the capsule may be color-coded for emergency medication or may include labels that identify the medication within the capsule. The capsule may also include a locking element that prevents the capsule from atomizing the medication unless an access code is provided. The access code may be provided via the remote computing device (708 in FIG. 7) and may be a biometric element or an alphanumeric element.

The capsule may also include a processor 540 and a power source 545. In some embodiments, the method for atomizing the medication described herein may be performed by the processor 540 of the capsule. The power source may be a battery power source. In the present embodiment, the battery power source may be a battery power source, such as a standard dry cell battery commonly used in low-drain portable electronic devices (i.e., AAA batteries, AA batteries, etc.). Other types of batteries may be used including rechargeable batteries, aluminum air batteries, lithium batteries, paper batteries, lithium-ion polymer batteries, lithium iron phosphate batteries, magnesium iron batteries etc. Additionally, other types of battery applications may be used and are within the spirit and scope of the present invention. For example, a battery stripper pack may also be used. Additionally, other types of power sources may also be used and are within the spirit and scope of the present invention. In other embodiments, the power source may be an external power source. For example, the system may include a power cable that can connect to an electrical wall outlet. Other types of external power sources may be used and are within the spirit and scope of the present invention. The capsule may also include electrical contacts 1605 that pair with the electrical contacts in the second channel of the base unit.

Referring now to FIG. 4, a diagram 400 illustrating the main electrical components of the system for administering medication to a patient is shown, according to an example embodiment. Within the attachment 106, the sensor 156, the power source 154, the processor 148, and a pair of electrical contacts 152 are in electrical communication with each other. Additionally, within the capsule 108, the atomizer 110, the sensor 535, and a pair of electrical connectors 215 are in electrical communication with each other. When the two pairs of electrical contacts are contacting each other, the system provides electrical communication between the base unit and the capsule, such that the power source can power the atomizer when the processor of the base unit receives the signal to start the atomizer.

Figure 6B:
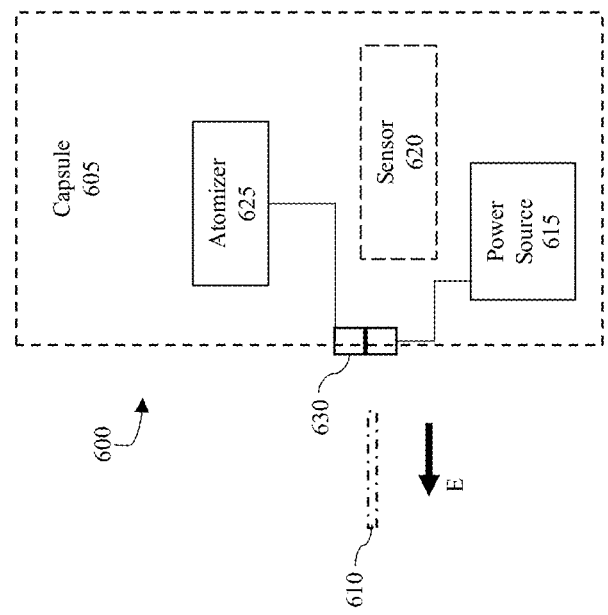
Figure 6A:
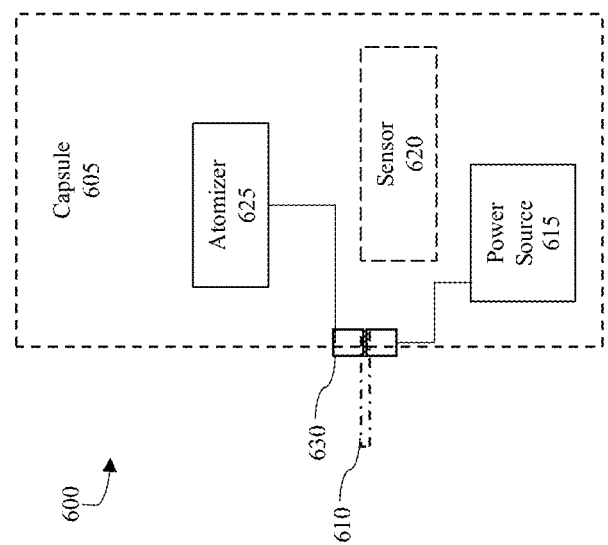

Referring now to FIG. 6A and FIG. 6B, a diagram 600 illustrating the main electrical components of the capsule 605 with an electrical insulator in the form of a tab 610 is shown, according to an example embodiment. In this embodiment, the capsule includes a power source 615, a sensor 620, and the atomizer 625 in electrical communication. The power source 615 is the same as the power source 545 described with reference to FIG. 5. The capsule also includes at least two contacts 630 that can provide electrical communication between the power source and the atomizer. In FIG. 6A, the electrical contacts are separated by a tab that blocks the electrical communication between the power source and the atomizer. The tab may be comprised of material including rubber, synthetic rubber, like latex or silicone, and plastics such as Polyvinyl Chloride, Teflon (PTFE-Polytetrafluoroethylene), and Polyethylene. However, other materials configured to insulate electricity may be used and are within the spirit and scope of the present invention. They offer excellent resistance to electricity, and their physical properties can be adjusted to suit specific applications.

When a user of the capsule pulls the tab out from between the electrical contacts, the electrical contacts can contact each other and provide electrical communication between the power source and the atomizer. In this embodiment, the amount of energy within the power source is configured to run out after all of the medication within the capsule is atomized. This is useful for medical emergencies because the rescuer can quickly pull out the tab and quickly insert the capsule into the base unit.

Figure 7:
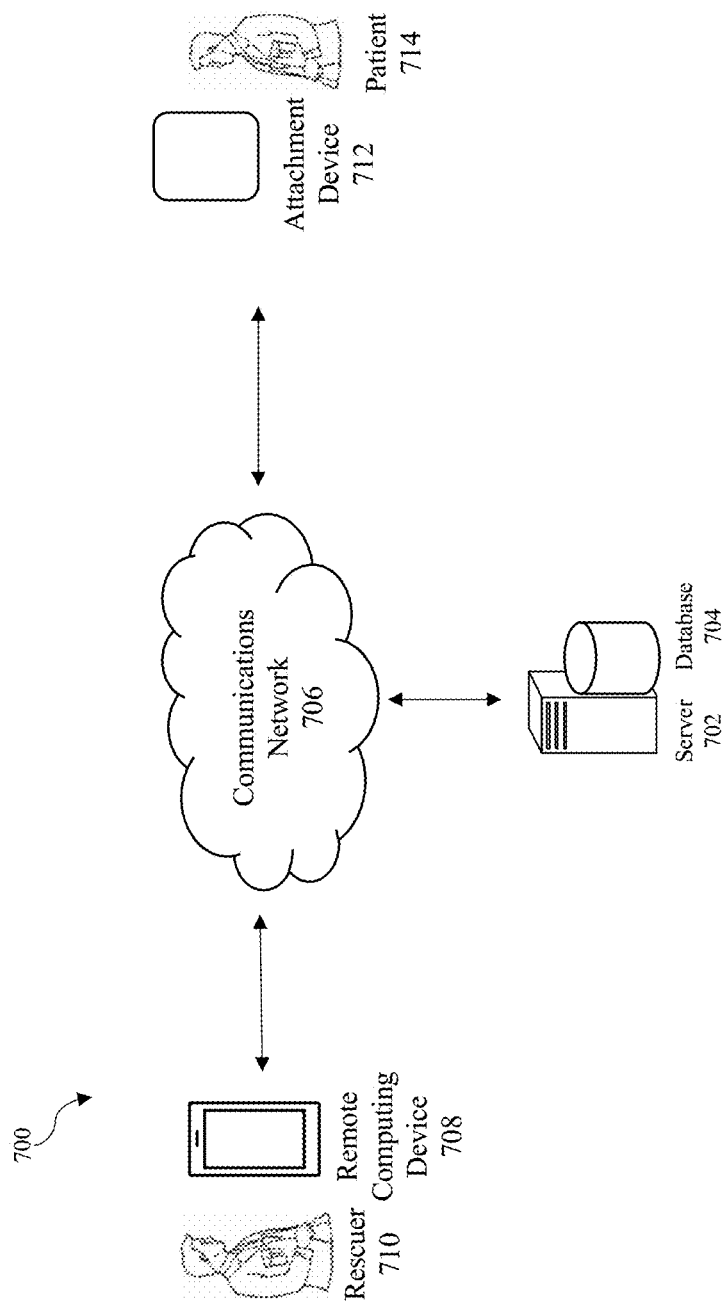

Referring now to FIG. 7. is a diagram of an operating environment 700 that supports a system of administering medication to a patient is shown, according to an example embodiment. FIG. 7 is a diagram of an operating environment that supports a system of administering medication to a patient, according to an example embodiment. The most prominent element of FIG. 7 is the server 702 associated with repository or repository 704 and further coupled with the communications network 706, which can be a circuit switched network, such as the Public Service Telephone Network (PSTN), or a packet switched network, such as the Internet or the World Wide Web, the global telephone network, a cellular network, a mobile communications network, or a Personal Area Network (PAN), such as Bluetooth® or any combination of the above. In one embodiment, network 706 is a secure network wherein communications between endpoints are encrypted so as to ensure the security of the data being transmitted. Server 702 is a central controller or operator for the functionality that executes on at least a remote computing device 708 and an attachment device 712, via various methods.

FIG. 7 further includes the remote computing device 708 and the attachment device 712, which are computing devices that each may be smart phones, mobile phones, tablet computers, handheld computers, laptops, or the like. The remote computing device corresponds to a rescuer 710, and the attachment device 712 corresponds to the attachment, or attachment (106 in FIG. 1), that is associated with the cardiopulmonary device positioned on the face of the patient 714. The remote computing device and attachment device may include transceivers for communicating over the network 706. In some embodiments, the capsule may also include a transponder such that a user can link the capsule to the attachment device. Each of the computing devices includes a user interface and/or graphical user interface. In certain embodiments, the system may communicate between the remote computing device and the attachment device, over the communications network, where the rescuer is a person who is providing aid to a patient, and the patient is a person needing medical attention. The users of the system input selections via a user interface on the remote computing device to be sent through the communications network via a data packet and to the attachment device.

FIG. 7 further shows that server 702 includes a database or repository 704, which may be one or more of a relational database comprising a Structured Query Language (SQL) database stored in a SQL server, a columnar database, a document database and a graph database. Computing devices 708 and 712 may also each include their own database. The repository 704 serves data from a database, which is a repository for data used by server 702 and the remote computing device during the course of operation of the invention. Repository 704 may be distributed over one or more nodes or locations that are connected via network 706.

FIG. 7 shows an embodiment wherein networked computing devices 708 and 712 may interact with server 702 and repository 704 over the network 706. Server 702 includes a software engine that delivers applications, data, program code and other information to networked computing devices 708 and 712. The software engine of server 702 may perform other processes such as audio and/or video streaming or other standards for transferring multimedia data in a stream of packets that are interpreted and rendered by a software application as the packets arrive. It should be noted that although FIG. 7 shows only two networked mobile computing devices 708 and 712, the system of the present invention supports any number of networked mobile computing devices connected via network 706, having at least the remote computing device 708 and the attachment device 712.

Server 702 also includes program logic comprising computer source code, scripting language code or interpreted language code that is compiled to produce executable file or computer instructions that perform various functions of the present invention. In another embodiment, the program logic may be distributed among more than one server 702, computing devices 708 and 712, or any combination of the above.

Note that although server 702 is shown as a single and independent entity, in one embodiment of the present invention, the functions of server 702 may be integrated with another entity, such as each of computing devices 708 and 712. Further, server 702 and its functionality, according to a preferred embodiment of the present invention, can be realized in a centralized fashion in one computer system or in a distributed fashion wherein different elements are spread across several interconnected computer systems.

Figure 1A:
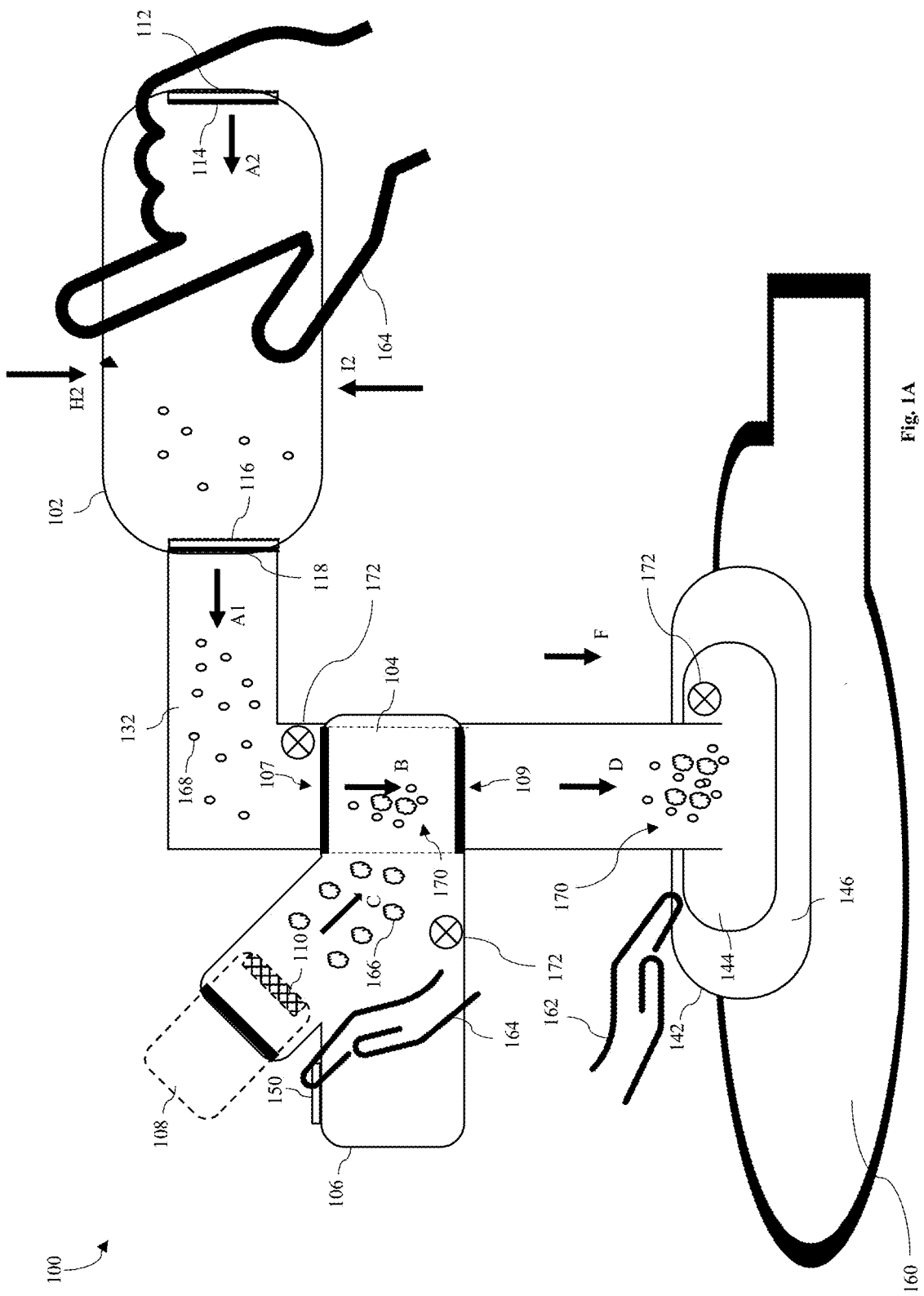
Figure 1B:
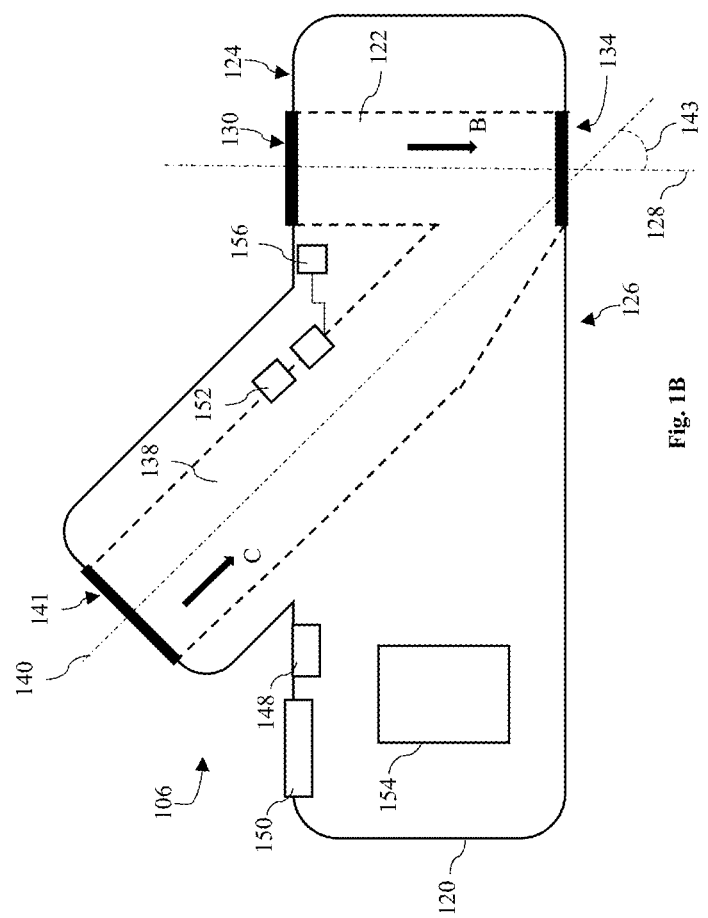
Figure 8:
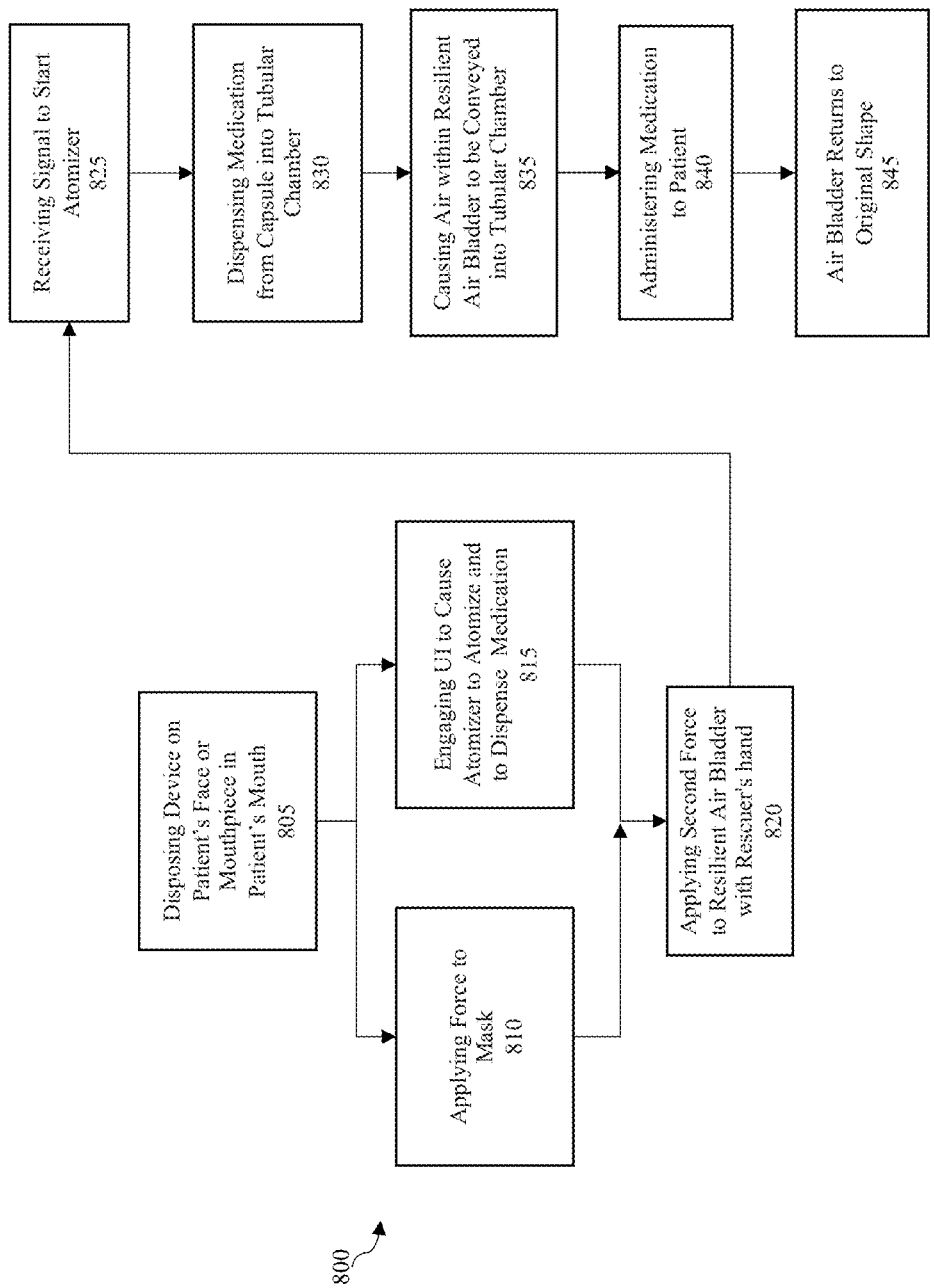

The process of administering medication to the patient will now be described with reference to FIG. 8 and FIG. 1A. FIG. 8 is a flowchart diagram illustrating steps for a method 800 of administering medication to a patient, according to an example embodiment. FIG. 1A is a diagram of the system 100 showing the patient's head 160 and the hands of the rescuer. In step 805, prior to dispensing the medication from the capsule, the rescuer disposes the mask of the device over the patient's mouth and nose and/or a mouthpiece to be inserted into the patient's mouth. In step 810, the rescuer uses a hand to apply a force to the mask to obtain a substantially air-tight seal against the patient's face. The substantially air-tight seal is created because the rim 146 surrounds the nose and mouth of the patient and is pressed against the patient's face. Shown in FIG. 1A, the rescuer uses a hand 162 to apply a force in direction F to hold the mask 142 over the patient's face. The force in the direction of F causes the substantially airtight seal. It is understood that the substantially airtight seal needs to allow most of the medication to be administered to a patient's face. In step 815, while applying the force with the hand to the mask, the rescuer engages, with a second hand (164 in FIG. 1A) of the rescuer, the user interface 150 on the device to cause the atomizer to atomize the medication (510 in FIG. 5) and to dispense the atomized medication 166 from the capsule. In step 820, while applying the force to the mask with the hand of the rescuer and either during or after engaging the user interface to cause the dispensing of the medication from the capsule, the rescuer applies a second force with the second hand 164 of the rescuer, to the resilient air bladder 102 so that the fresh air 168 within the resilient air bladder is conveyed via the conduit 132 from the resilient air bladder 102 and into the tubular chamber 104 such that the air conveyed from the resilient air bladder and the medication dispensed from the capsule is administered to the patient. In step 825, prior to dispensing the medication from the capsule, the system receives, with a processor, a signal to start the atomizer 110 to atomize the medication. In step 830, the system dispenses, using the atomizer, the medication from the capsule in fluid communication with the tubular chamber, into the tubular chamber. As mentioned above, the maximum amount of medication or amount of time the medication is atomized may be adjusted based on a variety of factors. The angle between the longitudinal axis of the second channel and the longitudinal axis of the first channel may be approximately 45 degrees so that the atomized medication can easily move and combine with air within the first channel.

In step 835, the system causes fresh air 168 within a resilient air bladder in fluid communication with the tubular chamber to be conveyed from the resilient air bladder 102 through the conduit 132. The fresh air then flows into the tubular chamber to mix with the atomized medication. In step 840, the air conveyed from the resilient air bladder and the medication dispensed from the capsule is administered to the patient. In step 845, the resilient air bladder 102 returns to its original shape such that the rescuer may squeeze it again to supply more fresh air into the system.

It is understood that this method is a continuous cycle and that each step of method 800 may operate concurrently with another step of method 800 to provide efficient administration of medication within the system. In other embodiments, the method may further include additional steps to promote efficient administration of medication consistent with the systems disclosed herein.

Figure 9:
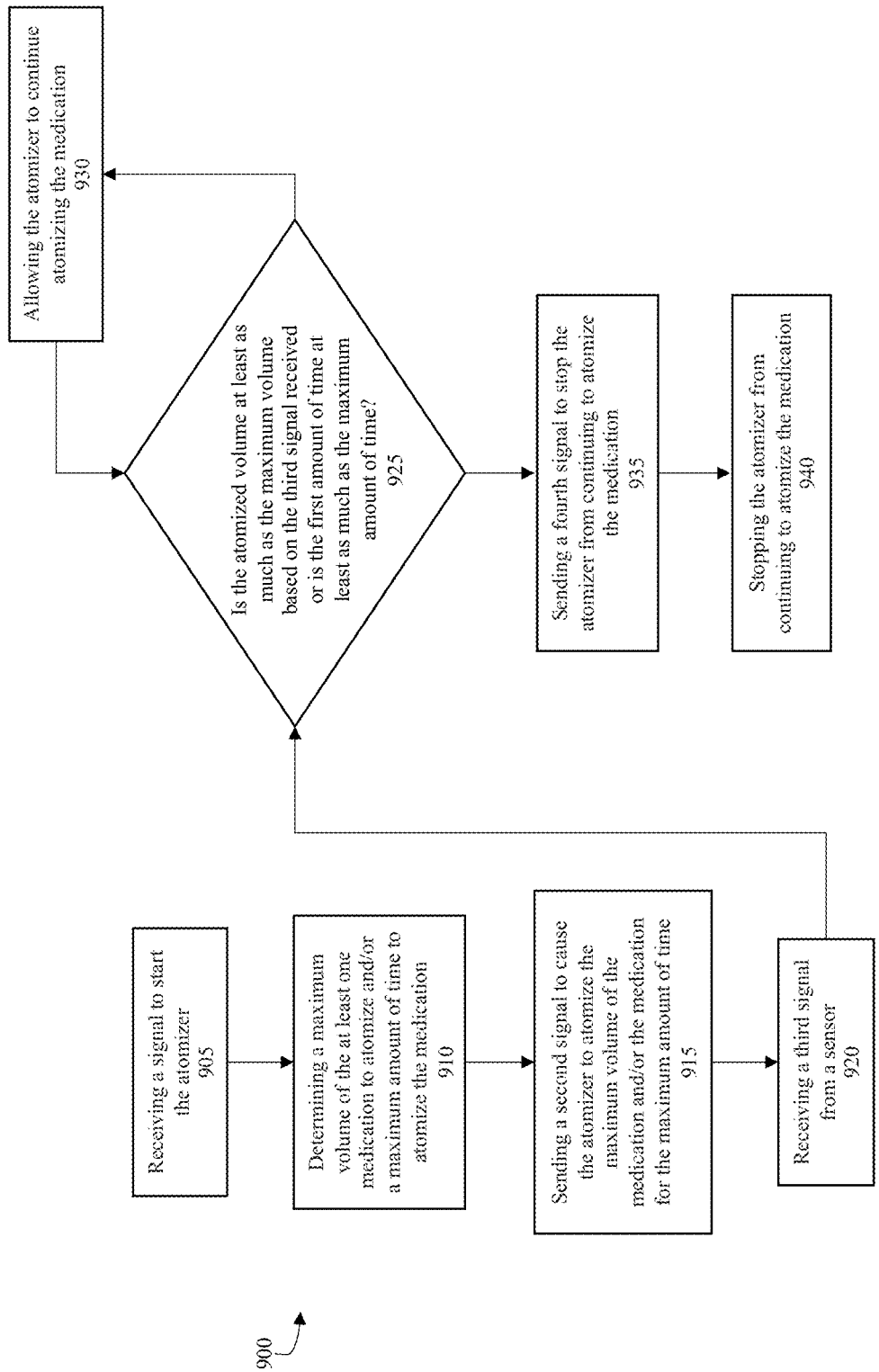
FIG. 9 is a flowchart diagram illustrating steps for a method of atomizing medication, according to an example embodiment.
Figure 10:
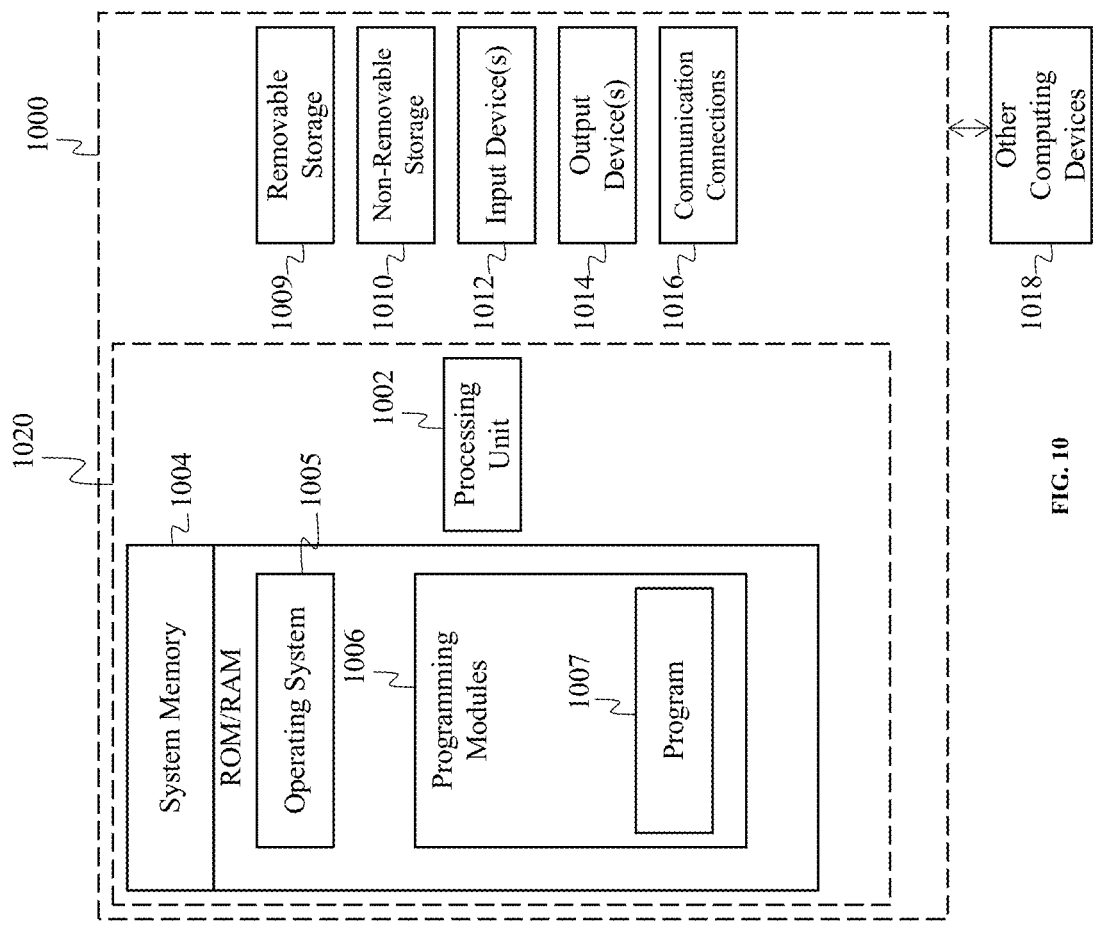
FIG. 10 is a block diagram of a system including a computing device and other computing devices, according to an exemplary embodiment of present technology.

With reference to FIG. 7 and FIG. 9, the process of atomizing the medication will be described. FIG. 9 is a flowchart diagram illustrating steps for a method 900 of atomizing medication, according to an example embodiment. The method 900 is performed by the processor of the attachment device. In step 905, the attachment device 712 receives a signal to start the atomizer to atomize the medication. The signal is received from the remote computing device. The signal may include data that allows the processor within the attachment device to determine that the atomizer should start to atomize medication within the capsule. Additionally, the data may include information to set the atomizer to atomize for a certain amount of time (for example a minimum or maximum) or certain amount of fluid (for example a minimum or maximum). This allows the rescuer or medical professional to control the dosage of the medication to the patient. The attachment device 712 may communicate with the remote computing device via Bluetooth®. The attachment device 712 may include security measures, such as requiring the rescuer to input a unique identifier, such as a security code or biometric information (such as a fingerprint) via the remote computing device to send the signal. For example, the rescuer may be a medical professional that is assigned a Personal Identification Number ("PIN") that, when entered into the remote computing device, allow the remote computing device to send the signal to start the atomizer within the capsule. Other examples of security codes may include, but are not limited to, a one-time-password, two-factor authentication codes, activation codes, or access codes. Other types of security measures configured to prevent unauthorized usage of the system may be used and are within the spirit and scope of the present invention.

In step 910, the attachment device determines, based on the signal, a maximum volume of the medication to atomize or a maximum amount of time to atomize the medication. The maximum amount of time can be set to a certain amount of time and can be adjusted during operation. For example, the maximum amount of time may be 2-10 seconds, 1 minute, etc. The maximum volume can be set to a certain volume and adjusted during operation. For example, the maximum volume may be 1, 2 or 4 milliliters. However, other embodiments may be used and are within the spirit and scope of the present invention. In step 915, the attachment device sends, to the atomizer, a second signal to cause the atomizer to atomize the maximum volume of the medication and/or the medication for the maximum amount of time. The maximum volume and the maximum amount of time depends on the signal sent by the remote computing device. In step 920, the attachment receives, from the atomizer, a third signal from the sensor that monitors an atomized volume of the medication within the capsule and/or a first amount of time the atomizer atomizes the medication. In step 925, the processor of the attachment device determines if the atomized volume is at least as much as the maximum volume based on the third signal received and/or the first amount of time is least as much as the maximum amount of time. In step 930, if the attachment device determines the atomized volume is not at least as much as the maximum volume based on the third signal received and/or the first amount of time is not at least as much as the maximum amount of time, the attachment device allows the atomizer to continue atomizing the medication. In step 935, after the attachment device determines the atomized volume is at least as much as the maximum volume based on the third signal received and/or the first amount of time is least as much as the maximum amount of time, the attachment device sends a fourth signal to stop the atomizer from continuing to atomize the medication within the capsule. In step 940, the attachment device stops the atomizer from continuing to atomize the medication within the capsule.

It is understood that this method is a continuous cycle and that each step of method 900 may operate concurrently with another step of method 900 to provide efficient atomization of medication within the system. In other embodiments, the method may further include additional steps to promote efficient atomization of medication consistent with the systems disclosed herein. In some embodiments, the steps of method 900 may be performed by a processor within the capsule.

Referring now to FIG. 10, a block diagram of a system including an example computing device 1000 and other computing devices is shown, according to an exemplary embodiment of present technology. Consistent with the embodiments described herein, the aforementioned actions performed by devices 708 and 712 may be implemented in a computing device, such as the computing device 1000 of FIG. 10. Any suitable combination of hardware, software, or firmware may be used to implement the computing device 1000. The aforementioned system, device, and processors are examples and other systems, devices, and processors may include the aforementioned computing device. Furthermore, computing device 1000 may include an operating environment for systems 100 and methods 800, 900 and others described herein. Methods 800, 900 and others described herein may operate in other environments and are not limited to computing device 1000.

With reference to FIG. 10, a system consistent with an embodiment of the invention may include a plurality of computing devices, such as computing device 1000. In a basic configuration, computing device 1000 may include at least one processing unit 1002 and a system memory 1004. Depending on the configuration and type of computing device, system memory 1004 may include, but is not limited to, volatile (e.g., random access memory (RAM)), non-volatile (e.g., read-only memory (ROM)), flash memory, or any combination or memory. System memory 1004 may include operating system 1005, and one or more programming modules 1006. Operating system 1005, for example, may be suitable for controlling computing device 1000's operation. In one embodiment, programming modules 1006 may include, for example, a program module 1007 for executing the actions of devices 708 and 712, for example. Furthermore, embodiments of the invention may be practiced in conjunction with a graphics library, other operating systems, or any other application program and is not limited to any particular application or system. This basic configuration is illustrated in FIG. 10 by those components within a dashed line 1020.

Computing device 1000 may have additional features or functionality. For example, computing device 1000 may also include additional data storage devices (removable and/or non-removable) such as, for example, magnetic disks, optical disks, or tape. Such additional storage is illustrated in FIG. 10 by a removable storage 1009 and a non-removable storage 1010. Computer storage media may include volatile and nonvolatile, removable and non-removable media implemented in any method or technology for storage of information, such as computer readable instructions, data structures, program modules, or other data. System memory 1004, removable storage 1009, and non-removable storage 1010 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information, and which can be accessed by computing device 1000. Any such computer storage media may be part of device 1000. Computing device 1000 may also have input device(s) 1012 such as a keyboard, a mouse, a pen, a sound input device, a camera, a touch input device, microphone for capturing audio sound (which may include commands to operate the device). Output device(s) 1014 such as a display, speakers, a printer, etc. may also be included. The aforementioned devices are only examples, and other devices may be added or substituted.

Computing device 1000 may also contain a communication connection 1016 that may allow device 1000 to communicate with other computing devices 1018, such as over a network in a distributed computing environment, for example, an intranet or the Internet. Communication connection 1016 is one example of communication media.

Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both computer storage media and communication media.

As stated above, a number of program modules and data files may be stored in system memory 1004, including operating system 1005. While executing on processing unit 1002, programming modules 1006 (e.g., program module 1007) may perform processes including, for example, one or more of the stages of the methods 800, 900 as described above. The aforementioned processes are examples, and processing unit 1002 may perform other processes. Other programming modules that may be used in accordance with embodiments of the present invention may include electronic mail and contacts applications, word processing applications, spreadsheet applications, database applications, slide presentation applications, drawing or computer-aided application programs, etc.

Generally, consistent with embodiments of the invention, program modules may include routines, programs, components, data structures, and other types of structures that may perform particular tasks or that may implement particular abstract data types. Moreover, embodiments of the invention may be practiced with other computer system configurations, including hand-held devices, multiprocessor systems, microprocessor-based or programmable user electronics, minicomputers, mainframe computers, and the like. Embodiments of the invention may also be practiced in distributed computing environments where tasks are performed by remote processing devices that are linked through a communications network. In a distributed computing environment, program modules may be located in both local and remote memory storage devices.

Furthermore, embodiments of the invention may be practiced in an electrical circuit comprising discrete electronic elements, packaged or integrated electronic chips containing logic gates, a circuit utilizing a microprocessor, or on a single chip (such as a System on Chip) containing electronic elements or microprocessors. Embodiments of the invention may also be practiced using other technologies capable of performing logical operations such as, for example, AND, OR, and NOT, including but not limited to mechanical, optical, fluidic, and quantum technologies. In addition, embodiments of the invention may be practiced within a general-purpose computer or in any other circuits or systems.

Embodiments of the present invention, for example, are described above with reference to block diagrams and/or operational illustrations of methods, systems, and computer program products according to embodiments of the invention. It is understood that, in certain embodiments, the functions/acts noted in the blocks may occur out of order as shown in any flowchart. For example, two blocks shown in succession may in fact be executed substantially concurrently or the blocks may sometimes be executed in the reverse order, depending upon the functionality/acts involved.

While certain embodiments of the invention have been described, other embodiments may exist. Furthermore, although embodiments of the present invention have been described as being associated with data stored in memory and other storage mediums, data can also be stored on or read from other types of computer-readable media, such as secondary storage devices, like hard disks, floppy disks, or a CD-ROM, or other forms of RAM or ROM. Further, the disclosed methods' stages may be modified in any manner, including by reordering stages and/or inserting or deleting stages, without departing from the invention.

Referring now to FIG. 17A through FIG. 17C views of capsule 1700 are shown, according to example embodiments. FIGS. 17A and 17B are cross-sections of a side view of the capsule 1700 illustrating two distinct chambers, according to an example embodiment. The capsule 1700 includes a first chamber 1705, a second chamber 1710, and the atomizer 1715. The first chamber includes the medication in a liquid formulation, and the second chamber is below and separate from the first chamber. A membrane 1720 is disposed between the first chamber and the second chamber. The capsule 1700 further includes a stop 1725 that inhibits or prevents the first chamber from translating relative to the second chamber. The stop may include an extruding tab 1730 that allows a user of the system to pull the stop. When a force is applied in direction J onto a top portion 1732 of the first chamber 1705, the first chamber translates relative to the second chamber such that the first chamber is pushed towards the second chamber. Then, the translation of the first chamber towards the second chamber ruptures the membrane to provide fluid communication between the first chamber and the second chamber. The capsule may include a rupturing element 1735, such as a needle, which can puncture the membrane between the first chamber and the second chamber.

When the membrane is ruptured, the gravity causes the liquid formulation to flow from the first chamber into the second chamber. An atomizer is disposed proximate to a portion 1740 or lower end of the second chamber that is distal to the first chamber. The second chamber abuts the atomizer such that gravity causes the medication in the second chamber to abut the atomizer. Gravity pushes the medication through the atomizer.

The use of a two-chamber capsule provides distinct advantages for shipping and transport of medications by enabling a controlled release mechanism. The first chamber serves as a storage compartment where the medication is securely held until activated, while the second chamber allows fluid communication with the medication after activation.

During shipping and transport, the medication remains confined within the first chamber of the two-chamber capsule, providing a stable and secure environment. This configuration prevents unintended exposure or premature mixing of the medication with any accompanying fluids or substances, ensuring the integrity and potency of the medication during transit. Upon activation, typically through a user-initiated action, the capsule's design allows for controlled fluid communication between the first and second chambers. This enables the release of the medication into the second chamber, where it becomes available for administration or further processing.

By separating the storage and activation stages, the two-chamber capsule minimizes the risk of premature degradation or alteration of the medication during shipping. This feature enhances the stability and shelf life of the medication, preserving its efficacy and therapeutic properties until it is ready for use. Moreover, the controlled release mechanism provided by the two-chamber design allows for precise dosing and administration. Activation at the desired time ensures that the medication is mixed with the accompanying fluid or solvent in the second chamber when it is most appropriate for administration. This feature is particularly beneficial for medications requiring reconstitution or those with specific timing requirements for optimal effectiveness. Overall, the two-chamber capsule's ability to store the medication separately from the accompanying fluid or solvent during shipping and transport provides advantages in terms of stability, potency, and controlled release. This design ensures that the medication remains protected until activation, allowing for safe and effective administration while maintaining the desired therapeutic outcomes.

FIG. 17C is a side view of the capsule 1701 having a pull clip 1745, according to an example embodiment. The pull clip is in attachment with the stop 1725 and allows a user to pull the stop out in direction G. The first chamber 1705 is a removable vial that may be stored separately. A removable vial would help improve the shelf life of the medication and keep the medication secure during transport. The second chamber 1710 includes a tapered section 1750, in which the cross-sectional diameter of the lower end of the second chamber is less than the cross-sectional diameter of the atomizer 1715. The tapered section acts as a ramp for the medication to direct the medication into the atomizer. The rupturing element is a sharp edge 1755 that punctures the membrane when the first chamber is pushed down. The sharp edge spans within the perimeter of the membrane. The user can push on the top portion 1732 of the first chamber in the direction of J, which causes the sharp blade to break the membrane 1720.

Figure 18B:
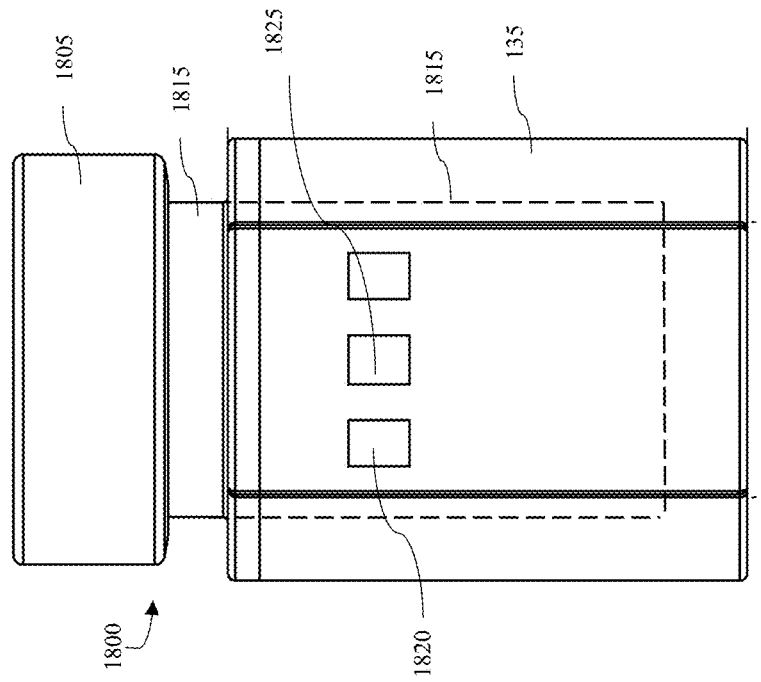
FIG. 18B is a side view of the capsule, according to the third example embodiment.
Figure 18A:
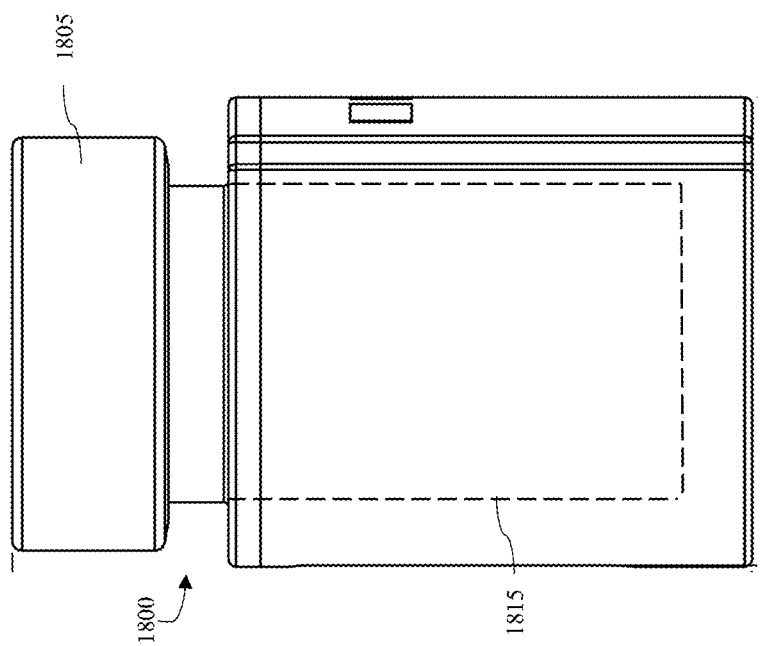
FIG. 18A is a side view of the capsule, according to a third example embodiment.
Figure 18C:
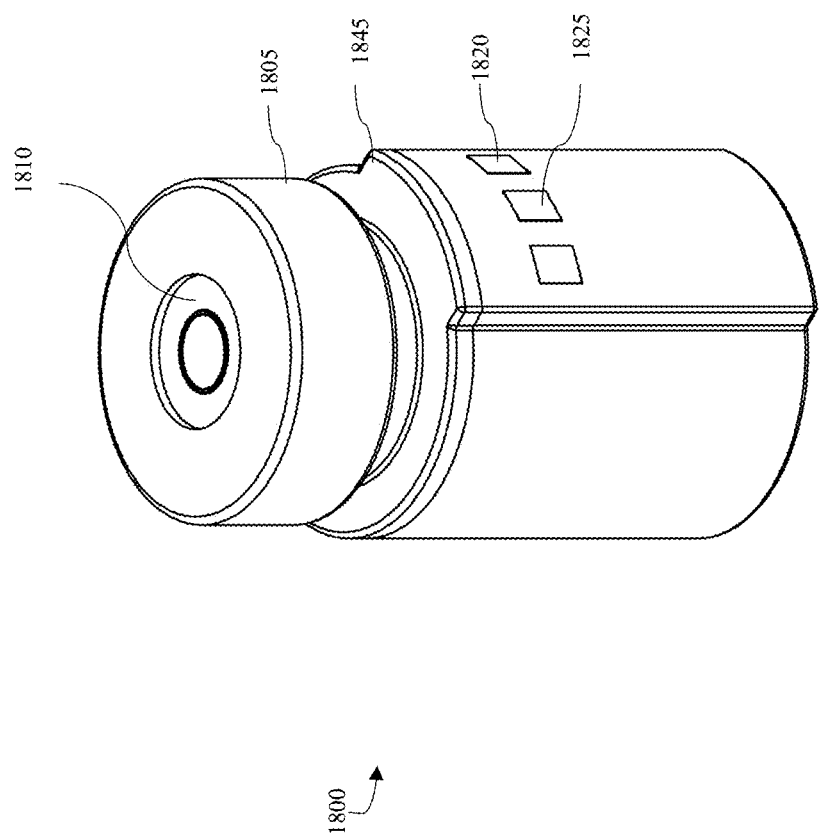
FIG. 18C is a perspective view of the capsule, according to the third example embodiment.
Figure 18D:
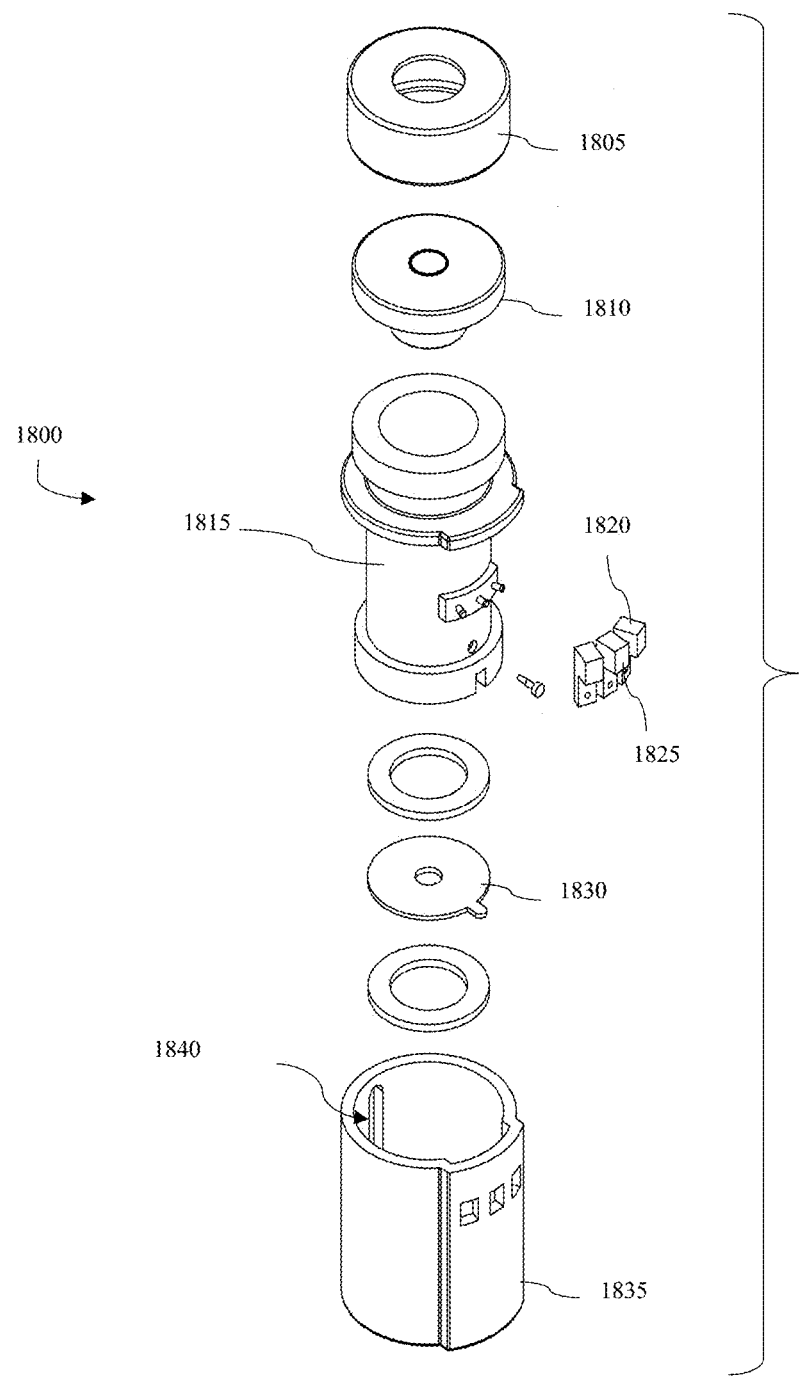
FIG. 18D is an exploded perspective view of the capsule, according to the third example embodiment.
Figure 26:
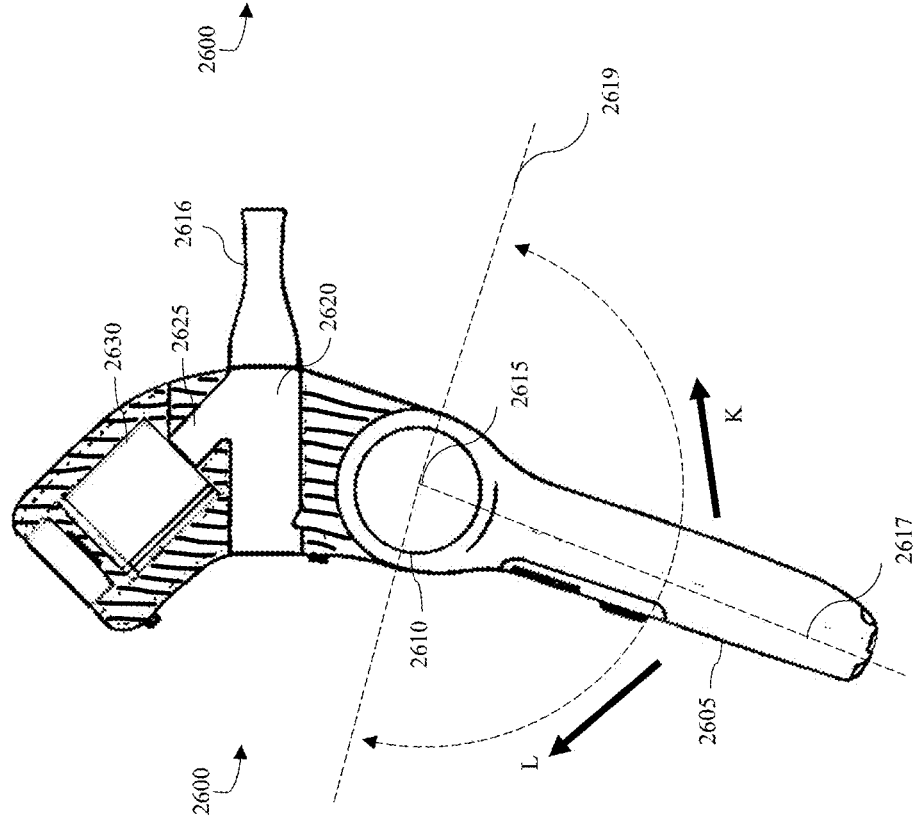
FIG. 26 illustrates the device for administering at least one medication to a patient in an unconscious state to a conscious state, according to a wand embodiment.
Figure 28:
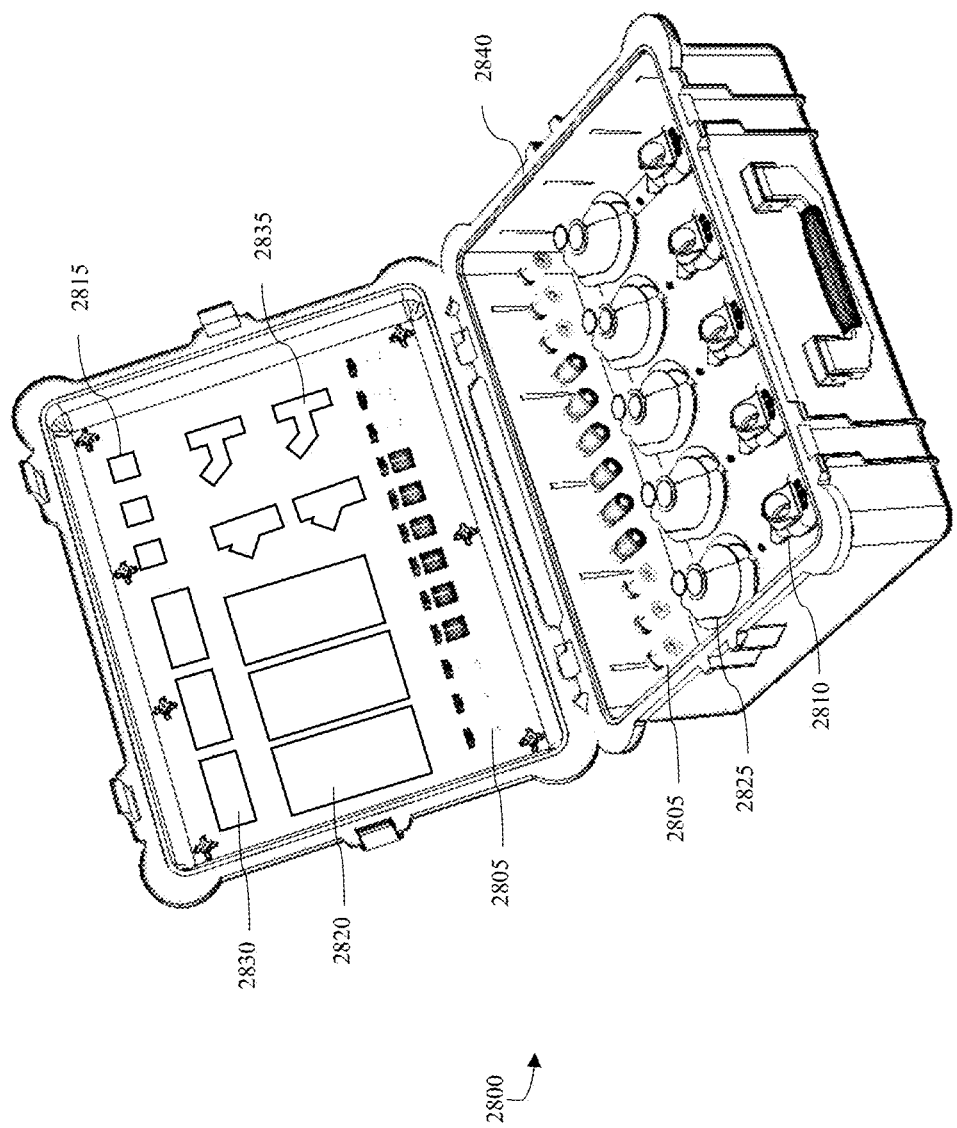
FIG. 28 illustrates a kit for converting a device for administering at least one medication to a patient in an unconscious state to a conscious state, according to an example embodiment.

Referring now to FIGS. 18A through 18B, the capsule 1800 is shown, according to an example embodiment. FIG. 18A is a side view of the capsule 1800, according to an example embodiment. FIG. 18B is a side view of the capsule 1800, according to an example embodiment. FIG. 18C is a perspective view of the capsule 1800, according to an example embodiment. FIG. 18D is an exploded perspective view of the capsule 1800, according to an example embodiment. Capsule 1800 may be used in the first embodiment, second embodiment, and third embodiment of the system for administering medication to a patient. Capsule 1800 may also be used in the inhaler embodiment shown in FIGS. 23 through 25 and in the wand, embodiment shown in FIGS. 26 through 27. The capsule 1800 is an advanced drug delivery system that incorporates innovative features to ensure precise administration and monitoring of medication and fluid levels. Capsule 1800 includes substantially similar components to the capsule 500 described above with reference to FIG. 5. As shown, capsule 1800 includes a crimp 1805, a rubberized seal 1810 to receive medication, at least one chamber 1815, electrical contacts 1820, at least one sensor 1825 for monitoring a level of medication and/or fluid, a mesh 1830, and a housing 1835. The crimp is a structural securing element used to hold the rubberized seal to the chamber. The crimp provides structural integrity and ensures the stability of the capsule's internal elements, contributing to the overall functionality and reliability of the device.

Rubberized seal 1810 is specifically designed to receive medication within capsule 1800. Composed of elastomeric materials, such as natural or synthetic rubber, this seal creates an airtight and secure enclosure for the medication, preventing leakage or contamination. The rubberized seal's resilience and deformable properties enable it to adapt to the medication's shape and size, ensuring a snug fit. The rubberized seal is an elastomeric component designed to facilitate the secure and airtight reception of medication boluses acting as a refillable container within the capsule. The seal exhibits resilient and deformable characteristics, allowing it to effectively enclose and retain the boluses while ensuring the integrity of the container's contents. The rubberized seal comprises a resilient material, typically composed of natural or synthetic rubber, or other suitable elastomers. This material possesses desirable properties such as flexibility, elasticity, and compression resistance, rendering it able to be pierced by a needle to inject medication within the seal and/or container. In its preferred embodiment, the rubberized seal is integrated into a refillable container, forming a tight and hermetic seal when engaged. The capsule may feature an opening or orifice in the crimp specially designed to receive the medication boluses or provide access to the rubberized seal to allow a user to inject medication into the rubberized seal by way of manual insertion or automated dispensing.

Capsule 1800 incorporates at least one chamber 1815 to hold the medication securely. These chambers are designed to accommodate the desired amount and formulation of medication, ensuring proper storage and controlled release. The number of chambers may vary based on the specific application and intended use of the capsule, such as FIG. 17A and FIG. 17B which employ a two-chamber capsule as described above. Electrical contacts 1820 are integrated into capsule 1800 to facilitate communication and power transfer between the device and the capsule. These contacts enable data exchange, power supply, or control signals, supporting functions such as monitoring, data recording, or activating specific features of the device. Capsule 1800 incorporates at least one sensor 1825 to monitor the level of medication and/or fluid within the capsule. These sensors may employ various technologies such as pressure sensors, level sensors, or other suitable sensing mechanisms. By accurately detecting and relaying this information, the sensor(s) enable precise medication dosage and monitoring.

Mesh 1830 is specifically designed to facilitate the atomization or aerosolization of the medication contained within the capsule. The atomizing mesh is composed of a fine material with micro-sized openings that allow for the breakup of the liquid medication into tiny droplets or particles, creating an inhalable or respirable mist. During the activation process, when the medication is intended for administration, the liquid medication is transferred or directed towards the atomizing mesh. As the medication flows through the mesh, it encounters the fine openings, which disrupt the liquid into a spray or mist-like form. The atomized medication, consisting of smaller droplets or particles, becomes suitable for inhalation or respiratory delivery. This mechanism allows for efficient and targeted delivery of the medication to the desired site within the respiratory system, maximizing its effectiveness and bioavailability.

Housing 1835 forms the outer structure of capsule 1800, providing a protective enclosure for the internal components. The housing may be composed of various materials, such as plastic, metal, or composite materials, offering durability and shielding the internal elements from external influences or damage. The housing may include a plurality of cutouts for the electrical components, namely, the sensor and the electrical contacts. Additionally, the housing may include a cutout which may be an opening 1840 allowing the user to see or visualize the level of medication within the at least one chamber 1815. The at least one chamber may be transparent and/or have a transparent section that corresponds to the window or opening 1840 and/or may include alphanumeric fluid level indicators.

In certain embodiments, as shown in FIG. 18C, the housing of the capsule exhibits an asymmetrical shape 1845 in the form of a protruding wedge or dovetail. This distinctive design feature serves a specific purpose within the invention, allowing for precise orientation and proper alignment of the capsule within the device. The protruding wedge or dovetail shape of the housing functions as a guiding mechanism for the capsule. It enables the user to align and insert the capsule into the device in a predetermined orientation, ensuring that the components and interfaces of the capsule correspond correctly with those of the device. The asymmetrical nature of the protrusion restricts the capsule from being inserted in any other position, ensuring that it is securely and accurately positioned within the device. This design consideration promotes reliable functionality and prevents potential errors or malfunctions that may arise from incorrect alignment.

Additionally, the protruding wedge or dovetail shape contributes to the overall stability and secure engagement of the capsule within the device. By creating a locking or interlocking mechanism between the capsule and the device, the asymmetrical shape enhances the overall robustness and reliability of the system. The incorporation of a protruding wedge or dovetail as an asymmetrical shape within the housing of the capsule represents an innovative aspect of the invention. It allows for intuitive and foolproof orientation and alignment, ensuring seamless operation and optimal performance of the device.

The inclusion of a refillable capsule in the disclosed invention represents a significant advancement over the prior art, offering a range of advantages and improvements. The refillable capsule introduces enhanced convenience, cost savings, and environmental benefits to the field of medication administration. By enabling multiple uses, the refillable capsule eliminates the need for single-use disposable capsules, leading to substantial cost savings for users. This economic advantage is further complemented by the reduction of waste, promoting sustainability and environmental stewardship. Moreover, the refillable nature of the capsule allows for personalized medication administration, as users can easily refill it with the specific medication and dosage required for their individual needs. This flexibility not only optimizes therapeutic outcomes but also simplifies medication management by eliminating the need for multiple specialized devices or capsules. Additionally, the user-friendly design facilitates a straightforward refilling process, ensuring ease of use and minimizing the likelihood of errors or confusion. Overall, the inclusion of a refillable capsule in the invention provides users with improved convenience, cost savings, and a more sustainable approach to medication administration.

Referring now to FIG. 19, a side view of a diagram 1900 of the device in operation for a patient in an intubated state, wherein the device 1902 is in attachment with an endotracheal tube 1905 and a conduit of a ventilator or a respiratory support device 1910, according to an example embodiment. The device includes a tubular chamber that is a removable modular tubular extension, according to the second embodiment or third embodiment shown in FIGS. 21 and 22, respectively. The removable modular tubular extension includes a first extension tubular chamber 1920, which includes a first extension receiving section 1925 and a second extension chamber receiving section 1930. The first extension tubular chamber defines the first channel 1935. The removable modular tubular extension further includes a second extension tubular chamber 1940 substantially in fluid communication with the first extension tubular chamber. The second extension tubular chamber is configured to be received by a device receiving section 1942 such that the second extension tubular chamber is in fluid communication with the second channel 1944 of the device, which also receives the capsule 1946. Therefore, when inserted into the second channel of the device, the second extension tubular chamber defines a portion 1945 of the second channel. The atomized medication forms a stable and uniform aerosol, or generally homogeneous aerosol, when combined with the air in the first channel. An endotracheal tube is in attachment with the first extension receiving section 1925 so that endotracheal tube is in fluid communication with the tubular chamber and the conduit. The conduit 1950 is received by the second extension receiving section 1930 and is in fluid communication with an air outlet of a respiratory support device 1910.

In some cases, the weight of the attachment device may be an issue when the user must put down the attachment device during usage. Therefore, in some embodiments, the capsule may be configured to be received directly by the modular tubular extension. The capsule and the attachment device may include a Universal Serial Bus ("USB") port such that a USB cord can provide electrical communication between the attachment device and the capsule. This allows the capsule and the modular tubular extension to rest on the patient without the weight of the device, which can be placed elsewhere.

Referring now to FIGS. 23 through 25 and FIGS. 34A through 34D, an inhaler embodiment of the device 2300 for administering medication to a patient is shown. The device 2300 includes an electrical insulator 2305 in the form of a tab that can be pulled by the user of the device. The electrical insulator prevents electrical communication between a replaceable power source 2310 and the capsule 2315. Once the electrical insulator is pulled, the replaceable power source can provide electrical power to the capsule such that the atomizer 2320 is powered by the power source. As described above with reference to FIGS. 17A and 17B, the user of the device must press on the capsule to allow the fluid medication to flow towards the atomizer. The atomized medication flows through the second channel 2325 towards the first channel 2330 leading to an outlet 2335 on which the patient can position their mouth. Device 2300 allows the patient to inhale the atomized medication from the second channel without the help of a medical professional or any other user. Device 2300 may also include an outlet covering or cap 2340 to cover the outlet of the device when stored. In the present embodiment, device 2300 does not include a resilient air bladder. However, in some embodiments, it may be configured to receive a resilient air bladder on an end 2345 that is distal to the outlet 2335.

In one example embodiment, as shown in FIGS. 34A through 34D, the device may include a button 3450. The button functions as a small control mechanism that serves various critical purposes. In one embodiment, the button may be designed to engage or disengage the device, activate the atomization process, or lock, unlock, or eject a capsule that contains the medication. The button may be mechanically or electronically linked to different components such as the atomizer, the capsule housing, or locking mechanisms. Pressing the button may initiate the flow of medication from the capsule to the atomizer, lock the capsule in place for use, unlock it for removal or replacement, or activate ejection mechanisms to release a spent capsule. The materials for the button could be chosen from durable plastics, metals, or other suitable materials that are both ergonomic and hygienic. The inclusion of a multifunction button represents an enhancement over previous designs by consolidating various control functions into a single, user-friendly interface. This consolidation enhances the usability of the inhaler, provides more precise control, and allows for more efficient handling. Moreover, it could be particularly beneficial for users with limited dexterity or those requiring quick and easy access to their medication, contributing to a more compact and streamlined design.

In certain embodiments, each press of the button may release a predetermined bolus of atomized medication. This function ensures exact control, allowing for the administration of a specific dose of atomized medication into the patient's respiratory system. The button may be intricately connected to the medication chamber, atomizer, and other system components, coordinating to atomize and meter the correct volume of medication for each press.

Referring now to FIGS. 26, 27, 36A through 36C, views of a wand embodiment of the device 2600 for administering medication to a patient are shown. FIG. 26 is a partial cross-sectional side view of the wand embodiment. FIG. 27 is a perspective view of the wand embodiment. FIGS. 36A through 36C show additional embodiments of the wand. The device 2600 includes a handle 2605 configured to be held a user to administer medication to a patient. The device 2600 includes a pivoting and/or rotating element 2610 configured to alter the angle between the handle and a mouthpiece. The rotating element may be a button to engage a locking mechanism to allow the handle 2605 to change position or relative angle. The rotating element allows the device to rotate and/or pivot about origin 2615. The handle may have at least 180 degrees of rotation—or at least 90 degrees or rotation from the position shown in FIG. 26 where the device is centered about axis 2617 and may rotate in any such direction toward axis 2619. This may allow the user to better visualize the display on the device.

Figure 27:
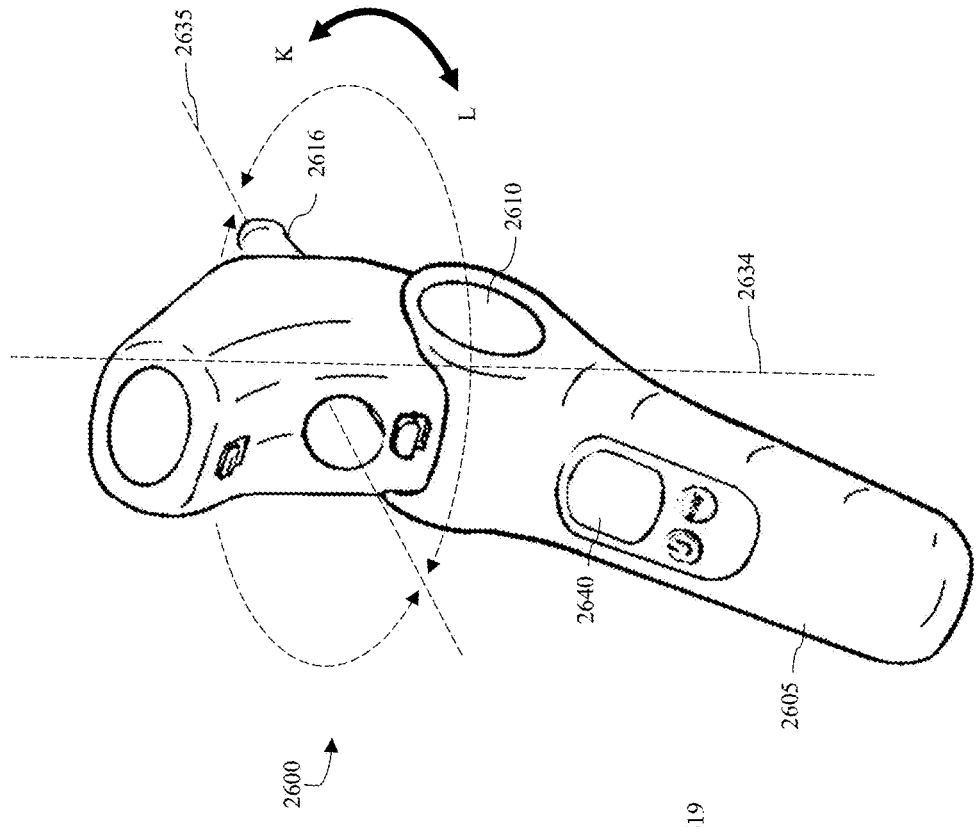
FIG. 27 illustrates the device for administering at least one medication to a patient in an unconscious state to a conscious state, according to an wand embodiment.

The mouthpiece 2616 is in fluid communication with the first channel 2620 and second channel 2625 that are configured to guide the flow of atomized medication from the capsule 2630. In some embodiments, as shown in FIG. 27, the device 2600 may be able to rotate about axis 2634 to reorient the mouthpiece direction relative to axis 2635. In one embodiment, the upper portion of the device may rotate, whereas in another embodiment, the lower portion of the device, namely, the handle, may rotate in the manner indicated by the arrows in FIG. 27. The rotation about axis 2634 may best be described as a twist or rotational motion. The rotation motion allows the administrator of the medication to view the display on the device and/or have access to the controls. For example, if the user is self-administering the atomized medication, the user may want visualization of the screen while they are using the mouthpiece, as shown in FIG. 36C. Similarly, if a third party is administering the device to another, maybe a child or unconscious person for example, then the administrator would want to visualize the screen or display 2640 on the device such that it opposed and/or faced away from the position of the mouthpiece and/or mask. It is understood that the device may have at least 180 degrees of rotation to allow the orientation of the display to align on the same side as the mouthpiece and or oppose the mouthpiece, as necessary. It is understood that FIG. 26 illustrates a first type of rotation, namely, rotating about an origin or pivoting, and FIG. 27 illustrates a second type of rotation, namely, rotating about an axis.

In some embodiments, the mouthpiece 2616 may be flexible and configured to be attached to the modular tubular extension. This allows device 2600 to be used as the attachment device shown in FIG. 19. Additionally, the handle 2605 may include arms or a cradle to maintain the device 2600 in an upright position when resting on a patient's chest.

Referring now to FIG. 28, a kit 2800 for converting a device for administering at least one medication to a patient in an unconscious state to a conscious state is shown, according to an example embodiment. The kit includes at least the components described in method 2900 below. The kit includes capsules 2805, the medical devices 2810 or base units, and removable caps 2815 to cover at least one receiving section of the medical device. The kit may further include resilient air bladders 2820 for removably attaching to receiving sections of the medical device, and mouthpieces and masks 2825 for removably attaching to a receiving section. The kit may further include power sources 2830 and modular tubular extensions 2835 for removably attaching to a receiving section. The kit also includes a case 2840 for enclosing the capsules, the medical devices, the caps, the resilient air bladders, the mouthpieces, the masks, the power sources, and the modular tubular extensions. The kit is configured to provide necessary components for various medical situations in which medication must be administered. The case may also include receiving sections or slots configured to securely hold each of the aforementioned components within the case.

The case may be comprised of metallic material such as carbon steel, stainless steel, aluminum, Titanium, other metals or alloys, composites, ceramics, polymeric materials such as polycarbonates, such as Acrylonitrile butadiene styrene (ABS plastic), Lexan™ and Makrolon™. other materials having waterproof type properties. The case may be made of other materials and is within the spirit and the disclosure. The case may be formed from a single piece or from several individual pieces joined or coupled together. The components of the case may be manufactured from a variety of different processes including an extrusion process, a mold, casting, welding, shearing, punching, folding, 3D printing, CNC machining, etc. However, other types of processes may also be used and are within the spirit and scope of the present invention.

In an embodiment, as illustrated in FIGS. 36D and 36F, a system for administering substance to a body part of the user is disclosed. The system comprises a wand embodiment of the device 3600 for delivering substance to the user. It is noted that the substance may be one of pharmaceutical, therapeutic, or cosmetic substances, to address specific conditions or enhance skin health. For example, pharmaceutical substances may include a medication, such as antibiotics or antifungal solutions designed to treat infections. In some embodiments, the medication may also include therapeutic substances including a regenerative medication targeting treatment of tissue repair and regeneration in the user.

Regenerative medications include bioactive agents or biological agents capable of stimulating cellular growth, differentiation, and repair. The medication may comprise a combination of growth factors, cytokines, stem cells, or other agents known to facilitate tissue regeneration and repair. In another embodiment, the medication comprises one of peptides, proteins, growth factors, cytokines, exosomes, and extracellular vesicles derived from human mesenchymal stem cells suspended and/or dissolved in an aqueous medium. In another embodiment, the medication is an aqueous suspension and solution comprising cells, cellular byproducts, and cell-derived products. The cells, the cellular byproducts, and cell-derived products are stem cells. It is noted that bioactive agent and biological agent may be used interchangeably throughout the document, as the biological agent may have a bioactive effect in some embodiments. Cosmetic substances may include hyaluronic acid or vitamin C serums for skin rejuvenation. The device atomizes and delivers these substances in a fine mist form to achieve targeted treatment or skincare benefits.

As noted above, the device 3600 includes a handle 2605 configured to be held by a user to administer medication to the user. In an embodiment, the device 3600 includes a pivoting and/or rotating element configured to alter the angle between the handle 2605 on a lower portion 3609 of the device and a conduit on an upper portion 3607 of the device, such as the conduit 3603. It is noted that the term "user" comprises, but is not limited to, a human being, an animal, or a patient, among other possible entities.

The device has a highly adaptable head unit or top, such as the upper portion 3607 designed to rotate by complete 3600 (degrees), providing flexibility in its application. The rotational capability allows the device to be easily adjusted to accommodate various configurations, during use of the device. For example, for direct application in a specific orientation or adjusting the angle to reach different areas effectively, the rotating head unit can have different configurations. In another example embodiment, the design of the device facilitates use by both individual users and others, such as healthcare professionals or caregivers, by simply changing the configuration of the head unit. For a single user, the device can be self-directed to the desired position, ensuring case of use and convenience. Conversely, when used by another person, such as a health professional or a nurse, the head unit can be adjusted to provide optimal access to the area being treated or worked on, thereby improving the effectiveness and comfort of the application. The device provides dual-use capability, enabled by the adjustable head unit in both personal and professional settings.

As shown in FIGS. 36D through 36K, and 36N, the conduit 3603 is attached to the base unit of the device by inserting within the opening 3634. The conduit is primarily cylindrical in shape but can also be designed in various other forms to suit different applications. Examples of alternative shapes include flexible, coiled, or even segmented designs to enhance maneuverability and access to difficult to reach areas. The conduit facilitates the easy attachment of a range of additional components, such as an ocular tube for eye treatments, a spraying catheter for precise delivery of substances, a mouthpiece for inhalation therapies, and the elongated tubes as depicted in FIGS. 36I, 36F, and 36N, respectively. These attachments expand the device's functionality, enabling it to serve a wide array of medical and cosmetic purposes. In various embodiments, the conduit itself can be directly utilized for delivering therapeutic or cosmetic substances to an affected skin area or for enabling substances to be inhaled by the user, showcasing its adaptability in the administration of treatment across different modalities and conditions as outlined in the disclosed embodiments of the specification. The conduit's design allows it to cover specific areas of the skin for targeted substance delivery, that can treat various conditions. This feature is particularly beneficial for administering treatments directly to areas affected by skin burns, where precise application of therapeutic substances can significantly aid the healing process. Additionally, the versatility of the conduit extends to applications involving the external and internal vaginal areas, offering a non-invasive means to deliver treatments for conditions affecting these sensitive regions. By conforming closely to the contours of the targeted area, the conduit ensures that the therapeutic or cosmetic substances are applied efficiently and effectively, maximizing the substance's contact with the skin or mucosal surfaces for optimal absorption and therapeutic effect.

The system comprises a removable capsule 3610 comprising a medication. In one example, the medication is exosomes. The removable capsule enhances both the functionality and user experience of the device. The removable capsule allows for easy replenishment of medication without needing to replace or service the entire device, facilitating continuous and flexible treatment management for users. This feature is particularly beneficial for individuals requiring regular doses of medication, as it enables them to conveniently carry and use the device on-the-go, ensuring timely medication administration. Moreover, the removable nature of the capsule permits the cleaning and maintenance of the device components separately, thereby improving hygiene and reducing the risk of contamination. Additionally, the removable capsule provides the flexibility to switch between different types of medications, dosages or any other liquid material. Exosomes are naturally occurring extracellular vesicles released by most cell types, and are used in therapeutic applications, in drug delivery and regenerative medicine. In the context of medication, exosomes can carry therapeutic agents, offering a targeted approach to treatment with reduced risk of adverse side effects. The utilization of a portable device for delivering exosome-based medications offers distinct advantages by enabling precise, controlled dosing and improving patient compliance through case of use. Such devices can be designed to administer doses at specific times or in response to physiological signals, enhancing the efficacy of treatment regimens. In the disclosed embodiment, the removable capsule contains the medication, however other embodiments disclosing a vial for containing substances other than medication, such as therapeutic and cosmetic substances are also covered within the spirit and scope of the invention.

The removable capsule has an atomizer disposed directly adjacent to a capsule chamber of the removable capsule. As shown in FIG. 36F, the removable capsule 3610 has the atomizer 3626 and the medication 3628 within the capsule chamber 3620. The atomizer is disposed such that the medication contacts the atomizer within the capsule chamber. In an example embodiment, the atomizer is disposed at a bottom portion of the removable capsule such that when the removable capsule is inserted in the device, the medication is in contact with the atomizer. The atomizer is positioned within the bottom portion of the removable capsule, ensuring that regardless of the capsule's orientation upon insertion into the device, the medication or any other substance within remains in consistent contact with the atomizer. This design ensures optimal utilization of the substance, as the atomizer can effectively convert the medication into a fine mist or aerosol for precise delivery, without the need for the capsule to be in a specific position. The positioning of the atomizer at the bottom portion of the capsule maximizes the effectiveness of the atomization process, ensuring that the entirety of the substance is readily available for conversion and delivery, thereby reducing waste and improving the overall delivery mechanism.

The device has a base unit 3622 including a mixing chamber 3624 and multiple openings 3634 and 3637 in fluid communication with the mixing chamber 3624. In the mixing chamber, multiple substances are combined or processed to obtain a mixture. For example, the atomized medication particles 3630 is combined with air molecules 3632 in the mixing chamber. Surrounding this mixing chamber, the base unit is equipped with the multiple openings. These openings are designed to facilitate fluid communication with the mixing chamber. This means that they allow for the passage of fluids into and out of the mixing chamber, enabling efficient mixing of materials, the introduction of new substances into the chamber, and the extraction of the resultant mixture, thereby supporting the device's intended functions. As shown in FIG. 36F, the mixing chamber 3624 receives the atomized medication particles 3630 and the air molecules 3632 for mixing and provide the mixture in form of a mist of medication. After the mixing, this mixture is then directed towards the user through the opening 3634, subsequently passing through the conduit 3603, to ensure efficient delivery. The mixing in the mixing chamber transforms the atomized medication and air particles into a homogenized mist, that can be readily inhaled by the user.

A removable air mover unit 3606 is attached to the base unit of the device via an opening 3608 of the plurality of openings on the base unit, such that such that a central axis of the removable air mover unit aligns with a central axis of the portion of the conduit. In the described embodiment, the air mover unit comprises a fan component and a frame component, with the fan securely nestled within the frame. The configuration optimizes airflow and ensures structural integrity. The air mover unit is further characterized by an outward surface 3611 to engage seamlessly with the inner wall 3604 of the opening of the device when attached. This precise interface between the air mover unit and the device ensures a tight and efficient connection, enhancing the unit's performance by minimizing air leakage and maximizing the directed airflow into the device. The air mover unit is attached to the base unit such that the outward surface 3611 of the removable air mover unit abuts the inner wall 3604 of the opening 3608 that receives the removable air mover unit. In an example, when the removable air mover unit is attached to the base unit, the air mover unit is in fluid communication with the mixing chamber of the base unit, the removable air mover unit is configured such that air conveyed from the removable air mover unit moves into the mixing chamber.

The air mover unit is small, compact, and designed to fit within the opening 3608 of the device's base unit. The depicted design of the air mover unit is rectangular, as shown in the figure. It is noted that different shapes and size of the air mover unit including circle or elliptical shape are covered within the spirit and scope of the invention. Further, the air mover unit is positioned within the base unit such that a fan component of the air mover unit specifically configured to direct airflow towards the base unit, thereby optimizing the device's performance through efficient air circulation.

In an embodiment, the air mover unit is a compact device equipped with an on-board battery, on-board circuitry, including a printed circuit board (PCB), and a Bluetooth connectivity module, making it a standalone, versatile tool for air circulation tasks. Once the air mover unit comes into contact with the base unit, electrical communication is established between them. This connection enables the base unit to power the air mover unit, activating its operational state. In one example, the Bluetooth connectivity module may establish a Bluetooth connection with a compatible controller of a user device, such as a smartphone or tablet. The user can then control activation or deactivation the air mover unit without needing to physically interact with the device. Additionally, the Bluetooth connectivity module allows for remote operation control and monitoring, enhancing the unit's functionality and user convenience. For example, the Bluetooth connectivity module may allow control of fan speed or direction via the user device. The Bluetooth connectivity module also detects the presence or attachment of the air mover unit to the base unit based on Bluetooth signals. Upon recognizing the air mover unit's proximity or connection, the module initiates an activation sequence through electrical communication between the air mover unit and the base unit. This seamless interaction ensures that the air mover unit is promptly activated and ready for operation, leveraging the wireless signals for recognition and efficient power management, thus enhancing the system's usability and performance.

The removable air mover unit is in direct electrical connection with the base unit of the device. A first electrical contact 3613 is disposed on the outward surface of the removable air mover unit and a second electrical contact 3614 is disposed on the inner wall of the opening of the base unit for providing electrical communication between the removable air mover unit and the base unit, shown in FIG. 36E. The electrical contacts establish a reliable electrical connection between two the base unit and the air mover unit in form of a cordless power connection. Examples of the electrical contacts include spring-loaded pins offering consistent contact force, blade and receptacle contacts, and leaf spring contacts. These contacts are widely used in battery connections, modular electronic devices, and connectors, for secure and repeatable electrical connection between the two devices.

In another embodiment, the air mover unit is equipped with an electrical power cord, designed to connect with a corresponding plug on the base unit. This configuration allows for the battery of the base unit to be electrically connected with the air mover unit. The electrical power cord provides device's connectivity and power supply. The cord allows the air mover unit to draw power from the battery of the device, ensuring it operates efficiently and consistently. In an example, the plug point is located on the back of the device, to provide a convenient and unobtrusive way to connect the power cord. The connection of the power cord of the air mover unit to the back of the device provides safety by reducing risk of accidental disconnections. Upon establishing this connection, the battery facilitates the activation of the air mover unit, powering it to function as intended. This design ensures that the air mover unit can be easily integrated into the system, providing a direct power source that enhances its operational efficiency and reliability.

In another embodiment, the air mover unit has a one-way valve such that in an assembled state, the on-way valve is positioned on the back of the device, for application in dental settings. This valve is used for preventing backflow, ensuring that if the user coughs or gags during a procedure, there is no reverse movement of air or fluids back into the device. The one-way valve maintains the hygiene and integrity of the air mover unit and also safeguards the user from potential cross-contamination. Such a configuration of the device having the one-way valve optimizes the device's safety and hygiene.

In an example, the airflow from the air mover unit is directed such that the mist, formed by the mixing of atomized medication and air in the mixing chamber, is channeled directly towards the opening 3634. From there, it is guided to exit through conduit 3603, as shown in FIG. 36F for delivery of the medicated mist to the user. The direction of airflow optimizes the delivery mechanism for the mist reaches the user in an effective and controlled manner. This specific airflow directionality enhances the efficiency of the medication delivery process providing a more effective solution for administering atomized medication. In an example, the air mover unit can be a fan such as an axial fan, a centrifugal fan or a blower, an exhaust fan, a crossflow fan, or a compressor. The integration of the air mover unit within the device offers a more compact, efficient, and effective solution for managing airflow, thereby enhancing the overall performance and user experience of the device.

It is noted that the air mover unit is shown to be positioned within the opening of the base unit, however in other embodiments, various other positions of the air mover unit is covered within the scope of the invention. For example, the air mover unit positioned adjacent the opening 3608 and not housed within the opening such that the axis of the air mover unit coincides with the axis of the opening. In such configuration the air mover unit directs the air flow towards the opening 3634 of the base unit. In another example, the air mover unit is positioned adjacent the conduit to direct the mixture that exits from the conduit toward the user. The ability to position the air mover unit in different orientations relative to the base unit provides flexibility and variability in its use, directly contributing to improved airflow dynamics within the system. This versatile design allows users to adjust the direction and intensity of the air flow according to specific needs or conditions, enhancing the overall efficiency and effectiveness of the air mover unit when operated in conjunction with the base unit. Such adaptability ensures optimal performance across a wide range of applications.

As noted above, the conduit is connected to the base unit. In an example, the conduit is in fluid communication with mixing chamber, and during use of the device by the user the conduit conveys the medication to the body part of the user. The exterior of the conduit has a slightly curved, tubular form, transitioning into a thicker, rounded shape towards one end attached to the base unit. The outer walls of the conduit provides durability and protection and are made from biocompatible materials. The conduit is designed to withstand external stresses and strains without deforming. Additionally, the surface of the outer walls is often treated with antimicrobial coatings to prevent biofilm formation and reduce the risk of infection. The inner walls are smooth for unhindered flow of fluids, gases or medication, minimizing turbulence and blockages. The smooth inner walls also prevent adherence of biological materials or other substances, that leads to contamination or obstruction. The conduit can be made from a diverse array of materials, based on properties and suitability for specific applications. For instance, flexible plastics such as polyvinyl chloride (PVC) and polyethylene (PE) are commonly used for their lightweight nature, flexibility, and chemical resistance. Metals like stainless steel and aluminum are chosen for their durability, resistance to high pressures, and ability to withstand extreme temperatures, lending themselves well to industrial and high-strength applications. Silicone, known for its flexibility, non-reactivity, and thermal stability, is often used that require a sterile environment and exposure to fluctuating temperatures. The conduit, as shown in the figure is cylindrical, to easily connect to the opening of the base unit on one end and to other additional components on the other end. It is noted that other shapes, such as rectangular, square, or elliptical shape are covered in the scope of the invention.

FIG. 36G shows a removable cap 3640 attached to the opening 3608 of the base unit. As shown in the figure, the device having the opening is covered by the removable cap 3640, and creates a capped chamber or a sealed compartment within the device. When the device is activated, the device induces the removable capsule's contents, the medication, to atomize into a fine mist by dispensing the medication from the capsule, which is in fluid communication with this capped chamber, into the capped chamber itself. Within this capped chamber, the atomized medication, released from the removable capsule, is effectively mixed with air. This process transforms the medication into the fine mist, which is then directed through an opening connected to a conduit, ultimately reaching the user. The resulting aerosolized medication is administered to the user. The capped chamber provides a consistent and efficient mixture of air and atomized medication. This mixing process creates the fine mist that can be easily inhaled, optimizing the delivery of the medication to the user's lungs. Additionally, the capped or sealed nature of the chamber prevents the escape of medication into the environment, minimizing waste and ensuring that the full dosage is delivered to the user. The design feature is particularly beneficial for individuals with respiratory conditions, as it ensures the delivery of medication in a manner that maximizes absorption and efficacy.

These removable caps may have various shapes and sizes, tailored to meet specific needs and preferences of the user. The shape of the cap can range from simple cylindrical or conical designs to more complex geometries that may include ergonomic features for easier handling. The size of the cap ensures a precise fit over the opening of the device to create an effective capped chamber for medication mixing. Larger caps may facilitate easier manipulation by users, and smaller caps can contribute to a more compact and portable device design.

In another embodiment, a resilient bladder 3642 is attached to the opening 3608 of the device, shown in FIG. 36H. The resilient bladder is attached such that the bladder is in fluid communication with the mixing chamber of the device. The air bladder has a bladder body 3644 and a connecting portion 3646, and manages the air flow within the device. The connecting portion, typically tubular in shape, is designed to attach or be partially inserted within the opening of the device, creating a seamless connection through which air can be directed. The primary function of the bladder is to be manually compressed by the user, thereby propelling air into the device to facilitate the mixing and delivery of the atomized medication.

Various size of the bladder is covered within the scope of the invention. A larger bladder allows for a greater volume of air to be stored and subsequently pushed through the device with each compression, potentially delivering a more potent dose of medication in a single breath. Conversely, a smaller bladder offers more precise control over the air flow, enabling a more measured and gentle delivery of medication. This can be particularly advantageous for users with sensitive respiratory conditions or those requiring a lower dosage of medication. The choice of bladder size should be aligned with the specific needs and capabilities of the user, ensuring that the device is both effective and comfortable to use.

The resilient air bladder provides the user with direct control over the air flow and, consequently, the dosage of medication delivered. This allows for a more personalized treatment regimen, catering to the varying needs of users with different respiratory conditions. Secondly, the manual operation of the air bladder eliminates the need for external power sources or complicated mechanisms, enhancing the device's portability and reliability. Further, the resilient air bladder provides a manual mechanism for air flow control, the device becomes more accessible and user-friendly, particularly for elderly users or those with limited technical proficiency.

In an embodiment, an ocular tube 3648 is attached to the conduit 3603. The ocular tube 3648 has a base tube 3649 and an eye cup 3651. In an example, the ocular tube houses the eye cup at a distant end for administering the medication in a mist form directly to eyes of the user. These tubes, designed to administer medication in mist form or liquid form directly to the eye. The ocular tube is made from a range of materials, each selected for their safety, durability, and compatibility with sensitive ocular tissues. Common materials include soft, flexible plastics that are gentle on the eye and minimize irritation or allergic reactions. The types of ocular tubes can vary based on their design, functionality, and the specific medication they are intended to deliver. Some are designed for single-use, disposable applications, ensuring sterility and preventing contamination, while others may be reusable for chronic conditions, featuring replaceable cartridges of medication. The use of ocular tubes offers a precise and controlled method of medication delivery, directly targeting the affected area and minimizing systemic absorption. This localized approach to treatment allows for lower dosages of medication, reducing the risk of side effects commonly associated with oral or injectable medications. Additionally, the design of these tubes ensures that the medication is distributed evenly across the surface of the eye, improving efficacy.

The ocular tube has an integrated eye cup. The eye cup has a scaling portion 3647 designed to securely cover and seal over a specific area of the skin. The sealing portion has a semi-spherical shaped body to enclose medication mist, ensuring that it remains concentrated near the treatment area. The semi-spherical shape of the cup provides a curved design that conforms over the area of the skin, ensuring that the medication is precisely targeted and contained to the area. This curved shape is beneficial because it creates an efficient seal against the skin, minimizing medication wastage and enhancing the concentration of treatment at the site of application, thereby increasing the efficacy of the therapy. This design is particularly beneficial for administering targeted therapy to areas affected by burns, lacerations, wounds, or lesions, as it creates an isolated environment that enhances the effectiveness of the treatment. By maintaining a high concentration of the therapeutic mist within the immediate vicinity of the affected area, the eye cup facilitates optimal absorption of the medication, thereby accelerating the healing process and improving treatment outcomes for various skin conditions.

The eye cup is designed to fit securely over the user's eye, creating a seal that prevents medication or other substances such as therapeutic or cosmetic substances from leaking out during administration. The connection is achieved through a snug-fitting mechanism where the ocular tube is either inserted into a central opening in the eye cup or attached via a flexible connector. This ensures that the medication is confined to the ocular area, maximizing absorption by the eye's surface and reducing waste. The eye cup is typically crafted from materials prioritizing safety, comfort, and effectiveness. Medical-grade silicone or rubber stands out as a preferred material, due to its flexibility, durability, and hypoallergenic properties. Silicone's softness ensures comfort against the sensitive skin around the eye, while its non-reactive nature prevents irritation or allergic reactions, making it ideal for direct contact with the eye area. Moreover, silicone's resilience allows for repeated use and easy cleaning, supporting both disposable and reusable eye cup designs, thus ensuring the safe and efficient delivery of various ocular treatments. The ocular tube and the eye cup improve the process of applying eye medication, particularly for elderly users or those with limited dexterity. The use of an eye cup reduces the risk of contamination, as the medication is transferred from the tube to the eye without coming into contact with external surfaces.

In an alternative embodiment, the ocular tube and the eye cup is utilized for delivering therapeutic and cosmetic substances directly to the user's face for skincare and eye treatments. Therapeutic substances can include hydrating serums and anti-inflammatory solutions aimed at treating eye-related conditions or providing relief to the sensitive skin around the eyes. For cosmetic applications, substances might range from anti-aging serums rich in vitamins and antioxidants, designed to diminish wrinkles and fine lines, brightening solutions that address dark circles and puffiness, revitalizing the skin's appearance. For delivering the substance, the ocular tube and the eye cup is correctly positioned on the face of the user. The eye cup is designed to fit snugly over the user's eye or against the targeted area on the face, creating a sealed environment that prevents spillage and ensures that the substance is confined to the desired area. This positioning improves effectiveness of the treatment, as it allows for direct application of the substance to the area that requires treatment or enhancement. Once the eye cup is securely in place, the pharmaceutical, therapeutic or cosmetic substance is gently released from the ocular tube into the eye cup in the form of a fine mist. The delivery is especially gentle on the sensitive skin around the eyes and allows for the substance to be evenly distributed across the targeted area. The fine mist ensures that the substance is absorbed efficiently by the skin, maximizing the therapeutic or cosmetic benefits. Thereafter, the eye cup is gently moved or hovered from one point to another over the entire targeted region. This movement helps to cover the entire area evenly, ensuring that no part of the targeted region is missed. This process not only enhances the effectiveness of the substance being applied but also contributes to a soothing and pleasant application experience for the user.

In another embodiment, a spraying catheter tube 3650 is attached to the conduit 3603, using an adapter 3652 in FIG. 36J. The spraying catheter tube 3650 has an elongated body having a flexible tube segment for inserting into a user's body, and an adjustable tip 3655 portion that can be oriented differently, allowing for directional adjustment of an outlet tip for medication delivery to a target region inside the user's body. In an example, the target region is a tooth within a mouth of the user or an internal organ of the user. The primary function of this spraying catheter tube is to facilitate targeted medication delivery during treatments that require localized drug administration. The elongated body of the tube incorporates the flexible segment, designed for safe and minimally invasive insertion into a patient's body. This design aspect ensures that the catheter can navigate through the body's pathways, reaching internal regions without causing significant discomfort or trauma to the patient. The adjustable tip portion can be oriented in various directions, allowing healthcare providers to adjust the outlet's direction to align with the target area for medication delivery accurately. Such a feature is particularly beneficial when addressing conditions localized within specific internal regions, requiring direct treatment application. The ability to adjust the direction of the medication outlet ensures that the drug is administered efficiently and effectively to the intended area, minimizing wastage and enhancing the treatment's impact.

The tip of the spraying catheter tube is made from materials distinct from those of the flexible tube segment. The flexible segment is made from materials for flexibility and biocompatibility to navigate the body's internal pathways without causing irritation or injury, the material of the tip is chosen for its durability and the precise control. In an example, medical-grade silicone or rubber is used for the flexible segment and the material for the tip is more rigid, and biocompatible material like polyurethane or a specialized polymer that can withstand repeated directional adjustments and exposure to various medications without degrading. This different materials of the flexible segment and the tip provides that the catheter combines the necessary flexibility for insertion and navigation with the robustness required for precise, repeated medication application.

The tip may be attached to the flexible segment using various techniques. This connection can be achieved through several methods, each designed to secure the tip while allowing for its necessary movement and orientation adjustments. One common approach is the use of a locking mechanism, where the tip snaps into a predefined position on the flexible segment, ensuring a secure yet adjustable connection. Another method involves the use of medical-grade adhesives that bond the tip to the segment without compromising the flexibility or adjustability required for operation. In another example, the tip and segment is manufactured as a single piece, using a dual-material injection molding process that seamlessly transitions from the flexible material of the segment to the more rigid material of the tip.

The adapter 3652 attaches the spraying catheter tube with the conduit of the device to provide a seamless and secure connection. The adapter accommodates the physical and operational disparities between the catheter and the device, facilitating a robust yet flexible link that can withstand the rigors of medical procedures. The adapter's provides a stable connection that maintains the integrity and functionality of the catheter while allowing for easy attachment and detachment from the device, catering to various clinical needs. In an example, the adapter has a locking mechanism, such as a latch or a twist-lock system, which secures the adapter to the flexible segment of the catheter. This ensures that once attached, the catheter remains firmly in place during use. For attachment to the flexible segment, methods such as mechanical fit, adhesives, or even a quick-release mechanism may be employed, offering flexibility in how the catheter is assembled and used. Additionally, the adapter has connection element with predefined dimension or threading, that matches the opening of the device. This design consideration allows for a snug and secure fit, minimizing the risk of disconnection or leakage during medication delivery. The adapters allow the spray catheter to be easily attached and detached from the device either for replacement, cleaning, or to adapt the device for different uses.

In another embodiment, a mouthpiece 3654 as shown in FIG. 36K is attached to the conduit of the device. The mouthpiece defines a tubular shaped body to be inserted into a user's mouth. The mouth piece has predefined dimensions to fit comfortably within the user's mouth. Its attachment to the conduit facilitates a direct pathway for medication from the device to the target area within the mouth, such as specific teeth, gums, or other oral tissues requiring treatment. The mouthpiece may be fitting snugly and comfortably within the user's mouth, to ensure that the medication is delivered precisely where it is needed, maximizing the efficacy of the treatment while minimizing waste and exposure to non-targeted areas. The material composition and ergonomic design of the mouthpiece are crucial for ensuring patient comfort and effective delivery of medication. The mouth piece is made from medical-grade materials that are both durable and non-irritating to the sensitive tissues within the mouth, the mouthpiece is designed to withstand repeated use while maintaining its shape and integrity. The attachment mechanism between the mouthpiece and the conduit is designed for secure yet easily adjustable connections, allowing healthcare providers to quickly attach or detach the mouthpiece as needed for cleaning, replacement, or adjustment. The material used for the mouthpiece may include medical-grade silicone, thermoplastic elastomers (TPE), and polyurethane. Medical-grade silicone is widely used for its flexibility, resistance to bacterial growth, and comfort against soft tissues. Thermoplastic elastomers offer a unique blend of plastic and rubber properties, providing a softer, more adaptable fit within the user's mouth while ensuring case of cleaning and sterilization. Polyurethane provides toughness and flexibility, capable of withstanding repeated use without losing shape or integrity.

In operation, with reference to FIG. 36F, the device 3600 has a base unit that defines the channel 3629 and various openings 3634 and 3637. The removable capsule 3610, which contains the medication 3628, is placed into the channel 3629 within the device. This initial step ensures that the capsule is properly aligned and secured for the subsequent atomization process. Following this, the atomizer 3626 within the device is powered on, initiating the transformation of the contained medication into a fine mist form. This atomization process breaks down the medication into minuscule particles, making it easier for the body to absorb and increasing the efficacy of the treatment. Once atomized, the atomized medication particles 3630 are then introduced into the mixing chamber 3624, where they are thoroughly mixed with air molecules 3632. The mixing forms the homogenized mixture, ensuring that the medication is evenly distributed within the air, ready for delivery to the user.

In conveying the homogenized mixture to the user, the device employs distinct mechanisms in different embodiments, the air mover unit and the resilient bladder. In the first example, the air mover unit 3606 propels the mixture through a portion of the conduit 3603 and out of the device, utilizing a fan or similar mechanism to generate airflow in the direction of arrows 3636. This method is particularly effective for a consistent and controlled delivery of the medication. Alternatively, in another embodiment, a resilient bladder, such as the resilient bladder 3642 shown in FIG. 36H is used to convey the mixture. The bladder, through its expansion and contraction, forces the medication-air mixture through the conduit, offering a different method of delivery that can be precisely controlled based on the degree of pressure applied. Both methods ensure that the medication is delivered efficiently and directly to the required site, highlighting the device's flexibility and adaptability in meeting various medical needs.

In another embodiment, a wearable headset or a mask designed for direct connection to the conduit of the base unit, may be attached to the conduit of the base unit. The headset or the mask may facilitate delivery of nebulized medicine to the user's face and/or eyes. This wearable device is equipped with a connecting tubular portion that seamlessly inserts into the opening of the base unit, establishing a secure and efficient pathway for the nebulized substance. Incorporated within the headset or mask are finely calibrated nozzles, placed to uniformly distribute the fine mist across the facial or ocular regions of the user. These nozzles are meticulously designed to ensure that the nebulized medication or therapeutic substance is delivered in an evenly dispersed manner, optimizing the effectiveness of treatment and enhancing the user experience. Furthermore, the headset or mask may be used therapeutic and cosmetic uses as well. The headset or the mask may be used to deliver medications, therapeutic substances for relaxation and skin care, or cosmetic products for hydration and rejuvenation. The uniform dispersion of substances through the nozzles ensures that the fine mist reaches the target area effectively, maximizing absorption and benefits. The mask may fit over targeted areas, providing a versatile solution for delivering substances to treat a variety of conditions. The mask allows covering general skin surfaces affected by burns, facilitating direct treatment and healing, and more sensitive regions such as the external and internal vaginal areas. This capability ensures that treatments can be applied in a precise, controlled manner, directly where needed, while maintaining the comfort and privacy of the user. The mask's ability to conform to different body contours and effectively seal the treatment area optimizes the delivery and absorption of therapeutic or cosmetic substances, enhancing the efficacy of the treatment for skin rejuvenation, healing of burns, or addressing conditions specific to the vaginal areas.

Figure 29A:
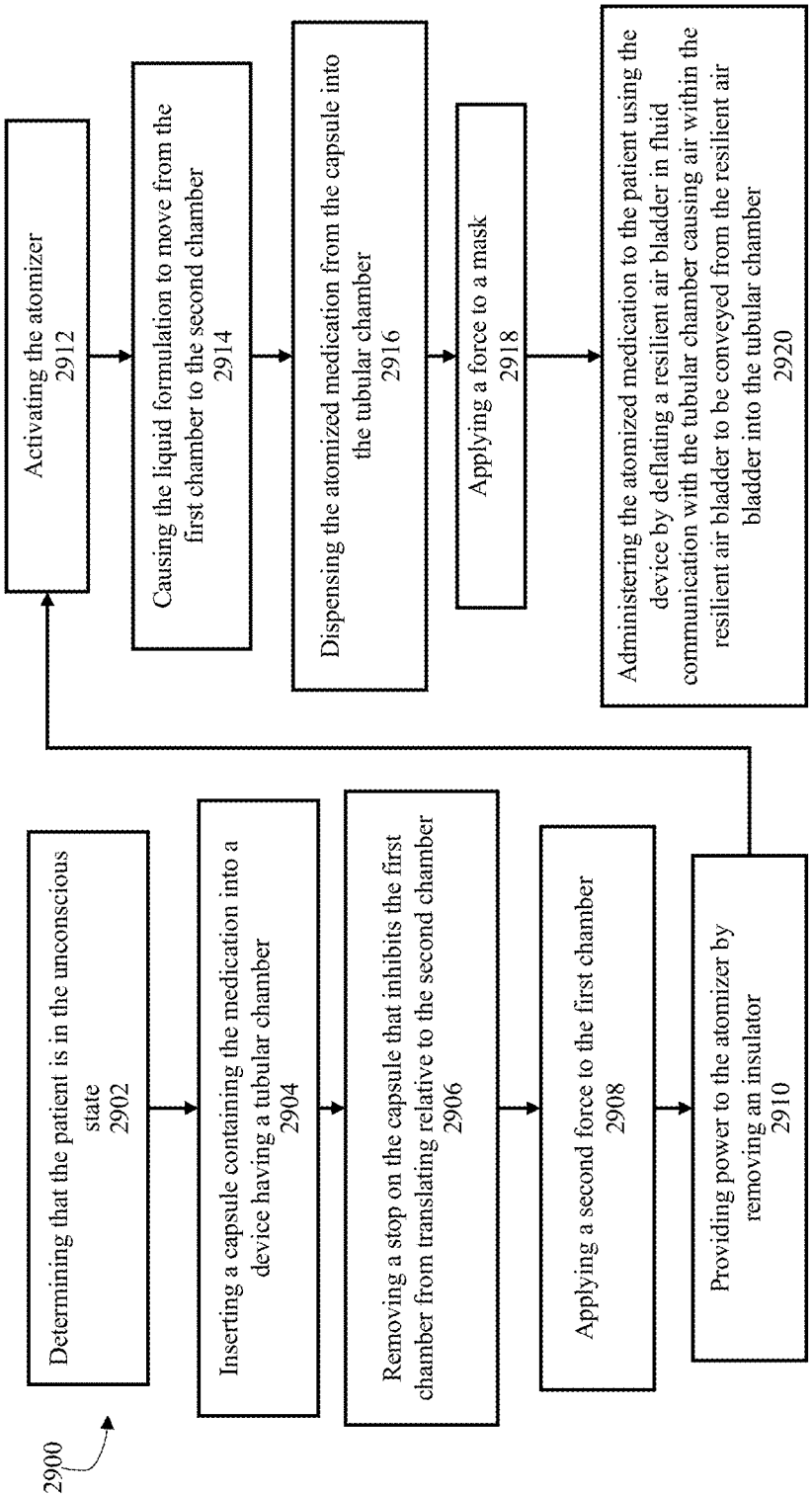
FIG. 29A is a flowchart diagram illustrating steps for a method for converting a device for administering at least one medication to a patient in an unconscious state to a conscious state, according to an example embodiment.
Figure 29B:
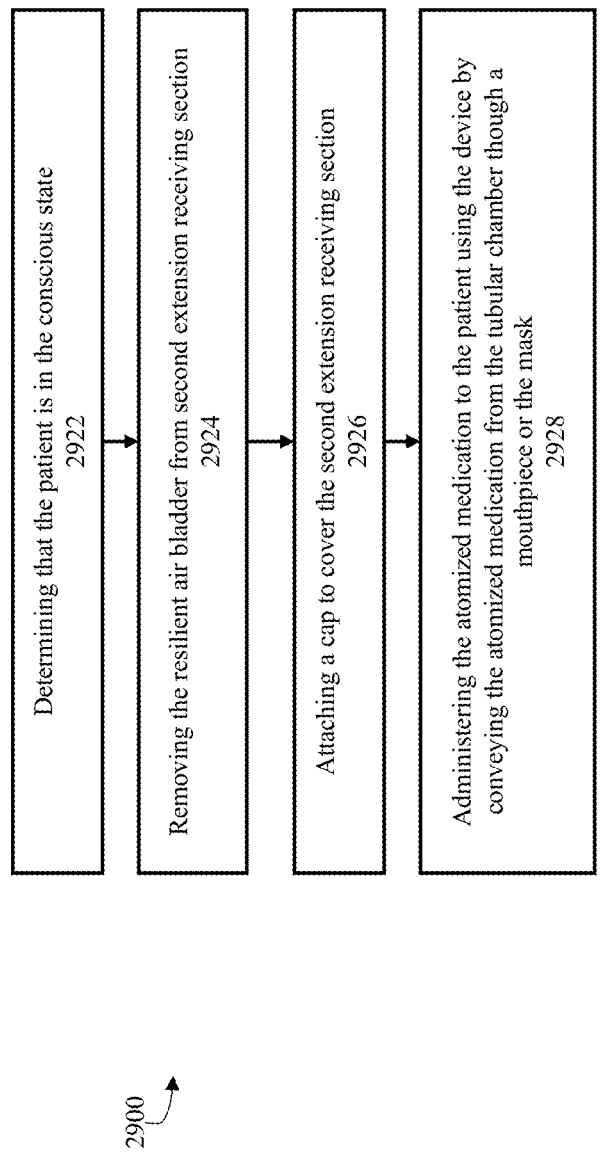
FIG. 29B is a flowchart diagram illustrating steps for a method for converting a device for administering at least one medication to a patient in an unconscious state to a conscious state, according to an example embodiment.
Figure 29C:
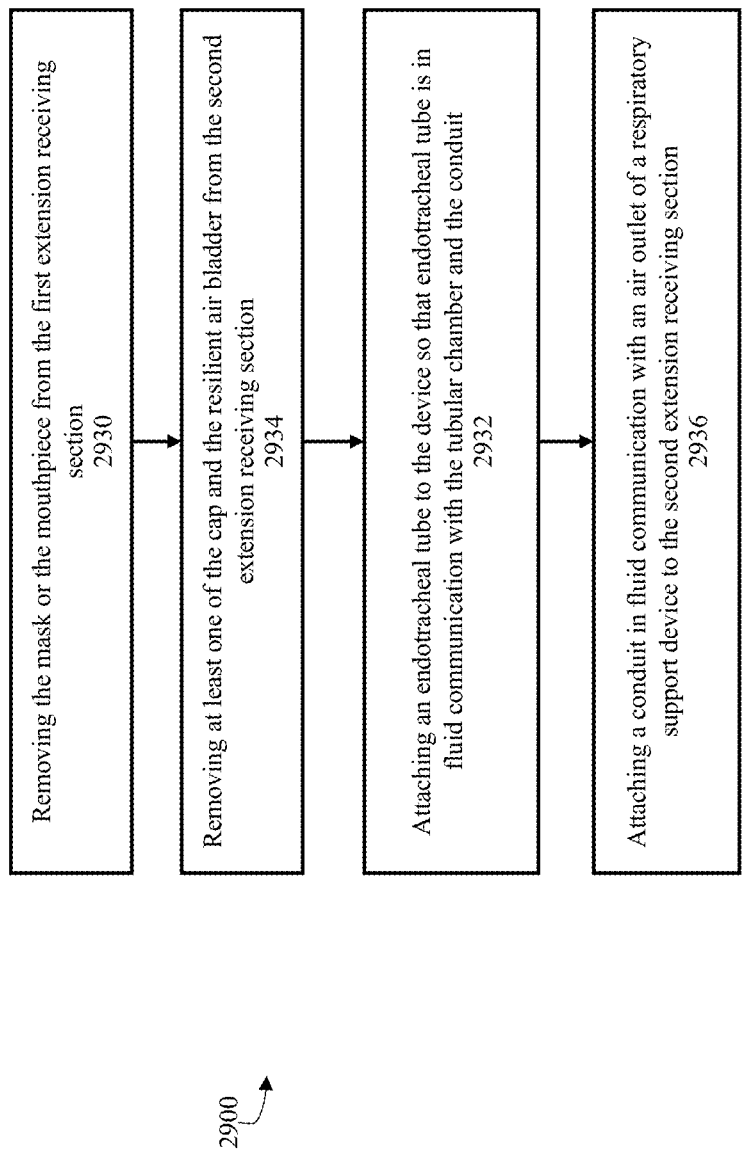
FIG. 29C is a flowchart diagram illustrating steps for a method for converting a device for administering at least one medication to a patient in an unconscious state to a conscious state, according to an example embodiment.

Referring specifically to FIGS. 29A through 29C, with intermittent reference to FIGS. 1 through 28 as indicated below, a flowchart diagram of a method 2900 for administering at least one medication to a patient when the patient is unconscious and when the patient is consciousness and for converting a device for administering at least one medication to a patient in an unconscious state to a conscious state is shown, according to an example embodiment. Unless otherwise stated, generally, the method described herein is not limited to the particular order of the disclosed steps. While the disclosed order provides certain improvements over the prior art, it should be understood that the method steps can be rearranged, modified, or performed in alternative sequences without departing from the scope of the disclosure. In certain embodiments, the method steps may occur concurrently, simultaneously, independently, dependently, or in any other suitable manner, as determined by the specific implementation and requirements. The flexibility of the method allows for adaptability and optimization based on various factors, such as system resources, data availability, and user preferences. Therefore, the specific arrangement and order of the method steps should be interpreted as illustrative rather than limiting, and the disclosure encompasses all variations, modifications, and alternatives falling within the scope of the appended claims.

Method 2900 begins with step 2902, wherein a user determines that the patient is in the unconscious state. Method 2900 includes removing and inserting the second extension tubular chamber of the removable modular tubular extension into a device receiving section depending on the state of the patient. For example, in most unconscious states or conscious states, the device will be in attachment with the first embodiment of the removable modular tubular extension 2000 shown in FIG. 20. The system 100 in FIG. 1A may incorporate this removable modular tubular extension. In an intubated state, the device will be in attachment with the second embodiment, or third embodiment of the removable modular tubular extension shown in FIGS. 21 and 22. Shown in FIGS. 20 through 22, the removable modular tubular extensions 2000, 2100, and 2200 include a first extension tubular chamber 2005 and a second extension tubular chamber 2010. The first extension tubular chamber includes a first extension receiving section 2015 and a second extension receiving section 2020. The first extension tubular chamber defines the first channel 2025 that provides fluid communication between the second channel, the attachments, such as the endotracheal tube and the conduit of the ventilator, received by the first extension receiving section and the second extension receiving section. When inserted into the device, the second extension tubular chamber defines a portion 2030 of the second channel on the device.

Referring to FIGS. 35A through 35C, the removable modular tubular extension 2000 is shown according to additional example embodiments. The y-shaped extension includes a receiving section 3505 in fluid communication with the second extension tubular chamber 2010. The receiving section 3505 is configured for receiving a capsule 3508. Capsule 3508 is understood to represent any embodiment of a capsule consistent with the present disclosure. It is further understood, that capsule 3508 may represent and/or include, in certain embodiments, a medicine vial. A standard medicine vial, a prevalent form in which medications are often stored, typically consists of a cylindrical container made of glass or plastic with a sealed cap. These vials are designed to hold liquid or powdered medications and are available in standard volumes. Common volumes for standard medicine vials range from smaller 1-milliliter units to larger sizes, such as 10, 20, 30, or even 50 milliliters, allowing for the containment of various quantities of medication. This adaptability of the device and/or capsule 3508 to receive a standard medicine vial or other described capsules enhances the flexibility of the system, ensuring that it can be tailored to specific needs and applications in administering medication.

In certain embodiments, the receiving section may further include a cross section corresponding to the cross-sectional shape of the capsule to facilitate the insertion of the capsule into the device. In certain embodiments, the receiving section may also include electrical contacts on the interior surface of the receiving section to align with the electrical contacts on the capsule. Extension 2000 may further include a button 3450 being the button disclosed in the embodiment of FIGS. 34A through 34D and as described herein. Moreover, the device may include a pull tab electrical insulator 2305 as shown and described herein in reference to FIGS. 23 through 25.

The removable modular tubular extension may be comprised of metallic material such as carbon steel, stainless steel, aluminum, Titanium, other metals or alloys, composites, ceramics, polymeric materials such as polycarbonates, such as Acrylonitrile butadiene styrene (ABS plastic), Lexan™, and Makrolon™. Other materials having waterproof type properties. The removable modular tubular extension may be made of other materials and is within the spirit and the disclosure. The removable modular tubular extension may be formed from a single piece or from several individual pieces joined or coupled together. The components of the removable modular tubular extension may be manufactured from a variety of different processes including an extrusion process, a mold, casting, welding, shearing, punching, folding, 3D printing, CNC machining, etc. However, other types of processes may also be used and are within the spirit and scope of the present invention. The modular tubular extension, as an integral component of the medical device, can also be constructed from a variety of materials that conform to the stringent requirements of medical device applications. Examples of suitable materials include medical-grade plastics such as polyethylene (PE), polypropylene (PP), polyvinyl chloride (PVC), and thermoplastic elastomers (TPE). These plastics offer a combination of biocompatibility, flexibility, and case of manufacturing, making them well-suited for medical device tubing. Silicone, known for its excellent biocompatibility, high-temperature resistance, and flexibility, is commonly utilized in medical tubing and catheters. For applications requiring strength and durability, stainless steel may be employed due to its corrosion resistance. Titanium and titanium alloys, renowned for their strength, low density, and biocompatibility, find utility in medical implants. Nitinol, a shape memory alloy, is employed in devices necessitating dynamic shape changes. Biodegradable polymers like polylactic acid (PLA) and polyglycolic acid (PGA) are used for temporary medical devices that degrade over time. The choice of material for the modular tubular extension depends on factors such as the intended use, desired properties, biocompatibility, sterilization compatibility, and regulatory compliance, all of which ensure patient safety and device performance within the confines of medical device regulations.

It should be noted that the device may be comprised of the same materials as the modular tubular extension. The utilization of the same materials for both the modular tubular extension and the medical device holds significant importance within the present invention. Consistency in material composition ensures compatibility and minimizes the risk of material interactions or incompatibilities that could compromise device performance or patient safety. This approach assures biocompatibility throughout the device, reducing the likelihood of adverse reactions or complications. Moreover, employing identical materials simplifies manufacturing and processing, eliminating the need for additional material compatibility testing and streamlining production processes. From a regulatory perspective, employing consistent materials facilitates the submission and approval process, as it provides a clear and well-documented rationale for material selection and ensures compliance with relevant standards. By maintaining material consistency, the device's structural integrity, durability, and performance characteristics remain consistent, fostering reliability and enhancing the overall quality of the medical device.

In the second embodiment of removable modular tubular extension 2100, the second extension tubular chamber includes a first section 2105 and a second section 2110. The first section is configured to be received by the device and has an angle 2115 relative to the second section. Angle 2115 is approximately 135 degrees. The second section 2110 is perpendicular to the first extension tubular chamber such that the angle between the second section and the first extension tubular chamber is at angle 2120, which is approximately 45 degrees. This allows the atomized medication to travel through the second channel into the first channel such that the flow of fresh air can push the atomized medication upwards in the first channel. Shown in FIG. 22, the third embodiment of the removable modular tubular extension is similar to the second embodiment. However, the third embodiment includes a rotating element 2205 that alters angle 2115 between the first section and the second section. The rotating element allows the device and the tubular chamber to be positioned at an angle that is optimal for various positions of the patient.

In one embodiment, the second extension tubular chamber may include a variable angle and/or partial composition from a flexible material, thereby enabling a variable angle within the conduit. By incorporating a variable angle within the conduit, the invention provides increased flexibility and adaptability in fluid communication with the first extension tubular chamber. The conduit can be adjusted to different angles or orientations, accommodating diverse system configurations or specific requirements. This adjustability allows for precise routing of fluids, optimizing flow dynamics and enhancing the overall performance of the system. Furthermore, the conduit's composition may be comprised of a flexible material in at least a portion of the conduit, namely the portion requiring the variable bend and/or angle, which contributes to the variable angle capability. The flexible nature of the material enables the conduit to bend or flex at the desired angle, facilitating seamless fluid communication with the first channel. This flexibility allows for smooth and uninterrupted flow, minimizing pressure losses or restrictions within the system. The incorporation of a conduit with a variable angle and flexibility within the invention presents numerous advantages. It enables the adaptation of fluid routing to specific needs, optimizing system performance and efficiency. The variable angle capability ensures accurate and targeted fluid delivery, promoting precise control and distribution within the system. Additionally, the flexibility of the conduit material enhances durability and resilience, mitigating the risk of damage or failure during operation.

Next, in step 2904, the user. Inserts the capsule containing the medication into the device, or base unit, having the tubular chamber. In step 2906, the user removes the stop on the capsule that inhibits the first chamber from translating relative to the second chamber. In step 2908, the user applies a second force to the first chamber causing the first chamber to translate relative to the second chamber rupturing a membrane disposed between the first chamber and the second chamber thus providing fluid communication between the first chamber and the second chamber. In step 2910, the user provides power to the atomizer by removing an insulator that prevents electrical communication between the atomizer and a power source. In step 2912, the processor activates the atomizer to atomize the medication to generate at least one atomized medication comprising a plurality of particles. Each particle of said plurality of particles is at most four microns in diameter. In step 2914, gravity causes the liquid formulation to move from the first chamber to the second chamber. In step 2916, the device dispenses the atomized medication from the capsule into the tubular chamber. In step 2918, the user applies a force to a mask that is positioned over the patient's nose and the patient's mouth and in fluid communication with the tubular chamber. In step 2920, the user administers the atomized medication to the patient using the device by at least partially deflating a resilient air bladder in fluid communication with the tubular chamber causing air within the resilient air bladder to be conveyed from the resilient air bladder into the tubular chamber.

With reference to FIG. 29B, in step 2922, the user determines that the patient is in the conscious state. Therefore, the user must convert the device such that the patient can inhale the atomized medication by themselves. Next, in step 2924, the user removes the resilient air bladder from the second extension receiving section. In step 2926, the user attaches a cap to cover the second extension receiving section. Steps 2922 through 2926 convert the device into the device illustrated in FIGS. 11A through 12, in which a cap is covering the first receiving section and a mouthpiece or mask is in attachment with the second receiving section. In step 2928, the user administers the atomized medication to the patient using the device by conveying the at least one atomized medication from the tubular chamber though the mouthpiece that is in fluid communication with the tubular chamber or the mask that is positioned over the patient's nose and the patient's mouth and in fluid communication with the tubular chamber.

With reference to FIG. 29C, in step 2930, the user removes the mask or the mouthpiece from the first extension receiving section. In step 2932, the user removes the cap or the resilient air bladder from the second extension receiving section. In one embodiment, it is understood that instead of removing the resilient air bladder, mouthpiece, cap, and/or mask, the method 2900 may include removing the removable modular tubular extension from the device and inserting a second removable modular tubular extension. Then, the user inserts the second modular tubular extension into a device receiving section such that the second extension tubular chamber is in fluid communication with the second channel of the device and such that the second extension tubular chamber defines a portion of the second channel. The second removable modular tubular extension may be those of embodiments shown in FIGS. 21 and 22. If the third embodiment of the removable modular tubular extension is inserted, then the user adjusts the angle (2115 in FIG. 22) between the first extension tubular chamber and the second extension tubular chamber of the second extension tubular chamber to a predetermined angle. Additionally, the user locks the angle between the first section and the second section at the predetermined angle. In step 2934, the user attaches an endotracheal tube to the device so that endotracheal tube is in fluid communication with the tubular chamber and the conduit. In step 2936, the user attaches a conduit in fluid communication with an air outlet of a respiratory support device to the second extension receiving section. Steps 2930 through 2936 convert the device to the example embodiment shown in FIG. 19. These steps allow the device to be used when the patient is in an intubated state.

Referring now to FIGS. 30A and 30B, views of a capsule 3000 for use with a medical device for administering at least one atomized medication to a patient are shown, according to an example embodiment. The capsule system includes at least one chamber, the medication 510 disposed within the chambers, and an atomizer 1715 at a lower end portion 3010 of the capsule system. The atomizer converts liquid into a fine spray or mist. The chambers include a first chamber 1705 disposed above a second chamber 1710. The first chamber includes the medication, and the second chamber includes the atomizer. The atomizer is disposed proximate to a bottom portion 3015 of the second chamber. The configuration of having the first chamber containing the medication situated above the second chamber with the atomizer ensures that the medication flows or is directed from the first chamber into the second chamber by the force of gravity. The materials for the chambers may include, but are not limited to, biocompatible materials that are suitable for storing medication and for constructing an atomizer, such as medical-grade plastics, stainless steel, ceramics, or other non-reactive materials. Two separate chambers facilitate case of cleaning or replacing parts, reduce the risk of contamination, and contribute to a more compact and streamlined design of the capsule system.

The second chamber includes tapered sections 1750 to direct the at least one medication toward the mesh of the atomizer. The tapered wall sections refer to a compartment or space featuring a sloping or gradually narrowing wall within its structure. This specific design is implemented to guide or direct the medication toward the atomizer. The tapered wall section serves to concentrate the medication flow towards the atomizer, thus enhancing the atomization process and ensuring that the medication is uniformly spread. This optimizes the flow path of the medication, thus potentially improving the consistency and efficiency of the atomization process, and thereby enhancing the overall effectiveness of the medication delivery.

The capsule system further includes a stopper 3020 in fluid communication with the second chamber. The stopper is a self-sealing rubber stopper that covers the open side of the first chamber. The materials for this self-sealing stopper may include, but are not limited to, elastomers, silicone rubber, or other flexible and resilient materials that provide a tight seal while allowing temporary access when needed. In a medical context, a self-sealing rubber stopper is used to seal containers like vials or chambers, and it can be punctured by a syringe or other device to access the contents without permanently compromising the seal. The stopper is self-sealing, meaning that it automatically returns to a closed or sealed position after being accessed or penetrated, such as during a refilling process. This ensures that the integrity of the chamber's contents is maintained without requiring manual resealing. The materials for this self-sealing stopper may include, but are not limited to, elastomers, silicone or butyl rubber, or other flexible and resilient materials that that have been carefully formulated to offer the right balance of elasticity, resilience, and chemical resistance. These materials provide a tight seal while allowing temporary access when needed. The material must be compliant with pharmaceutical or medical standards. The rubber stopper enhances the usability of the device, particularly in scenarios where repeated access to the chamber is required, such as for refilling. It ensures a consistent and secure seal, thereby maintaining sterility and preventing leaks, and it simplifies the handling of the device, reducing the potential for user error.

The capsule system also includes a housing 3025 that substantially encloses the chambers. The housing is a protective case or enclosure designed to contain and protect internal components. This provides a controlled environment for the medication contained within the chamber. The composition of the capsule and the chamber may include, but are not limited to, materials suitable for medical applications, such as medical-grade plastics or bio-compatible metals, ensuring safe and effective operation within the medical device environment.

The capsule includes a capsule width 3030 and the chambers includes a chamber width 3035 such that the chamber width substantially spans the capsule width. In some embodiments, the chamber width may span at least 50 percent of the capsule width. In other embodiments, the chamber width may span at least 50 percent of the capsule width. In this embodiment, the walls of the chambers are designed to abut the walls of the housing, thereby forming a connection that often provides stability, containment, and precise alignment within the system. This alignment may facilitate the controlled flow of medication, prevent leakage, and contribute to the correct orientation and functioning of other components, such as sensors, atomizers, or electrical contacts. The chambers substantially occupy a cavity with the capsule without any voids between a chamber wall of the chamber and a housing wall of a housing of the capsule. This means that the size of the chamber, as determined by its transverse dimension or diameter, is almost as large as that of the capsule system itself. Therefore, the chamber effectively maximizes the available internal space of the capsule, minimizing any wasted or unused space within the capsule system. This arrangement of the chamber width substantially spanning the capsule width represents an improvement over prior art in the field of medical devices. It allows for efficient use of space within the capsule system, potentially accommodating larger medication volumes or multiple functionalities within the same capsule size. This leads to increased utility of the medical device without necessitating a proportional increase in its physical size, thus improving the overall efficiency and user experience.

A membrane 1720 preventing fluid communication is disposed between the first chamber from the second chamber. The membrane is a thin, flexible layer or barrier that prevents the passage of liquid. The membrane may include, but is not limited to, a range of impermeable materials that are compatible with the medication and the atomizer, such as certain plastics, elastomers, or composite materials that are engineered to provide a secure yet breakable or penetrable barrier. The membrane allows precise control over the release and flow of medication into the atomizer. This can lead to reduced risk of contamination or spillage and the possibility of more sophisticated release mechanisms that can be tailored to specific medical needs or patient preferences.

At least one rupturing element is in attachment with the first chamber 1705 or the second chamber 1710 such that the at least one rupturing element configured to engage the membrane 1720 when a first force is applied to translate the first chamber relative to the second chamber 1710. This rupturing element is configured to engage with a membrane that separates two chambers. Engagement occurs when a predetermined force, termed a first force, is applied, translating the first chamber relative to the second. This relative movement prompts the rupturing element to come into contact with the membrane, puncturing or tearing it to allow fluid communication between the chambers. Such a mechanism can enable the flow of medication or another substance from one chamber to the other or activate specific functionalities within the medical device. Compared to previous designs, the careful configuration of the rupturing element for engagement with the membrane in response to a specific force represents a controlled, precise mechanism for regulating fluid communication within the system. It allows for more control over medication dosage, timing, or mixing of components and enhances safety by ensuring that the membrane is ruptured under controlled conditions.

When the first chamber is pushed towards the second chamber, the rupturing elements pierce and break the membrane such that the membrane becomes a ruptured membrane 3040 to allow the medication to flow out of the first chamber and into the second chamber. A stop 1725 is disposed between the first chamber and the second chamber inhibiting the first chamber from translating relative to the second chamber.

The rupturing element may be composed of materials that provide the necessary strength, sharpness, and resilience for the intended function. Materials such as stainless steel, hard plastics, or other biocompatible materials may be used to provide the necessary strength, sharpness, and resilience to ensure that the rupturing element performs effectively without compromising the integrity or sterility of the contents.

The capsule further includes a plug 3045 disposed at the lower end portion 3010 of the capsule system. The plug includes a plug receiver 3046 and a plug cap 3048. The plug's primary function is to provide a seal or barrier at the lower end portion. The plug cap includes a protruding section 3050 configured to be received by a dimple 3055 of the plug receiver. The diameter of the dimple is slightly smaller than the diameter of the protruding section 3050 such that the protruding section is tightly received by the plug dimple 3055. This provides a tight seal that prevents leakage of liquid solution. By being strategically positioned, the plug prevents the atomizer from leaking medication and contamination from external sources. Its role in the capsule system ensures that the contents of the chamber(s) are managed according to the device's operational requirements. The plug offers a targeted solution to potential issues related to leakage, flow control, and hygiene. Its presence thus contributes to the overall efficiency and effectiveness of the capsule system, marking an improvement over previous designs in the field. The plug may be constructed from, but is not limited to, various materials, such as rubber, silicone, or other elastomers, which offer properties like flexibility, resilience, and resistance to chemical interaction with the medication. The selection of materials would depend on the specific demands of the capsule system and its intended medical application.

Referring now to FIGS. 31A through 31D, views of the capsule systems 3100, 3101 for use with a medical device for administering at least one atomized medication to a patient are shown, according to an example embodiment. FIG. 31A is a cross-section of a side view of a capsule system 3100, according to an example embodiment. FIG. 31B is a cross-section of a side view of the capsule system 3100, wherein the removable container is inserted, according to an example embodiment. Capsule system 3100 includes a first chamber 3105 having an open top side and a first chamber width that substantially spans a capsule width. A rupturing element 3110 is disposed at least proximate to the first chamber. An atomizer 1715 is disposed at a lower end portion of the capsule system.

The capsule system 3100 also includes a removable container 3115 including a removable container width. The removable container is a vial having a fluid volume of 10 milliliters. Other fluid volumes may be used and are within the spirit and scope of the present invention. A seal 3120 is on the removable container. A second chamber 3125 is positioned within the removable container. The medication 510 is disposed within the second chamber. The removable container is disposed within the first chamber 3105 through the open top side of the first chamber. The container width spans substantially the first chamber width. When a force is applied on the removable container towards the first chamber, the rupturing element penetrates the seal to provide fluid communication between the first chamber and the second chamber.

The removable container functions as a specialized chamber within the capsule system, allowing for specific medications or substances to be enclosed and protected. Its removable nature offers flexibility in handling, refilling, or changing the contents without altering other parts of the system. Users of the capsule may have multiple removable containers, each labeled and containing different medications similar to commonly used medical vials. Therefore, the removable containers allow for efficient replacement or replenishment of medication for the capsule. When inserted, it integrates seamlessly with other elements such as the rupturing element and first chamber, providing a cohesive function within the overall medical device. The removable container presents a significant advancement in managing and delivering medication in medical devices. By facilitating easy insertion and removal, the container enables efficient handling, customization, and maintenance of the system. The feature of being removable allows for easier cleaning, sterilization, or replacement, thereby enhancing usability and hygiene. Its precise construction to fit within the existing chambers ensures that the functionality and integration within the device remain consistent, thus overcoming limitations found in previous designs. The removable container may be comprised of materials suitable for medical applications, ensuring biocompatibility, strength, and resistance to contamination. This could include medical-grade plastics, glass, or other sterilizable materials that comply with relevant regulatory standards. However, other materials may be used and are within the spirit and scope of the present invention.

FIG. 31C is a side perspective view of the capsule system 3101, according to an example embodiment. FIG. 31D is an exploded perspective view of the capsule system 3101, according to an example embodiment. The housing 1835 includes an asymmetrical transverse cross-sectional shape. The shape of the housing of the capsule system, when cut or viewed in a plane perpendicular to its length 3135, is not symmetrical about its center. This unique configuration ensures a specific orientation when the capsule is inserted into a medical device, allowing for accurate alignment and connection with other components within the system. The housing may be constructed from, but is not limited to, materials suitable for medical applications, such as medical-grade plastics, stainless steel, or other materials that meet necessary biocompatibility and sterility requirements. The distinct asymmetrical design of the housing provides improvements over prior art by ensuring precise alignment and engagement with corresponding components, thereby reducing the risk of improper installation or handling, and enhancing the overall functionality and reliability of the capsule system. The portion of the housing that creates the asymmetrical shape may harbor the main electrical components of the capsule system, such as the sensors, electrical contacts, and/or processor.

The capsule system 3101 further includes at least one electrical contact 1820 and at least one sensor. The sensor is a fluid sensor that can detect various properties related to the fluid, such as its level, flow rate, or presence. The fluid sensor is configured to detect and monitor the level or presence of medication within the first chamber and/or second chamber of the capsule system. The fluid sensor operates in coordination with other components to ensure proper dispensing of medication. By continually monitoring the fluid level, it provides real-time feedback, enabling precise control over the dosage and alerting the system if the medication reaches a critical level. The fluid sensor adds an additional layer of control and safety in the medication administration process, reducing the risk of administering incorrect dosages, and enhancing the ability to provide tailored treatment regimens. The capsule system 3101 may include a fluid sensor for the removable container 3115 and a second fluid sensor for the first chamber 3105. The electrical contacts are in electrical communication with a power source. The electrical contacts refer to the conductive interface designed to establish a connection within an electronic circuit. The electrical contacts may be composed of, but are not limited to, conductive materials such as copper, gold, or alloys, providing efficient energy transmission without significant loss. This provision for electrical communication with a power source offers improvements over prior art by allowing for consistent and controlled operations of the capsule system, enhancing both reliability and performance, particularly in comparison with manually operated or less sophisticated electronically controlled systems.

Figure 32:
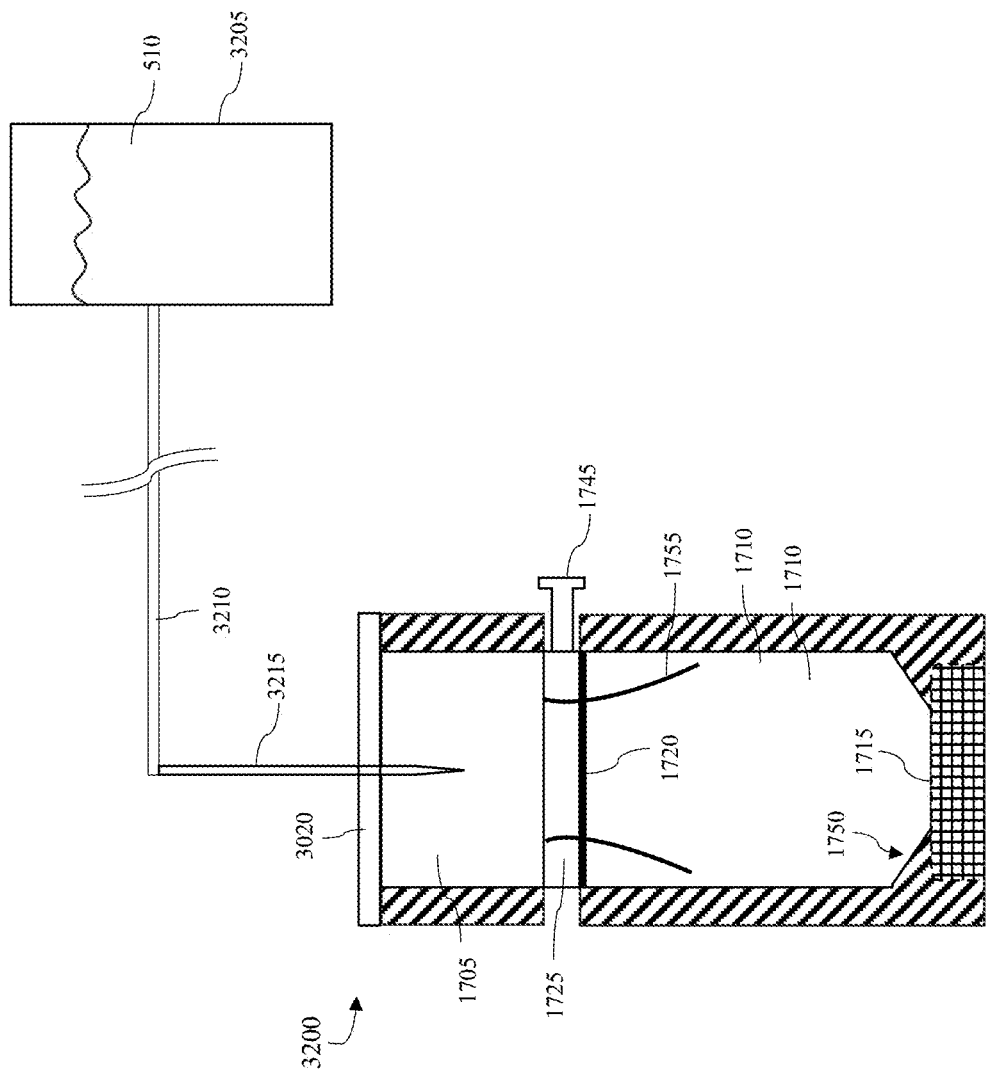
FIG. 32 is a cross-section of a side view of the capsule system, wherein an external container is in fluid communication with the capsule system, according to an example embodiment.
Figure 34B:
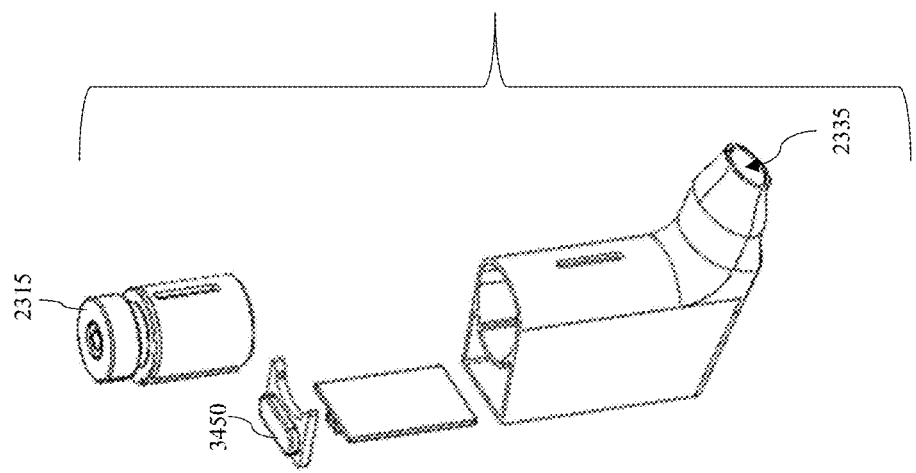
FIG. 34B is an exploded perspective view of the medical device, according to an example embodiment.
Figure 34A:
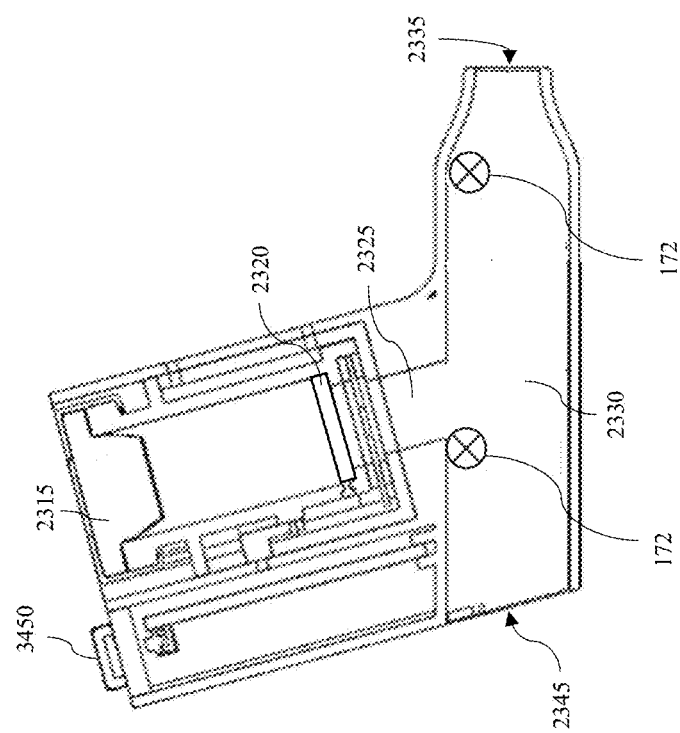
FIG. 34A is a cross-section of a side view of the medical device, according to an example embodiment.
Figure 34D:
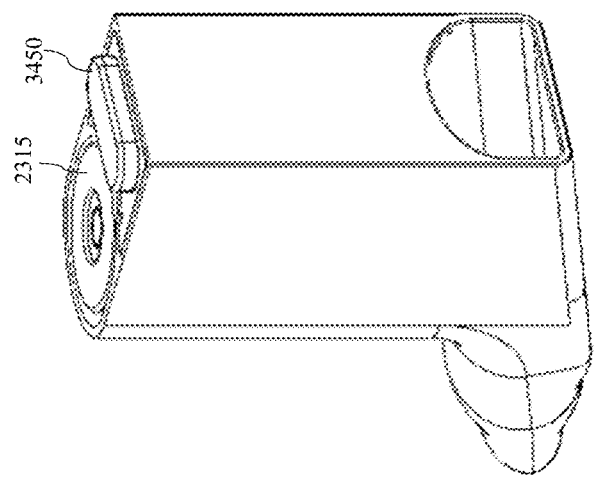
FIG. 34D is a perspective back view of the medical device, according to an example embodiment.
Figure 34C:
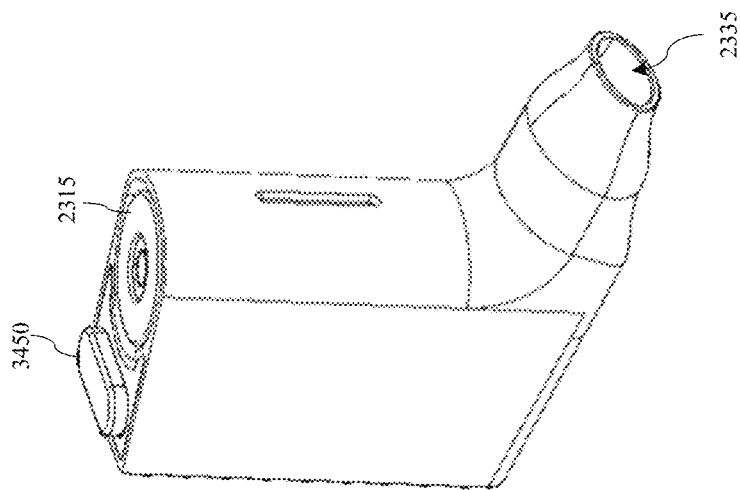
FIG. 34C is a perspective front view of the medical device, according to an example embodiment.

With reference to FIG. 32, a cross-section of a side view of the capsule 3200, wherein an external container 3205 is in fluid communication with the capsule system, is shown, according to an example embodiment. The first chamber 1705 is in fluid communication with an external container via an elongated tube 3210. The external container has the medication 510. In some embodiments, the external container is an intravenous line ("IV") solution bag that holds the medication solution. The external container is an intravenous bag or infusion bag being a sterile, flexible container holding fluids, medications, and/or other solutions. The external container may be made of medical-grade plastic materials that are compatible with the solutions they contain. The external container and tube enable the controlled transfer of medication or other substances. This connection allows the capsule system to draw the medication from an external source, either continuously or in measured quantities, depending on the requirements of the medical device and treatment protocol. The elongated tube serves as the conduit for this transfer, maintaining a controlled and sterile pathway between the components.

The most common IV bags are typically made of polyvinyl chloride (PVC) or polyolefin, which are flexible, transparent, and resistant to chemical interactions with the fluids and medications inside. The elongated tube and connecting elements that facilitate this fluid communication may be constructed of biocompatible and inert materials, such as medical-grade silicone, polyurethane, or other suitable polymers. These materials ensure that the integrity and purity of the medication are maintained during transfer.

The elongated tube provides fluid communication between the first chamber and the external container. The fluid and/or the medication from the bag flows through tubing connected to the IV catheter. The elongated tube is in attachment with the first chamber of the capsule. In one embodiment, a medical needle 3215 is attached to the distal end of the elongated tube, and the needle is inserted into the self-sealing rubber stopper of the capsule and partially into the first chamber. The medication will continuously drip, at an adjustable flow rate, into the at least one chamber of the capsule.

The external container and elongated tube permit the medical device to access larger volumes of medication or other fluids stored externally, thus enabling longer or more complex treatment regimens without the need to refill the internal chamber frequently. The ability to connect with external containers also allows for versatility in medication types and concentrations, providing customization to individual patient needs. By maintaining a secure and sterile pathway for fluid transfer, this embodiment ensures safety and efficiency in delivering medication.

With reference to FIG. 33, a diagram of the capsule system 3300 for use with a medical device for administering atomized medication to a patient is shown, according to an example embodiment. The capsule system further includes an electrical conductor 3305 connecting the capsule to a remote-control device 3315 such that the capsule includes a port 3310. The remote-control device 3315 may be the medical device or base unit that includes a display, a processor, and a power source. In certain embodiments, the medical device may have a port 3320. The display allows for visual feedback and interaction, the processor controls the operations and data processing, and the power source provides energy for the system. The conductor enables data and control signals to be sent between the capsule and the remote-control device, ensuring synchronized operation and real-time control of the medication administering process. In certain embodiments, the remote-control device is separate from the device which receives the capsule. A remote-control device typically refers to an electronic device used to operate another device from a distance, typically wirelessly. Within the capsule system, the remote-control device interacts with the capsule through an electrical conductor connecting to a port. It may comprise elements such as a display, a processor, and a power source. This integration allows healthcare providers or patients to monitor, adjust, and control the capsule system's operation, facilitating tailored treatment regimens and responsive care.

An electrical conductor is any material or substance through which electric current can pass easily. It includes not only wires and cables but also components like metal bars, plates, or even certain liquids and gases. Conductors are characterized by their ability to carry electrical charges with minimal resistance. The capsule may include more than one conductor as well. The electrical conductor may be an electrical lead. An electrical lead is a conductor or wire that is used to connect an electrical device to a power source, such as a charger connecting a device to an outlet—or in the context of this invention, connect the capsule to the medical device. The electrical conductor may be made from, but are not limited to, materials such as copper, silver, or gold, known for their high electrical conductivity and reliability. The insulation surrounding the conductor would typically be made of materials resistant to medical environments, such as Teflon or other medical-grade polymers.

The port is a specific interface or receptacle on an electronic device or apparatus that facilitates the transfer of data, electrical signals, power, or other information between the device and external components, such as cables, connectors, or peripherals. The port typically comprises a well-defined physical and electrical structure designed to accommodate compatible connectors, ensuring secure and reliable connections. The structure of the port may correspond to the electrical lead such that the port is configured with a compatible shape, size, and electrical layout that matches the design of the electrical lead. The port typically includes male or female terminals, pins, or contacts, strategically positioned within the receptacle to match the corresponding connectors or plugs on the electrical lead. The electrical lead, in turn, features complementary male or female connectors designed to fit precisely into the corresponding terminals of the port. The port's structural design may also incorporate additional features such as locking mechanisms, shielding, or protective covers to enhance durability, prevent accidental disconnections, and safeguard against potential hazards. It is understood that the term "port" should be construed to encompass a broad range of configurations, including but not limited to, input/output (I/O) ports, charging ports, data transfer ports, audio ports, video ports, or any other interface specifically engineered to enable communication, interaction, or power exchange between the capsule and external entities or devices.

The electrical conductor and ports enhance the functionality, flexibility, and user experience of the medical device. Unlike previous designs that may rely solely on manual control or limited interface, this configuration allows for precise control, monitoring, and customization of the treatment. The integration with a remote-control device equipped with a display, processor, and power source enables a more sophisticated and tailored approach to medication administration, potentially improving treatment outcomes, patient compliance, and healthcare professionals' efficiency. This represents a significant advancement over prior art, adding value to the medical field by increasing the utility and effectiveness of the capsule system. For example, this embodiment allows the capsule and the modular tubular extension to rest on the patient without the weight of the remote-control device, which can be placed elsewhere.

FIG. 36L is a flowchart diagram illustrating steps for a method for conveying substance to a subject using the removable air unit. The method is explained with reference to FIGS. 36D through 36F. In an example, the term subject includes a user, a plant, agricultural crops, ornamental plants, trees, shrubs, and grasses, among others, and an animal. In step 3656, the method initiates with providing a removable capsule having an atomizer. The capsule is a container for the medication but also houses the atomizer for creating a fine mist or aerosol of the medication, facilitating more efficient and targeted delivery within the body. As shown in FIGS. 36D and 36F, the removable capsule 3610 is inserted within the channel 3629. The atomizer 3626 provides the substance that can be administered in a form that is readily absorbed by the body's tissues.

In an embodiment, the substance comprises a fertilizer material for delivering in mist form to plants, providing essential nutrients to plants through a fine spray or aerosol. This provides a more direct and efficient uptake of nutrients by the plants' leaves and roots. The device may be used in agricultural practices such as hydroponics or aeroponics, that utilizes water-soluble fertilizers dissolved in water to form a nutrient-rich solution. Examples of such fertilizer materials include but are not limited to, nitrogen, phosphorus, and potassium compounds, which are crucial for plant growth, along with trace elements like iron, manganese, and zinc. The delivery mechanism involves nebulizing the solution into tiny droplets that can be evenly distributed over the plants, allowing for immediate absorption through the stomata on the leaves, and the roots. The mist form of the fertilizer optimizes water and nutrient use and promotes healthier, more robust plant growth by ensuring that plants receive a balanced supply of essential nutrients directly to their active growth sites.

In the next step 3658, the process involves inserting the removable capsule into a channel specifically designed within the base unit of the device. This step ensures that the capsule is correctly positioned to interface with the device's internal systems, such as the mixing chamber and the atomizer activation mechanism. The channel within the base unit accommodates the capsule snugly, securing it in place to prevent any displacement during operation and ensuring an optimal alignment with the device's delivery and mixing systems. After insertion of the capsule, step 3660 involves dispensing, using the atomizer, the substance from the removable capsule to the mixing chamber of the base unit. FIG. 36F shows the atomized substance, such as medication particles 3630 in mist form that is dispensed from the atomizer 3626 to the mixing chamber 3624. This action dispenses the medication in a finely atomized form, directing it into the mixing chamber of the base unit. The mixing chamber serves as the area where the atomized medication is prepared for inhalation or delivery by mixing with the air molecules 3632, ensuring a uniform and controlled mixture. Thereafter, in step 3662, using the removable air mover unit, causing air and the substance within the mixing chamber to be conveyed from the mixing chamber to the conduit. FIG. 36F shows the removable air unit 3606 blowing air in the direction of arrows 3636 towards the opening 3634. The air mover unit is integral to the system, propelling air through the mixing chamber, thereby conveying the atomized medication from the mixing chamber 3624 into the conduit 3603 via the opening 3634. The conduit then serves as the passage through which the medication-air mixture is delivered to the user. This sequence of steps highlights a methodical approach to medication delivery, emphasizing precision, control, and patient safety in administering treatments. As noted above, additional application of the device are covered within the scope of the present invention. The device can also be used to administer substances for therapeutic and cosmetic purposes. In addition to health-related treatments, the device can be utilized for cosmetic treatments, providing a versatile tool for both medical professionals and for personal care and cosmetic enhancements. Therapeutically, it can administer medications such as bronchodilators and corticosteroids for respiratory conditions, insulin for diabetes management, and antibiotics or antivirals for infections, providing a non-invasive route of administration that enhances patient comfort and compliance. Additionally, it can deliver pain management medications, offering an alternative for those seeking quick relief without the need for oral intake or injections. On the cosmetic front, the device can be used to apply substances like hydrating mists, anti-aging treatments, and targeted skin serums. These cosmetic applications benefit from the atomization process, which allows for a finer and more even distribution of the product, potentially increasing absorption and efficacy. Whether for managing health conditions or enhancing beauty routines, this device opens up new possibilities for delivering a variety of substances directly and efficiently to the user.

FIG. 36M is a flowchart diagram of a method for administering the medication to the user from the capped chamber. In step 3664, the method includes attaching a cap to cover an opening of the base unit, for a capped chamber. In an example, the cap is the removable cap 3640 that is fitted inside the opening 3608, as shown in FIG. 36G, to completely cover the opening and form the capped chamber. In the next step 3666, the method includes dispensing, using the atomizer, the substance from the removable capsule to the capped chamber of the base unit. The process of dispensing medication from the removable capsule into the capped chamber of the base unit via an atomizer ensures precise and efficient delivery of treatment. The atomizer within the capsule transforms the substance into a fine mist, facilitating its controlled release into the capped chamber. The atomized medication particles 3630 are shown to be introduced in the mixing chamber 3624 of FIG. 36F. Following atomization, the atomized substance, such as the medication is introduced into the mixing chamber, where it combines with air. The introduction of the atomized medication into the mixing chamber creates a pressure on the mixture and acts as a driving force, propelling the mixture through the conduit in a controlled manner. This method ensures that the medication is not only effectively atomized for optimal delivery but also efficiently conveyed through the device, ensuring a precise and consistent dosage reaches the user.

In the next step 3668, the method involves administering the substance to the user by conveying the substance from the capped chamber. This chamber, designed to temporarily hold the atomized medication, serves as a mixing area where the substance or the medication is stabilized and readied for patient administration. The method optimizes the delivery of medication by ensuring a consistent dosage and improves patient comfort by providing a non-invasive means of administration of the medication. The capped chamber ensures that the mixture is contained securely, minimizing loss or dispersion of the medication into the surrounding environment, thereby maximizing the efficiency of the delivery of the medication.

FIG. 36N illustrates an embodiment having a skin care cup and an elongated tube attached to the base unit of the device. As shown, the skincare cup 3674 is attached to one end of the elongated tube 3672, and the elongated tube 3672 is attached to the base unit of the device 3600 via the adaptor 3652. The adaptor is attached to the conduit 3603 of the device. It is noted that the elongated tube is attached to the device via the adaptor and the elongated tube. In alternative embodiments, the elongated tube can be directly inserted into opening 3634 of device 3600 for attachment.

The skin care cup 3674 has a sealing member 3676 to form a seal with a skin of the user 3670 when the substance is applied on a portion of the skin 3671 using the device. It is noted that the substance can be pharmaceutical, therapeutic, or cosmetic compounds, that are directly to the user's skin, for treating various skin conditions such as lesions, boils, sores, acne, or allergies. Other skin conditions, such as eczema, characterized by patches of itchy, inflamed skin, psoriasis, and rosacea, fine lines, wrinkles, and age spots, can also be treated using the device. For instance, a pharmaceutical substance could be an antibiotic solution targeted at bacterial skin infections, effectively reducing inflammation and promoting healing. A therapeutic substance might include aloe vera or hyaluronic acid-based serums, renowned for their soothing and moisturizing properties, thereby aiding in the recovery of damaged skin and enhancing hydration. On the cosmetic front, substances like vitamin C or retinol serums could be atomized through the device, offering anti-aging benefits, improving skin texture, and reducing the appearance of fine lines and discoloration. The versatility of this device lies in its ability to atomize these substances into a fine mist, ensuring deep penetration and uniform distribution across the affected area, thereby maximizing the efficacy of the treatment and offering a tailored approach to skin care. This multifaceted device, with its ability to deliver a variety of substances, presents a revolutionary method for addressing a wide spectrum of skin issues, providing users with a personalized and effective skin care solution.

FIG. 36N shows the substance particles 3678 is released on the affected skin portion having lesions marks 3680 on the skin. The specific portion of the skin affected by the condition is identified, such as the portion of the skin having the lesion marks 3680. Subsequently, the sealing member of the skin care cup is positioned over the identified area. The sealing member is then engaged to form a tight seal against the skin, ensuring that the portion in contact is effectively isolated for treatment. Once a secure seal is established, the chosen substance, be it a pharmaceutical, therapeutic, or cosmetic compound, is atomized and released into the sealed area, facilitating direct application to the affected skin. The substance released is thoroughly absorbed by the skin, ensuring that the active ingredients are delivered precisely for healing and rejuvenation of the skin.

The sealing member creates an airtight environment over the treated skin area. This isolation facilitates a concentrated and uninterrupted interaction between the skin and the therapeutic or cosmetic substance being administered. By preventing the dispersion of the substance into the surrounding air, the sealing ensures that a maximum amount of the active ingredients directly contacts the skin, enhancing absorption and efficacy. Moreover, this method minimizes external contaminant exposure and reduces the risk of evaporation of the substance, ensuring that the skin receives a full dose of the treatment. This targeted delivery improves the effectiveness of the treatment for various skin conditions and maximizes the efficient use of the substance.

In an embodiment, the device is used for delivering substance, such as a pharmaceutical, a therapeutic or a cosmetic substance. As noted above, pharmaceutical substances may include a medication, such as antibiotics or antifungal solutions. In some embodiments, the medication may also include therapeutic substances including a regenerative medication targeting treatment of tissue repair and regeneration in the user. Regenerative medications include bioactive agents or biological agents capable of stimulating cellular growth, differentiation, and repair. The medication may comprise a combination of growth factors, cytokines, stem cells, or other agents known to facilitate tissue regeneration and repair. In another embodiment, the medication comprises one of peptides, proteins, growth factors, cytokines, exosomes, and extracellular vesicles derived from human mesenchymal stem cells suspended and/or dissolved in an aqueous medium. In another embodiment, the medication is an aqueous suspension and solution comprising cells, cellular byproducts, and cell-derived products. The cells, the cellular byproducts, and cell-derived products are stem cells. The bioactive agent and biological agent may be used interchangeably throughout the document, as the biological agent may have a bioactive effect in some embodiments. In an embodiment, the biological agent including one of stem cells, or exosomes are delivered in a mist form directly to the skin or other targeted regions, such as teeth in the mouth or in open heart surgeries. As noted above, exosomes are small extracellular vesicles, approximately 30 to 150 nanometers in diameter, that are secreted by virtually all cell types. The exosomes provide cell-to-cell communication, carrying proteins, lipids, and nucleic acids between cells. Exosomes can carry and protect bioactive molecules and function as a medium for delivering therapeutic substances to specific areas of the body. Administering exosomes using the described medical device involves atomizing the exosome-containing solution or substance into a fine mist that can be directly applied to the skin or affected regions. The device's sealing member ensures that the exosome-laden mist is confined to the target area, enhancing the local concentration of exosomes and facilitating their absorption and interaction with the skin cells. This method of delivery is particularly beneficial for skin rejuvenation, wound healing, and the treatment of various dermatological conditions. Exosomes can promote tissue repair and regeneration by delivering growth factors, cytokines, and genetic materials that stimulate the body's natural healing processes. Additionally, the targeted delivery of exosomes via the device minimizes wastage and ensures a high efficiency of treatment, providing a focused approach that enhances the therapeutic outcomes. This innovative application of exosome technology heralds a new era in personalized and precision medicine, offering a powerful tool for addressing a wide range of health concerns.

In one embodiment, the device enables the application of exosomes to the affected skin portion, as depicted in the figure, while in other embodiments, it facilitates the application to different areas of the body, adapting to a wide range of treatment needs. In an embodiment, exosomes can be applied to external and internal regions of the vagina, including the skin around the vagina, offering significant therapeutic benefits. The application of exosomes to the vaginal areas promotes tissue regeneration, enhances cellular communication, and supports healing of mucosal injuries. Further, the anti-inflammatory properties of exosomes reduces inflammation and preventing infections in these sensitive areas. Apart from vaginal health, such an application of exosomes allows for the treatment of other delicate regions, such as oral mucosa, internal wounds, or even the scalp, where exosomes can aid in tissue repair, soothe irritation, and stimulate regenerative processes.

In one embodiment, the application of exosomes to treat affected skin areas is using a spray mechanism that atomizes the exosome-containing solution into a fine mist. This method allows for a gentle and even distribution of exosomes over the skin, ensuring that the therapeutic agents are directly and efficiently delivered to the target area. Spraying the mist enables a non-invasive, painless application process, ideal for sensitive or damaged skin, and enhances the absorption of exosomes into deeper layers of the skin. The spraying maximizes the contact between the exosomes and the skin cells, facilitating the delivery of proteins, RNA, and other bioactive molecules to promote healing, reduce inflammation, and encourage tissue regeneration.

In another embodiment, the device may be used to deliver stem cells and regenerative medicines directly to targeted areas of the body. Examples of stem cells that may be delivered include mesenchymal stem cells (MSCs), that promotes tissue repair, and induced pluripotent stem cells (iPSCs), that can be generated from adult cells and have the potential to treat a wide range of diseases. As for regenerative medicines, growth factors and cytokines may be administered to stimulate the body's healing processes. The device atomizes these stem cells or regenerative medicines into a fine mist, allowing for precise application and deep penetration into the skin or affected tissues. The stem cells and regenerative medicines repair damaged tissues, reduce inflammation, and improve the functionality of organs and tissues. This delivery system maximizes the potential benefits of these treatments by ensuring targeted, efficient, and minimally invasive application.

Referring now to FIG. 37, a diagram of a system 3700 for veterinary administration of at least one medication to an animal is shown, according to an example embodiment. The animal is a mammal. More specifically, the animal may be cattle. In the present embodiment, the animal is a horse 3705. In other embodiments, other animals may be treated using system 3700. System 3700 includes the medical device in fluid communication with the mask 3710 and the resilient air bladder 102. In some embodiments, instead of the resilient air bladder, the system may be in attachment with a respiratory support device configured to provide airflow to the system. The mask 3710 is a standard medical mask that is commonly used in the veterinary field. The mask 3710 is configured to cover the muzzle 3715 of the horse. The muzzle, or snout, of an animal is the projecting jaws and nose of the animal. Other types of medical masks may be used depending on the animal being treated.

The medication may be an aqueous suspension or a solution including at least one of cells, cellular byproducts, and cell-derived products. The aqueous suspension refer to a liquid medium, primarily water-based, in which the cells or cell-derived materials are suspended or dissolved. Cells may include, but are not limited to, various types of biological cells, such as somatic cells, stem cells, or even specialized cells like nerve or muscle cells. Cells refer to living cells, such as stem cells, which can be used for regenerative therapies. Cellular byproducts may include, but are not limited to, elements like enzymes, waste products, or signaling molecules produced by cells. Cell-derived products may include molecules synthesized by cells, such as proteins, lipids, or nucleic acids. The cells can be of any type suitable for veterinary applications, with properties that are deemed therapeutic. Cell byproducts are substances produced naturally by cells and may have therapeutic effects. Examples could include enzymes or antibodies that can have a direct therapeutic action or facilitate other biological processes beneficial to the animal's health. Cell-derived products are materials produced from cells but may not be naturally occurring. For example, proteins engineered for specific therapeutic actions would fall under this category. The use of an aqueous suspension as the medium for these cellular components offers significant advantages over prior art, such as improved bioavailability and rapid onset of therapeutic effects. The method of administration, via atomization and inhalation, represents a significant technological advancement, optimizing the delivery and efficacy of the medication. The components of the system, such as the tubular chamber and atomizer, may be composed of materials that are biologically inert, such as medical-grade plastics or metals, to maintain the medication's integrity throughout the administration process. The inclusion of cells, cellular byproducts, and cell-derived products as the constituents of the medication underscores the present invention's utility in cutting-edge veterinary treatments, such as regenerative medicine.

In some embodiments, the cells, the cellular byproducts, and cell-derived products are stem cells. Generally, stem cells are unspecialized cells with the unique capacity to differentiate into various cell types and possess self-renewal capabilities. Specifically, these stem cells can be adult stem cells, embryonic stem cells, or induced pluripotent stem cells, among other types. The stem cells serve as the active agent in the aqueous suspension and are intended for therapeutic applications in veterinary medicine. The inclusion of stem cells as the active ingredient offers significant improvements over the prior art, notably in the areas of tissue regeneration and healing. Due to their unique properties of differentiation and self-renewal, stem cells provide a highly efficacious treatment option for various degenerative and acute conditions in animals. The aqueous suspension containing stem cells can be specifically formulated to be compatible with the device's materials, which may include biocompatible plastics or metals. This ensures the integrity and efficacy of the stem cells from the point of encapsulation to the point of administration. In a veterinary context, this could mean regenerating tissues damaged by injury, disease, or age.

In some embodiments, the cell-derived products are exosomes. Exosomes are nanoscale, membrane-bound vesicles that are secreted by most cell types, including stem cells. They are a subset of extracellular vesicles that typically range in size from about 30 to 150 nanometers. Exosomes contain various bioactive molecules such as proteins, lipids, and nucleic acids (like RNA). They play a key role in cell-to-cell communication and have been found to be involved in a variety of physiological and pathological processes. Exosomes are natural carriers of biological information, functioning almost like tiny 'message parcels' between cells. They can modulate immune responses, facilitate tissue repair, and even transfer genetic material. The use of exosomes in the aqueous solution offers improvements over prior art by facilitating targeted delivery of bioactive molecules to specific cells or tissues. This enhances the treatment's efficacy and potentially reduces side effects. The exosome-containing solution is designed to be compatible with the materials of the device, which may include medical-grade plastics or metals, thereby preserving the integrity and activity of the exosomes throughout the administration process.

In some embodiments, the medication includes at least one of peptides, proteins, growth factors, cytokines, exosomes, and extracellular vesicles derived from human mesenchymal stem cells ("hMSCs") suspended and/or dissolved in an aqueous medium. These bioactive agents derived from hMSCs are either suspended or dissolved in the aqueous medium. The hMSCs exhibit a multipotent differentiation potential, which means they can differentiate into various cell lineages, specifically those of mesenchymal origin. This includes, but is not limited to, osteocytes (bone cells), chondrocytes (cartilage cells), and adipocytes (fat cells).

Peptides and proteins may include amino acid sequences involved in cellular signaling or structural functions. Growth factors are proteins that regulate cell growth and division, while cytokines are small proteins involved in cell signaling. Exosomes and extracellular vesicles are membrane-bound carriers of bioactive molecules. This form of medication offers improvements over the prior art by providing a targeted and efficient method of delivering a complex mixture of bioactive molecules. These molecules interact synergistically to promote tissue repair, modulate immune responses, and carry out other therapeutic functions, thereby enhancing the overall efficacy of the treatment. The aqueous medium and the bioactive molecules are specifically formulated to be compatible with the materials of the device, which may be composed of medical-grade plastics or metals, ensuring that the integrity and bioactivity of the medication are maintained throughout the administration process.

In some embodiments, the medication includes no preservatives. Preservatives are substances added to medications to prolong shelf life by inhibiting microbial growth or chemical degradation. The absence of preservatives offers several advantages over the prior art, one of which is the potential for reduced risk of allergic reactions or sensitivities in the animal receiving treatment. Additionally, a preservative-free formulation can be advantageous in maintaining the biological activity and integrity of sensitive bioactive agents like peptides, proteins, or cellular components. The medication and the device are engineered to be compatible, often using medical-grade plastics or metals to ensure that the integrity of the preservative-free medication is maintained throughout the administration process.

In some embodiments, the medication includes bioactive molecules including proteins, lipids, and ribonucleic acid (RNA). Bioactive molecules are substances that exert a biological effect on living tissues. In this particular formulation, proteins may act as enzymes, signal molecules, or structural components; lipids could serve as signaling molecules or membrane components; and RNA may act as a template for protein synthesis or have other regulatory functions. The inclusion of these bioactive molecules offers several advantages over prior art, such as the potential for multi-target therapeutic effects, given the diverse functional roles of proteins, lipids, and RNA. Additionally, this formulation may provide more natural or physiologically compatible treatment options, reducing the likelihood of adverse reactions. The materials constituting the device through which this medication passes are carefully selected, typically involving medical-grade plastics or metals, to ensure that the bioactive molecules maintain their integrity and activity throughout the administration process.

The medication is a regenerative medication targeting treatment of tissue repair and regeneration in the animal. Regenerative medications include bioactive agents capable of stimulating cellular growth, differentiation, and repair. The medication may include a combination of growth factors, cytokines, stem cells, or other agents known to facilitate tissue regeneration and repair. Compared to prior art, this specific type of medication provides several advantages, such as a targeted and potentially more effective approach to tissue repair and regeneration. This innovation minimizes the need for surgical intervention or long recovery periods, thereby offering a more convenient and less invasive treatment option. The regenerative medication and the materials of the device, which may include medical-grade plastics or metals, are formulated to be compatible, thus maintaining the medication's bioactivity and efficacy throughout the administration process.

Aerosol administration of the abovementioned medication embodiments allow for direct deposition into the respiratory tract, facilitating rapid absorption into the bloodstream. This ensures immediate bioavailability, which can be crucial for timely therapeutic effects. Aerosol administration avoids the need for injections or surgical interventions, reducing the risk of complications such as infections or tissue damage. This non-invasive method is also more patient-friendly and can be more easily accepted by animals, especially when considering veterinary applications. For conditions affecting the respiratory system, aerosol administration can provide a localized delivery, ensuring a high concentration of therapeutic entities at the target site. This is especially beneficial for treating lung diseases or injuries. By delivering these entities directly to the target site, systemic exposure can be reduced, potentially minimizing side effects or adverse reactions in other parts of the body. The nano-size of exosomes and some vesicles allows for efficient penetration into deeper lung tissues, ensuring a wide distribution and reaching cells that might be inaccessible with larger particles. Aerosolizing these entities in an appropriate medium can help in preserving their structural and functional integrity, ensuring that they retain their therapeutic potential upon administration. The present disclosure can be calibrated to deliver precise doses, ensuring consistent and controlled administration of these therapeutic entities. Aerosol administration can be more convenient than repeated injections or infusions, leading to better compliance, especially in chronic conditions.

Referring now to FIG. 38A, a flowchart diagram illustrating steps for a method 3800 for veterinary administration of at least one medication to an animal is shown, according to an example embodiment. In this embodiment, method 3800 begins with step 3802, in which the user inserts the capsule into the device. The capsule may be any one of the previously mentioned capsules, such as capsule 500, 1600, 1700, 1701, 1800, 3000, 3200, and capsule system 3100, 3101. The device may be the base unit/attachment, also referred to as medical device, such as base unit 300, device 1500, and 3315. Depending on the situation, different modular tubular extensions may be in attachment with the device. For example, the animal may be unconscious and lying on the ground. Therefore, the device and modular tubular extension must be configured to treat an animal laying on the ground. Then, in step 3804, the user activates the atomizer within the capsule to generate atomized medication, which travels to the tubular chamber. In step 3806, the user partially deflates the resilient air bladder to provide airflow and convey fresh air towards the tubular chamber. This causes the fresh air to mix with the atomized medication in the tubular chamber. Deflating the resilient air bladder also conveys the mixture of fresh air and atomized medication toward the mask. In some embodiments, airflow can be provided using other means, such as the respiratory support device previously described. Then, in step 3808, the user administers the atomized medication to the animal using the device.

Referring now to FIG. 38B, a flowchart diagram illustrating steps for a method 3801 for veterinary administration of at least one medication to an animal is shown, according to an example embodiment. FIG. 37 will also be reference relative to method 3800. Method 3801 begins with step 3810, in which the user inserts a capsule containing the medication into a device in fluid communication with a tubular chamber. The capsule may be any one of the previously mentioned capsules, such as capsule 500, 1600, 1700, 1701, 1800, 3000, 3200, and capsule systems 3100, and 3101. The device may be the base unit/attachment, also referred to as medical device, such as base unit 300, device 1500, and 3315. Next, in step 3812, prior to activating the atomizer, the user provides power to the atomizer by removing an insulator that prevents electrical communication between the atomizer and a power source. The insulator may be the insulator 2305 shown in FIG. 23. Then, in step 3814, the user activates the atomizer to atomize the medication to generate atomized medication.

In step 3816, prior to administering the atomized medication to the animal using the device, the user applies force K to the mask 3710, positioned over an animal's muzzle and in fluid communication with the tubular chamber. This mask is tailored to fit securely over the facial structure or "muzzle" of an animal, which is the projecting part of the face that includes the nose and mouth. Applying a force could be manual, such as pressing or adjusting the mask onto the animal's muzzle, or it could be mechanized, involving components like straps, clamps, or inflatable sections. For example, in one embodiment a strap 3711 or plurality of straps may be used to attach the mask to the animal. This applied force ensures that the mask remains in place, offering a consistent and effective seal during the procedure so that a minimum amount of medication is dispersed outside of the mask. By applying force to the mask, unintentional loss of medication is minimized, and the desired concentration of the medication can be maintained within the mask, ensuring effective delivery.

In step 3818, prior to causing the liquid formulation to move from the first chamber to the second chamber, the user removes a stop on the capsule that inhibits the first chamber from translating relative to the second chamber. Removing a stop entails physically disengaging, dislodging, or eliminating the device or mechanism that imposes the aforementioned restriction. By doing so, the first chamber is now allowed to move or adjust its position relative to the second chamber. Such movement could be in the form of sliding, rotating, tilting, or any other type of translational motion, depending on the design of the capsule. However, other forms of disengagement of the stop may be used and are within the spirit and scope of the present disclosure. For example, in another embodiment, the stop may be the stop 1725 shown in FIGS. 17A-17C.

In step 3820, after removing the stop of the capsule, the user applies a second force L to the first chamber causing the first chamber to translate relative to the second chamber rupturing the membrane disposed between the first chamber and the second chamber thus providing fluid communication between the first chamber and the second chamber. Causing the first chamber to translate in relation to the second chamber denotes a controlled movement or repositioning of the first chamber with respect to the second chamber. Translation may include sliding, shifting, or any relative motion that brings two chambers closer together or further apart. Once the membrane is ruptured, the previously isolated chambers are now connected, establishing "fluid communication" between them. This means that substances, such as liquids or gases, can now flow or transfer freely from one chamber to the other. This provides precise control over the timing and conditions of interaction between the chamber contents, enhancing the system's adaptability and functionality. This modular approach ensures that interactions or mixings between the chambers occur only when desired, maximizing the capsule's efficiency and potential applications, and distinguishing it from less flexible systems. Then, in step 3822, because rupturing the membrane provides fluid communication between the first chamber and second chamber, the liquid formulation moves from the first chamber to the second chamber.

In step 3824, the user at least partially deflates the resilient air bladder in fluid communication with the tubular chamber causing air within the resilient air bladder to be conveyed from the resilient air bladder into the tubular chamber. Deflating the resilient air bladder causes fresh air contained within it to be pushed or conveyed out. The released air flows directly into the tubular chamber within the device. The tubular chamber, being a conduit or passage, receives this air and may be used to aid in the process of conveying atomized medication and fresh air.

In step 3826, deflating the resilient air bladder further conveys the atomized medication through the second tubular chamber 3720. The second tubular chamber is disposed between the animal's muzzle and the tubular chamber. Conveying fresh air towards the second tubular chamber causes the atomized medication to form a substantially stable and uniform aerosol with the fresh air. Then, in step 3828, the user administers the atomized medication to the animal using the device.

It is understood that this method is a continuous cycle and that each step of method 3800 may operate concurrently with another step of method 3800 to provide efficient administration of medication to an animal within the system. In other embodiments, the method may further include additional steps to promote efficient administration of medication consistent with the systems disclosed herein.

The embodiments described in the context of the disclosed invention serve as examples and are non-limiting. While specific configurations, functionalities, and arrangements of elements like the button, atomizer, chambers, and sensors have been detailed, these descriptions are illustrative and not intended to restrict or confine the invention to these exact embodiments. The invention's underlying principles and concepts allow for various modifications, adaptations, and variations. Different designs and arrangements can be developed to meet particular needs or applications without departing from the scope and spirit of the invention. This flexibility ensures that the invention can be tailored to a broad array of medical devices, enhancing the application in diverse scenarios and providing improvements over the existing art in multiple contexts.

FIG. 38C is a flowchart diagram for a method 3830 of conveying the medication using the resilient air bladder. The method for medication delivery utilizing a resilient bladder, such as the resilient bladder of 3642 of FIG. 36H provides precise and controlled dispensing. The resilient bladder functions as an intermediary storage and propulsion device to facilitate the movement of medication. The initial step 3832 involves removing the cap from the base unit. The base unit houses the mixing chamber and provides an interface for various other components, including the resilient bladder. The cap functions as a protective element that secures the contents within the base unit and maintains the sterility of the internal environment. The removal of the cap exposes the opening of the base unit and creates an accessible pathway for subsequent attachment of the resilient bladder and the conveyance of medication. The next step 3834 entails connecting a portion of the resilient bladder with the base unit. The resilient bladder is designed to be flexible and durable, capable of withstanding the pressures associated with medication conveyance. The resilient bladder can be made from a range of materials, each selected for its specific properties to suit different applications. Common materials include silicone, latex, and various types of rubber, such as natural rubber or synthetic versions like neoprene and nitrile. Silicone is often chosen for its flexibility, durability, and resistance to temperature extremes for medical devices or environments with fluctuating temperatures. Latex, known for its high elasticity and resilience, is suitable for applications requiring tight seals and frequent expansions. Rubbers like neoprene offer excellent chemical resistance and strength, useful in industrial settings where the bladder might be exposed to oils or solvents. Each material brings distinct advantages, allowing the resilient bladder to be tailored to meet the specific requirements of its intended use, for medical devices administering fluids to users.

For connecting the resilient bladder with the base unit, the bladder is aligned with the designated attachment point or opening on the base unit. For example, the tubular connecting portion 3646 of FIG. 36H of the bladder is aligned with a corresponding receptacle or opening on the base unit. Once aligned, the tubular portion is gently inserted into the opening 3608, ensuring a snug and secure fit. This connection not only facilitates a seamless linkage between the bladder and the base unit but also ensures that there is no leakage or loss of air pressure when the device is operational. The design of the tubular connecting portion allows for easy attachment and detachment, providing flexibility and convenience in the maintenance and operation of the system. In an example, the connection between the bladder and the base unit is secure and leak-proof, such that there is no loss of medication during transfer. The design of the resilient bladder allows it to expand and contract during conveying of the medication. In step 3836, the method includes conveying the at least one medication from the mixing chamber to a portion of the conduit using the resilient bladder. This step leverages the elastic properties of the bladder to move medication with precision. As the bladder contracts, it exerts air pressure on the medication stored within, propelling it through the conduit towards the delivery point. In the embodiment, the resilient bladder ensures a consistent flow rate and volume of medication delivered to the user.

Referring to FIG. 38D, a method 3840 for conveying the medication from the mixing chamber to the conduit. The method includes providing a removable capsule having an atomizer, the removable capsule containing the medication in step 3842. In FIGS. 36D and 36F, the removable capsule 3610 is positioned inside the device 3600. The removable capsule 3610 has a capsule chamber 3620, the atomizer 3626 and the medication 3628, such as the medication contained in the removable capsule. It is noted that in other embodiment the medication 3628 contained inside the removable capsule can be a therapeutic substance or a cosmetic substance as noted above. In step 3844, the method includes providing a removable air mover unit in attachment with a base unit of a device. FIGS. 36D and 36F shows the removable air mover unit 3606 that is attached to the base unit via the opening 3637. The air mover unit is a compact unit having electrical contacts on the outer surface of the air mover unit, such that when the air mover unit is fitted within the opening 3637, the electrical contacts of the air mover unit comes in contact with the electrical contacts on an inner wall of the opening. The air mover unit is a compact device equipped with its on-board battery, on-board circuitry, including a printed circuit board (PCB), and a Bluetooth connectivity module. Once the air mover unit comes into contact with the base unit, electrical communication is established between them. This connection enables the base unit to power the air mover unit, activating its operational state. The integration of Bluetooth technology allows for remote operation and monitoring, enhancing the unit's functionality and user convenience.

In alternative embodiments, different communication standards may be used. For example, Wi-Fi offering a broader range and higher data transfer speeds, which could enhance the efficiency of signal transmission when the air mover unit is in proximity to or attached to the device may be used. In another example, Near Field Communication (NFC) for close-range interactions, enabling a simple tap-to-connect functionality that simplifies the pairing process. Infrared (IR) technology that provides a direct line of sight communication method, ensuring secure connections in controlled environments may be used in between the air mover unit and the device. Additionally, Radio Frequency (RF) communication, including technologies like Zigbee or Z-Wave, can be utilized for their low-power consumption and reliable connectivity over varying distances.

In step 3846, the method includes providing a spraying catheter tube connected to the conduit, using an adapter. The spraying tube is connected to the conduit through the use of an adapter. The adapter serves as an interface for securing a linkage between the catheter tube and the conduit. During surgeries, the spray catheter tube provides targeted spraying of medication and therapeutic agents directly to the surgical site, minimizing tissue disturbance and enhancing the efficacy of the medication. This targeted approach facilitates rapid healing, reduces the risk of infection, and ensures that the medication is applied uniformly across the affected area. This configuration optimizes the delivery of fluids directly to the desired location but also enhances the precision and control of the spraying action.

In the next step 3848, the method includes inserting the removable capsule in a channel of the base unit. As shown in FIG. 36F, the removable capsule in inserted within the channel 3629. The channel 3629 accommodates the removable capsule and serves as a dedicated pathway for insertion and alignment of the removable capsule. This channel ensures that the capsule can be easily and securely positioned within the base unit, facilitating seamless integration with the system's overall functionality. The channel provides a snug fit, preventing any movement of the capsule that may disrupt the device operation. Additionally, this feature allows for the quick replacement or removal of the capsule, enhancing the system's versatility and maintenance efficiency. Thereafter, in step 3850, the method involves dispensing, using the atomizer, the at least one medication from the removable capsule to the mixing chamber. In the next step 3852, the method involves using the removable air mover unit, causing air and the medication within the mixing chamber to be conveyed from the mixing chamber to the conduit. By activating the air mover unit, air is propelled into the mixing chamber, where it interacts with the medication, creating a mixture that is efficiently conveyed through the conduit. This process ensures a homogenous distribution of medication within the air stream, optimizing the delivery mechanism for therapeutic applications. The inclusion of a removable air mover unit enhances the system's flexibility and ensures precise control over the medication delivery rate.

Delivering medication through a long spraying catheter that incorporates multiple bends can present challenges due to the potential for uneven medication distribution and resistance to flow, which may result in reduced efficacy of delivery to the targeted site. The complexity of navigating the medication through the catheter's turns can lead to accumulation at bends, thereby affecting the uniformity and speed of the medication's travel. The air mover unit addresses these challenges by propelling a consistent stream of air through the mixing chamber, where the medication is held, into the conduit and subsequently through the spraying catheter. This air stream acts as a carrier for the medication, ensuring that it remains suspended and mixed within the air flow. As a result, the medication is able to maintain a uniform distribution throughout its transfer, even when navigating through the catheter's lengthy path and turns. The air mover unit's mechanism significantly improves the precision and effectiveness of medication delivery, ensuring that the medication is evenly dispersed and reaches the intended site with optimal coverage.

FIG. 38E illustrates a method 3860 for attaching an ocular tube to the conduit of the base unit. In step 3862, the method involves removing the spraying catheter tube from the conduit of the base unit. In one example, the spraying catheter tube 3650 of FIG. 36J is detached from the conduit 3603 of the base unit for cleaning, or replacement purposes. The removing of the spraying catheter is performed carefully to ensure that the connection between the catheter tube and the conduit is safely disconnected without damaging either component. The removal process begins by gently disengaging any locking mechanism or an adapter, such as the adapter 3652 that secures the catheter tube to the conduit, followed by a controlled withdrawal of the tube from the conduit's opening. In another example, the step of removing the spray catheter may be performed for attaching any other component to the conduit. In the next step 3864, the method includes attaching an ocular tube to the conduit, the ocular tube housing an eyepiece at a distant end for administering the at least one medication in a mist form directly to eyes of the user.

For example, the ocular tube 3648 is attached to the conduit 3603 of the base unit as shown in FIG. 36I. The attachment of an ocular tube equipped with an eye cup to the conduit serves a specialized and crucial purpose in medical applications, particularly in administering treatments directly to the eye. This design facilitates precise and gentle delivery of medication or therapeutic solutions to the delicate ocular surface. The eye cup, when attached to the ocular tube and subsequently to the conduit, forms a sealed environment around the eye, minimizing the risk of medication spillage or dispersal to surrounding areas. This targeted delivery mechanism not only enhances the efficacy of the treatment by ensuring that the medication is concentrated at the site of application but also improves patient comfort and safety by preventing irritation to adjacent tissues. Furthermore, this setup is instrumental in treatments requiring controlled and localized administration of medication, offering a high degree of accuracy and effectiveness in ocular therapy.

Referring now to the Figures, FIG. 39 is a side view of an active vibrating instrument ("AVI") 3900, according to an example embodiment. The AVI includes a reservoir 3905 the contains a liquid solution 3910. The reservoir is in attachment with an inner surface of a vibrating mesh membrane 3915. The solution is provided in a sterile, scaled syringe 3935. A channel 3920 is in attachment with an outer surface of the vibrating mesh membrane 3915. The AVI is configured to produce particles 3925 having a particle diameter ranging from about 1.5 micrometers (μm, or microns) to about 6 micrometers. As the solution passes through the vibrating mesh membrane 3915 nebulizes the solution to create a nebulized solution that includes particles 3925. The vibrating mesh membrane 3915 produces nebulized solution by vibrating at high frequency to trigger particle, or droplet, formation from the solution 3910 against an inner surface of the membrane on an outer surface of the membrane. The inner surface of the membrane faces the reservoir, and the outer surface of the membrane faces a channel 3920. The vibrating mesh membrane is a metal piece or plate having a plurality of openings extending through the piece, such that the metal piece, when electrically stimulated to undergo piezoelectric vibration, oscillates against the solution 3910 in the reservoir 3905, causing some of the solution to move through the openings and form small particles on or above the outer surface of the vibrating mesh membrane 3915. The vibrating mesh membrane 3915 vibrates at between about 150 kHz and about 300 kHz upon electrical stimulation by an AC|DC current directed to the vibrating mesh membrane. The vibrating mesh membrane includes material such as pure titanium, platinum, or palladium, or alloys thereof or the like, or laminated layers of titanium, platinum, or palladium or the like, to produce a piezoelectric effect that results in mesh vibration and particle formation over the outer surface of the mesh in the mouthpiece interior volume. Piezoelectricity is the ability of a material to develop electric charge in response to applied mechanical stress.

The particles are atomized droplets of the solution 3910. Particles that are larger than 5 micrometers are unable to penetrate into the alveoli of the lungs and are thus of reduced efficiency in being rapidly absorbed by the circulatory system and/or body tissues. The ability of particles to penetrate into the lungs and be absorbed by the depends on the size of the particles. Inhalable particles, ranging in size from 1.5 micrometers to about 6 micrometers, penetrate into the lungs as far as the bronchi because the cilia of the lungs filter the inhalable particles from further travel into the lung volume. Particles ranging in size from 1.5 micrometers to about 5 micrometers are able to penetrate into the alveoli in the lungs and are readily absorbed through the alveoli into the circulatory system and body tissues. The AVI 3900 further includes a channel 3920 that encloses the atomized droplets of the nebulized solution created by the AVI. The atomized droplets flow in the direction A towards a user of the AVI. The opening 3930 in the channel 3920 may be attached to a mouthpiece and/or nosepiece configured to be positioned on the user's face. In some embodiments, the AVI may be used within a disposable pen-type vaporizer. The pen-type vaporizer would provide more portability than a standard nebulizer and thus would be more convenient.

Referring now to FIG. 40, a block diagram 4000 of a solution 4005 for use with the AVI is shown, according to an example embodiment. The solution includes an aqueous solution 4005 that includes an active ingredient 4010 and sodium chloride 4015. The active ingredient includes at least one of nicotine 4310 of FIG. 43C, caffeine 4315 of FIG. 43D, a plurality of vitamins, kratom 4320 of FIG. 43E, Vitamin B12 4325 of FIG. 43F, cotinine 4300 of FIG. 43G, adalimumab 4305 of FIG. 43B, cannabidiol ("CBD") 4330, tetrahydrocannabinol ("THC") 4335, psilocybin 4340 of FIG. 43I, cannabis 4335 of FIG. 43H, ketamine 4345 of FIG. 43J and any combination thereof. The active ingredient may also include analgesics, antifungals, antibiotics, anti-inflammatory, anti-gout, cardiovascular agents, central nervous system stimulants and/or depressants, diabetic agents, diuretics, immunologic agents, gastrointestinal agents, common biologics like Humira, Lantus, Remicade, Enbrel, vaccines, psychotherapeutic agents, opiate partial antagonists, pulmonary agents, hormonal agents, weight loss agents, and vitamins/minerals/supplements.

The solution further includes a buffer and/or stabilizer 4020. The buffer helps stabilize and maintain the pH level of the solution. The active ingredient includes approximately up to 10% of the solution. Sodium chloride includes approximately between 10% to 90% of the solution. The buffer includes approximately between 1% to 5% of the total solution.

The solution is sterile, non-pyrogenic, additive and preservative free, and provided in sterile unit-of-use, blow-fill-seal cartridges/capsules. The solution being mixed into an aqueous solution allows for its long-term storage. The capsules are configured to conveniently fill up the reservoir of the AVI. For smaller, portable AVI, cartridges may be used such that the solution is quickly replaced when a cartridge is emptied. The cartridges are conveniently detachable from the AVI.

Referring to FIG. 41, the solution has a pH 4105 of approximately between 4 pH and 7.5 pH, as shown in the pH scale 4100. The pH range is critical to decrease the effects that the active ingredient may have on the body when inhaled, e.g., an increased amount of acute toxicity which may be present in unprotonated active ingredients above a certain pH.

Referring now to FIG. 42, a flow diagram of a method 4200 of administering the solution for use with the AVI, according to an example embodiment. Method 4200 begins with step 4201 which includes mixing the solution. In step 4205, mixing the solution includes combining the active ingredient and the sodium chloride into an aqueous solution. Then, step 4210 includes combining buffer and/or stabilizers with the aqueous solution created in step 4205. In step 4215, mixing the solution further includes adding sugar alcohol and water to the aqueous solution. The sugar alcohol may include erythritol, mannitol, sorbitol, xylitol, lactitol, isomalt, maltitol, and hydrogenated starch hydrolysates. Other sugar alcohols may be used and are within the spirit and scope of the present invention. The solution created by steps 4205, 4210, and 4215. Method 4200 then includes providing the solution in a sterile, sealed syringe in step 4220. In step 4225, the method includes filling the reservoir of the AVI with the solution using the syringe. Next, in step 4230, the method includes nebulizing the solution across the vibrating mesh membrane. Nebulizing the solution generates the nebulized solution in step 4235. Finally, in step 4240, the method includes administering the nebulized solution to the user. It is understood that this method is a continuous cycle and that each step of method 4200 may operate concurrently with another step of method 4200 to administer medication through an AVI within the system. In other embodiments, the method may further include additional steps to administer medication through an AVI consistent with the systems disclosed herein.

With reference now to FIGS. 43A, 43B, 43C, 43D, 43E, 43F, 43G, 43H, 43I, 43J, 43K, 43L several embodiments of the solution for use with the AVI will be described. In a first embodiment, the solution is for at least deceasing a plurality of withdrawal symptoms of a person addicted to nicotine. Said solution includes cotinine being the active ingredient in the solution including approximately between 0.5% and 8% of the solution and a sugar alcohol 4500 of FIG. 45 including approximately between 0.5% to 3% of the solution. The solution further includes a buffer including ethyl alcohol 4400 of FIG. 44A and citric acid 4405 of FIG. 44B. The ethyl alcohol includes approximately between 0.1% to 3% of the solution, and the citric acid comprising approximately between 0.1% to 3% of the solution. Cotinine helps reduce symptoms of nicotine withdrawal. The sugar alcohol and citric acid act as sweetener to counter the bitterness of cotinine when inhaled. In another embodiment, the solution of the first embodiment may be mixed with a small dose of nicotine.

In a second embodiment, the solution is a pulmonary irrigation solution. The solution includes adalimumab being the active ingredient including approximately between 1% to 10% of the solution and a sugar alcohol 4500 including approximately between 0.1% to 1% of the solution. The solution further includes a stabilizer including polyol including approximately between 0.1% to 5% of the solution and surfactant comprising approximately between 0.1% to 5% of the solution. The polyol is at least one of sucrose 4410 of FIG. 44C, histidine 4415 of FIG. 44D, and succinate 4420 of FIG. 44E. The surfactant is polyetherimide 4440 of FIG. 44I. At least one of the buffer and the stabilizer includes at least one buffer selected from the group consisting of histidine, succinate, phosphate 4430 of FIG. 44G, citrate 4435 of FIG. 44H, acetate 4425 of FIG. 44F, sodium bicarbonate 4445 of FIG. 44J, maleate 4450 of FIG. 44K, and tartrate 4455 buffers of FIG. 44L. The buffer does not include a combination of a citrate buffer and a phosphate buffer. Adalimumab is a therapeutic biologic used in the treatment of various autoimmune and inflammatory conditions. As a monoclonal antibody, it specifically targets and neutralizes tumor necrosis factor alpha (TNF-α), a substance in the body that contributes to inflammation and immune system activity. Adalimumab is widely used in the management of rheumatoid arthritis, a condition characterized by chronic joint inflammation. Its efficacy extends to other autoimmune disorders such as psoriatic arthritis, which affects the skin and joints, and ankylosing spondylitis, a type of spinal arthritis. Additionally, Adalimumab has shown effectiveness in treating inflammatory bowel diseases, including Crohn's disease and ulcerative colitis, where it helps in reducing inflammation of the gastrointestinal tract. It is also used in certain dermatological conditions like plaque psoriasis, providing relief from skin symptoms. The broad application of Adalimumab in these conditions underscores its role as a critical therapeutic agent in the management of various chronic inflammatory and autoimmune disorders.

In a third embodiment, the active ingredient is naloxone 4350. Naloxone rapidly counters and/or reverses the effects of opioids. Naloxone is the standard treatment to counter opioid overdoses. Inhalation of naloxone through a portable AVI could quickly save the life of opioid users who overdose.

In a fourth embodiment, the active ingredient is colloidal silver 4600 in FIG. 46. Colloidal silver is a liquid solution 4605 including a plurality of silver particles 4610. Colloidal silver treatment can heal a variety of infections, such as the common cold or respiratory infections.

In a fifth embodiment, the active ingredient is glucagon 4355 of FIG. 43L.

Glucagon is a hormone that raises blood glucose levels and the concentration of fatty acids in the bloodstream. Glucagon treatment helps people who suffer from hypoglycemia. Hypoglycemia occurs when the blood glucose levels are lower than the standard range.

Referring now to FIGS. 43K and 47 through 50, multiple pharmaceutical compositions are illustrated. In the disclosed embodiments, various pharmaceutical solutions are presented for use with a vibrating mesh nebulizer, each tailored for specific therapeutic purposes. These solutions are meticulously formulated with precise concentrations of active ingredients and are designed to operate within a defined pH range, ensuring both efficacy and stability for nebulization.

Generally, the pH of these pharmaceutical compositions is between 3 pH to 7.5 pH. In other embodiments, the pH may be more ideally maintained between 4 pH and 7.5 pH. This precise pH control is critical for several reasons integral to the efficacy, stability, and safety of the compositions. Firstly, the stability of active ingredients such as naloxone, yohimbine, albuterol, and tolazoline is highly pH-dependent. Deviations from the optimal pH range can lead to the degradation or alteration of these compounds, thereby compromising the therapeutic effectiveness and shelf-life of the pharmaceutical product. Secondly, the solubility of the active ingredients is influenced by pH, where maintaining the pH within this defined range ensures consistent dissolution, crucial for effective delivery, particularly in nebulizer applications.

Furthermore, aligning the pH range with physiological levels minimizes potential irritation or discomfort upon administration, especially pertinent for mucosal or inhaled routes. This consideration is vital for patient compliance and comfort. Additionally, the prescribed pH range facilitates appropriate chemical interactions within the composition, preventing undesirable reactions between the active ingredients, excipients, and stabilizers, thus preserving the intended pharmacological action. Moreover, certain pH levels play a pivotal role in inhibiting microbial growth, thus contributing to the preservative efficacy of the formulation. This aspect is especially critical in ensuring the safety and longevity of the pharmaceutical composition.

The disclosed pharmaceutical composition are designed for treating conditions such as opioid overdose and opioid dependency. This composition is characterized by its versatility and precision in formulation, catering to varying therapeutic needs. At its core, the composition includes an aqueous solution of sodium chloride, providing a stable and biocompatible medium. Incorporated within this solution is at least one active ingredient, chosen from a group comprising naloxone, yohimbine, and albuterol. The concentration of this active ingredient is carefully calibrated to be between 0.025% and 25% of the aqueous solution, ensuring optimal therapeutic efficacy. Critical to the composition's stability and compatibility with human physiology is the maintenance of a pH range approximately between 3 and 7.5. This pH range is chosen to maximize the stability of the active ingredients, ensure patient comfort upon administration, and maintain the chemical integrity of the composition.

In embodiments where naloxone is the active ingredient, its concentration is finely tuned to approximately 4% to 6% of the aqueous solution, aligning with its optimal therapeutic window for treating opioid overdose. For compositions containing yohimbine, the concentration is adjusted to approximately 2.5% to 6%, catering to its pharmacological role in opioid dependency management. In the case of albuterol, its concentration is maintained at a precise range of approximately 0.025% to 0.075%, leveraging its therapeutic benefits while ensuring safety and efficacy. Additionally, some embodiments may include tolazoline, constituting approximately 50% to 75% of the aqueous solution, broadening the composition's therapeutic spectrum.

The disclosed dosages are calibrated based on a standard human adult weight of 150 pounds. For administering these compositions, specific dosing guidelines are established: for example, a dose of 0.1 ml is nebulized and delivered in 3 breaths, while a larger dose of 0.3 ml is nebulized across 9 breaths. The achievement of the total intended dose is reached upon the nebulization and administration of 0.3 ml of the pharmaceutical composition. When these pharmaceutical compositions are prepared and stored in capsules, they are formulated in quantities sufficient to allow for a number of breaths, providing flexibility in dosing. This approach is particularly advantageous as it negates the need to alter the pharmaceutical composition itself to accommodate variations in patients' body weights. For example, the capsule may contain 3 mL of the pharmaceutical composition, a volume that accommodates multiple dosing regimens for flexible treatment. This capacity is particularly beneficial for varying patient needs, allowing for adjustable dosing, such as 0.1 ml in 3 breaths or 0.3 ml in 9 breaths, without the need for frequent refills. This design ensures efficient and consistent delivery of medication, crucial in treatments like opioid overdose and dependency. Depending on the patient's specifications, the dosage can be effectively adjusted by modifying the number of breaths through which the composition is administered. This method ensures that each patient receives a tailored dose proportional to their body weight, enhancing the precision and efficacy of the treatment.

To further streamline this process, the nebulizing device can be equipped with a functionality that requires the input of the patient's body weight. Upon receiving this input, the device is programmed to automatically administer the correct number of breaths corresponding to the appropriate dose. This feature adds a layer of convenience and accuracy, reducing the potential for manual errors in dosage calculation. It ensures that patients receive the optimal amount of medication based on their individual needs, aligning with the overarching goal of personalized medical care. This integration of patient-specific dosing with intuitive device functionality represents a significant advancement in the field of pharmaceutical delivery, particularly for treatments involving complex dosing regimens like those for opioid overdose and dependency.

In variations of the pharmaceutical composition, the active ingredient(s) may be dissolved in a diluent selected from a group consisting of sterile water, normal saline, and sodium chloride. It is noted that normal saline has a specific concentration (usually 0.9% sodium chloride in water), which is physiologically compatible with the body's fluids. This selection offers flexibility in formulation, accommodating different administration routes and patient tolerances. Furthermore, the composition may be enhanced with a buffer chosen from a group comprising histidine, succinate, phosphate, citrate, acetate, sodium bicarbonate, maleate, and tartrate buffers. These buffers aid in maintaining the desired pH range, contributing to the stability and efficacy of the composition.

In an ideal embodiment of the pharmaceutical composition for use with a vibrating mesh nebulizer, buffers may be excluded to accommodate patients who may experience adverse reactions, such as vasoconstriction, from these additives. Eliminating buffers is particularly critical for sensitive patients or those with specific health conditions where additional compounds might complicate treatment.

To ensure the sterility and purity of the composition in the absence of buffers, the capsules are meticulously hermetically sealed. This scaling is crucial for maintaining a bacteria-free environment, thus preserving the medication's sterility from manufacture to administration. This scaling plays a crucial role in ensuring the sterility of the pharmaceutical composition from the point of manufacture through to administration. By creating an airtight and bacteria-free environment within each capsule, the risk of contamination is significantly minimized. This approach not only maintains the purity and efficacy of the medication but also reduces the likelihood of introducing external pathogens that could be detrimental to patient health.

Below are various example embodiments of the pharmaceutical compositions contemplated by this disclosure.

Regarding a first pharmaceutical composition, or first solution being a naloxone-based pharmaceutical composition; this pharmaceutical composition comprises naloxone 4350 as the active ingredient, dissolved in an aqueous solution of sodium chloride, where the sodium chloride concentration is maintained between 0.6% and 3%. Naloxone constitutes approximately 4% to 6% of the total composition. In certain embodiments, the composition may solely consist of these elements, while in other embodiments, it may include additional components such as buffers for pH stability, stabilizers to enhance shelf-life, or other active ingredients that synergize with naloxone, all falling within the scope of this disclosure.

Regarding a second pharmaceutical composition, or second solution being a naloxone and yohimbine 4700 based pharmaceutical composition; this composition features a combination of naloxone and yohimbine in an aqueous sodium chloride solution. The sodium chloride concentration ranges from 0.6% to 3%, with naloxone present at 4% to 6%, and yohimbine at 2.5% to 6%. While certain embodiments focus solely on these components, others might include additional elements such as buffers for pH stability, stabilizers, or other active ingredients compatible with naloxone and yohimbine, adhering to the intended therapeutic application of the composition.

Regarding a third pharmaceutical composition, or third solution being a naloxone, yohimbine, and albuterol 4800 based pharmaceutical composition; this comprehensive pharmaceutical composition integrates naloxone 4350, yohimbine 4700, and albuterol 4800 in an aqueous sodium chloride base. The sodium chloride concentration is from 0.6% to 3%, with naloxone at 4% to 6%, yohimbine at 2.5% to 6%, and albuterol between 0.025% to 0.075%. Some embodiments of this composition may be limited to these ingredients, while others could incorporate additional components like buffers, stabilizers, or other active ingredients that complement the primary agents without departing from the intended scope of the composition.

Regarding a fourth pharmaceutical composition, or fourth solution being a naloxone 4350 and tolazoline 4900 based pharmaceutical composition; this composition pairs naloxone with tolazoline in an aqueous sodium chloride solution, where the sodium chloride concentration ranges from 0.6% to 3%. Here, naloxone comprises approximately 4% to 6% of the composition, while tolazoline is included at a concentration of about 50% to 75%. Alternative embodiments may include buffers for pH adjustment, stabilizers, or other active ingredients that fit within the therapeutic objectives of the solution.

Regarding a fifth pharmaceutical composition, or fifth solution being a yohimbine, based pharmaceutical composition; this solution contains yohimbine 4700 as the sole active ingredient in an aqueous sodium chloride base, where the sodium chloride concentration is between 0.6% and 3%. Yohimbine constitutes approximately 2.5% to 6% of the composition. Some embodiments might be exclusively yohimbine-based, whereas others could include additional components like buffers, stabilizers, or other active ingredients that are consistent with yohimbine's pharmacological profile and therapeutic goals.

Regarding a sixth pharmaceutical composition, or sixth solution being a naloxone and albuterol based pharmaceutical composition; in this pharmaceutical composition, naloxone 4350 and albuterol 4800 are combined in an aqueous sodium chloride solution, with the sodium chloride concentration ranging from 0.6% to 3%. Naloxone is formulated at approximately 4% to 6% of the composition, while albuterol is between 0.025% to 0.075%. While certain embodiments concentrate solely on these two active ingredients, others might encompass additional components like buffers, stabilizers, or other active ingredients that are compatible and supportive of the therapeutic objectives.

Regarding a seventh pharmaceutical composition, or seventh solution being a yohimbine and albuterol based pharmaceutical composition; this pharmaceutical composition combines yohimbine and albuterol in an aqueous sodium chloride base. The sodium chloride concentration ranges from 0.6% to 3%, with yohimbine between 2.5% to 6%, and albuterol between 0.025% to 0.075%. While the basic composition includes just these components, alternative embodiments could incorporate additional elements such as buffers, stabilizers, or other active ingredients, as long as they align with the intended therapeutic use and overall.

Regarding an eighth pharmaceutical compound, a pharmaceutical composition specifically formulated to address opioid dependency is disclosed. This composition combines the active ingredient naloxone, a potent opioid antagonist, with buprenorphine 5000, a partial opioid agonist. The buprenorphine component plays a critical role in this formulation by adhering to the mu-opioid receptors, thereby facilitating the targeted delivery of naloxone to these receptors. Notably, naloxone is typically unable to effectively reach the mu-opioid receptors without the presence of buprenorphine. This synergistic relationship between buprenorphine and naloxone is central to the efficacy of the medication, known commercially as Suboxone® and Zubsolv®. This embodiment leverages the unique pharmacological properties of both naloxone and buprenorphine, offering an effective treatment modality for patients grappling with opioid dependency, and aligns with current therapeutic protocols in addiction medicine. Various pharmaceutical compositions comprising buprenorphine and/or naloxone are contemplated and disclosed herein. In the disclosed embodiments below, a series of pharmaceutical compositions are designed for use with a vibrating mesh nebulizer, focusing on the administration of buprenorphine, both alone and in combination with naloxone, for the treatment of pain and opioid use disorder. These formulations consider the pharmacokinetics of buprenorphine, including its half-life and morphine equivalent dosing, and are pioneering in exploring the potential of inhaled buprenorphine.

First, said composition includes buprenorphine 5000 as the active ingredient, dissolved in sterile water with a sodium chloride content ranging from 0% to 3%. The buprenorphine concentration is approximately 0.02% to 0.045% (0.2 mg/ml to 0.45 mg/ml). The solution's pH, adjusted using hydrochloric acid, is maintained between 3.5 and 7.8. Such a formulation may be applicable for administering said medication in situations that require immediate acute pain relief, such as in the field of military and first responder application. In certain embodiments, this composition may further includes a cytochrome P450 3A inhibitor at a predetermined strength, alongside buprenorphine. The inhibitor's inclusion aims to decrease the clearance of buprenorphine, potentially extending its half-life. Such a formulation may be used for treating chronic pain relief and also for naloxone sensitive opioid dependency.

Second, in this formulation, buprenorphine 5000 is combined with naloxone. Both active ingredients are dissolved in sterile water, maintaining sodium chloride ranging from 0% to 3% . . . . The buprenorphine concentration varies between 0.01% and 0.4% (0.1 mg/ml to 4 mg/ml), and naloxone between 0.025% and 0.2% (0.25 mg/ml to 2 mg/ml). The pH is similarly adjusted to fall between 3.5 and 7.8. Such a formulation may be applicable for treating opioid dependency. In certain embodiments, this solution may combine buprenorphine and naloxone with a cytochrome P450 3A inhibitor. The inclusion of the inhibitor is intended to enhance the pharmacological effectiveness of buprenorphine.

These pharmaceutical compositions including a cytochrome P450 3A inhibitor improve over the prior art by extending the half-life of buprenorphine, particularly in its hydrochloride form, where the half-life is notably shortened. This reduction in half-life can impede the effectiveness of buprenorphine in achieving the desired goals of decreasing tolerance at the cellular level, which is crucial for chronic pain relief and managing opioid dependence. To address this challenge, the composition includes the addition of a Cytochrome P450 3A inhibitor, such as a specified amount of citalopram. The incorporation of this inhibitor is a deliberate strategy to prolong the half-life of buprenorphine. By doing so, the composition effectively reinstates the original objective of diminishing opioid receptor activity and reducing tolerance. This enhancement is particularly significant in Formula 2, designed for opioid dependence treatment, where maintaining the therapeutic effectiveness of buprenorphine over a prolonged period is crucial for successful patient outcomes. The addition of the P450 3A inhibitor thus represents a critical improvement in the formulation, optimizing its efficacy for both chronic pain management and opioid dependency treatments.

Overall, these formulations are directed towards the administration of buprenorphine 5000 and its combinations, utilizing nebulizer technology for potentially more effective and controlled delivery. The versatility in concentration ranges and the addition of a metabolic inhibitor demonstrate an innovative step in optimizing drug delivery for pain management and opioid use disorder treatment. The active ingredients, naloxone and/or buprenorphine, may be combined in an aqueous solution of sodium chloride, providing a stable and biocompatible medium. The concentration of this active ingredient is carefully calibrated to be between 0.025% and 25% of the aqueous solution, ensuring optimal therapeutic efficacy. Critical to the composition's stability and compatibility with human physiology is the maintenance of a pH range approximately between 3 and 7.5. This formulation provides a means of atomized administration of the medication for treatment of opioid exposure and/or dependency.

In the context of the aforementioned pharmaceutical compositions, specifically designed for the treatment of opioid overdose and dependency and xylazine exposure, said pharmaceutical compositions are meticulously prepared and stored within capsules for atomized administration to patients. The process begins with the precise selection and measurement of active ingredients, such as naloxone, yohimbine, albuterol, tolazoline, and buprenorphine. These ingredients are quantified to achieve the desired concentrations, ranging from 0.025% to 25% of the total composition. Concurrently, an aqueous solution of sodium chloride, or alternative diluents such as sterile water or normal saline, is prepared, ensuring a sodium chloride concentration between 0.6% and 3%.

Subsequently, the active ingredients are dissolved in this aqueous medium, ensuring complete dissolution and uniform distribution. Critical to the stability and patient compatibility of the composition is the adjustment of pH, typically maintained within the range of 3 to 7.5. This is achieved through the judicious use of buffers, including but not limited to histidine, succinate, phosphate, citrate, acetate, sodium bicarbonate, maleate, or tartrate. Upon formulation, the composition undergoes rigorous quality control testing to confirm the accuracy of active ingredient concentrations, appropriate pH levels, and overall stability.

Once the pharmaceutical composition meets all specified criteria, it is carefully filled into specially designed capsules. These capsules are tailored for compatibility with vibrating mesh nebulizers and are fabricated from materials that are inert to the composition. Ensuring the integrity of the composition, the capsules are hermetically sealed, safeguarding against environmental factors such as moisture, light, and air, which could otherwise compromise the active ingredients.

The storage of these capsules is managed under controlled conditions, typically at temperatures conducive to maintaining the stability of the pharmaceutical composition. This aspect of the invention is crucial for preserving the therapeutic efficacy of the composition until the point of administration.

For patient administration, a capsule is loaded into a vibrating mesh nebulizer. The capsule is inserted into a device equipped with a device chamber. This device includes a receiving section with an opening, which is covered by a removable cap to define what is termed as a capped chamber. Upon activation, the device induces the capsule's contents, the pharmaceutical composition, to atomize into a fine mist by dispensing the pharmaceutical composition from the capsule, which is in fluid communication with this capped chamber, into the capped chamber itself. The resulting aerosolized medication is administered to the patient by being conveyed from this capped chamber, then inhaled by the patient, facilitating rapid, targeted, controlled, and effective delivery of the active ingredients directly to the respiratory tract.

In certain embodiments, the medical situation of the respective patient, or multiple patients, may involve removing the removable cap from the receiving section of the device. The initial act of removing the cap serves a dual purpose: it not only prepares the device for the impending atomization process but also establishes an open interface for the subsequent attachment of the air bladder. This opening is essential for facilitating the fluid communication requisite for effective atomization.

Subsequently, the resilient air bladder is attached to the receiving section of the device. Upon the attachment of the resilient air bladder, a seamless fluidic pathway is established between the bladder and the chamber of the device. This air bladder is designed to be in fluid communication with the chamber via the opening, facilitating an enhanced mechanism for conveying the atomized pharmaceutical composition to the patient. This addition of the air bladder aids in the efficient and effective delivery of the medication, ensuring that the therapeutic agents are administered in an optimized manner suitable for the treatment of opioid-related conditions.

With reference to FIGS. 30A through 31D, the specific configuration for administering a pharmaceutical composition with yohimbine as the active ingredient is of notable interest, particularly given yohimbine's known instability in liquid form. This capsule system, designed for atomized administration, solves this challenge through its dual-reservoir structure.

The capsule comprises a first reservoir, which is dedicated to containing the active ingredient, yohimbine hydrochloride. The concentration of yohimbine hydrochloride is meticulously calibrated within the range of 0.05 to 0.25 mg per kg of a patient's body weight. Considering yohimbine's inherent instability when dissolved, it is crucially stored in a powdered or solid form in this first reservoir. This approach is essential to maintain the integrity and efficacy of yohimbine until the moment of administration, circumventing the stability issues associated with liquid formulations. In certain embodiments, the amount of dry weight yohimbine may be suitable such that, when mixed with the diluent, the amount of yohimbine comprises approximately between 2.5% and 6% of the aqueous solution.

Adjacent to this is the second reservoir, which is distinctively formulated to include a diluent, chosen from options such as sterile water, normal saline, and sodium chloride, and may also contain a buffer selected from a group including histidine, succinate, phosphate, citrate, acetate, sodium bicarbonate, maleate, and tartrate buffers. The presence of these buffers aids in maintaining the desired pH level, crucial for the stability and effectiveness of the yohimbine once it is in solution.

The method, as outlined above, includes the critical step of moving the yohimbine from the first reservoir to the second reservoir to combine the yohimbine with the diluent to formulate the pharmaceutical composition. In one embodiment, this transfer is facilitated by rupturing a membrane that separates these two compartments, thereby allowing fluid communication between them. The membrane's rupture, triggered at the time of administration, ensures that yohimbine is mixed with the diluent and/or buffer only immediately prior to administration, thus effectively addressing the stability concerns.

In certain embodiments, the capsule system may be configured for administering light-sensitive pharmaceuticals. Accordingly, said capsule, and/or the respective reservoirs or chambers, may be darkly tinted or non-transparent. This is crucial for protecting active ingredients, like yohimbine, from light-induced degradation. The dark tint or non-transparency effectively blocks harmful light, particularly UV and visible light, maintaining the integrity and efficacy of the medication. The materials used are selected for their light-blocking properties and compatibility with pharmaceutical standards, ensuring the safety and stability of the contents. This approach simplifies storage and handling, allowing for safer and more convenient use in various settings. Thus, the design of darkly tinted or non-transparent capsules or vials is a key feature in preserving the potency and effectiveness of light-sensitive medications.

A further aspect of the method of administering the pharmaceutical composition involves the removal of a stop that initially inhibits the movement of the first reservoir relative to the second reservoir. This stop's removal is a key activation step, enabling the translation of the first reservoir towards the second and the subsequent engagement of the rupturing mechanism. This design ensures that the mixing of yohimbine with the diluent and/or buffer is a controlled and deliberate process, occurring only when the pharmaceutical composition is intended to be administered.

By causing the first chamber or first reservoir to be in fluid communication with the second chamber or second reservoir, the active ingredient is then mixed with the diluent and/or buffer within the capsule chamber, which is typically the second chamber/reservoir. This chamber contains the diluent and/or buffer, while the active ingredient, like yohimbine, is initially segregated in a separate reservoir. The mixing process is activated by a user or an automated mechanism, leading to the rupture of a membrane barrier that separates the active ingredient from the diluent and buffer. This rupture, facilitated by a built-in rupturing element, enables the active ingredient in its powdered or solid form to merge with the diluent, such as sterile water, normal saline, or sodium chloride. If included, the buffer-which could be histidine, succinate, phosphate, citrate, acetate, sodium bicarbonate, maleate, or tartrate-assists in maintaining an optimal pH level, crucial for the stability and efficacy of the resultant solution.

Upon the mixing of these components, a homogeneous pharmaceutical composition is formed within the capsule chamber. This composition is then ready for the final stage of atomized administration. The capsule system, typically equipped with a vibrating mesh atomizer proximate to the capsule chamber, transforms the liquid composition into a fine aerosol. This aerosolized form is ideal for inhalation, ensuring efficient and effective delivery of the medication to the patient. In certain embodiments of this pharmaceutical system, the system is configured to cater to specific medical emergencies, ensuring the precise and controlled mixing of the active ingredients with the diluent and buffer for effective administration. In one embodiment, the system includes the administration of naloxone, an active ingredient renowned for its efficacy in reversing opioid overdose. However, it is noteworthy that naloxone alone generally does not address opioid dependency, a condition that may be more effectively managed by a combination of buprenorphine and naloxone. This embodiment, therefore, may encompass a formulation specifically targeting opioid overdose scenarios. In another embodiment, the system is adapted for the administration of yohimbine. Unlike naloxone, yohimbine does not counteract opioid overdose but is effective in reversing the effects of xylazine, an emerging concern in public health. This embodiment ensures that yohimbine is delivered in a controlled manner, suitable for addressing complications arising from xylazine exposure.

Each embodiment of this system reflects a dedicated focus on addressing the distinct requirements of different medical emergencies, be it opioid overdose or Xylazine-related complications. This versatility in design underscores the commitment to advancing pharmaceutical administration's efficiency and efficacy, particularly in critical care settings where precise and targeted treatment is paramount.

In summary, this capsule system represents a sophisticated and highly effective solution for administering yohimbine, particularly given its instability in liquid form. The dual-reservoir design, coupled with a precise rupturing mechanism and the careful separation of yohimbine from the diluent until the point of use, ensures the stability, potency, and efficacy of the medication, thereby addressing a significant challenge in the pharmaceutical administration of yohimbine.

The two-reservoir capsule design, exemplified by the innovative system described herein, offers a versatile and efficient solution for isolating various active ingredients prior to administration. It is understood that this capsule system can be adapted for a wide range of pharmaceutical compositions, including those requiring multiple active ingredients. In such scenarios, the capsule may be configured to include one or more first reservoirs or chambers, each initially housing a distinct active ingredient. These first chambers are effectively isolated from a second reservoir, typically containing a diluent or buffer, by one or more membranes. The membranes serve as a barrier, maintaining separation of the active ingredients from the diluent or buffer until the point of administration. This separation is crucial for preserving the stability and efficacy of the active ingredients, especially those sensitive to premature mixing or environmental factors. When required, the membranes can be ruptured or otherwise breached, allowing for the controlled release of each active ingredient into the second reservoir. This results in a combined pharmaceutical composition that is ready for atomized delivery. The adaptability of this at least two-reservoir system to accommodate multiple active ingredients in separate chambers underscores its potential in providing tailored and sophisticated medication delivery solutions, particularly in treatments requiring complex pharmaceutical regimens.

The pharmaceutical composition comprising yohimbine hydrochloride, formulated for treating opioid overdose and dependency, is adaptable for various methods of administration, each tailored to optimize efficacy and patient convenience. The pharmaceutical composition includes the active ingredient, yohimbine hydrochloride, and a diluent selected from the group consisting of sterile water, normal saline, and sodium chloride.

When combined with sterile water as a diluent, the pharmaceutical composition is suitable for intramuscular injection. This method involves injecting the yohimbine hydrochloride solution, with a concentration ranging from 0.05 to 0.25 mg per kg of the patient's body weight, directly into the muscle tissue. Intramuscular injection offers a relatively quick onset of action, as the drug is absorbed into the bloodstream through the muscle fibers. This route is particularly useful in emergency scenarios where swift response is crucial and when intravenous access is not readily available.

Alternatively, when the composition uses normal saline as the diluent, the pharmaceutical composition is configured for intravenous administration. This method involves delivering the yohimbine hydrochloride solution directly into the bloodstream through a vein. Intravenous administration ensures rapid distribution of the medication throughout the body, offering immediate therapeutic effects, which is essential in acute care situations like opioid overdose.

In cases where sodium chloride is used as the diluent, the composition is prepared for atomized aerosol delivery as describe above. Each of these administration methods offers distinct benefits. Intramuscular and intravenous injections provide rapid drug delivery in emergency situations, while atomized aerosol delivery offers a non-invasive alternative with direct respiratory system delivery. The flexibility in the choice of diluent and the inclusion of suitable buffers ensure that the pharmaceutical composition remains stable and effective, regardless of the chosen method of administration. This adaptability underscores the composition's versatility in addressing the varied needs of patients suffering from opioid overdose or dependency.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

The invention claimed is:

1. A method for administering at least one substance to a subject, the method comprising:
   providing a removable capsule having an atomizer;
   inserting the removable capsule in a channel of a base unit of a device, the channel in fluid communication with a mixing chamber of the base unit, the base unit defining openings on the base unit configured to receive a portion of a conduit and a removable air mover unit, wherein the removable air mover unit is electrically connected directly to the base unit;
   dispensing, using the atomizer, the at least one substance from the removable capsule to the mixing chamber of the base unit, wherein the at least one substance is combined with air in the mixing chamber; and
   using the removable air mover unit, causing air and the at least one substance within the mixing chamber to be conveyed from the mixing chamber to the conduit such that air and the at least one substance dispensed from the removable capsule exits the conduit.

2. The method of claim 1 further comprising attaching an ocular tube to the conduit, the ocular tube housing an eye cup at a distant end configured for administering the at least one substance in a mist form directly to eyes of a user.

3. The method of claim 1, wherein the removable air mover unit is in attachment with the base unit of the device, such that a central axis of the removable air mover unit aligns with a central axis of the portion of the conduit.

4. The method of claim 1 further comprising: removing the removable air mover unit from the base unit;
attaching a cap to cover an opening of the base unit, for a capped chamber;
dispensing, using the atomizer, the at least one substance from the removable capsule to the capped chamber of the base unit; and
administering the at least one substance to a user by conveying the at least one substance from the capped chamber.

5. The method of claim 4 further comprising:
removing the cap from the base unit;
connecting a portion of a resilient bladder with the base unit, such that the resilient bladder in in fluid communication with the mixing chamber of the base unit; and
conveying the at least one substance from the mixing chamber to a portion of the conduit though the resilient bladder.

6. The method of claim 1, wherein the removable air mover unit is in direct electrical connection with the base unit of the device and an outward surface of the removable air mover unit abuts an inner wall of an opening that receives the removable air mover unit, wherein a first electrical contact is disposed on the outward surface of the removable air mover unit, and a second electrical contact is disposed on the inner wall of an opening that receives the removable air mover unit to provide electrical communication between the removable air mover unit and the base unit of the device.

7. The method of claim 1 wherein the removable air mover unit is disposed adjacent to the base unit such that the removable air mover unit is in fluid communication with the mixing chamber of the device.

8. The method of claim 1, wherein the removable air mover unit comprises a fan, an on-board battery, on-board circuitry, and a power cord, the power cord configured to connect with the base unit for electrical communication.

9. The method of claim 1, wherein the at least one substance comprises a fertilizer for delivering in mist form to a plant.

10. The method of claim 1 comprising connecting a spraying catheter tube to the conduit, using an adapter, wherein the spraying catheter tube has an elongated body comprising a flexible tube segment configured for inserting into a user's body, and an adjustable tip portion that is oriented differently for allowing directional adjustment of an outlet tip for medication delivery to a target region inside the user's body, wherein the target region is a tooth within a mouth or an internal organ of the user.

11. A method for administering at least one substance to a body part of a user, the method comprising:
providing a removable capsule having an atomizer, the removable capsule containing the at least one substance, wherein the at least one substance is one of a medication, a therapeutic substance and a cosmetic substance;
providing a removable air mover unit in attachment with a base unit of a device, the base unit defining openings on the base unit configured to receive a portion of a conduit and the removable air mover unit such that the removable air mover unit is in fluid communication with a mixing chamber within the device;
providing a spraying catheter tube connected to the conduit, using an adapter, wherein the spraying catheter tube has an elongated body comprising a flexible tube segment configured for inserting into a user's body, and an adjustable tip portion that is oriented differently for allowing directional adjustment of the adjustable tip portion for medication delivery to a target region inside the user's body, wherein the target region is a tooth within a mouth of the user or an internal organ of the user;
inserting the removable capsule in a channel of the base unit, the channel in fluid communication with a mixing chamber of the base unit,
dispensing, using the atomizer, the at least one substance from the removable capsule to the mixing chamber of the base unit, wherein the at least one substance is combined with air in the mixing chamber; and
using the removable air mover unit, causing air and the at least one substance within the mixing chamber to be conveyed from the mixing chamber to the conduit such that air and the at least one substance dispensed from the removable capsule exits the conduit.

12. The method of claim 11, wherein an outward surface of the removable air mover unit abuts an inner wall of an opening that receives the removable air mover unit and the removable air mover unit is in direct electrical connection with the base unit, wherein a first electrical contact is disposed on the outward surface of the removable air mover unit, and a second electrical contact is disposed on the inner wall of the opening that receives the removable air mover unit for providing electrical communication between the removable air mover unit and the base unit of the device.

13. The method of claim 12 further comprising:
removing the removable air mover unit from the base unit;
attaching a cap to cover the opening of the base unit, for a capped chamber;
dispensing, using the atomizer, the at least one substance from the removable capsule to the capped chamber of the base unit; and
administering the at least one substance to the user by conveying the at least one substance from the capped chamber.

14. The method of claim 13 further comprising:
removing the cap from the base unit;
connecting a portion of a resilient bladder with the base unit, such that the resilient bladder in in fluid communication with the mixing chamber of the base unit; and
conveying the at least one substance from the mixing chamber to a portion of the conduit though the resilient bladder.

15. The method of claim 14, further comprising:
removing the spraying catheter tube from the conduit of the base unit; and
attaching an ocular tube to the conduit, the ocular tube housing an eye cup at a distant end for administering the at least one substance in a mist form directly to eyes and skin of the user.

* * * * *